US008865672B2

(12) United States Patent
Isenberg et al.

(10) Patent No.: US 8,865,672 B2
(45) Date of Patent: Oct. 21, 2014

(54) PREVENTION OF TISSUE ISCHEMIA AND RELATED METHODS

(75) Inventors: Jeffrey S. Isenberg, Mt. Lebanon, PA (US); David D. Roberts, Bethesda, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 275 days.

(21) Appl. No.: 13/546,931

(22) Filed: Jul. 11, 2012

(65) Prior Publication Data
US 2012/0295956 A1 Nov. 22, 2012

Related U.S. Application Data

(62) Division of application No. 12/444,364, filed as application No. PCT/US2007/080647 on Oct. 5, 2007, now Pat. No. 8,236,313.

(60) Provisional application No. 60/850,132, filed on Oct. 6, 2006, provisional application No. 60/864,153, filed on Nov. 2, 2006, provisional application No. 60/888,754, filed on Feb. 7, 2007, provisional application No. 60/910,549, filed on Apr. 6, 2007, provisional application No. 60/956,375, filed on Aug. 16, 2007.

(51) Int. Cl.
*A61K 48/00* (2006.01)
*C07K 14/78* (2006.01)
*G01N 33/68* (2006.01)

(52) U.S. Cl.
CPC ............... *C07K 14/78* (2013.01); *A61K 48/00* (2013.01); *G01N 33/6887* (2013.01); *G01N 33/6893* (2013.01); *G01N 2333/705* (2013.01)
USPC .................... 514/44 A; 424/184.1; 536/23.1; 536/24.5

(58) Field of Classification Search
None
See application file for complete search history.

(56) References Cited

U.S. PATENT DOCUMENTS

| 4,877,810 | A | * | 10/1989 | Mickle et al. .................. 514/456 |
| 5,192,744 | A | | 3/1993 | Bouck et al. |
| 5,399,667 | A | | 3/1995 | Frazier et al. |
| 5,627,265 | A | | 5/1997 | Frazier et al. |
| 5,750,141 | A | * | 5/1998 | Roberts et al. .................. 424/449 |
| 5,750,502 | A | | 5/1998 | Jessell et al. |
| 5,789,447 | A | | 8/1998 | Wink, Jr. et al. |
| 5,840,692 | A | | 11/1998 | Deutch et al. |
| 6,235,716 | B1 | | 5/2001 | Ben-Sasson |
| 6,469,138 | B1 | | 10/2002 | Frazier et al. |
| 6,727,063 | B1 | | 4/2004 | Lander et al. |
| 6,812,339 | B1 | | 11/2004 | Venter et al. |
| 6,900,016 | B1 | | 5/2005 | Venter et al. |
| 7,097,618 | B1 | * | 8/2006 | Benditt et al. ................. 600/363 |
| 2004/0101526 | A1 | | 5/2004 | Freyberg et al. |
| 2008/0131431 | A1 | | 6/2008 | Smith et al. |

FOREIGN PATENT DOCUMENTS

| WO | WO 97/27873 A1 | 8/1997 |
| WO | WO 99/40940 A1 | 8/1999 |
| WO | WO 03/090694 | 11/2003 |
| WO | WO 2004/018995 | 3/2004 |

OTHER PUBLICATIONS

Mongardon et al., Br J Anaesth. Jul. 2009;103(1):82-8. doi: 10.1093/bja/aep135. Epub May 21, 2009.*
Soto-Pantoja et al., J Genet Syndr Gene Ther. Oct. 2011;2(2). pii: 1000105. Epub Sep. 26, 2011.*
Agah et al., "The lack of thrombospondin-1 (TSP1) dictates the course of wound healing in double-TSP1/TSP2-null mice," *Am. J. Pathol.*, 161:831-839, 2002.
Agbanyo et al., "Thrombospondin-Platelet Interactions: Role of Divalent Cations, Wall Shear Rate, and Platelet Membrane Glycoproteins," *J. Clin. Invest.*, 92:288-296, 1993.
Aiken et al., "Identification of a New Class of Inducible Receptors on Platelets: Thrombospondin Interacts with Platelets via a GPIIb-IIIa-independent Mechanism," *J. Clin. Invest.*, 78:1713-1716, 1986.
Antignani, "Treatment of chronic peripheral arterial disease," *Curr. Vasc. Pharmacol.*, 1(2):205-216, 2003.
Armstrong and Bornstein, "Thrombospondins 1 and 2 function as inhibitors of angiogenesis," *Mat. Biol.*, 22(1):63-71, 2003.
Aronow, "Management of peripheral arterial disease," *Cardiol. Rev.*, 13:61-68, 2005.
Asch et al., "Isolation of the Thrombospondin Membrane Receptor," *J. Clin. Invest.*, 79:1054-1061, 1987.
Atiyeh et al., "New technologies for burn wound closure and healing-review of the literature," *Burns*, 31(8):944-956, 2005.
Bamberger et al., "A cell surface receptor complex for fibrillar beta-amyloid mediates microglial activation," *J. Neurosci.*, 23:2665-2674, 2003.
Barazi et al., "Regulation of Integrin Function by CD47 Ligands: Differential Effects on $\alpha v\beta 3$ and $\alpha 4\beta 1$ Integrin-Mediated Adhesion," *J. Biol. Chem.*, 277(45):42859-42866, 2002.
Bocci et al., "Thrombospondin 1, a mediator of the antiangiogenic effects of low-dose metronomic chemotherapy," *Proc. Natl. Acad. Sci. USA*, 100:12917-12922, 2003.

(Continued)

*Primary Examiner* — Michael Szperka
(74) *Attorney, Agent, or Firm* — Klarquist Sparkman, LLP

(57) ABSTRACT

Provided herein are methods for preventing, ameliorating, and/or reducing tissue ischemia and/or tissue damage due to ischemia, increasing blood vessel diameter, blood flow and tissue perfusion in the presence of vascular disease including peripheral vascular disease, atherosclerotic vascular disease, coronary artery disease, stroke and influencing other conditions, by suppressing CD47 and/or blocking TSP1 and/or CD47 activity or interaction. Influencing the interaction of CD47-TSP1 in blood vessels allows for control of blood vessel diameter and blood flow, and permits modification of blood pressure and cardiac function. Under conditions of decreased blood flow, for instance through injury or atherosclerosis, blocking TSP1-CD47 interaction allows blood vessels to dilate and increases blood flow, tissue perfusion and tissue survival.

31 Claims, 51 Drawing Sheets

(56) References Cited

OTHER PUBLICATIONS

Bolz et al., "Nitric oxide-induced decrease in calcium sensitivity of resistance arteries is attributable to activation of the myosin light chain phosphatase and antagonized by the RhoA/Rho kinase pathway," *Circulation*, 107(24):3081-3087, 2003.

Bonnefoy et al., "A Model of Platelet Aggregation Involving Multiple Interactions of Thrombospondin-1, Fibrinogen, and GPIIbIIIa Receptor," *J. Biol. Chem.*, 276:5605-5612, 2001.

Bonnefoy et al., "Thrombospondin-1 controls vascular platelet recruitment and thrombus adherence in mice by protecting (sub)endothelial VWF from cleavage by ADAMTS13," *Blood*, 107(3):955-964, 2006.

Bornstein et al., "The role of thrombospondins 1 and 2 in the regulation of cell-matrix interactions, collagen fibril formation, and the response to injury," *Int. J. Biochem. Cell Biol.*, 36(6):1115-1125, 2004.

Bornstein, "Thrombospondins as matricellular modulators of cell function," *J. Clin. Invest.*, 107(8):929-934, 2001.

Boukerche et al., "Characterization of an anti-thrombospondin monoclonal antibody (P8) that inhibits human blood platelet functions. Normal binding of P8 to thrombin-activated Glanzmann thrombasthenic platelets," *Eur. J. Biochem.*, 171:383-392, 1988.

Boyce and Warden, "Principles and practices for treatment of cutaneous wounds with cultured skin substitutes," *Am. J. Surg.*, 183(4):445-456, 2002.

Brown and Frazier, "Integrin-associated protein (CD47) and its ligands," *Trends Cell Biol.*, 11(3):130-135, 2001.

Brown et al., "Integrin-associated protein: a 50-kD plasma membrane antigen physically and functionally associated with integrins," *J. Cell Biol.*, 111:2785-2794, 1990.

Budhani et al., "Vascular response to intra-arterial injury in the thrombospondin-1 null mouse," *J. Mol. Cell. Cardiol.*, 43:210-214, 2007.

Carlson et al., "Structure of the calcium-rich signature domain of human thrombospondin-2," *Nat. Struct. Mol. Biol.*, 12:910-914, 2005.

Cauwels et al., "Anaphylactic shock depends on PI3K and eNOS-derived NO," *J. Clin. Invest.*, 116(8):2244-2251, 2006.

Chan, "Role of nitric oxide in ischemia and reperfusion injury," *Current Medicinal Chemistry—Anti-Inflammatory and Anti-Allergy Agents*, 1(1):1-13, 2002.

Chen et al., "Antibody blockade of thrombospondin accelerates reendothelialization and reduces neointima formation in balloon-injured rat carotid artery," *Circulation*, 100:849-854, 1999.

Chen et al., "The cell biology of thrombospondin-1," *Matrix Biol.*, 19:597-614, 2000.

Chung et al., "Thrombospondin Acts via Integrin-associated Protein to Activate the Platelet Integrin $\alpha_{IIb}\beta_3$," *J Biol. Chem.*, 272:14740-14746, 1997.

Chung et al., "Thrombospondin-1 Acts Via IAP/CD47 to Synergize With Collagen in $\alpha_2\beta_1$-Mediated Platelet Activation," *Blood*, 94:642-648, 1999.

Cordeiro et al., "The protective effect of L-arginine on ischemia-reperfusion injury in rat skin flaps," *Plast. Reconstr. Surg.*, 100(5):1227-1233, 1997.

Danielewski et al., "The NO/cGMP pathway inhibits Rap 1 activation in human platelets via cGMP-dependent protein kinase I," *Thromb. Haemost.*, 93:319-325, 2005.

Dawson et al., "CD36 mediates the In vitro inhibitory effects of thrombospondin-1 on endothelial cells," *J. Cell. Biol.*, 138:707-717, 1997.

de Fraipont et al., "Thrombospondins and tumor angiogenesis," *Trends Mol. Med.*, 7(9):401-407, 2001.

Desjardins and Balligand, "Nitric oxide-dependent endothelial function and cardiovascular disease," *Acta Clin. Belg.*, 61(6):326-334, 2006.

Dimmeler et al., "Activation of nitric oxide synthase in endothelial cells by Akt-dependent phosphorylation," *Nature*, 399:601-605, 1999.

DiPietro et al., "Thrombospondin 1 Synthesis and Function in Wound Repair," *Am. J. Pathol.*, 148(6):1851-1860, 1996.

Dixit et al., "A monoclonal antibody against human thrombospondin inhibits platelet aggregation," *Proc. Natl. Acad. Sci. U S A*, 82(10):3472-3476, 1985.

Dorahy et al., "Stimulation of Platelet Activation and Aggregation by a Carboxyl-terminal Peptide from Thrombospondin Binding to the Integrin-associated Protein Receptor" *J. Biol. Chem.*, 272:1323-1330, 1997.

Dzavik et al., "Effect of nitric oxide synthase inhibition on haemodynamics and outcome of patients with persistent cardiogenic shock complicating acute myocardial infarction: a phase II dose-ranging study," *Eur. Heart J.*, 28(9):1109-1116, 2007.

Eldesoky, "Effect of acute inhibition of nitric oxide synthesis by L-NAME on cardiovascular responses following peripheral autonomic blockade in rabbits," *Fundam. Clin. Pharmacol.*, 202:39-45, 2006.

Esemuede et al., "The role of thrombospondin-1 in human disease," *J. Surg. Res.*, 122:135-142, 2004.

Favier et al., "Critical overexpression of thrombospondin-1 in chronic leg Ischaemia," *.J. Pathol.*, 207(3):358-366, 2005.

Frangogiannis et al., "Critical role of endogenous thrombospondin-1 in preventing expansion of healing myocardial infarcts," *Circulation*, 111:2935-2942, 2005.

Frazier et al., "The Thrombospondin Receptor Integrin-associated Protein (CD47) Functionally Couples to Heterotrimeric Gi," *J. Biol. Chem.*, 274:8554-8560, 1999.

Freedman et al., "Deficient platelet-derived nitric oxide and enhanced hemostasis in mice lacking the NOSIII gene," *Circ. Res.*, 84:1416-1421, 1999.

Fujimoto et al., "Thrombospondin-bound Integrin-associated Protein (CD47) Physically and Functionally Modifies Integrin $\alpha$IIb$\beta$3 by Its Extracellular Domain," *J. Biol. Chem.*, 278:26655-26665, 2003.

Fukumura et al., "Predominant role of endothelial nitric oxide synthase in vascular endothelial growth factor-induced angiogenesis and vascular permeability," *Proc. Natl. Acad. Sci. USA*, 98:2604-2609, 2001.

Furchgott and Vanhoutte, "Endothelium-derived relaxing and contracting factors," *Faseb J.*, 3:2007-2018, 1989.

Gao et al., "Integrin-associated Protein Is a Receptor for the C-terminal Domain of Thrombospondin," *J. Biol. Chem.*, 271:21-24, 1996.

Gao et al., "Thrombospondin modulates $\alpha_v$ $\beta_3$ function through integrin-associated protein," *J. Cell Biol.*, 135(2):533-544, 1996.

Gatti et al., "Intravenous nitroglycerin as a means of improving ischemic tissue hemodynamics and survival," *Ann. Plast. Surg.*, 16(6):521-526, 1986.

GenBank Accession No. NM_001777, *Homo sapiens* CD47 molecule (CD47), transcript variant 1, mRNA, Jun. 24, 2005.

Good et al., "A tumor suppressor-dependent inhibitor of angiogenesis is immunologically and functionally indistinguishable from a fragment of thrombospondin," *Proc. Natl. Acad. Sci. USA*, 87(17):6624-6628, 1990.

Gresham et al., "A novel member of the integrin receptor family mediates Arg-Gly-Asp-stimulated neutrophil phagocytosis," *J. Cell Biol.*, 108:1935-1943, 1989.

Gribbe et al., "Effects of nitric oxide synthase inhibition on blood flow and survival in experimental skin flaps," *J. Plast. Reconstr. Aesthet. Surg.*, 60(3):287-293, 2007.

Guo et al., "Differential roles of protein kinase C and pertussis toxin-sensitive G-binding proteins in modulation of melanoma cell proliferation and motility by thrombospondin 1," *Cancer Res.*, 58(14):3154-3162, 1998.

Hamano et al., "Thrombospondin-1 associated with tumor microenvironment contributes to low-dose cyclophosphamide-mediated endothelial cell apoptosis and tumor growth suppression," *Cancer Res.*, 64:1570-1574, 2004.

Han et al., "Reconstructing and deconstructing agonist-induced activation of integrin $\alpha_{IIb}\beta_3$," *Curr. Biol.*, 16:1796-1806, 2006.

Hankey et al., "Medical treatment of peripheral arterial disease," *JAMA*, 295(5):547-553, 2006.

(56) References Cited

OTHER PUBLICATIONS

Harris and Rumbaut, "Age-related responses of the microcirculation to ischemia-reperfusion and inflammation," *Pathophysiology*, 8(1):1-10, 2001.
Haviv et al., "Thrombospondin-1 mimetic peptide inhibitors of angiogenesis and tumor growth: design, synthesis, and optimization of pharmacokinetics and biological activities," *J. Med. Chem.*, 48:2838-2846, 2005.
Haynes et al., "Inhibition of nitric oxide synthesis increases blood pressure in healthy humans," *J. Hypertens.*, 11(12):1375-1380, 1993.
Hermann et al., "Nitric oxide in hypertension," *J. Clin. Hypertens.* (Greenwich), 8:17-29, 2006.
Hermann et al., "The Vitronectin Receptor and its Associated CD47 Molecule Mediates Proinflammatory Cytokine Synthesis in Human Monocytes by Interaction with Soluble CD23," *J. Cell Biol.*, 144(4): 767-775, 1999.
Higuchi et al., "Assay of antioxidant and anti-inflammatory activity of nitric oxide in vivo," *Methods Enzymol.*, 301:424-436, 1999.
Hiscott et al., "Thrombospondin 1, thrombospondin 2 and the eye," *Prog. Retin. Eye Res.*, 25:1-18, 2006.
Hochberg et al., "Development and evaluation of an in vivo mouse model for studying myocutaneous flap microcirculation and viability before and after suturing or stapling," *Int. J. Microcirc. Clin. Exp.*, 14(1-2):67-72, 1994.
Hoekstra et al., "Phase 1 safety, pharmacokinetic, and pharmacodynamic study of the thrombospondin-1 mimetic angiogenesis inhibitor ABT-510 in patients with advanced cancer," *J. Clin. Oncol.*, 23:5188-5197, 2005.
Holmes et al., "Preservation of platelet responsiveness to nitroglycerine despite development of vascular nitrate tolerance," *Br. J. Clin. Pharmacol.*, 60:355-363, 2005.
Ignarro et al., "Endothelium-derived nitric oxide: actions and properties," *Circ. Res.*, 90:21-28, 2002.
Ignarro, "Biological actions and properties of endothelium-derived nitric oxide formed and released from artery and vein," *Circ. Res.*, 65:1-21, 1989.
Ignarro, "Nitric oxide as a unique signaling molecule in the vascular system: a historical overview," *J. Physiol. Pharmacol.*, 53(4 Pt. 1):503-514, 2002.
Ii et al., "Endothelial progenitor thrombospondin-1 mediates diabetes-induced delay in reendothelialization following arterial injury," *Circ. Res.*, 98(5):697-704, 2006.
Iruela-Arispe et al., "Inhibition of angiogenesis by thrombospondin-1 is mediated by 2 independent regions within the type 1 repeats," *Circulation*, 100:1423-1431, 1999.
Isenberg et al., "Blockade of thrombospondin-1-CD47 interactions prevents necrosis of full thickness skin grafts," *Ann Surg.*, 247(1):180-190, 2008.
Isenberg et al., "Blocking thrombospondin-1/CD47 signaling alleviates deleterious effects of aging on tissue responses to ischemia," *Arterioscler. Thromb. Vasc. Biol.*, 27(12):2585-2588, 2007.
Isenberg et al., "CD47 is Necessary for Inhibition of Nitric Oxide-stimulated Vascular Cell Responses by Thrombospondin-1," *J. Biol. Chem.*, 281(36):26069-26080, 2006.
Isenberg et al., "CD47: A New Target in Cardiovascular Therapy," *Arterioscler. Thromb. Vasc. Biol.*, 28:615-621, 2008.
Isenberg et al., "Differential effects of ABT-510 and a CD36-binding peptide derived from the type 1 repeats of thrombospondin-1 on fatty acid uptake, nitric oxide signaling, and caspase activation in vascular cells," *Biochem. Pharmacol.*, 75(5):875-885, 2008.
Isenberg et al., "Differential interactions of thrombospondins-1, -2 and -4 with CD47 and effects on cGMP signaling and ischemic injury responses," *J. Biol. Chem.*, 284(2):1116-1125, 2009.
Isenberg et al., "Endogenous thrombospondin-1 is not necessary for proliferation but is permissive for vascular smooth muscle cell responses to platelet-derived growth factor," *Matrix Biol.*, 24:110-123, 2005.
Isenberg et al., "Enhancing cardiovascular dynamics by inhibition of thrombospondin-1/CD47 signaling," *Curr. Drug. Targets*, 9(10):833-841, 2008.

Isenberg et al., "Gene silencing of CD47 and antibody ligation of thrombospondin-1 enhance ischemic tissue survival in a porcine model: Implications for human disease," *Ann. Surg.*, 247(5):860-868, 2008.
Isenberg et al., "Guanylyl cyclase-dependent chemotaxis of endothelial cells in response to nitric oxide gradients," *Free Radic. Biol. Med.*, 40(6):1028-1033, 2006.
Isenberg et al., "In vivo Applications of Morpholino Oligonucleotides," *Gene and Cell Therapy*, 3$^{rd}$ ed:487-496, 2008.
Isenberg et al., "Increasing survival of ischemic tissue by targeting CD47," *Circ. Res.*, 100(5):712-720, 2007.
Isenberg et al., "Modulation of angiogenesis by dithiolethione-modified NSAIDs and valproic acid," *Br J. Pharmacol.*, 151(1):63-72, 2007.
Isenberg et al., "Nitric oxide in wound-healing," *Microsurgery*, 25(5):442-451, 2005.
Isenberg et al., "Nitric oxide modulation of low-density mononuclear cell transendothelial migration," *Microsurgery*, 25(5):452-456, 2005.
Isenberg et al., "Regulation of nitric oxide signalling by thrombospondin 1: implications for anti-angiogenic therapies," *Nat. Rev. Cancer*, 9(3):182-194, 2009.
Isenberg et al., "Thrombospondin 1 and vasoactive agents indirectly alter tumor blood flow," *Neoplasia*, 10(8):886-896, 2008.
Isenberg et al., "Thrombospondin-1 and CD47 limit cell and tissue survival of radiation injury," *Am. J. Pathol*, 173(4)1100-1112, 2008.
Isenberg et al., "Thrombospondin-1 and CD47 regulate blood pressure and cardiac responses to vasoactive stress," *Matrix Biol.*, 28(2):110-119, 2009.
Isenberg et al., "Thrombospondin-1 antagonizes nitric oxide-stimulated vascular smooth muscle cell responses," *Cardiovasc Res.*, 71(4):785-793, 2006.
Isenberg et al., "Thrombospondin-1 inhibits endothelial cell responses to nitric oxide in a cGMP-dependent manner," *Proc. Natl. Acad. Sci. U.S.A.*, 102(37):13141-13146, 2005.
Isenberg et al., "Thrombospondin-1 inhibits nitric oxide signaling via CD36 by inhibiting myristic acid uptake," *J. Biol. Chem.*, 282(21):15404-15415, 2007.
Isenberg et al., "Thrombospondin-1 limits ischemic tissue survival by inhibiting nitric oxide-mediated vascular smooth muscle relaxation," *Blood*, 109(5):1945-1952, 2007.
Isenberg et al., "Thrombospondin-1 stimulates platelet aggregation by blocking the antithrombotic activity of nitric oxide/cGMP signaling," *Blood*, 111(2):613-623, 2008.
Isenberg et al., "Thrombospondin-1: a physiological regulator of nitric oxide signaling," *Cell. Mol. Life Sci.*, 65(5):728-742, 2008.
Isenberg et al., "Thrombospondin-1-CD47 blockade and exogenous nitrite enhance ischemic tissue survival, blood flow and angiogenesis via coupled NO-cGMP pathway activation," *Nitric Oxide*, May 27, 2009 (Epub ahead of print).
Isenberg et al., "Treatment of liver ischemia-reperfusion injury by limiting thrombospondin-1/CD47 signaling," *Surgery*, 144(5):752-761, 2008.
Isenberg, "Nitric oxide modulation of early angiogenesis," *Microsurgery*, 24(5):385-391, 2004.
Janeway et al., *Immunobiology*, 3$^{rd}$ edition, 1997, Garland Publications, Inc., 3:1-3:11.
Jiménez et al., "Signals leading to apoptosis-dependent inhibition of neovascularization by thrombospondin-1," *Nat. Med.*, 6(1): 41-48, 2000.
Jurk et al., "Thrombospondin-1 mediates platelet adhesion at high shear via glycoprotein Ib (GPIb): an alternative/backup mechanism to von Willebrand factor," *Faseb J.*, 17:1490-1492, 2003.
Kanda et al., "Role of thrombospondin-1-derived peptide, 4N1K, in FGF-2-induced angiogenesis," *Exp. Cell Res.*, 252:262-272, 1999.
Kang et al., "Impaired angiogenesis in the aging kidney: vascular endothelial growth factor and thrombospondin-1 in renal disease," *Am. J. Kidney Dis.*, 37:601-611, 2001.
Kapila et al., "Nitric oxide and the angiogenic response: can we improve the results of therapeutic angiogenesis?," *Expert Opin. Investig. Drugs*, 14:37-44, 2005.
Kasirer-Friede et al., "Complementary roles for fibrin(ogen), thrombospondin and vWF in mediating shear-dependent aggregation

(56) References Cited

OTHER PUBLICATIONS of platelets stimulated at threshold thrombin concentrations," *Thromb. Haemost.*, 86:653-659, 2001.

Khatib et al., "Basal and induced nitric oxide and cGMP productions are decreased in senescent cultured rat articular chondrocytes," *Mech. Ageing Dev.*, 101:21-32, 1998.

Khiabani and Kerrigan, "The effects of the nitric oxide donor SIN-1 on ischemia-reperfused cutaneous and myocutaneous flaps," *Plast. Reconstr. Surg.*, 110:169-176, 2002.

Knox et al., "Nitric oxide synthase inhibitors improve skin flap survival in the rat." *Microsurgery*, 15(10):708-711, 1994.

Komorowska-Timek et al. "The effect of single administration of vascular endothelial growth factor or L-arginine on necrosis and vasculature of the epigastric flap in the rat model," *Br. J. Plast. Surg.*, 57(4):317-325, 2004.

Kopp et al., "Thrombospondins deployed by thrombopoietic cells determine angiogenic switch and extent of revascularization," *J. Clin. Invest.*, 116(12):3277-3291, 2006.

Kuntscher et al., "Role of nitric oxide in the mechanism of preclamping and remote ischemic preconditioning of adipocutaneous flaps in a rat model," *J. Reconstr. Microsurg.*, 19:55-60, 2003.

Kuo et al., "Nitrosoglutathione improves blood perfusion and flap survival by suppression iNOS but protecting eNOS expression in the flap vessels after ischemia/reperfusion injury," *Surgery*, 135:437-446, 2004.

Kuo et al., "Nitrosoglutathione modulation of platelet activation and nitric oxide synthase expression in promotion of flap survival after ischemia/reperfusion injury," *J. Surg. Res.*, 119:92-99, 2004.

Kuznetsova and Roberts, "Functional regulation of T lymphocytes by modulatory extracellular matrix proteins," *Int. J. Biochem. Cell Biol.*, 36:1126-1134, 2004.

Kvansakul et al., "Structure of a thrombospondin C-terminal fragment reveals a novel calcium core in the type 3 repeats," *Embo J.*, 23:1223-1233, 2004.

Lamy et al., "CD47 and the 19 kDa Interacting Protein-3 (BNIP3) in T Cell Apoptosis," *J. Biol. Chem.*, 278(26):23915-23921, 2003.

Lamy et al., "Interactions between CD47 and thrombospondin reduce inflammation," *J Immunol.*, 178(9):5930-5939, 2007.

Lawler et al., "Thrombospondin-1 Is Required for Normal Murine Pulmonary Homeostasis and its Absence Causes Pneumonia," *J. Clin. Invest.*, 101:982-992, 1998.

Lawler, "The functions of thrombospondin-1 and -2," *Curr. Opin. Cell Biol.*, 12(5):634-640, 2000.

Lawler, "Thrombospondin-1 as an endogenous inhibitor of angiogenesis and tumor growth," *J. Cell Mol. Med.*, 6:1-12, 2002.

Legrand et al., "Selective inhibition of platelet macroaggregate formation by a recombinant heparin-binding domain of human thrombospondin," *Arterioscler Thromb.*, 14(11):1784-1791, 1994.

Leung, "Role of Thrombospondin in Platelet Aggregation," *J. Clin. Invest.*, 74:1764-1772, 1984.

Li et al., "Interactions of thrombospondins with α4β1 integrin and CD47 differentially modulate T cell behavior," *J. Cell Biol.*, 157(3):509-519, 2002.

Li et al., "Sequential activation of p38 and ERK pathways by cGMP-dependent protein kinase leading to activation of the platelet integrin $\alpha_{IIb}\beta_3$," *Blood*, 107:965-972, 2006.

Li et al., "Thrombospondin-1 inhibits TCR-mediated T lymphocyte early activation," *J. Immunol.*, 166(4):2427-2436, 2001.

Lin et al., "Differential Regulation of Thrombospondin-1 and Thrombospondin-2 After Focal Cerebral Ischemia/Reperfusion," *Stroke, J. Am. Heart Assoc.*, 34:177-186, 2003.

Lindberg et al., "Decreased resistance to bacterial infection and granulocyte defects in IAP-deficient mice," *Science*, 274:795-798, 1996.

Lindberg et al., "Integrin-associated Protein Immunoglobulin Domain Is Necessary for Efficient Vitronectin Bead Binding," *J. Cell Biol.*, 134(5):1313-1322, 1996.

Lindberg et al., "Molecular cloning of integrin-associated protein: an immunoglobulin family member with multiple membrane-spanning domains implicated in $\alpha_v\beta_3$-dependent ligand binding," *J. Cell Biol.*, 123:485-496, 1993.

Liu et al., "Functional elements on SIRPα IgV domain mediate cell surface binding to CD47," *J. Mol. Biol.*, 365(3):680-693, 2006.

Lopes et al., "Thrombospondin 2 regulates cell proliferation induced by Rac1 redox-dependent signaling," *Mol. Cell Biol.*, 23:5401-5408, 2003.

Lucchesi, B.R., *Arzneimittel-Forschung*, 44:420-32, 1994.

Magnetto et al., "CD36 mediates binding of soluble thrombospondin-1 but not cell adhesion and haptotaxis on immobilized thrombospondin-1," *Cell Biochem. Funct.*, 16:211-221, 1998.

Manna and Frazier, "CD47 Mediates Killing of Breast Tumor Cells via Gi-Dependent Inhibition of Protein Kinase A," *Cancer Res.*, 64:1026-1036, 2004.

Manna and Frazier, "The mechanism of CD47-dependent killing of T cells: heterotrimeric Gi-dependent inhibition of protein kinase A," *J. Immunol.*, 170(7):3544-3553, 2003.

Manna et al., "CD47 Augments Fas/CD95-mediated Apoptosis," *J. Biol. Chem.*, 280(33):29637-29644, 2005.

Marin, "Age-related changes in vascular responses: a review," *Mech. Ageing Dev.*, 79(2-3):71-114, 1995.

Markovic et al., "A phase II study of ABT-510 (thrombospondin-1 analog) for the treatment of metastatic melanoma," *Am. J. Clin. Oncol.*, 30:303-309, 2007.

McAllister and Laughlin, "Vascular nitric oxide: effects of physical activity, importance for health," *Essays Biochem.*, 42:119-131 2006.

McDonald et al., "An amyloid-like C-terminal domain of thrombospondin-1 displays CD47 agonist activity requiring both VVM motifs," *Biochemistry*, 42:10001-10011, 2003.

McDonald et al., "Cholesterol-independent Interactions with CD47 Enhance αvβ3 Avidity" *J. Biol. Chem.*, 279:17301-17311, 2004.

McDonald et al., "Role of nitric oxide in skin flap delay," *Plast. Reconstr. Surg.*, 113:927-931, 2004.

Moncada and Higgs, "The L-arginine-nitric oxide pathway," *N. Engl. J. Med.*, 329:2002-2012, 1993.

Moore et al., "A CD36-initiated Signaling Cascade Mediates Inflammatory Effects of β-Amyloid," *J. Biol. Chem.*, 277:47373-47379, 2002.

Morbidelli et al., "Role of nitric oxide in the modulation of angiogenesis," *Curr. Pharm. Des.*, 9:521-530, 2003.

Moro et al., "cGMP mediates the vascular and platelet actions of nitric oxide: confirmation using an inhibitor of the soluble guanylyl cyclase," *Proc. Natl. Acad. Sci. U.S.A.*, 93:1480-1485, 1996.

Mosher et al., "Secreted thrombospondin-1 controls platelet sensitivity to NO," *Blood*, 111:473-474, 2008.

Mullane et al., *Ann NY Acad Sci.*, 524:103-21, 1988.

Muller-Delp et al., "Effects of aging on vasoconstrictor and mechanical properties of rat skeletal muscle arterioles," *Am. J. Physiol. Heart Circ. Physiol.*, 282:H1843-1854, 2002.

Mullershausen et al., "Direct activation of PDE5 by cGMP: long-term effects within NO/cGMP signaling," *J. Cell. Biol.*, 160:719-727, 2003.

Munzel et al., "Vascular consequences of endothelial nitric oxide synthase uncoupling for the activity and expression of the soluble guanylyl cyclase and the cGMP-dependent protein kinase," *Arterioscler. Thromb. Vasc. Biol.*, 25:1551-1557, 2005.

Murad, "Cyclic GMP: synthesis, metabolism, and function. Introduction and some historical comments," *Adv. Pharmacol.*, 26:1-5, 1994.

Murohara and Asahara, "Nitric oxide and angiogenesis in cardiovascular disease," *Antioxid. Redox. Signal.*, 4:825-831, 2002.

Murthy et al., "Efficacy of perioperative thromboprophylactic agents in the maintenance of anastamotic patency and survivial of rat microvascular free groin flaps," *Otolaryngol. Head Neck Surg.*, 129:176-182, 2003.

Napoli et al., "Beneficial effects of concurrent autologous bone marrow cell therapy and metabolic intervention in ischemia-induced angiogenesis in the mouse hindlimb," *Proc. Natl. Acad. Sci. U.S.A.*, 102:17202-17206, 2005.

Napoli et al., "Nitric oxide and atherosclerosis: an update," *Nitric Oxide*, 15(4):265-279, 2006.

(56) References Cited

OTHER PUBLICATIONS

Niezgoda and Mewissen, "The management of lower extremity wounds complicated by acute arterial insufficiency and ischemia," *Ostomy Wound Manage.*, 50:1-11, 2004.
Nowygrod et al., "Trends, complications, and mortality in peripheral vascular surgery," *J. Vasc. Surg.*, 43:205-216, 2006.
Oldenborg, "Role of CD47 in erythroid cells and in autoimmunity," *Leuk. Lymphoma.*, 45:1319-1327, 2004.
Ortiz and Garvin, "Cardiovascular and renal control in NOS-deficient mouse models," *Am. J. Physiol. Regul. Integr. Comp. Physiol.*, 284:R628-638, 2003.
Papapetropoulos et al., "Nitric Oxide Production Contributes to the Angiogenic Properties of Vascular Endothelial Growth Factor in Human Endothelial Cells," *J. Clin. Invest.*, 100:3131-3139, 1997.
Pimanda et al., "Role of Thrombospondin-1 in Control of von Willebrand Factor Multimer Size in Mice," *J. Biol. Chem.*, 279(20):21439-21448, 2004.
Qian et al., "Age-dependent acceleration of ischemic injury in endothelial nitric oxide synthase-deficient mice: potential role of impaired VEGF receptor 2 expression," *J. Cardiovasc. Pharmacol.*, 47(4):587-593, 2006.
Quesada et al., "In vivo upregulation of CD95 and CD95L causes synergistic inhibition of angiogenesis by TSP1 peptide and metronomic doxorubicin treatment," *Cell Death and Diff.*, 12:649-658, 2005.
Radomski et al., "An L-arginine/nitric oxide pathway present in human platelets regulates aggregation," *Proc. Natl. Acad. Sci. U.S.A.*, 87(13):5193-5197, 1990.
Rebres et al., "Membrane Raft Association of CD47 Is Necessary for Actin Polymerization and Protein Kinase C u Translocation in Its Synergistic Activation of T Cells" *J. Biol. Chem.*, 276(10):7672-7680, 2001.
Rebres et al., "Normal Ligand Binding and Signaling by CD47 (Integrin-associated Protein) Requires a Long Range Disulfide Bond between the Extracellular and Membrane-spanning Domains," *J. Biol. Chem.*, 276(37):34607-34616, 2001.
Reed and Edelberg, "Impaired angiogenesis in the aged," *Sci. Aging Knowledge Environ.*, 2004(7):pe7, 2004.
Reed et al., "Differential expression of SPARC and thrombospondin 1 in wound repair: immunolocalization and in situ hybridization," *J. Histochem. Cytochem.*, 41(10):1467-1477, 1993.
Rees et al., "Role of Endothelium-Derived Nitric Oxide in the Regulation of Blood Pressure," *Proc. Natl. Acad. Sci. U.S.A.*, 86:3375-3378, 1989.
Ribuffo et al., "Salvage of a free flap after late total thrombosis of the flap and revascularization," *Scand. J. Plast. Reconstr. Surg. Hand Surg.*, 38:50-52, 2004.
Ridnour et al., "Molecular mechanisms for discrete nitric oxide levels in cancer," *Nitric Oxide*, 19(2):73-76, 2008.
Ridnour et al., "Nitric oxide regulates angiogenesis through a functional switch involving thrombospondin-1," *Proc. Natl. Acad. Sci. U.S.A.*, 102:13147-13152, 2005.
Ridnour et al., "Nitric oxide regulates matrix metalloproteinase-9 activity by guanylyl-cyclase-dependent and -independent pathways," *Proc. Natl. Acad. Sci. U.S.A.*, 104(43):16898-06903, 2007.
Ridnour et al., "The biphasic nature of nitric oxide responses in tumor biology," *Antioxid. Redox. Signal.*, 8(7-8):1329-1337, 2006.
Riessen et al., "Immunolocalization of thrombospondin-1 in human atherosclerotic and restenotic arteries," *Am. Heart J.*, 135:357-364, 1998.
Roberts et al., "Nitric oxide and its gatekeeper thrombospondin-1 in tumor angiogenesis," *Clin. Cancer Res.*, 13(3):795-798, 2007.
Roberts, "Regulation of tumor growth and metastasis by thrombospondin-1," *Faseb J.*, 10:1183-1191, 1996.
Rofstad et al., "Antiangiogenic treatment with thrombospondin-1 enhances primary tumor radiation response and prevents growth of dormant pulmonary micrometastases after curative radiation therapy in human melanoma xenografts," *Cancer Res.*, 63:4055-4061, 2003.
Rofstad et al., "Thrombospondin-1 treatment prevents growth of dormant lung micrometastases after surgical resection and curative radiation therapy of the primary tumor in human melanoma xenografts," *Int. J. Radiat. Oncol. Biol. Phys.*, 58:493-499, 2004.
Roth et al., "Thrombospondin-1 is elevated with both intimal hyperplasia and hypercholesterolemia," *J. Surg. Res.*, 74:11-16, 1998.
Rudikoff et al., *Proc. Natl. Acad. Sci. USA*, 79:1979-1983, 1982.
Rush et al., "Vascular nitric oxide and oxidative stress: determinants of endothelial adaptations to cardiovascular disease and to physical activity," *Can. J. Appl. Physiol.*, 30(4):442-474, 2005.
Ryan, "The ageing of the blood supply and the lymphatic drainage of the skin," *Micron*, 35(3):161-171, 2004.
Rybalkin et al., "Cyclic GMP phosphodiesterases and regulation of smooth muscle function," *Circ. Res.*, 93:280-291, 2003.
Sarifakioglu et al., "The influence of sildenafil on random skin flap survival in rats: an experimental study," *Br. J. Plast. Surg.*, 57:769-772, 2004.
Sauzeau et al., "Cyclic GMP-dependent Protein Kinase Signaling Pathway Inhibits RhoA-induced Ca21 Sensitization of Contraction in Vascular Smooth Muscle" *J. Biol. Chem.*, 275:21722-21729, 2000.
Schultess et al., "Rap1GAP2 is a new GTPase-activating protein of Rap1 expressed in human platelets," *Blood*, 105:3185-3192, 2005.
Sezaki et al., "Thrombospondin-1 is induced in rat myocardial infarction and its induction is accelerated by ischemia/reperfusion," *Exp. Biol. Med. (Maywood)*, 230:621-630, 2005.
Shafiee et al., "Inhibition of retinal angiogenesis by peptides derived from thrombospondin-1," *Invest. Ophthalmol. Vis. Sci.*, 41(8):2378-2388, 2000.
Shizukuda et al., "Vascular endothelial growth factor-induced endothelial cell migration and proliferation depend on a nitric oxide-mediated decrease in protein kinase C delta activity," *Circ. Res.*, 85:247-256, 1999.
Short et al., "Inhibition of endothelial cell migration by thrombospondin-1 type-1 repeats is mediated by β1 integrins," *J. Cell. Biol.*, 168:643-653, 2005.
Snyder, "Treatment of nonhealing ulcers with allografts," *Clin. Dermatol.*, 23(4):388-395, 2005.
Sorbera and Bayes, "ABT-510: Oncolytic Angiogenesis Inhibitor," *Drugs of the Future*, 30:1081-8086, 2005.
Stenina et al., "Coronary artery disease and the thrombospondin single nucleotide polymorphisms," *Int. J. Biochem. Cell Biol.*, 36:1013-1030, 2004.
Stenina et al., "Increased expression of thrombospondin-1 in vessel wall of diabetic Zucker rat," *Circulation*, 107:3209-3215, 2003.
Streit et al., Thrombospondin-1 suppresses wound healing and granulation tissue formation in the skin of transgenic mice, *EMBO J.*, 19(13): 3272-3282, 2000.
Takahashi and Mendelsohn, "Synergistic activation of endothelial nitric-oxide synthase (eNOS) by HSP90 and Akt: calcium-independent eNOS activation involves formation of an SHP90-Akt-CaM-bound eNOS complex," *J. Biol. Chem.*, 278:30821-30827, 2003.
Tandon et al., "Adhesive functions of platelets lacking glycoprotein IV (CD36)," *Blood*, 78:2809-2813, 1991.
Taraboletti et al., "Platelet thrombospondin modulates endothelial cell adhesion, motility, and growth: a potential angiogenesis regulatory factor," *J. Cell. Biol.*, 111(2):765-772, 1990.
Thakar et al., "Identification of thrombospondin 1(TSP-1) as a novel mediator of cell injury in kidney ischemia," *J Clin Invest*, 115(12):3451-3459, 2005.
Tolsma et al., "Peptides derived from two separate domains of the matrix protein thrombospondin-1 have anti-angiogenic activity," *J. Cell Biol.*, 122:497-511, 1993.
Topol et al., "Single nucleotide polymorphisms in multiple novel thrombospondin genes may be associated with familial premature myocardial infarction," *Circulation*, 104(22):2641-2644, 2001.
Topp et al., "Role of nitric oxide in surgical flap survival," *J. Am. Coll. Surg.*, 201(4):628-639, 2005.
Tsao and Mousa, "Thrombospondin Mediates Calcium Mobilization in Fibroblasts via Its Arg-Gly-Asp and Carboxyl-terminal Domains" *J. Biol. Chem.*, 270:23747-23753, 1995.
Tulasne et al., "C-terminal peptide of thrombospondin-1 induces platelet aggregation through the Fc receptor g-chain—associated signaling pathway and by agglutination," *Blood*, 98:3346-3352, 2001.

(56) References Cited

OTHER PUBLICATIONS

Tuszynski et al., "Thrombospondin promotes platelet aggregation," *Blood*, 72:109-115, 1988.

Urbich et al., "Dephosphorylation of endothelial nitric oxide synthase contributes to the anti-angiogenic effects of endostatin," *FASEB J.*, 16:706-708, 2002.

van Beek et al., "Signal regulatory proteins in the immune system," *J. Immunol.*, 175:7781-7787, 2005.

Vogel et al., "Modulation of endothelial cell proliferation, adhesion, and motility by recombinant heparin-binding domain and synthetic peptides from the type I repeats of thrombospondin," *J. Cell Biochem.*, 53:74-84, 1993.

Volpert et al., "A human fibrosarcoma inhibits systemic angiogenesis and the growth of experimental metastases via thrombospondin-1," *Proc. Natl. Acad. Sci. U.S.A.*, 95:6343-6348, 1998.

Wang and Frazier, "The thrombospondin receptor CD47 (IAP) modulates and associates with $\alpha 2\beta 1$ integrin in vascular smooth muscle cells," *Mol. Biol. Cell.*, 9:865-874, 1998.

Wang et al., "Integrin-associated protein stimulates $\alpha 2\beta 1$-dependent chemotaxis via Gi-mediated inhibition of adenylate cyclase and extracellular-regulated kinases," *J. Cell Biol.*, 147:389-400, 1999.

Wang et al., "Recipient bed vascularity and the survival of ischaemic flaps," *Br. J. Plast. Surg.*, 50(4):266-271, 1997.

Watkins et al., "Single-chain antibody fragments derived from a human synthetic phage-display library bind thrombospondin and inhibit sickle cell adhesion," *Blood*, 102(2):718-724, 2003.

Weinzweig and Gonzalez, "Free tissue failure is not an all-or-none phenomenon," *Plast. Reconstr. Surg.*, 96:648-660, 1995.

Wheeler et al., "Age-dependent changes in particulate and soluble guanylyl cyclase activities in urinary tract smooth muscle," *Mol. Cell Biochem.*, 169:115-124, 1997.

Wilson et al., "Beta 1 integrin- and proteoglycan-mediated stimulation of T lymphoma cell adhesion and mitogen-activated protein kinase signaling by thrombospondin-1 and thrombospondin-1 peptides," *J. Immunol.*, 163:3621-3628, 1999.

Woodman et al., "Selected Contribution: Aging impairs nitric oxide and prostacyclin mediation of endothelium-dependent dilation in soleus feed arteries," *J. Appl. Physiol.*, 95(5):2164-2170, 2003.

Yamamoto et al., "Normal aggregations of glycoprotein IV (CD36)-deficient platelets from seven healthy Japanese donors," *Br. J. Haematol.*, 81(1):86-92, 1992.

Yamasaki et al., "Reversal of impaired wound repair in iNOS-deficient mice by topical adenoviral-mediated iNOS gene transfer," *J. Clin. Invest.*, 101:967-971, 1998.

Yan et al., "Effects of early enteral arginine supplementation on resuscitation of severe burn patients," *Burns*, 33(2):179-184, 2007.

Yap et al., "Metronomic low-dose chemotherapy boosts CD95-dependent antiangiogenic effect of the thrombospondin peptide ABT-510: a complementation antiangiogenic strategy," *Clin. Cancer Res.*, 11:6678-6685, 2005.

Yee et al., "Expression of the type-1 repeats of thrombospondin-1 inhibits tumor growth through activation of transforming growth factor-beta," *Am. J. Pathol.*, 165(2):541-552, 2004.

Yu et al., "Endothelial nitric oxide synthase is critical for ischemic remodeling, mural cell recruitment, and blood flow reserve," *Proc. Natl. Acad. Sci. U.S.A.*, 102:10999-11004, 2005.

Zakarija and Soff, "Update on angiogenesis inhibitors," *Curr. Opin. Oncol.*, 17:578-583, 2005.

Zhou et al., "Type I collagen is a molecular target for inhibition of angiogenesis by endogenous thrombospondin-1," *Oncogene*, 25(4):536-545, 2006.

Ziche et al., "Nitric Oxide Synthase Lies Downstream from Vascular Endothelial Growth Factor—induced but Not Basic Fibroblast Growth Factor—induced Angiogenesis," *J. Clin. Invest.*, 99:2625-2634, 1997.

Zwicker et al., "The thrombospondin-1 N700S polymorphism is associated with early myocardial infarction without altering von Willebrand factor multimer size," *Blood*, 108:1280-1283, 2006.

Database UniProt (online), "Putative uncharacterized protein DKFZp686G02190 (Fragment)," retrieved from EBI accession No. UNIPROT: Q6MZL6, Database accession No. Q6MZL6n, first deposited Jul. 5, 2004.

International Search Report issued in International Application No. PCT/US2007/080647 on Oct. 5, 2007 (8 pages).

Written Opinion of the International Searching Authority issued in International Application No. PCT/US2007/080647 on Oct. 5, 2007 (9 pages).

Grimbert et al., "Thrombospondin/CD47 Interaction: A Pathway to Generate Regulatory T Cells from Human CD4 $^+$CD25$^-$ T Cells in Response to Inflammation," *J Immunol*, 177:3534-3541, 2006.

\* cited by examiner

Figure 1
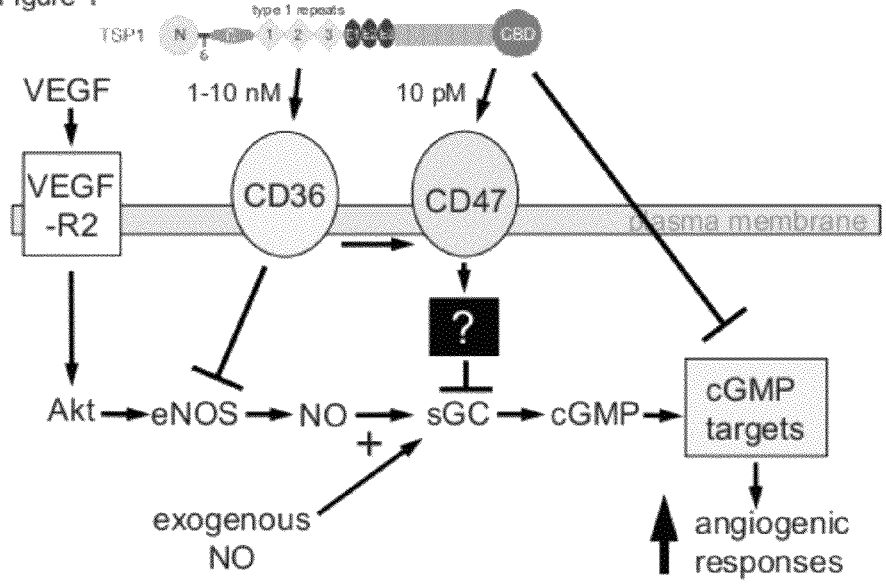
Figure 2
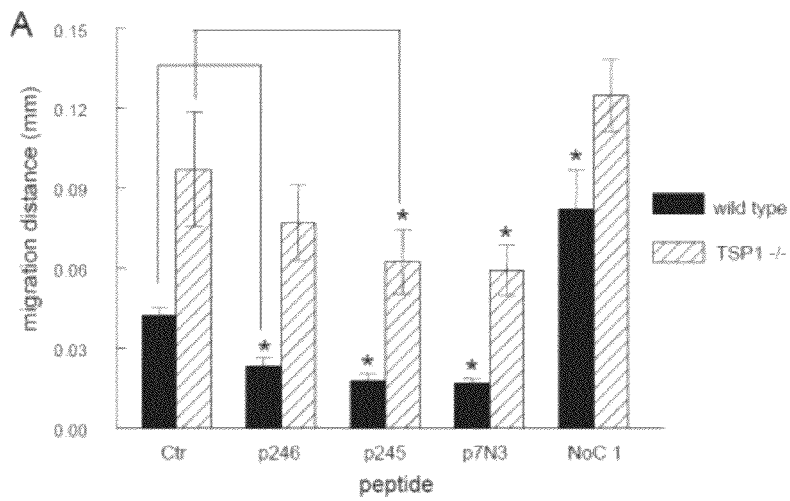
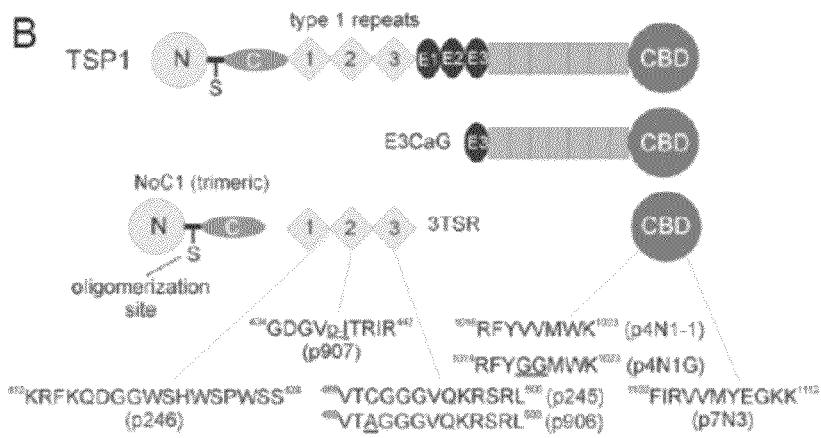

Figure 7
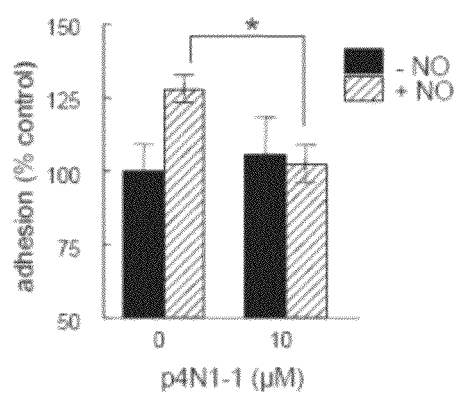
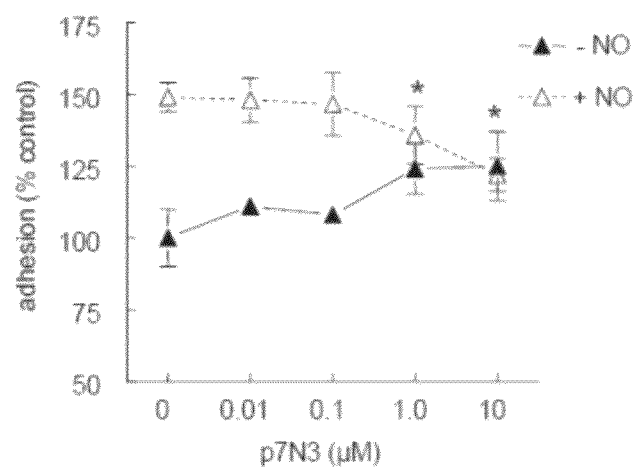

Figure 16
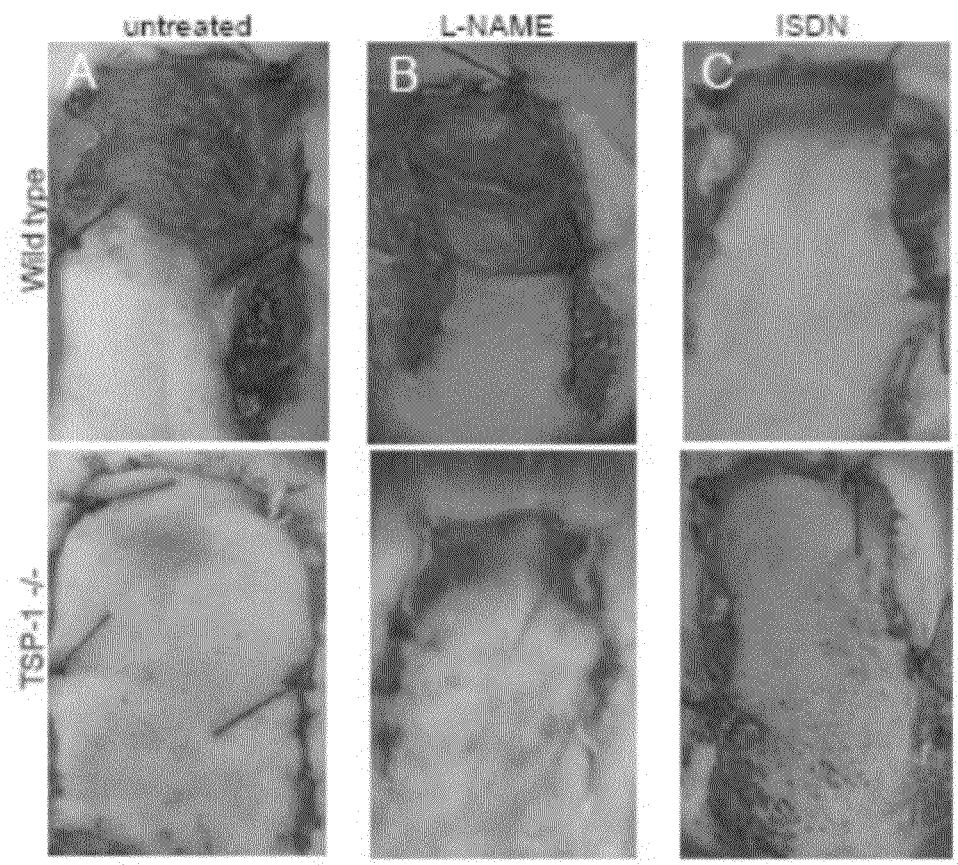
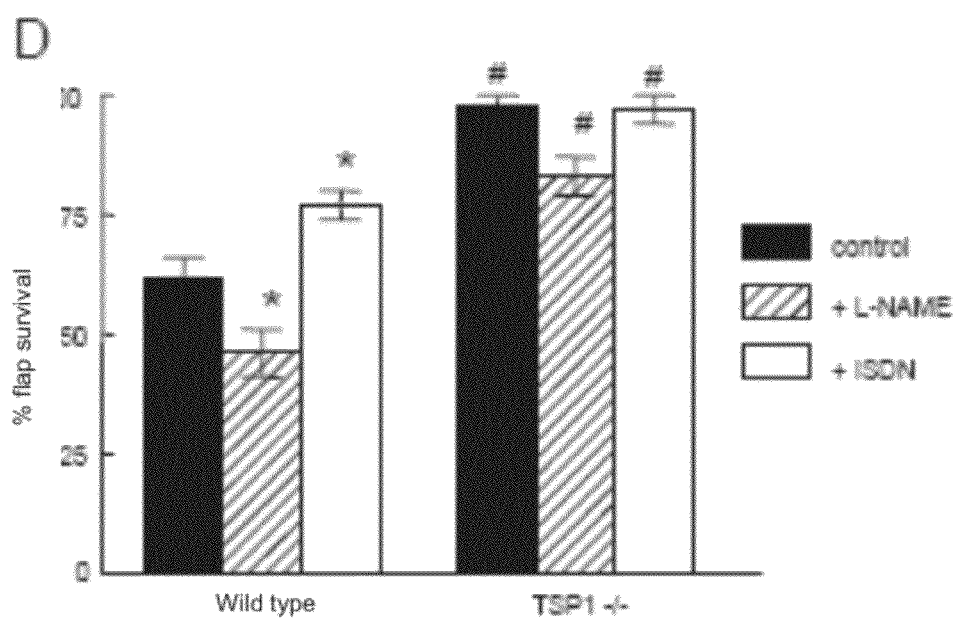

Figure 17
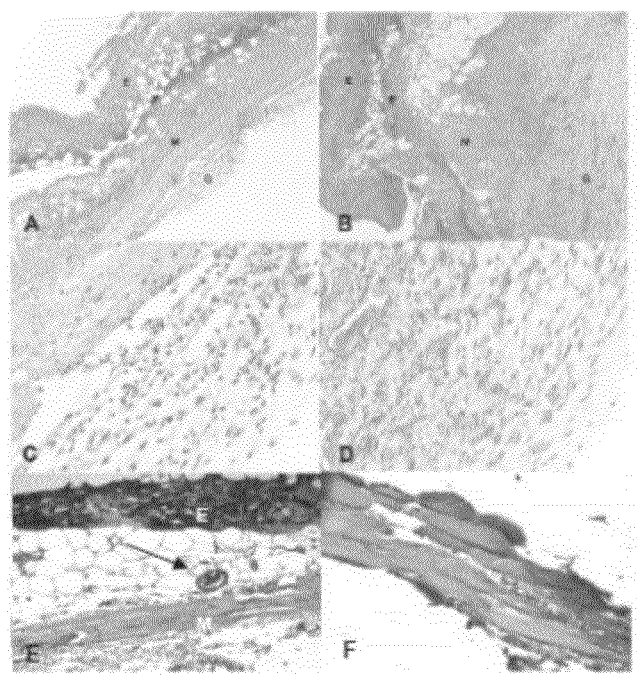
Figure 18
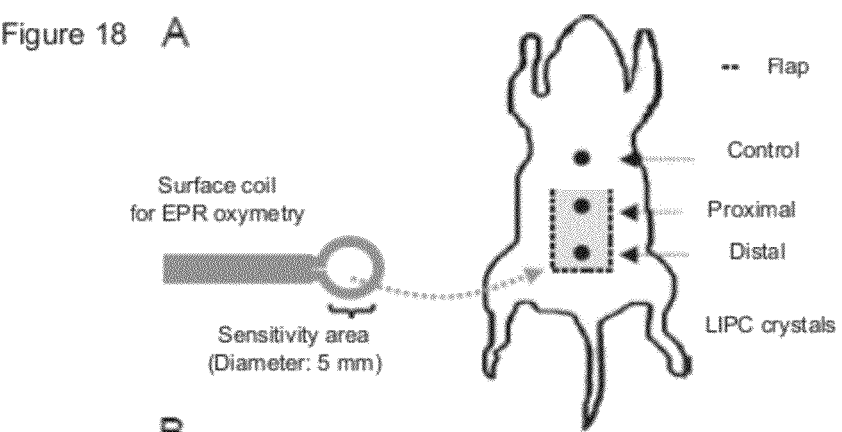
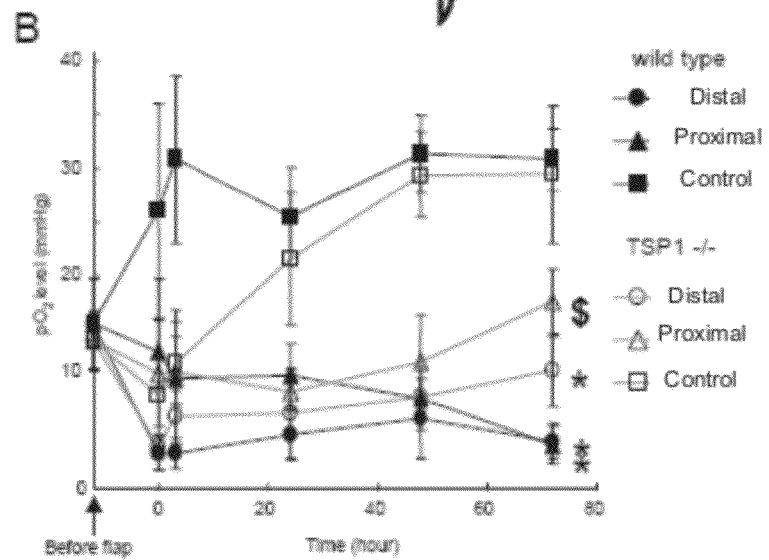

Wild type    TSP1 -/-

Wild type    TSP1 -/-

CD36 -/-    CD47 -/-

Figure 24A
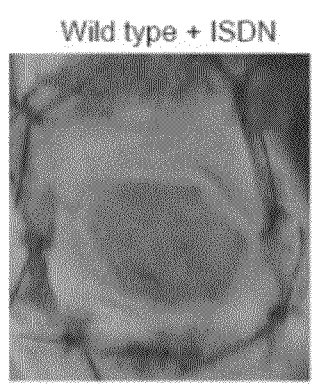
Wild type + ISDN
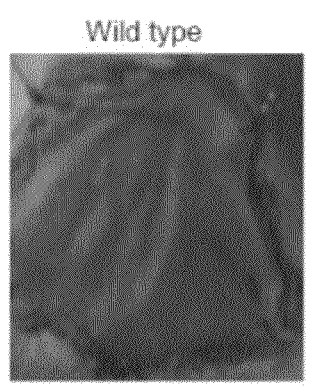
Wild type
Figure 24B
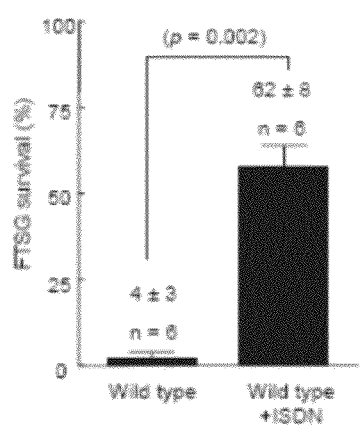
Figure 24C
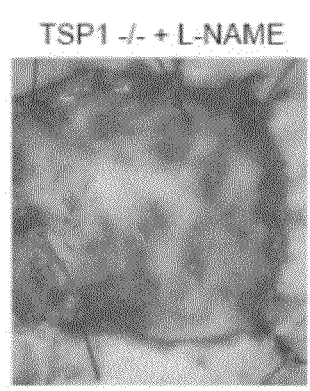
TSP1 -/- + L-NAME
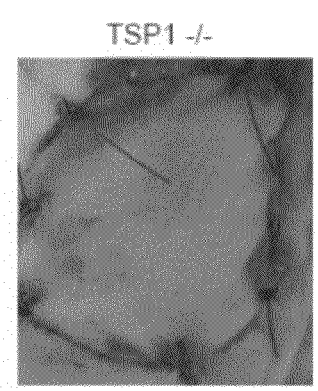
TSP1 -/-
Figure 24D
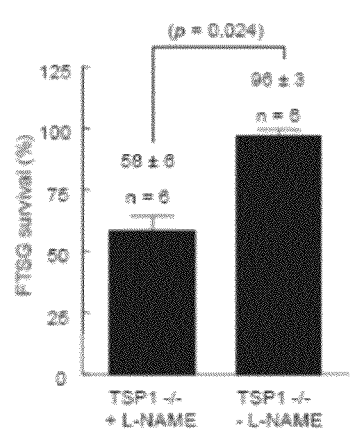

Wild type    CD36 -/-    CD47 -/-    TSP1 -/-

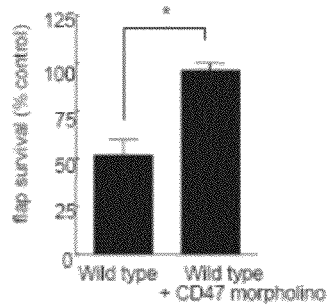
Figure 31E 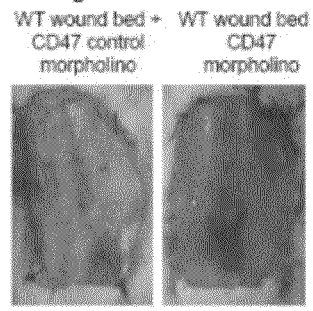 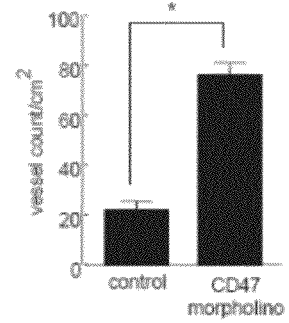

CD47 -/-   CD36 -/-

Figure 43
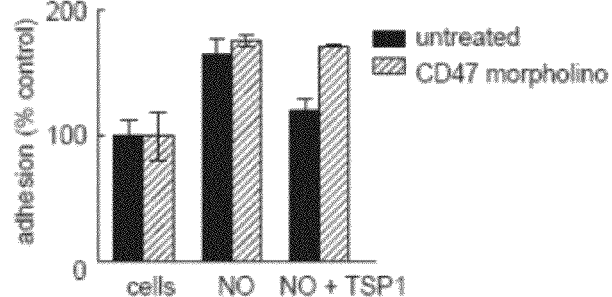
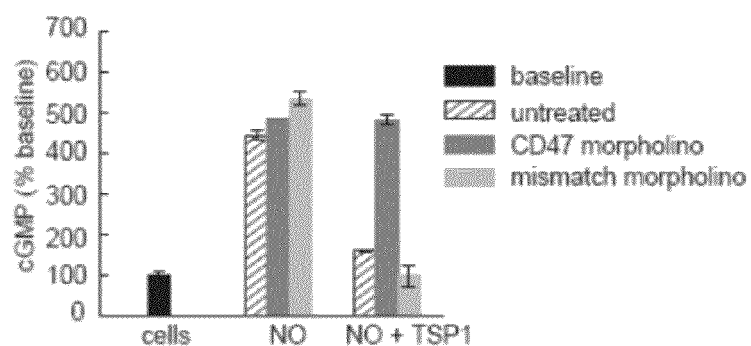
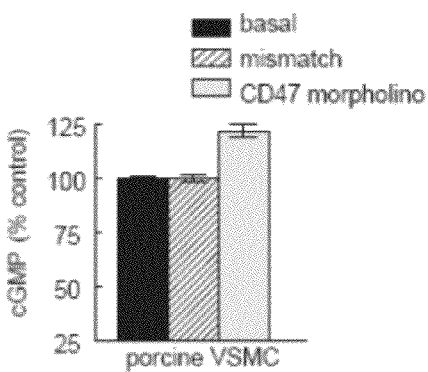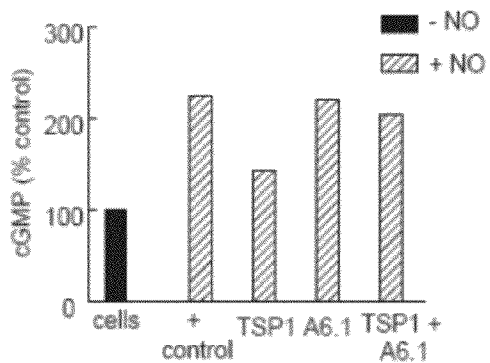

Figure 44
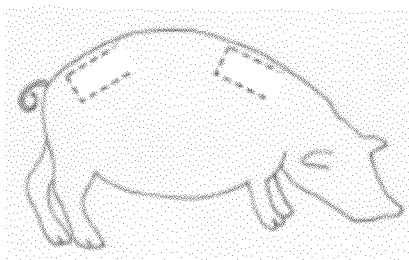
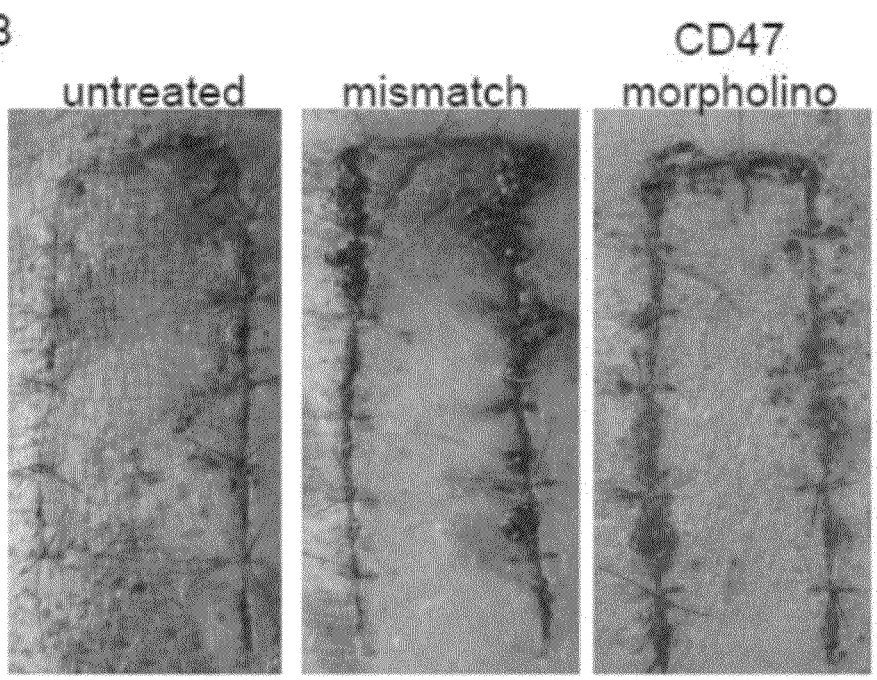
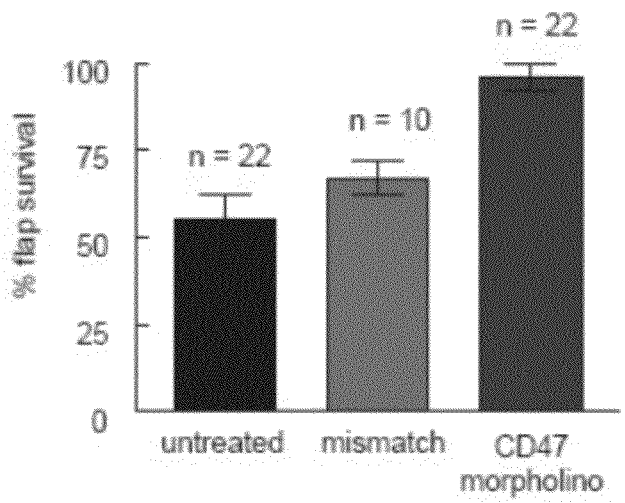

Figure 46
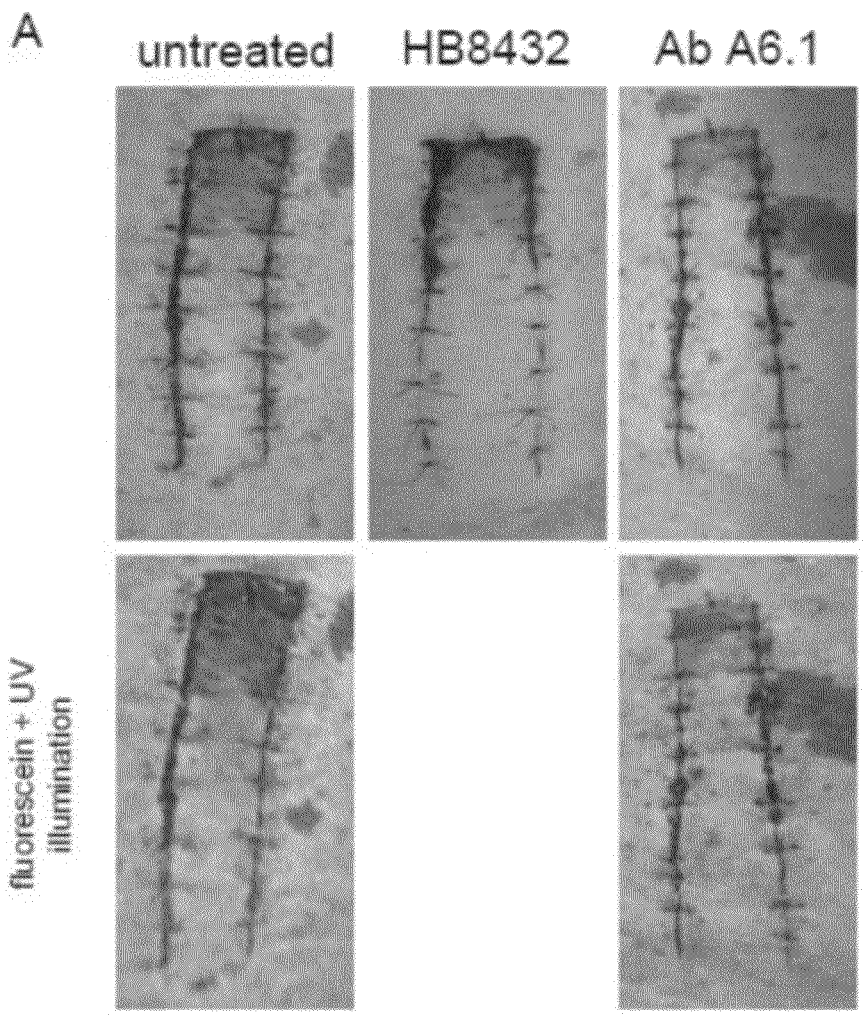
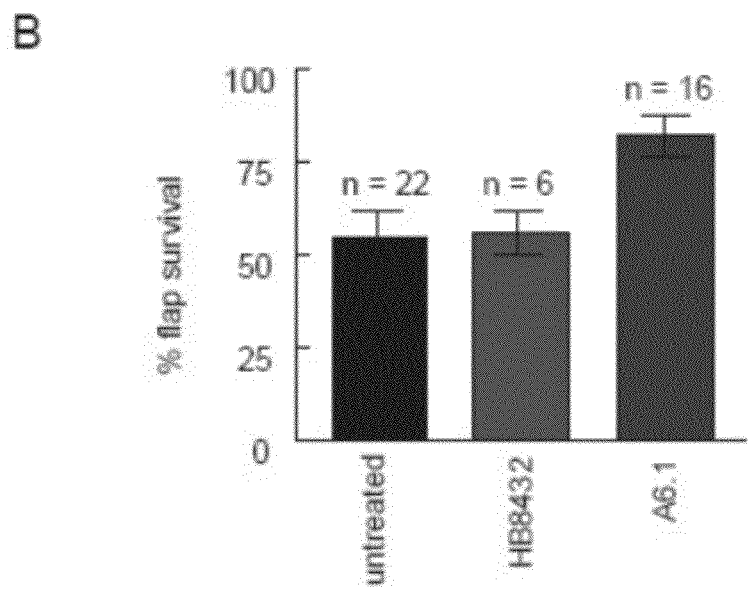

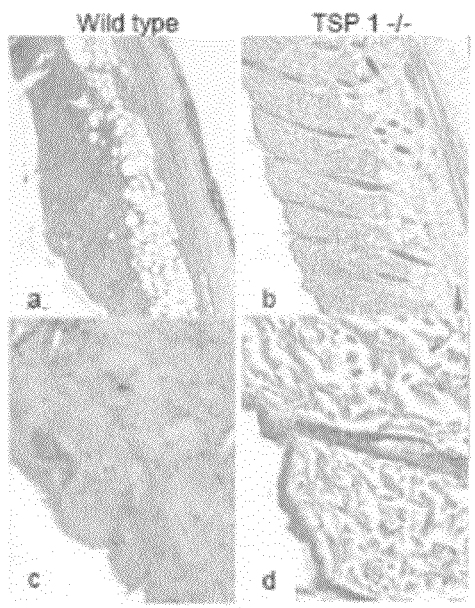
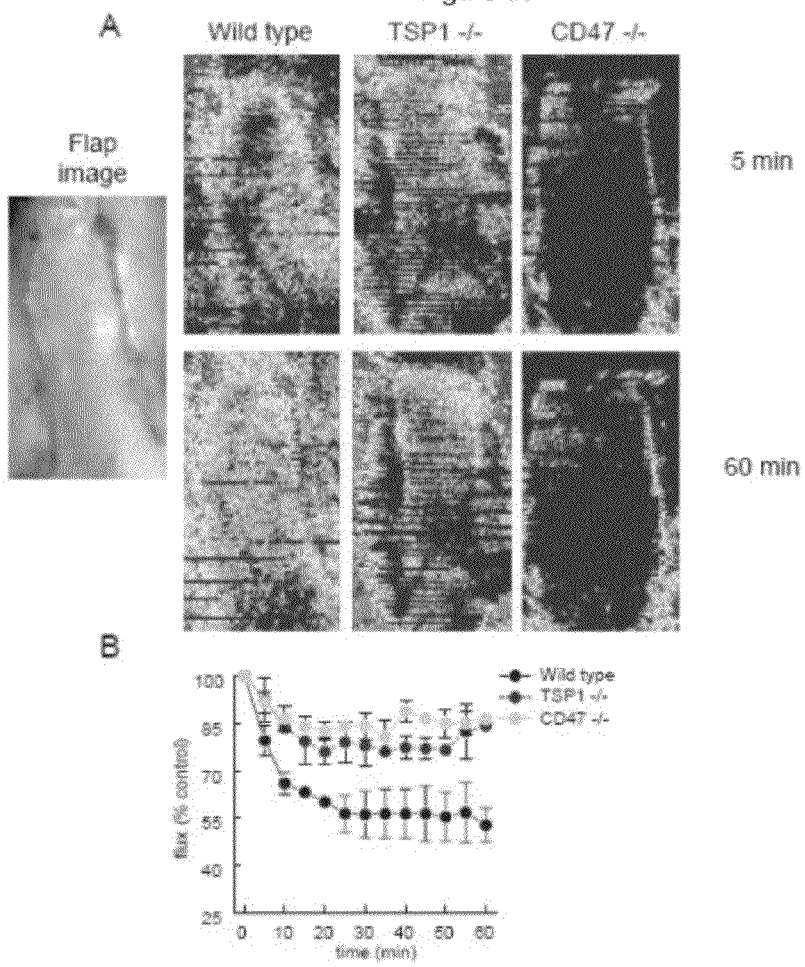

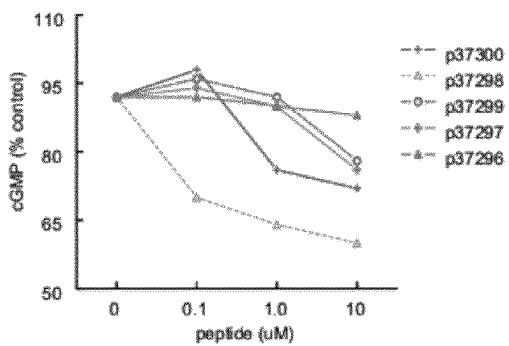
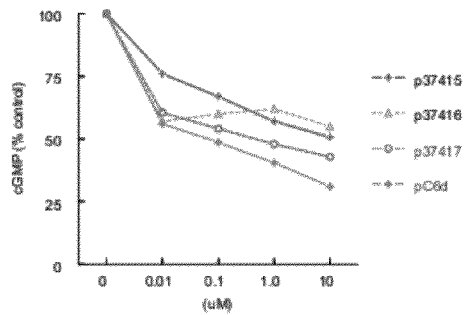
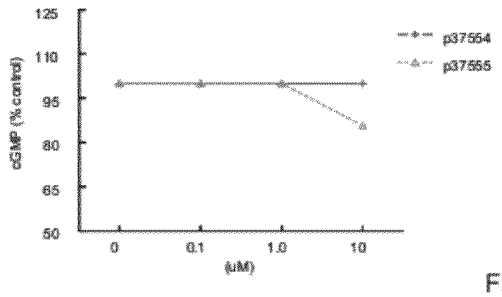
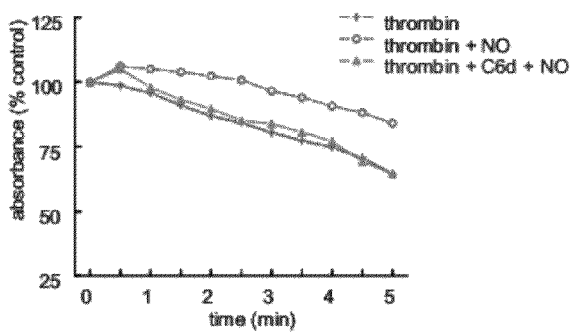

SEQUENCE LISTING

```
<160> NUMBER OF SEQ ID NOS: 33

<210> SEQ ID NO 1
<211> LENGTH: 10
<212> TYPE: PRT
<213> ORGANISM: Artificial sequence
<220> FEATURE:
<223> OTHER INFORMATION: Synthetic Peptide

<400> SEQUENCE: 1

Ile Gly Trp Lys Asp Phe Thr Ala Tyr Arg
1               5                   10

<210> SEQ ID NO 2
<211> LENGTH: 8
<212> TYPE: PRT
<213> ORGANISM: Artificial sequence
<220> FEATURE:
<223> OTHER INFORMATION: Synthetic Peptide

<400> SEQUENCE: 2

Trp Lys Asp Phe Thr Ala Tyr Arg
1               5
```

```
<210> SEQ ID NO 3
<211> LENGTH: 10
<212> TYPE: PRT
<213> ORGANISM: Artificial sequence
<220> FEATURE:
<223> OTHER INFORMATION: Synthetic Peptide

<400> SEQUENCE: 3

Ile Gly Trp Lys Asp Phe Thr Ala Tyr Arg
1               5                   10

<210> SEQ ID NO 4
<211> LENGTH: 10
<212> TYPE: PRT
<213> ORGANISM: Artificial sequence
<220> FEATURE:
<223> OTHER INFORMATION: Synthetic Peptide

<400> SEQUENCE: 4

Ile Gly Trp Lys Asn Phe Thr Ala Tyr Arg
1               5                   10

<210> SEQ ID NO 5
<211> LENGTH: 10
<212> TYPE: PRT
<213> ORGANISM: Artificial sequence
<220> FEATURE:
<223> OTHER INFORMATION: Synthetic Peptide

<400> SEQUENCE: 5

Ile Gly Trp Lys Asp Phe Ala Ala Tyr Arg
1               5                   10

<210> SEQ ID NO 6
<211> LENGTH: 14
<212> TYPE: PRT
<213> ORGANISM: Artificial sequence
<220> FEATURE:
<223> OTHER INFORMATION: Synthetic Peptide

<400> SEQUENCE: 6

Ile Gly Trp Lys Asp Glu Thr Ala Tyr Arg Trp Arg Leu Ser
1               5                   10

<210> SEQ ID NO 7
<211> LENGTH: 15
<212> TYPE: PRT
<213> ORGANISM: Artificial sequence
<220> FEATURE:
<223> OTHER INFORMATION: Synthetic Peptide

<400> SEQUENCE: 7

His Ile Gly Trp Lys Asp Phe Thr Ala Tyr Arg Trp Arg Leu Ser
1               5                   10                  15

<210> SEQ ID NO 8
<211> LENGTH: 17
<212> TYPE: PRT
<213> ORGANISM: Artificial sequence
<220> FEATURE:
<223> OTHER INFORMATION: Synthetic Peptide

<400> SEQUENCE: 8

Lys Arg Phe Lys Gln Asp Gly Gly Trp Ser His Trp Ser Pro Trp Ser
1               5                   10                  15

Ser
```

<210> SEQ ID NO 9
<211> LENGTH: 13
<212> TYPE: PRT
<213> ORGANISM: Artificial sequence
<220> FEATURE:
<223> OTHER INFORMATION: Synthetic Peptide

<400> SEQUENCE: 9

```
Val Thr Cys Gly Gly Gly Val Gln Lys Arg Ser Arg Leu
1               5                   10
```

<210> SEQ ID NO 10
<211> LENGTH: 11
<212> TYPE: PRT
<213> ORGANISM: Artificial sequence
<220> FEATURE:
<223> OTHER INFORMATION: Synthetic Peptide

<400> SEQUENCE: 10

```
Phe Ile Arg Val Val Met Tyr Glu Gly Lys Lys
1               5                   10
```

<210> SEQ ID NO 11
<211> LENGTH: 11
<212> TYPE: PRT
<213> ORGANISM: Artificial sequence
<220> FEATURE:
<223> OTHER INFORMATION: Synthetic Peptide

<400> SEQUENCE: 11

```
Phe Ile Arg Gly Gly Met Tyr Glu Gly Lys Lys
1               5                   10
```

<210> SEQ ID NO 12
<211> LENGTH: 11
<212> TYPE: PRT
<213> ORGANISM: Artificial sequence
<220> FEATURE:
<223> OTHER INFORMATION: Synthetic Peptide

<400> SEQUENCE: 12

```
Phe Ile Arg Val Ala Ile Tyr Glu Gly Lys Lys
1               5                   10
```

<210> SEQ ID NO 13
<211> LENGTH: 10
<212> TYPE: PRT
<213> ORGANISM: Artificial sequence
<220> FEATURE:
<223> OTHER INFORMATION: Synthetic Peptide

<400> SEQUENCE: 13

```
Lys Arg Phe Tyr Val Val Met Trp Lys Lys
1               5                   10
```

<210> SEQ ID NO 14
<211> LENGTH: 8
<212> TYPE: PRT
<213> ORGANISM: Artificial sequence
<220> FEATURE:
<223> OTHER INFORMATION: Synthetic Peptide

<400> SEQUENCE: 14

```
Arg Phe Tyr Val Val Met Trp Lys
1               5
```

```
<210> SEQ ID NO 15
<211> LENGTH: 8
<212> TYPE: PRT
<213> ORGANISM: Artificial sequence
<220> FEATURE:
<223> OTHER INFORMATION: Synthetic Peptide

<400> SEQUENCE: 15

Arg Phe Tyr Gly Gly Met Trp Lys
1               5

<210> SEQ ID NO 16
<211> LENGTH: 10
<212> TYPE: PRT
<213> ORGANISM: Artificial sequence
<220> FEATURE:
<223> OTHER INFORMATION: Synthetic Peptide

<400> SEQUENCE: 16

Ile Gly Trp Lys Ala Phe Thr Ala Tyr Arg
1               5                   10

<210> SEQ ID NO 17
<211> LENGTH: 7
<212> TYPE: PRT
<213> ORGANISM: Artificial sequence
<220> FEATURE:
<223> OTHER INFORMATION: Synthetic Peptide

<400> SEQUENCE: 17

Arg Lys Arg Ser Arg Ala Glu
1               5

<210> SEQ ID NO 18
<211> LENGTH: 13
<212> TYPE: PRT
<213> ORGANISM: Artificial sequence
<220> FEATURE:
<223> OTHER INFORMATION: Synthetic Peptide

<400> SEQUENCE: 18

Val Thr Ala Gly Gly Gly Val Gln Lys Arg Ser Arg Leu
1               5                   10

<210> SEQ ID NO 19
<211> LENGTH: 9
<212> TYPE: PRT
<213> ORGANISM: Artificial sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: This isoleucine is dextro-rotatory-isoleucine
      (d-isoleucine, or D-I)

<400> SEQUENCE: 19

Gly Asp Gly Val Ile Thr Arg Ile Arg
1               5

<210> SEQ ID NO 20
<211> LENGTH: 10
<212> TYPE: PRT
<213> ORGANISM: Artificial sequence
<220> FEATURE:
<223> OTHER INFORMATION: Synthetic Peptide

<400> SEQUENCE: 20
```

```
Ile Gly Trp Lys Asp Tyr Thr Ala Tyr Arg
1               5                   10
```

<210> SEQ ID NO 21
<211> LENGTH: 25
<212> TYPE: DNA
<213> ORGANISM: Artificial sequence
<220> FEATURE:
<223> OTHER INFORMATION: Synthetic oliogonucleotide

<400> SEQUENCE: 21
cgtcacaggc aggacccact gccca                                              25

<210> SEQ ID NO 22
<211> LENGTH: 25
<212> TYPE: DNA
<213> ORGANISM: Artificial sequence
<220> FEATURE:
<223> OTHER INFORMATION: Synthetic oliogonucleotide

<400> SEQUENCE: 22
cgtgacagcc acgaccgact gcgca                                              25

<210> SEQ ID NO 23
<211> LENGTH: 19
<212> TYPE: DNA
<213> ORGANISM: Artificial sequence
<220> FEATURE:
<223> OTHER INFORMATION: Synthetic oliogonucleotide

<400> SEQUENCE: 23
ctgctccaga cacctgagg                                                     19

<210> SEQ ID NO 24
<211> LENGTH: 20
<212> TYPE: DNA
<213> ORGANISM: Artificial sequence
<220> FEATURE:
<223> OTHER INFORMATION: Synthetic oliogonucleotide

<400> SEQUENCE: 24
cgtcttagta ctctccaatc                                                    20

<210> SEQ ID NO 25
<211> LENGTH: 10
<212> TYPE: PRT
<213> ORGANISM: Artificial sequence
<220> FEATURE:
<223> OTHER INFORMATION: Synthetic Peptide

<400> SEQUENCE: 25

```
Ile Gly Trp Lys Gly Phe Thr Ala Tyr Arg
1               5                   10
```

<210> SEQ ID NO 26
<211> LENGTH: 9
<212> TYPE: PRT
<213> ORGANISM: Artificial sequence
<220> FEATURE:
<223> OTHER INFORMATION: Synthetic Peptide

<400> SEQUENCE: 26

```
Gly Ala Lys Asp Phe Thr Ala Tyr Arg
1               5
```

```
<210> SEQ ID NO 27
<211> LENGTH: 10
<212> TYPE: PRT
<213> ORGANISM: Artificial sequence
<220> FEATURE:
<223> OTHER INFORMATION: Synthetic Peptide

<400> SEQUENCE: 27

Ile Gly Trp Lys Asp Phe Thr Ala Ala Arg
1               5                   10

<210> SEQ ID NO 28
<211> LENGTH: 10
<212> TYPE: PRT
<213> ORGANISM: Artificial sequence
<220> FEATURE:
<223> OTHER INFORMATION: Synthetic Peptide

<400> SEQUENCE: 28

Ile Gly Trp Lys Asp Phe Thr Ala Tyr Lys
1               5                   10

<210> SEQ ID NO 29
<211> LENGTH: 10
<212> TYPE: PRT
<213> ORGANISM: Artificial sequence
<220> FEATURE:
<223> OTHER INFORMATION: Synthetic Peptide

<400> SEQUENCE: 29

Ile Gly Trp Ala Asp Phe Thr Ala Tyr Arg
1               5                   10

<210> SEQ ID NO 30
<211> LENGTH: 10
<212> TYPE: PRT
<213> ORGANISM: Artificial sequence
<220> FEATURE:
<223> OTHER INFORMATION: Synthetic Peptide

<400> SEQUENCE: 30

Ile Gly Trp His Asp Phe Thr Ala Tyr Arg
1               5                   10

<210> SEQ ID NO 31
<211> LENGTH: 10
<212> TYPE: PRT
<213> ORGANISM: Artificial sequence
<220> FEATURE:
<223> OTHER INFORMATION: Synthetic Peptide

<400> SEQUENCE: 31

Ile Gly Trp Lys Glu Phe Thr Ala Tyr Arg
1               5                   10

<210> SEQ ID NO 32
<211> LENGTH: 10
<212> TYPE: PRT
<213> ORGANISM: Artificial sequence
<220> FEATURE:
<223> OTHER INFORMATION: Synthetic Peptide

<400> SEQUENCE: 32

Ala Gly Trp Lys Asp Phe Thr Ala Tyr Arg
1               5                   10

<210> SEQ ID NO 33
```

```
<211> LENGTH: 10
<212> TYPE: PRT
<213> ORGANISM: Artificial sequence
<220> FEATURE:
<223> OTHER INFORMATION: Synthetic Peptide

<400> SEQUENCE: 33

Ile Gly Tyr Lys Asp Phe Thr Ala Tyr Arg
1               5                   10
```

PREVENTION OF TISSUE ISCHEMIA AND RELATED METHODS

CROSS REFERENCE TO RELATED APPLICATIONS

This is a divisional application of co-pending U.S. application Ser. No. 12/444,364, filed Apr. 3, 2009, which is the U.S. National Stage of International Application No. PCT/US2007/080647, filed Oct. 5, 2007, which was published in English under PCT Article 21(2). Benefit is also claimed to each of the following U.S. Provisional Applications: 60/850,132, filed Oct. 6, 2006; 60/864,153, filed Nov. 2, 2006; 60/888,754, filed Feb. 7, 2007; 60/910,549, filed Apr. 6, 2007; and 60/956,375, filed Aug. 16, 2007. Each of the listed prior applications is incorporated herein by reference in its entirety.

GOVERNMENT INTEREST STATEMENT

Aspects of this invention were developed with government support under Grant Nos. HL54390 and GM57573, awarded by the National Institutes of Health. The government has certain rights in aspects of the invention. The government also has certain rights in the invention due to at least one inventor's employment by the National Institutes of Health.

FIELD

This application relates to the field of ischemia and blood flow. More specifically, this application relates to acute reversal and/or prevention of tissue ischemia, and related and associated tissue and cell damage, as well as compositions and methods for such.

BACKGROUND

The body depends upon adequate blood flow. At the level of organs and tissue, blood flow is controlled by vascular smooth muscle cells. These cells line every blood vessel of the body. The contraction of these cells determines the amount of blood that flow through a certain vessel and on to organs and tissues. The contraction (and relaxation) of vascular smooth muscle cells is in turn controlled by the bioactive gas nitric oxide (NO) which is constantly produced by blood vessels. NO causes blood vessels to dilate and increases blood flow to tissues and organs. Disruption of this process leads to significant diseases, morbidity and mortality including peripheral vascular disease, ischemic heart disease, stroke and diabetes. Additionally, lack of blood flow causes tissue death and wound healing problems both during and after surgery.

Resolution of acute and chronic ischemia, be it in soft tissue flaps or skin grafts, requires restoration of tissue perfusion and blood flow. Treatments to address these factors including hyperbaric oxygen, intravenous thrombolytics, anti-inflammatory agents, and local application of angiogenesis promoters have been developed but have yielded only limited success.

BRIEF SUMMARY

The inventors have made the revolutionary discovery that a matrix protein thrombospondin-1 (TSP1) blocks effects of NO in the vascular system, and prevents NO from dilating blood vessels and increasing blood flow to organs and tissues. Further, the inventors also discovered that TSP1 acts through the cell receptor CD47 to block the effects of NO on blood vessels. Relief of this inhibition in genetically altered (knock-out) mice lacking either TSP1 or CD47 results in dramatically improved blood flow and increased tissue oxygenation. Further, by using reagents such as monoclonal antibodies (mAbs), and peptides that block the TSP1-CD47 interaction, or agents (such as antisense oligonucleotides or morpholinos) that reduce the level of CD47 or TSP1, blood flow can be dramatically increased to ischemic tissues.

Decreasing CD47 expression using antisense oligonucleotides significantly increases blood flow and tissue perfusion under conditions of acute or chronic ischemia. Under conditions of acute loss of blood flow and ischemia as found in surgery and skin grafting, blocking TSP1 or suppressing CD47 dramatically increases blood flow and tissue survival. Equally startling and unexpected was the discovery that in models of chronic vascular pathology similar to those occurring in patients with atherosclerotic vascular disease targeting TSP1 or CD47 significantly improves tissue blood flow and survival. Finally, it was discovered that blocking TSP1 or CD47 can alter platelet function and prevent platelets from forming clots. The implications of these discoveries and the therapeutics based on the same are tremendous and would extend to almost every disease process afflicting our aging population, including people who suffer from diabetes, atherosclerotic peripheral vascular disease, scleroderma, Reynaud's disease, coronary artery disease and myocardial infarction, stroke, Alzheimer's disease, dementia of old age and macular degeneration. The therapeutics described herein can also be employed to limit or reverse endothelial dysfunction (NO insufficiency) and suppress inflammatory activation of the endothelium thus having application in inflammatory diseases such as arthritis, Crohn's disease, and so forth. Further, the therapeutics identified herein can be applied to improve tissue survival and wound healing during surgery and to burn victims before and after undergoing skin grafting. The therapeutic agents herein identified may also be applied to patients with bleeding disorders to increase or decrease the clotting process.

The extent of the described discoveries and inventions based thereon goes beyond the ability to regulate blood vessel and vascular cell responses. Nitric oxide is one of the central regulators, via cGMP, of mammalian physiology. A majority of cell types in the body utilize NO and cGMP to control vital cell signaling functions. Discoveries presented herein represent a novel method of controlling NO signaling through cGMP and hence will have an impact on almost every cell in the body. The discovery that thrombospondin-1 via CD47 blocks NO-driven signaling in mammalian cells permits for the first time harnessing beneficial effects of NO.

Provided herein are methods and compositions useful in exploiting the discoveries that TSP1 and CD47 influence and control tissue survival in response to ischemia. Included are the use of therapeutic compounds and compositions that block TSP1 and thereby increase tissue survival to ischemia, as well as use of therapeutic compounds and compositions that block CD47 and thereby increase tissue survival to ischemia. Also included are compositions (including for instance nucleic acid and protein/peptide compositions) useful in such methods. Specific example compounds useful as therapeutics include anti-CD47 antibodies (such as Ab 301, discussed herein) and anti-TSP1 antibodies that have similar effect on the interaction between CD47 and TSP1, as well as morpholinos (e.g., CD47 or TSP1 morpholinos), and peptides derived from CD47 or TSP1 and other known TSP family members, TSP2-TSP5 inclusive, and additional CD47 ligands including members of the family of Signal Inhibitory Receptor Proteins (SIRPα, β, γ).

Particular contemplated methods include tissue preservation following surgery, and as part of surgery, such as reconstructive surgery and reattachment of severed body parts (e.g., fingers, toes, hands, feet, ears, limbs and soft tissue units; increased tissue survival in the treatment of burns, both through decreasing tissue loss secondary to the burn injury and increasing skin graft survival and take; increased tissue survival in peripheral vascular interruption or disease secondary to amputation, clot and thrombosis and stroke; and restoration of blood flow in diseases of chronic vascular obstruction secondary to diabetes, hypertension and primary peripheral vascular disease.

Particular contemplated methods also include modulation of blood clotting through targeting of TSP1 and CD47 on the cell surface of platelets, for instance with antibodies or peptides or small molecule inhibitors, thus increasing or decreasing the tendency of platelets to form aggregates and thrombotic clots. Such therapeutics are useful in minimizing complications from excessive clotting such as occurs in stroke and coronary artery disease. They may also play a role in helping to restore clotting in cases of bleeding disorders, such as hemophilia, injuries, surgeries and so forth.

Yet further embodiments are provided herein, and we claim all methods and compositions described.

The foregoing and other features and advantages will become more apparent from the following detailed description of several embodiments, which proceeds with reference to the accompanying figures.

BRIEF DESCRIPTION OF THE FIGURES

FIG. 1. Regulation of NO signaling by TSP1 via CD36 and CD47. Endogenous NO synthesis is stimulated via Akt-mediated phosphorylation of endothelial nitric oxide synthase (eNOS) downstream of VEGF receptor (Dimmeler et al, FEBS Lett, 477:258-262, 2000). Ligation of either CD36 or CD47 is sufficient to inhibit activation of soluble guanylyl cyclase (sGC) mediated by endogenous or exogenous NO. CD47 is downstream of CD36 because ligation on CD36 can not inhibit signaling in the absence of CD47. The requirement for CD47 is consistent with lateral interactions with CD36 or with CD36 signaling requiring a convergent CD47 signal at some point upstream of sGC. The mechanism by which CD47 ligation regulates sGC is not known. TSP1 also inhibits NO signaling downstream of cGMP (Isenberg et al, *PNAS*, 102: 13141-13146, 2005), at the level of cGMP protein kinase (PKG) (Isenberg et al, *Blood*, Epub Sep. 21, 2007).

FIG. 2A-2B. NO-stimulated vascular cell out growth is modulated by ligation of several TSP1 receptors. (FIG. 2A) Wild type and TSP1−/− muscle biopsies were explanted in three dimensional collagen matrices and incubated in growth medium in the presence of exogenous NO (10 μM) and cell migration measured at day 7. Explants were treated with TSP1-derived peptides specific for heparin sulfate proteoglycans (peptide 246, 10 μM), CD36 (peptide 245, 10 μM), CD47 (peptide 7N3, 10 μM), or NoCl (0.1 μg/ml), which binds to several $\beta_1$ integrins. Results are representative of three experiments with those differing from the respective controls with p<0.05 indicated by *. (FIG. 2B) Origins of the recombinant proteins and peptides. Amino acid residues differing from the native TSP1 sequence are underlined. Shown are p907 (SEQ ID NO: 19), p246 (SEQ ID NO: 8), p4N1-1 (SEQ ID NO: 14), p4N1G (SEQ ID NO: 15), p245 (SEQ ID NO: 9), p906 (SEQ ID NO: 18), and p7N3 (SEQ ID NO: 10).

(FIG. 3A) CD47−/− muscle biopsies were explanted in 3D collagen matrix and incubated in growth medium. Explants were treated with a slow release exogenous NO-donor (DETA/NO 0.1-100 μM) with or without TSP1 (1 μg/ml). Cell migration was determined at 7 days as described. Results are representative of three experiments. Representative photo micrographs are shown of CD47−/− explants incubated in basal medium, ±DETA/NO (10 μM)±TSP1 (1 μg/ml). (Scale bars: 50 μm). (FIG. 3B) CD36−/− muscle biopsies were explanted in 3D collagen matrix and incubated in growth medium with or without TSP1 (1 μg/ml) and exogenous NO-donor (DETA/NO 0.1-100 μM). Cell migration was determined at 7 days. Results are representative of three experiments. Representative photo micrographs are shown of CD 36−/− explants incubated in basal medium, ±DETA/NO (10 μM)±TSP1 (1 μg/ml). (Scale bars: 50 μm).

(FIG. 4A) HUVEC ($1 \times 10^4$ cell/well) were plated in 96-well culture dishes pre-coated with type I collagen (5 μg/ml), pre-incubated with the CD36 binding peptides p906 or p907 (10 μM) or CD36 antibodies FA6-152 (FIG. 4B) (0.1 μg/ml), SMΦ (FIG. 4C) (0.1 μg/ml) and 185-1G2 (FIG. 4D) (0.1 μg/ml) and exposed to DEA/NO (10 μM). Cells were also concurrently and under similar conditions treated with isotype-matched control antibodies ($IgG_1$, IgM and $IgG_{2a}$ respectively) (0.1 μg/ml). Following incubation for 1 hour at 37° C., the plates were washed, the cells fixed, stained, developed and read at 570 nm. Results are expressed as a percent of the untreated control and represent the mean±SD of at least three separate experiments.

(FIG. 5A) HASMC ($1 \times 10^4$ cell/well) were plated in 96-well culture dishes pre-coated with type I collagen (5 μg/ml), pre-incubated with the CD36 monoclonal antibody FA6-152 (0.01-1 μg/ml) or IgG1 control and exposed to DEA/NO (10 μM). Following incubation for 1 h at 37° C. plates were washed and cells fixed, stained, developed and read at 570 nm. (FIG. 5B) HASMC cells were plated ($5 \times 10^3$ cells/well) 96-well plates and weaned over 24 h from serum, then treated in serum-free medium with 0.1% BSA with DEA/NO (10 μM)±FA6-152 (1 μg/ml) or an isotype control antibody (1 μg/ml) for 5 minutes, cells lysed, and cGMP levels determined by ELISA.

(FIG. 6A) Murine ASMC from wild type and CD36 null animals ($1 \times 10^4$ cell/well) were plated in 96-well culture dishes pre-coated with type I collagen (5 μg/ml), and incubated in SM-GM+0.1% BSA with DEA/NO (10 μM)±exogenous TSP1 (0.022-22 nM). Following incubation for 1 hour at 37° C. plates were washed and cells fixed, stained, developed and read at 570 nm. Results are expressed as percent control and represent the mean±SD of at least three separate experiments. (FIG. 6B) Wild type and CD36 null ASMC cells were plated ($5 \times 10^3$ cells/well) 96-well plates and weaned over 24 h from serum, then treated in serum-free medium with 0.1% BSA with DEA/NO (10 μM)±TSP1 (1 μg/ml) for 5 minutes, cells lysed and cGMP levels determined by ELISA. Results presented are representative of those obtained in three independent experiments.

FIG. 7A-7B. TSP-1 based peptide ligation of CD47 is sufficient to block NO-driven endothelial cell adhesion. (FIG. 7A) HUVEC ($1 \times 10^4$ cell/well) were plated in 96-well culture dishes pre-coated with type I collagen (5 μg/ml), and incubated in EGM+0.1% BSA±DEA/NO (10 μM) and CD47 peptides p4N1-1 and (FIG. 7B) p7N3 at the indicated concentrations. Following incubation for 1 hour at 37° C. plates were washed and cells fixed, stained, developed and read at 570 nm. Results are expressed as percent control and represent the mean±SD of at least three separate experiments.

(FIG. 8A) HASMC ($1\times10^4$ cell/well) were plated in 96-well culture dishes pre-coated with type I collagen (5 µg/ml) and incubated in EGM+0.1% BSA±DEA/NO (10 µM)±the recombinant CBD or E3CaG1 (0.4-40 nM). Following incubation for 1 h at 37° C. plates were washed and cells fixed, stained, developed and read at 570 nm. (FIG. 8B) HASMC ($5\times10^3$/well) were plated in 96-well culture plates, treated with CBD (0.42-420 nM)±DETA/NO (10 µM) and incubated for 72 hours at 37° C. in a 5% $CO_2$ atmosphere, then developed with MTS reagent and read at a wavelength of 490 nm. Results are expressed as percent of control and represent the mean±SD of at least three separate experiments. (FIG. 8C) HASMC were plated ($5\times10^3$ cells/well) in 96-well plates and weaned over 24 h from serum, then treated in serum-free medium with 0.1% BSA with DEA/NO (10 µM)±CBD (0.42-420 nM) for 5 minutes, cells lysed and cGMP levels determined by ELISA. Results presented are representative of those obtained in three independent experiments. In other experiments HASMC (FIG. 8D) or HUVEC (FIG. 8E) were plated ($5\times10^3$ cells/well) in 96-well plates, weaned of serum and treated with E3CaG1 (0.39-39 nM)±DEA/NO (10 µM) and cGMP levels determined as described.

(FIG. 10A) Murine wild type and CD47 null ASMC ($1\times10^4$ cell/well) were plated in 96-well culture dishes pre-coated with type I collagen (5 µg/ml) and incubated in SM-GM+0.1% BSA with DETA/NO (10 µM)±TSP1 (0.022-22 nM) for 1 h, plates washed, cells fixed, stained, developed and read on a microplate reader at 570 nm. In other experiments, wild type and CD47 null ASMC ($5\times10^3$ cell/well) were plated on 96-well culture plates and incubated for 72 h in SM-GM+1% FCS with DETA/NO (10 µM)±TSP1 (0.022-2.2 nM) (FIG. 10B) or 3TSR (0.002-2 nM) (FIG. 10C) and proliferation determined as described. In other experiments wild type and null cells were plated in 96-well culture dishes pre-coated with type I collagen (5 µg/ml) and incubated in SM-GM+0.1% BSA with DETA/NO (10 µM)±peptide 907 (0.1-100 µM) for 1 h, plates washed, cells fixed, stained, developed and read at 570 nm FIG. 10(D). Wild type and CD47 null ASMC were plated ($5\times10^3$ cells/well) in 96 well plates and weaned over 24 h from serum, then treated in serum-free medium with 0.1% BSA with DEA/NO (10 µM)±TSP1 (1 µg/ml) (FIG. 10E), 3TSR (0.2 nM) (FIG. 10F), or CD36 binding peptides derived from the second (p907, 1 µM) or third type 1 repeats (p906, 1 µM) (FIG. 10G) for 5 minutes. The cells were cells lysed and intracellular cGMP levels determined.

(FIG. 11A) Murine CD47 null ASMC or (FIG. 11B) CD36 null ASMC were plated ($5\times10^3$ cells/well) in 96-well plates, weaned from serum over 24 hours and treated in serum-free medium with 0.1% BSA with DEA/NO (10 M)±CBD (1 µg/ml), peptide 7N3 (1 M) or peptide 907 (1 M) for 5 minutes, the cells lysed, and cGMP levels determined. Results are expressed as percent of control and represent the mean±SD of at least three separate experiments.

was injected with saline via an intra-rectal cannula 5 minutes after starting the scan. Green and red colors show positive and negative BOLD MRI signals, respectively at the indicated times after NO administration. The BOLD images were superimposed with the corresponding anatomic images to determine exact locations in the lateral thigh sections. (FIG. 15C) BOLD MRI signal changes as a function of time after NO challenge. The plots above the 0 axis are of increased BOLD MRI signal and the plots below the 0 axis of decreased BOLD MRI signals. Values are presented as mean±SD from five and four experiments in WT and TSP1 null mice, respectively.

FIG. 16A-16D. Endogenous TSP1 and NO modulate tissue survival under ischemic conditions. (FIG. 16A) Representative random flaps were photographed seven days following surgery for untreated WT and TSP1 null mice, WT and TSP1 null mice receiving L-NAME (500 mg/L, FIG. 16B) or mice receiving ISDN (1 mg/ml, FIG. 16C) in the drinking water during the post-operative period. (FIG. 16D) Flap survival is expressed as percent of the total involved area. Results are the mean±SD of 24 animals (12 age and sex matched pairs) of untreated WT and TSP1 null mice, 16 animals (8 matched pairs) treated with L-NAME, and 16 animals (8 matched pairs) treated with ISDN. * $P<0.05$ vs. control, one-way ANOVA. # $P<0.05$ vs. wild type, two-way ANOVA.

FIG. 17. Increased angiogenic and spindle cell responses in random ischemic flaps in the absence of endogenous TSP1. Sections from necrotic areas of the excised skin flap in WT (FIG. 17A) and TSP1 null (FIG. 17B) mice are shown. In WT mice, the epidermis (E) is necrotic and heavily infiltrated by polymorphonuclear leukocytes (P). A layer of loose granulation tissue (G) is present under the muscular layer (M). The layer of granulation tissue is significantly thicker and more heavily vascularized in the skin flap of the TSP1 null mouse. H+E, original magnification ×4. Higher magnification of the granulation tissue in the WT (FIG. 17C) and TSP1 null (FIG. 17D) flap shows more prominent spindle cell proliferation and capillary formation in the TSP1 null flap. H+E, original magnification ×20. Immunohistochemical staining with a TSP1 monoclonal antibody of wild type flaps at 4 hours (FIG. 17E) and 72 hours (FIG. 17F) post-operatively was performed. Tissue obtained 4 hours post-operatively demonstrated diffuse TSP1 staining of the epidermis, subcutaneous arterioles (arrow), extracellular matrix, striated muscle and inflammatory cells. At 72 hours post-operatively staining was localized to muscle cell borders and extracellular matrix with less staining in other areas. Original magnification ×20.

FIG. 18A-18B. Tissue $pO_2$ in WT and TSP1 null mice after flap treatment using EPR oximetry. (FIG. 18A) Schematic showing LiPc crystal placement in relation to a dorsal random myocutaneous flap. LiPc crystals were implanted in the dorsal subdermal area of mice 7 days prior to flap elevation. Initial measurements were performed by 700 MHz EPR spectroscopy with a small surface coil to confirm crystal location and calculate basal $pO_2$ levels. Body temperature of the animals was maintained between 37.5±0.5° C. Following flap elevation and suturing, measurements were recorded at the indicated times (FIG. 18B). The data represent the mean±SE of measurements from four animals in each group.

FIG. 24A-24D. Exogenous nitric oxide improves FTSG survival in wild type animals. Age and sex matched wild type and TSP1-null mice underwent autologous FTSG to the dorsal back and received ISDN (1 mg/ml) (FIGS. 24A, 24B) or L-NAME (0.5 mg/ml) in the drinking water post-operatively (FIGS. 24C, 24D). Graft survival was evaluated on post-operative day 7. Results represent the mean±SD of 6 age and sex matched animals in each group. p=0.002 (B) and 0.024 (D) versus respective controls.

p=0.006 (FIG. 26A) versus respective controls. p=0.001 (FIG. 26C) versus wild type, one-way ANOVA.

Figure 27A:
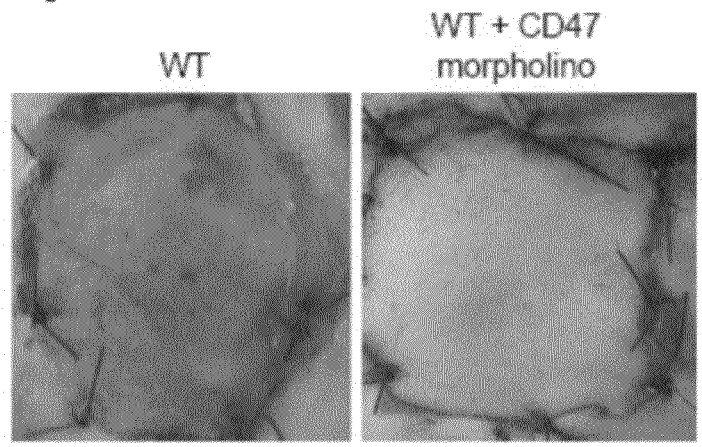
Figure 27B:
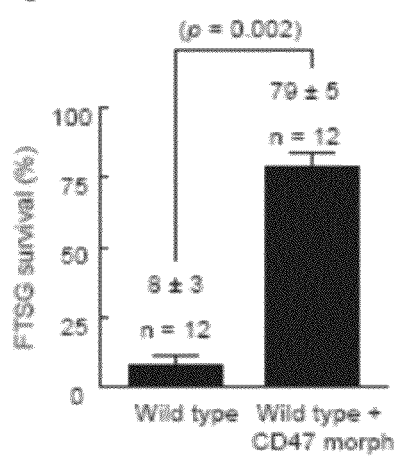
Figure 27D:
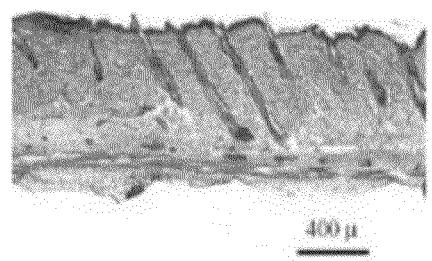
Figure 27E:
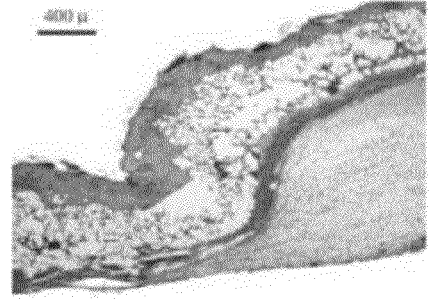
Figure 27C:
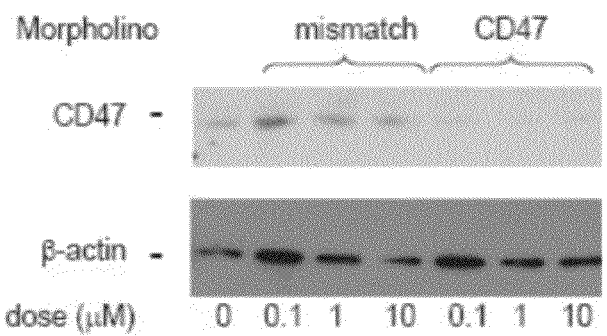

FIG. 27A-27D. CD47 suppression increases FTSG survival. Wild type FTSG and wound beds were infiltrated with a CD47 morpholino (10 µM in 100 µl PBS to the graft and wound bed) or mismatch control and grafts survival determined at 7 days (FIGS. 27A, 27B). Results represent the mean±SD of 12 pairs of animals. HUVEC were treated in standard growth medium with a CD47 or control morpholino (0.1-10 µM) for 48 hours and cell lysates prepared. Blots were developed with a CD47 specific antibody (clone B6H12). Results presented are a representative blot from 3 separate experiments (FIG. 27C). H & E staining of CD47 morpholino treated (FIG. 27D) versus untreated wild type FTSG (FIG. 27E). p=0.002 (B) versus control.

Figure 28A:
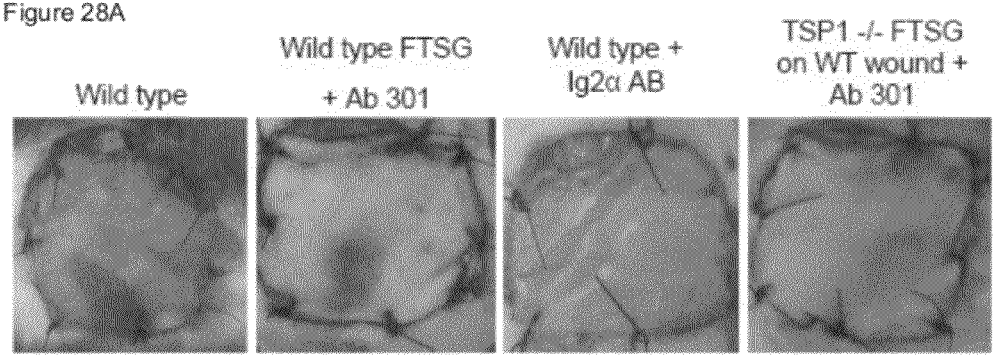
Figure 28B:
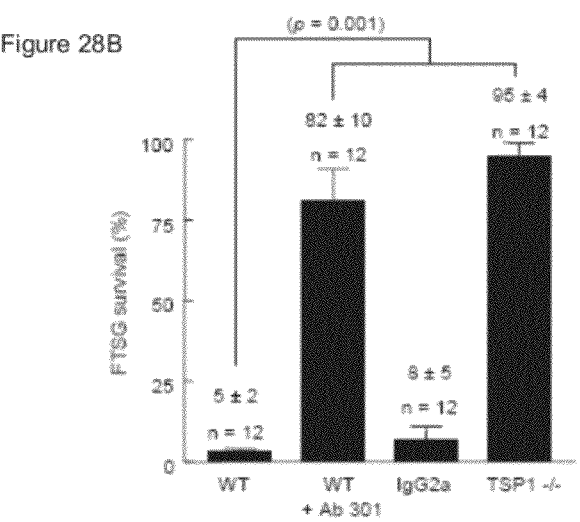
Figure 28C:
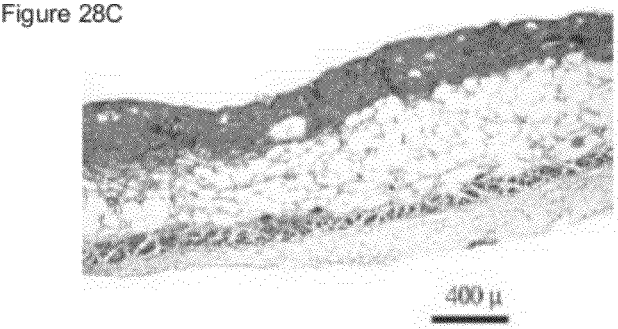

FIG. 28A-28C. CD47 ligation with monoclonal antibody increases wild type autologous FTSG survival. Age and sex matched wild type and TSP1-null mice underwent allograft FTSG to the dorsal back (FIGS. 28A, 28B). Infiltration of FTSG and wound beds with Ab 301 (40 µg in 200 µl PBS) or an isotype matched control antibody (IgG2a) was performed prior to graft suturing. Results represent the mean±SD of 12 animals in the indicated groups. H & E staining of wild type FTSG treated with a TSP1 monoclonal antibody clone Ab 301 (FIG. 28C). p=0.001 (B) versus wild type, one-way ANOVA.

Figure 29A:
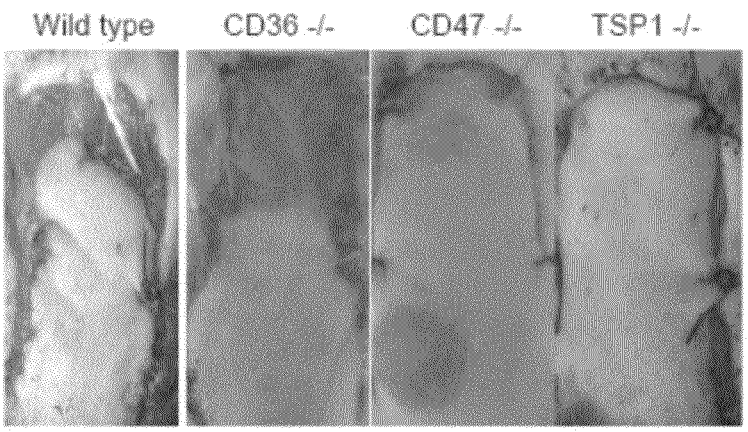
Figure 29B:
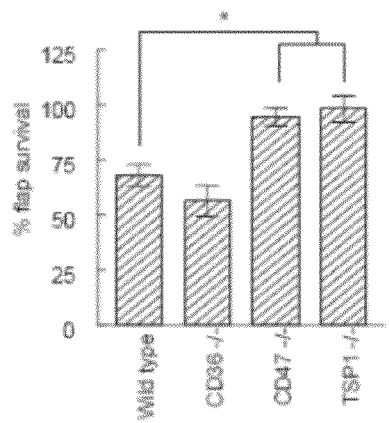

FIG. 29A-29D. CD47, but not CD36, limits ischemic soft tissue survival. Random flaps were created in transgenic mice and evaluated on post-operative day seven. Representative flaps were photographed for untreated WT, CD36-null, CD47-null, and TSP1-null mice (FIG. 29A). Flap survival is expressed as percent of total area and determined as described in the methods (FIG. 29B). Results are the mean±SD of 48 animals (12 age and sex matched pairs of WT and TSP1-, CD47-, and CD36-null mice). Type I collagen gel (3 mg/ml) was seeded with either WT or CD47-null VSMC (50,000 cells in 75 µl of gel/well), aliquoted to 96-well plates (Nunc, Denmark), and incubated overnight. Wells treated with TSP1 (2.2 nM) were pre-incubated overnight. Following the release of gels, contraction was initiated with either 10% FCS (FIG. 29C) or S1P (100 nM) (FIG. 29D)±DETA/NO (10 µM) and contraction determined. Results represent the mean±SD of three separate experiments.

Figure 30A:
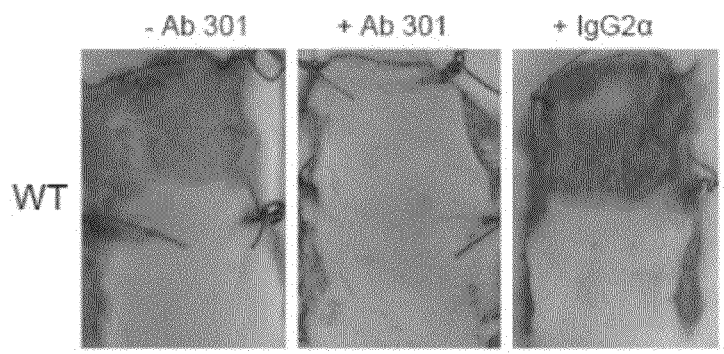
Figure 30B:
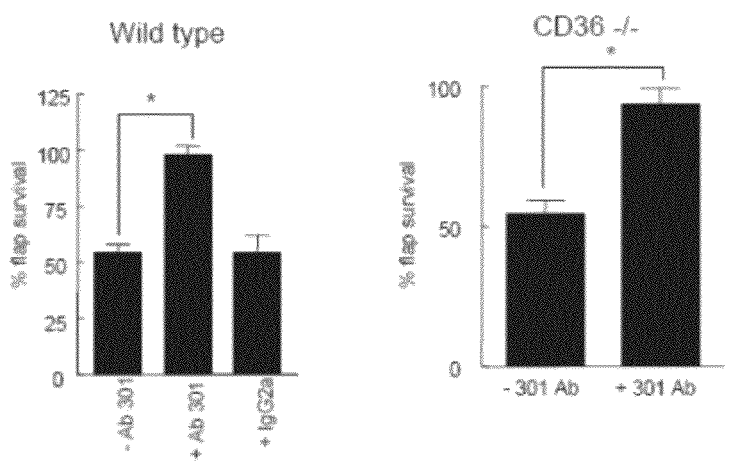
Figure 30C:
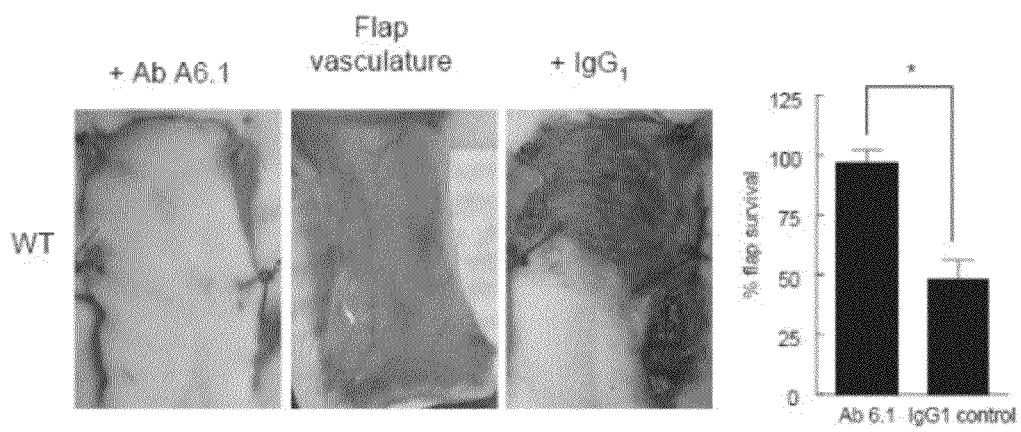

FIG. 30A-30C. Antibody blockade of CD47 or TSP1 increases ischemic tissue survival. Wild type and CD36-null mice (FIG. 30A) underwent random flap surgery. One hour pre-operatively, flaps were infiltrated with either PBS vehicle, a CD47 antibody clone 301 (40 µg delivered as 10 µl of a 4 mg/ml stock in 90 µl PBS), (FIG. 30B) a TSP1 monoclonal antibody clone A6.1 (2.4 µg in 90 µl PBS) or an isotype matched control IgG2a antibody (2.4 µg in 90 µl PBS). Flaps were photographed and tissue survival determined on post-operative day seven. Results represent the mean±SD of 12 animals (six age and sex matched pairs of wild type and CD36-null mice).

FIG. 31A-31G. CD47 knockdown increases survival of random myocutaneous flaps. (FIG. 31A) Human aortic VSMC were treated 48 hours with a CD47 morpholino oligonucleotide or a control morpholino (10 µM), lysates prepared and protein expression of CD47 determined. (FIG. 31B) Human aortic VSMC were pre-treated with a CD47 morpholino (10 µM) or a control and seeded into collagen gel, contraction initiated with 10% FCS and responses to DETA/NO (10 µM) and TSP1 (2.2 nM) determined. (FIG. 31C) Human aortic VSMC were cultured in the presence of CD47 or control morpholino for 48 hours and then in SM-BM+0.1% BSA treated with an NO donor (DEA/NO 10 µM)±TSP1 (1 µg/ml) and cGMP determined by immunoassay. (FIG. 31D) Wild type flaps were treated with either a CD47 targeted or control morpholino (10 µM) delivered in equal volumes of PBS to the flap and wound bed and tissue survival determined. In other experiments, treated or untreated flaps were sectioned and stained for CD47 with a murine monoclonal antibody. (FIG. 31E) Both random flaps and underlying wound beds were treated with the indicated morpholino and vascular indexes determined. Results represent the mean±SD of 16 animals (eight age and sex matched pairs of wild type mice). Sections from random flaps in CD36-null (FIG. 31F) and CD47-null (FIG. 31G) mice are shown.

FIG. 32A-32D. Tissue survival in ischemic hindlimbs is increased in the absence of TSP1. (FIG. 32A) Wild type and TSP1-null mice underwent ligation of the proximal arterial inflow of the left hindlimb, as described. At seven days post-operatively, tissue necrosis scores were determined, animals euthanized and tissue harvested for analysis of mitochondrial viability and histology. (FIG. 32B) Mitochondrial viability of muscle from the tibialis anterior was determined via conversion of MTT reagent to the formazan salt and quantified. (FIG. 32C) Visible vessels on the surface of the vastus medialis were quantified using 5× magnification. Results represent the mean±SD of 24 animals (12 sex and age matched pairs of wild type and TSP1 null animals). (FIG. 32D) Histology of transverse hindlimb sections of wild type and TSP1 null animals post vascular ligation.

Figure 33A:
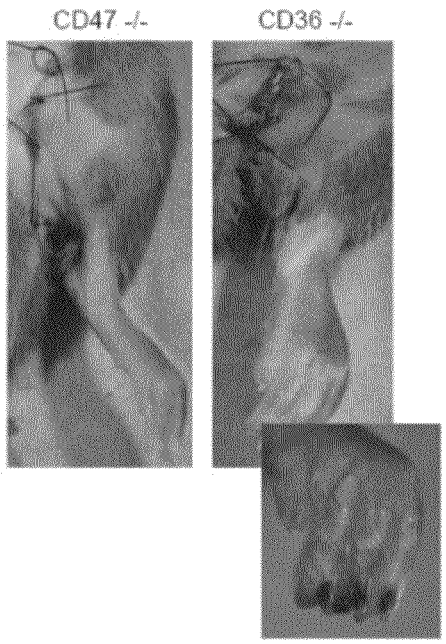
Figure 33B:
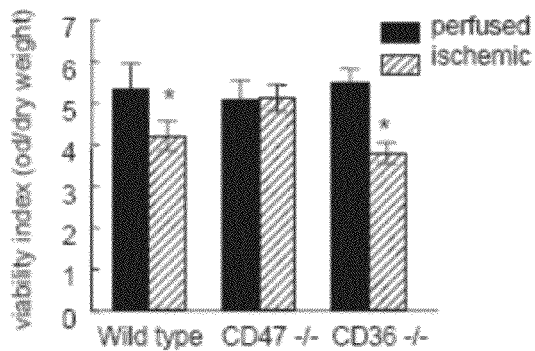
Figure 33C:
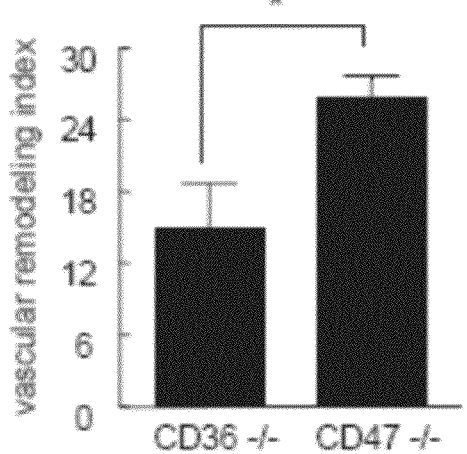
Figure 33D:
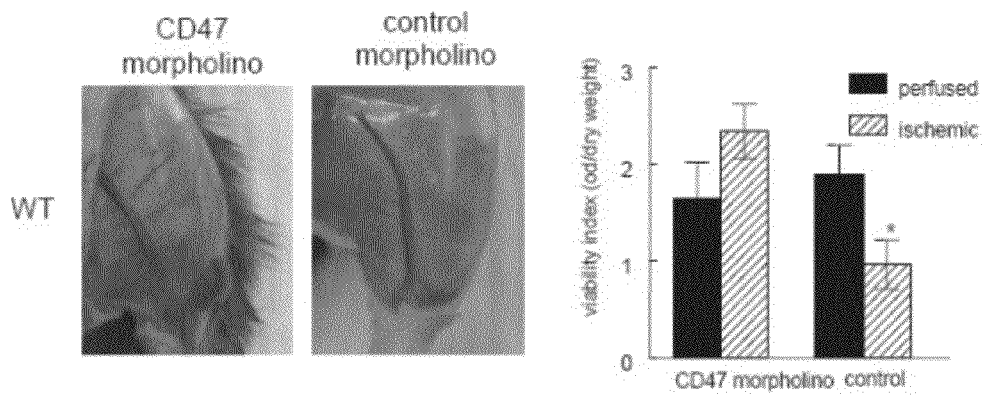

FIGS. 33A-33D. Tissue survival in ischemic hindlimbs is limited by CD47 but not by CD36. (FIG. 33A) CD47-null and CD36-null mice underwent ligation of the proximal arterial inflow of the left hindlimb, as described. At postoperative day seven, tissue necrosis scores were determined, animals euthanized and tissue harvested for analysis of mitochondrial viability and histology. (FIG. 33B) Mitochondrial viability of muscle from the tibialis anterior was determined via conversion of MTT reagent to the formazan salt and quantified. (FIG. 33C) Using 5× magnification, visible vessels on the surface of the vastus medialis were quantified. Results represent the mean±SD of 16 animals (four sex and age matched pairs of CD47-null and CD36-null animals). (FIG. 33D) Wild type animals underwent vascular ligation as described, and received either a CD47 targeted or control morpholino (125 µl of 10 µM morpholino in PBS to thigh musculature). *, p<0.05 vs. perfused (FIGS. 33B, 33D).

Figure 34:
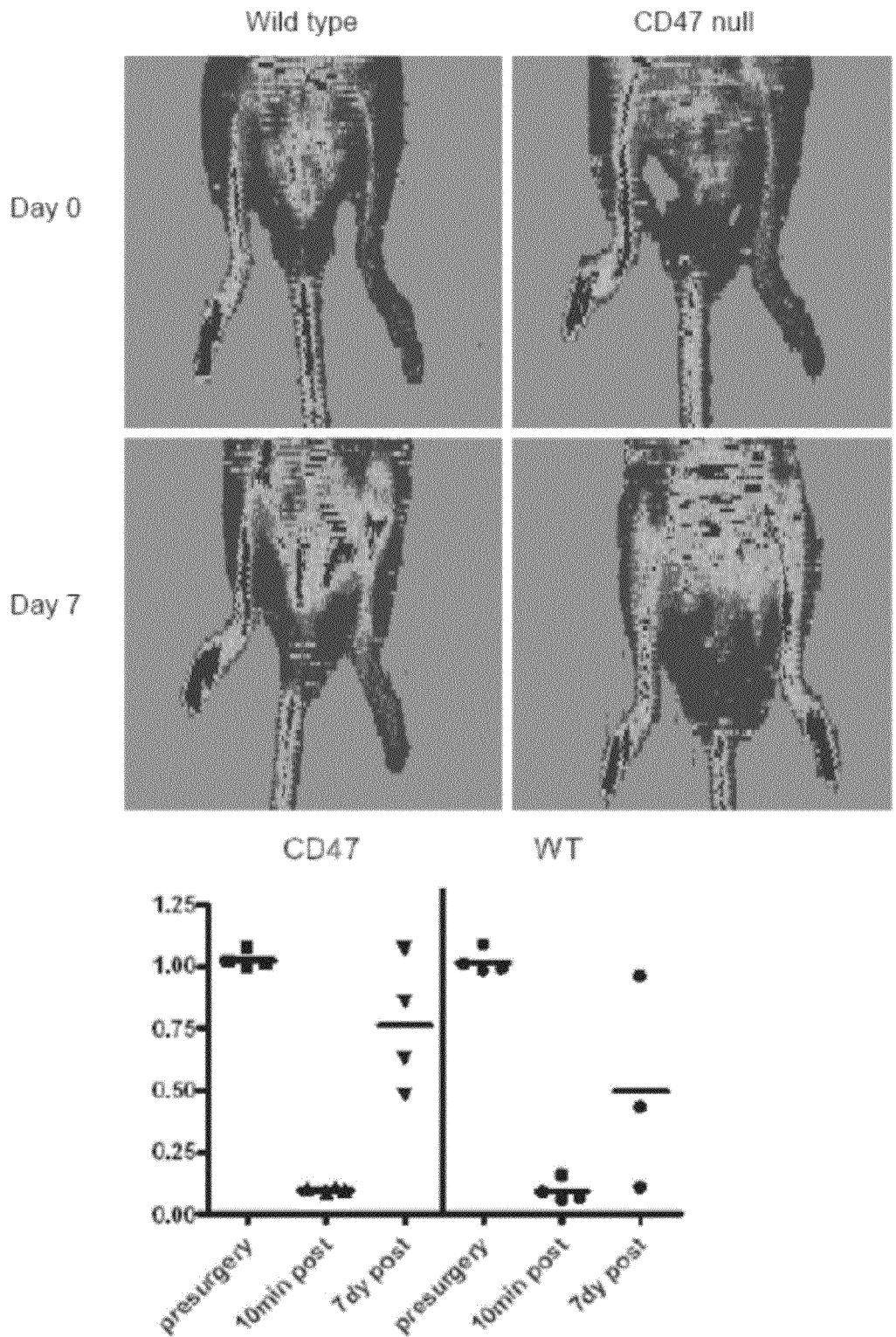

FIG. 34. Increased recovery of hindlimb perfusion in the absence of CD47. Wild type and transgenic knock out mice underwent laser Doppler analysis of limb perfusion following vascular ligation. Results from wild type and CD47-null hindlimbs are shown. Images are representative from a minimum of four animals in each group. Data were acquired pre-ligation, and 10 minutes and seven days post-ligation. Perfusion ratios are determined from average perfusion obtained in ligated limbs compared to non-ligated limbs.

Figure 35:
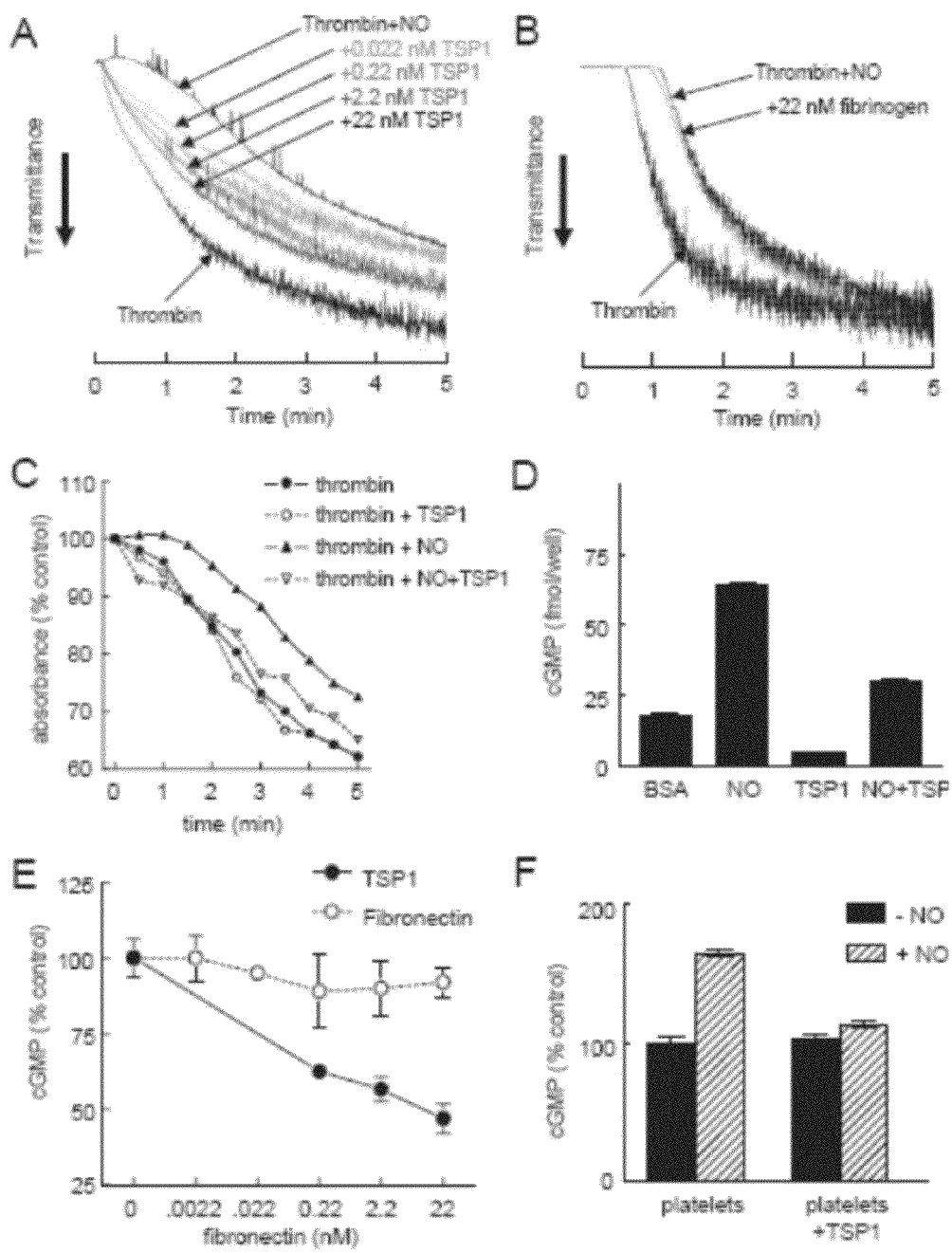

FIG. 35A-35F. Exogenous TSP1 reverses the delay of platelet aggregation by NO. Washed human platelets in Tyrode's buffer ($2\times10^5$ platelets/µl) were incubated in the presence of thrombin (0.2 U/ml) and exogenous NO (DEA/NO 10 µM) for 5 minutes under high shear (1200 rpm, FIGS. 35A, 35B) or static conditions (FIG. 35C) and absorbance recorded. In other experiments, fresh washed human platelets in Tyrode's buffer (500 µl) and treated with TSP1 (2.2 nM) (FIG. 35D) or the indicated concentrations of TSP1 or fibronectin (FIG. 35E) and DEA/NO (10 µM) for 5 minutes, lysed, and cGMP determined via immunoassay. Platelets in PRP were treated with TSP1 (2.2 nM) for 15 minutes followed by NO (DEA/NO 10 µM) for 5 minutes, lysed, and cGMP determined via immunoassay (FIG. 35F). Data presented are representative of at least three experiments (FIG. 35A-35C). Results are the mean±SD of at least three experiments (FIG. 35D-35F).

Figure 36:
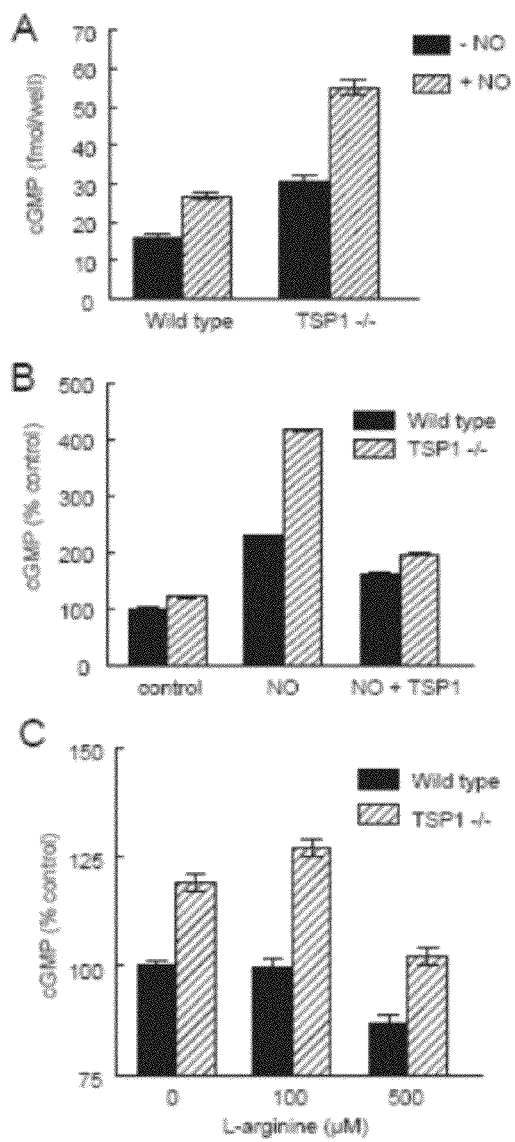

FIG. 36A-36C. Endogenous TSP1 limits NO/cGMP signaling in murine platelets. Equal numbers of murine C57BL/6 WT and TSP1-null platelets were incubated in Tyrode's buffer in the presence of 10 µM DEA/NO for 5 minutes, and cGMP was determined by immunoassay (FIG. 36A). In other experiments WT and TSP1-null platelets were pre-incubated with exogenous TSP1 (2.2 nM) for 15 minutes and then treated with NO (10 µM DEA/NO) (FIG. 36B) or treated with L-arginine at the indicated doses for 20 minutes and cGMP levels determined via immunoassay (FIG. 36C). Results are the mean±SD of at least three experiments.

Figure 37:
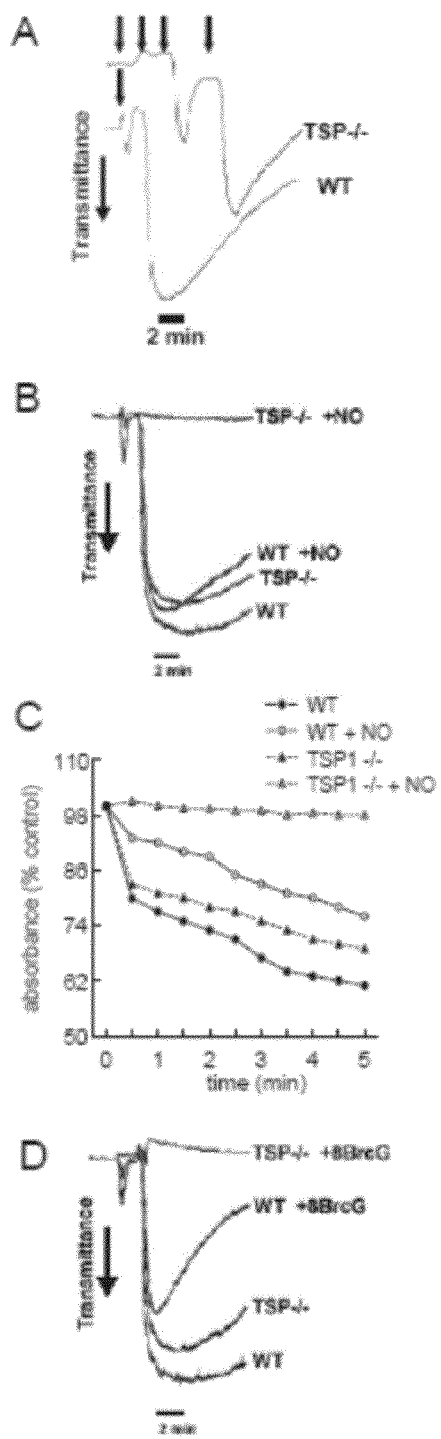

FIG. 37A-37D. Endogenous TSP1 is necessary for platelet aggregation in the presence of NO. Equal numbers of murine C57BL/6 WT and TSP1-null platelets were incubated under standard high shear (FIGS. 37A, 37B) or static aggregation conditions (FIG. 37C). Aggregation profiles were determined in the presence of a titrated dose of thrombin (0.1 U/ml added at time points indicated by arrows, A) or a fixed thrombin dose (0.2 U/ml, FIGS. 37B, 37C)±DEA/NO (10 µM). Alternatively, equal numbers of WT and TSP1-null platelets were treated with a fixed dose of thrombin (0.2 U/ml) and 8-BrcGMP (10 µM) under high shear conditions and aggregation determined (FIG. 37D). Data presented are representative of at least three experiments.

Figure 38:
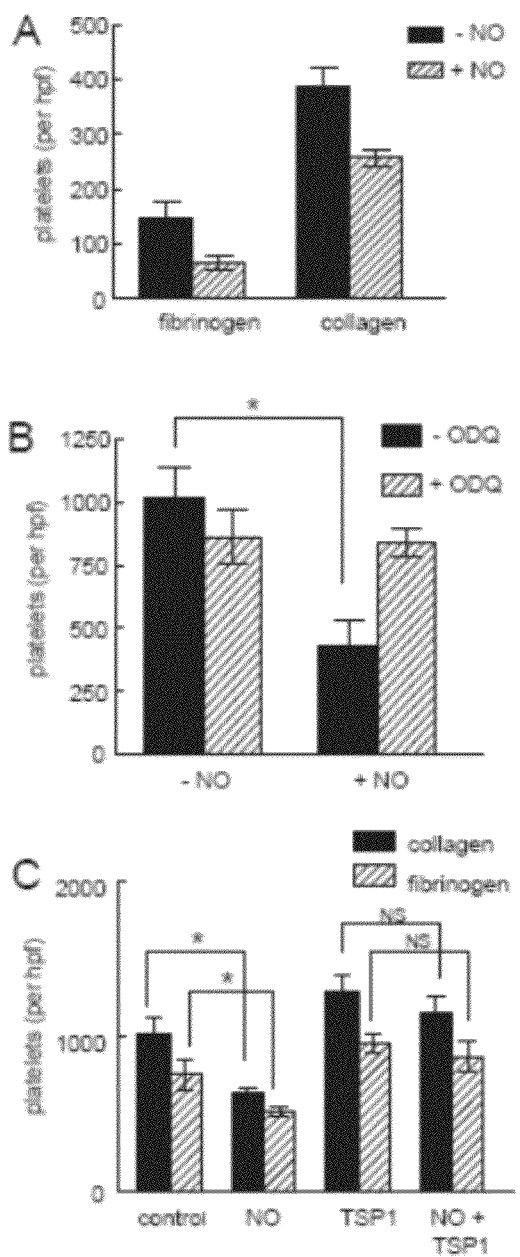

FIG. 38A-38C. Regulation of platelet adhesion by NO is blocked by TSP1. Fresh washed human platelets were added to 35×10 mm plastic dishes pre-coated with either type I collagen (3 µg/ml) or fibrinogen (5 µg/ml) (FIG. 38A) and incubated in Tyrode's buffer and the indicated treatment agents for 1 hr at 37° C. Wells were washed and platelets fixed, stained and counted. Human platelets were incubated on collagen coated plates in the presence of DEA/NO (10 µM)±ODQ (10 µM) (FIG. 38B) or collagen and fibrinogen coated plates±exogenous TSP1 (2.2 nM) (FIG. 38C) and adhesion determined. Results are the mean±SD of at least three experiments.

Figure 39:
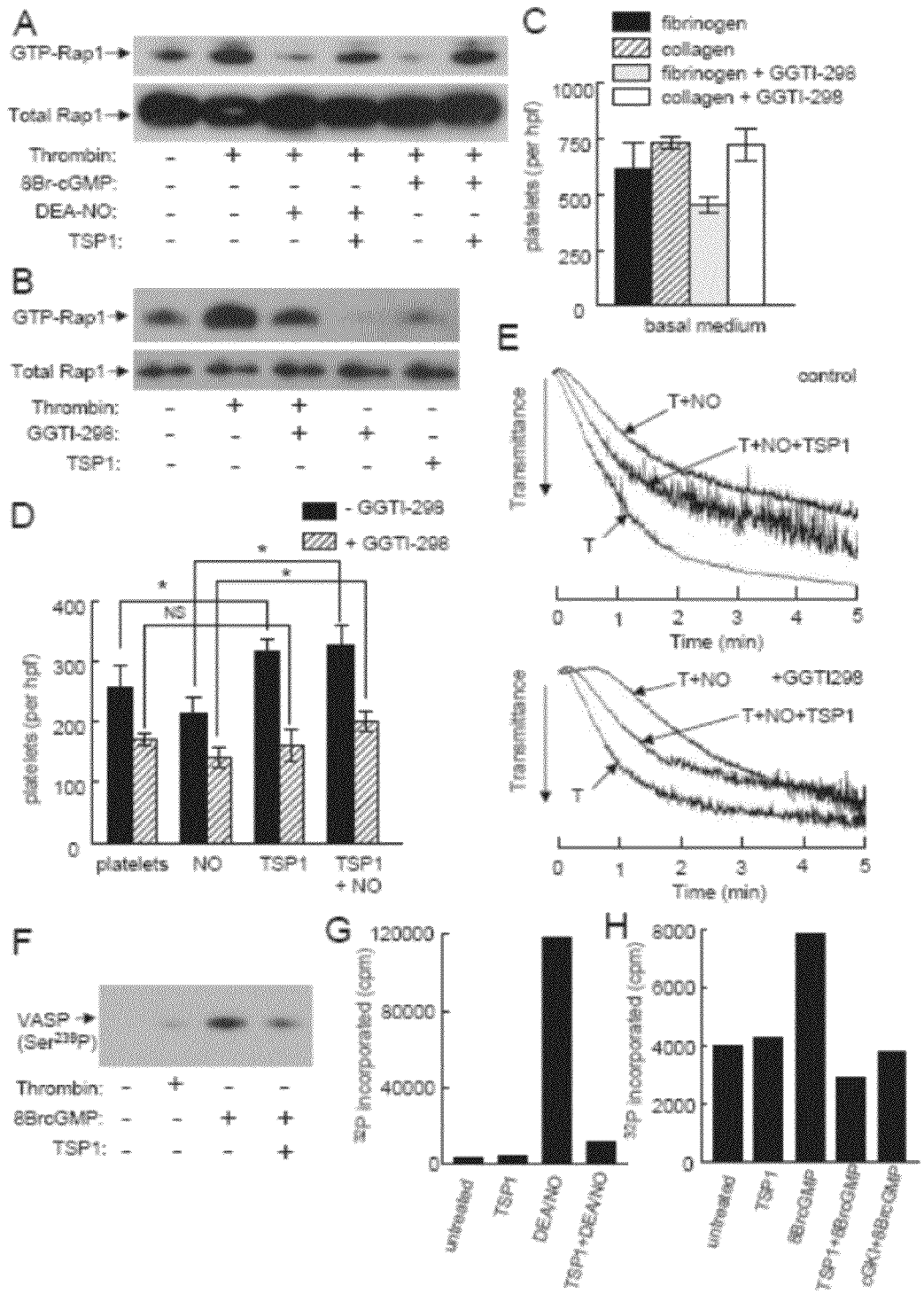

FIG. 39A-39H. TSP-1 enhances platelet adhesion by antagonizing NO and 8Br-cGMP signaling via Rap1 and blocks VASP-Ser239 phosphorylation by inhibiting cGK. Platelets preincubated in the presence or absence of TSP-1 (2.2 nM) were treated with DEA/NO (10 µM) or 8Br-cGMP (100 µM) 2 minutes prior to stimulation with 0.5 U/mL thrombin (FIG. 39A). Rap1 activation was analyzed by affinity purification using GST-RalGDS-RBD fusion protein immobilized on Glutathione-Sepharose beads. Platelets incubated at 37° C. in the presence or absence of GGTI-298 (10 µM for 30 minutes) before addition of 1 U/mL thrombin for 1 minute, or incubated with TSP1 (2.2 nM for 15 minutes), were lysed and subjected to a Rap activation assay (FIG. 39B). Fresh washed human platelets were used directly or preincubated in the presence of GGTI-298 for 30 min then added to 35 mm plastic dishes pre-coated with either type I collagen (3 µg/ml) or fibrinogen (5 µg/ml) (FIGS. 39C, 39D) and incubated in Tyrode's buffer and the indicated treatment agents for 1 hr at 37° C. Wells were washed and platelets fixed, stained and counted. Washed human platelets in Tyrode's buffer (2×105 platelets/µl) incubated in the presence of thrombin (0.2 U/ml) and exogenous NO (DEA/NO 10 µM)±TSP1 (2.2 nM) for 5 minutes or preincubated with GGTI-298 for 30 minutes and treated as above for 5 minutes and aggregation determined under high shear (FIG. 39E). Washed human platelets, either untreated or treated with thrombin (0.1 U/mL), 8Br-cGMP (100 µM for 2 minutes) or 2.2 nM TSP1 followed by 8BrcGMP, were lysed, resolved on SDS gels, blotted, and probed with a polyclonal antiserum against Ser239-phosphorylated VASP (FIG. 39F). Washed human platelets were pre-incubated with TSP1 (2.2 nM) or Rp-8 pCPT-cGMP (5 µM) for 15 minutes prior to treatment with NO (DEA-NO 10 µM) for 5 minutes (FIG. 39G) or 8Br-cGMP (100 µM) for 1 minute (FIG. 39H). The platelets were chilled to terminate the reaction, washed, lysed, and centrifuged. Lysate supernatants containing equal amounts of protein (100 µg) were assayed for phosphorylation of the cGK-1-selective substrate Arg-Lys-Arg-Ser-Arg-Ala-Glu. Data is representative of at least three experiments (FIGS. 39A, 39B, 39E-39H). Results are the mean±SD of at least three experiments (FIGS. 39C, 39D).

Figure 40:
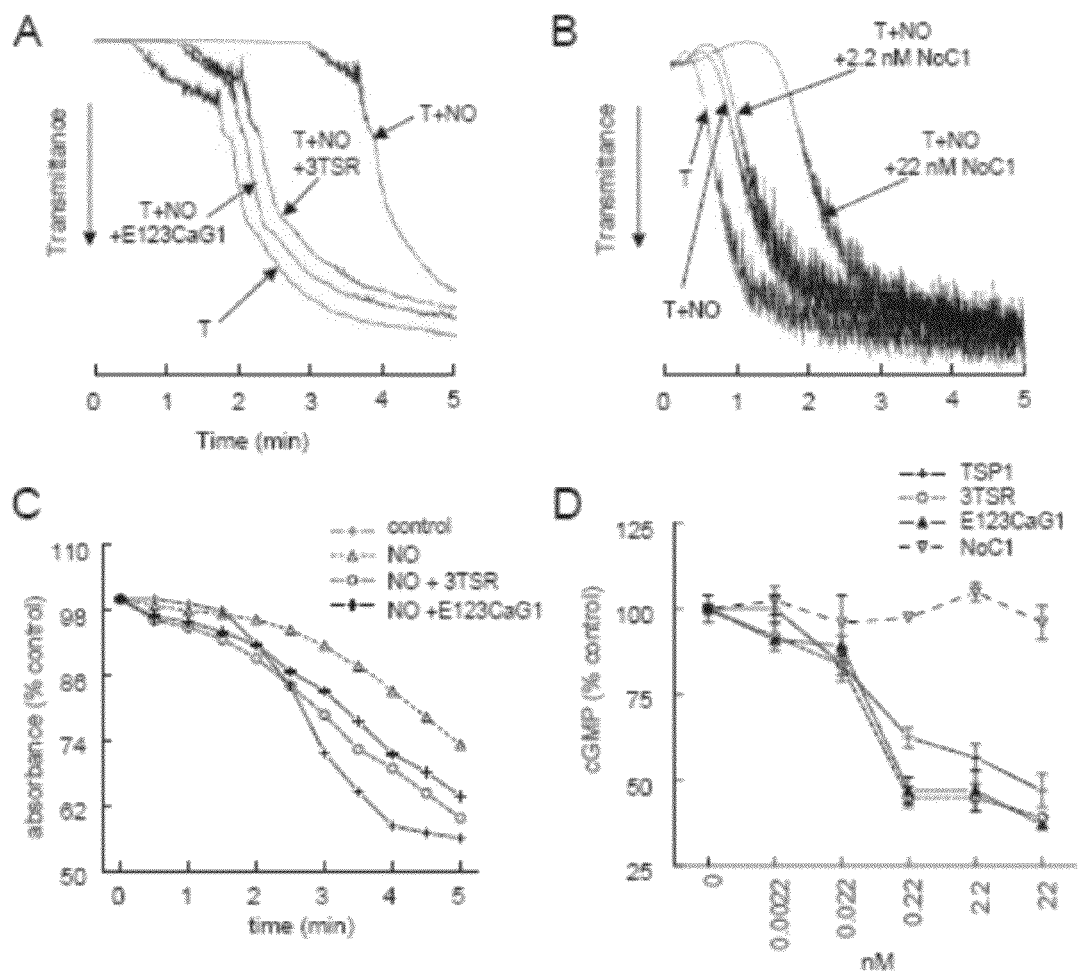

FIG. 40A-40D. CD36- and CD47-binding domains of TSP1 block NO-driven delay of platelet aggregation. Washed human platelets (2×105 platelets/µl) were incubated in the presence of thrombin (0.2 U/ml) and exogenous NO (DEA/NO 10 µM) for 5 minutes in the presence of recombinant TSP1 constructs 3TSR and E123CaG-1 (2.2 nM) or NoC1 (2.2-22 nM) and aggregation determined under high shear (FIGS. 40A, 40B) or low shear conditions (FIG. 40C). In other experiments washed platelet were pre-incubated with the indicated concentrations of recombinant fragments and treated with DEA/NO (1 µM) for 60 seconds, lysed and cGMP levels determined by immunoassay (FIG. 40D). Data is representative of at least three experiments (FIG. 40A-40C). Results are the mean±SD of at least three experiments (FIG. 40D).

Figure 41:
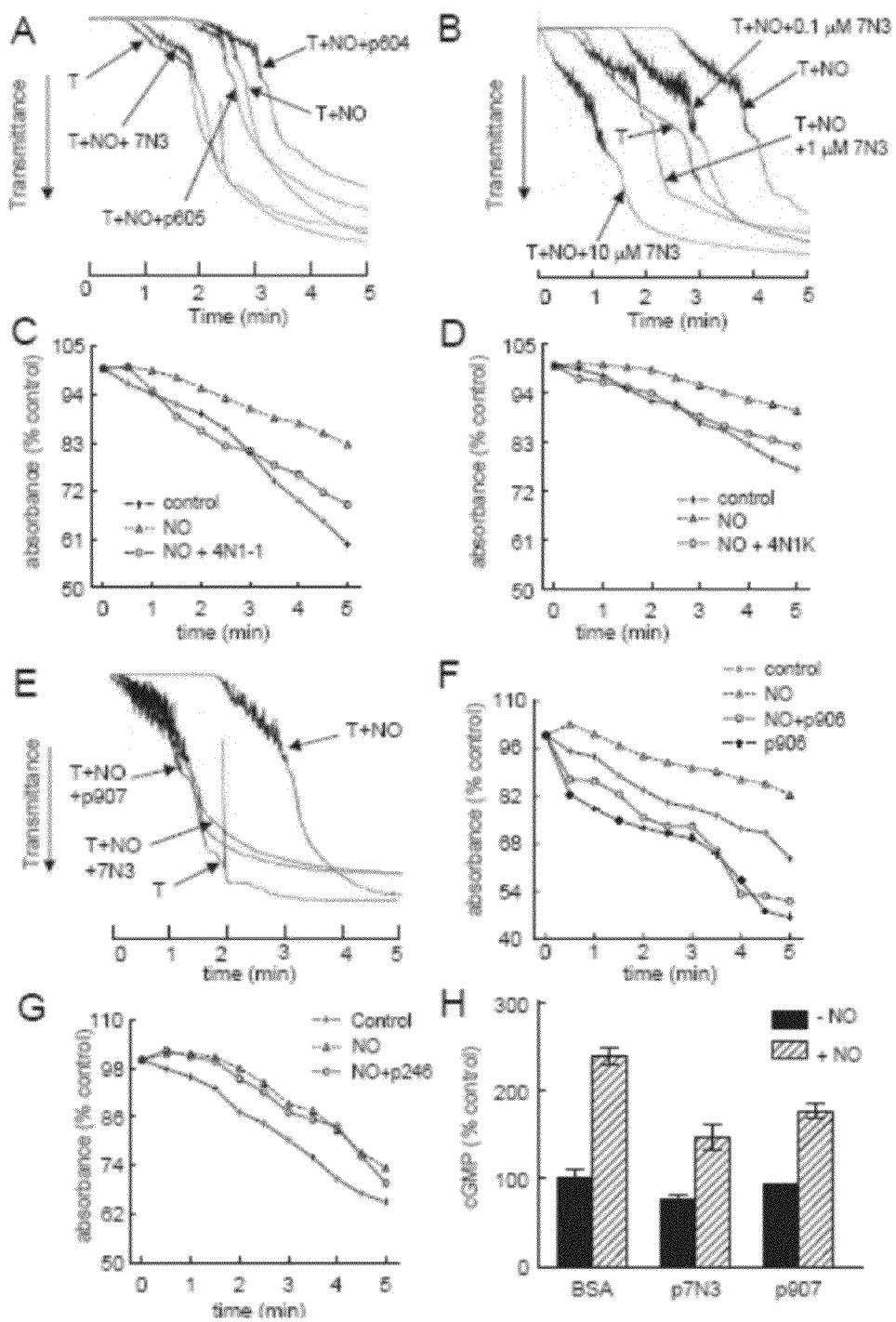

FIG. 41A-41H. CD47- and CD36-binding peptides antagonize the NO delay in platelet aggregation. Washed human platelets (2×10$^5$ platelets/µl) were incubated in Tyrode's buffer in the presence of thrombin (0.2 U/ml) and exogenous NO (DEA/NO 10 µM) for 5 minutes and peptide sequences derived from relevant domains of TSP1 including 7N3 (FIRVVMYEGKK, 10 µM; SEQ ID NO: 10) and control peptides for the same (p604, FIRGGMYEGKK, 10 µM and p605, FIRVAIYEGKK, 10 µM; SEQ ID NOs: 11 & 12, respectively) (FIG. 41A), p7N3 (0.1-10 µM) (FIG. 41B) and absorbance determined under high shear, or p459 (4N1-1, RFYVVMWK, 10 µM, FIG. 41C; SEQ ID NO: 14), 4N1K (KRFYVVMWKK, 10 µM, FIG. 41D; SEQ ID NO: 13) and absorbance determined under low shear conditions. Washed human platelets in Tyrode's buffer (2×105 platelets/µl) were incubated in the presence of thrombin (0.2 U/ml) and exogenous NO (DEA/NO 10 µM) for 5 minutes and peptide sequences derived from TSP1 including p7N3 and p907 (GDGV(D-I)TRIR, FIG. 41E; SEQ ID NO: 19) (10 µM) and aggregation determined under high shear, and p906 (VTAGGGVQKRSRL, FIG. 41F; SEQ ID NO: 18) (10 µM) and p246 (KRFKQDGGWSHWSPWSS, FIG. 41G; SEQ ID NO: 8) (10 µM) and absorbance measured under low shear. Human platelets were pre-treated with TSP1-based peptides p907 and p7N3 (10 µM) before adding DEA/NO (10 µM) and cGMP levels determined (FIG. 41H). Data is representative of at least three experiments (FIG. 41A-41G). Results are the mean±SD of at least three experiments (FIG. 41H).

Figure 42:
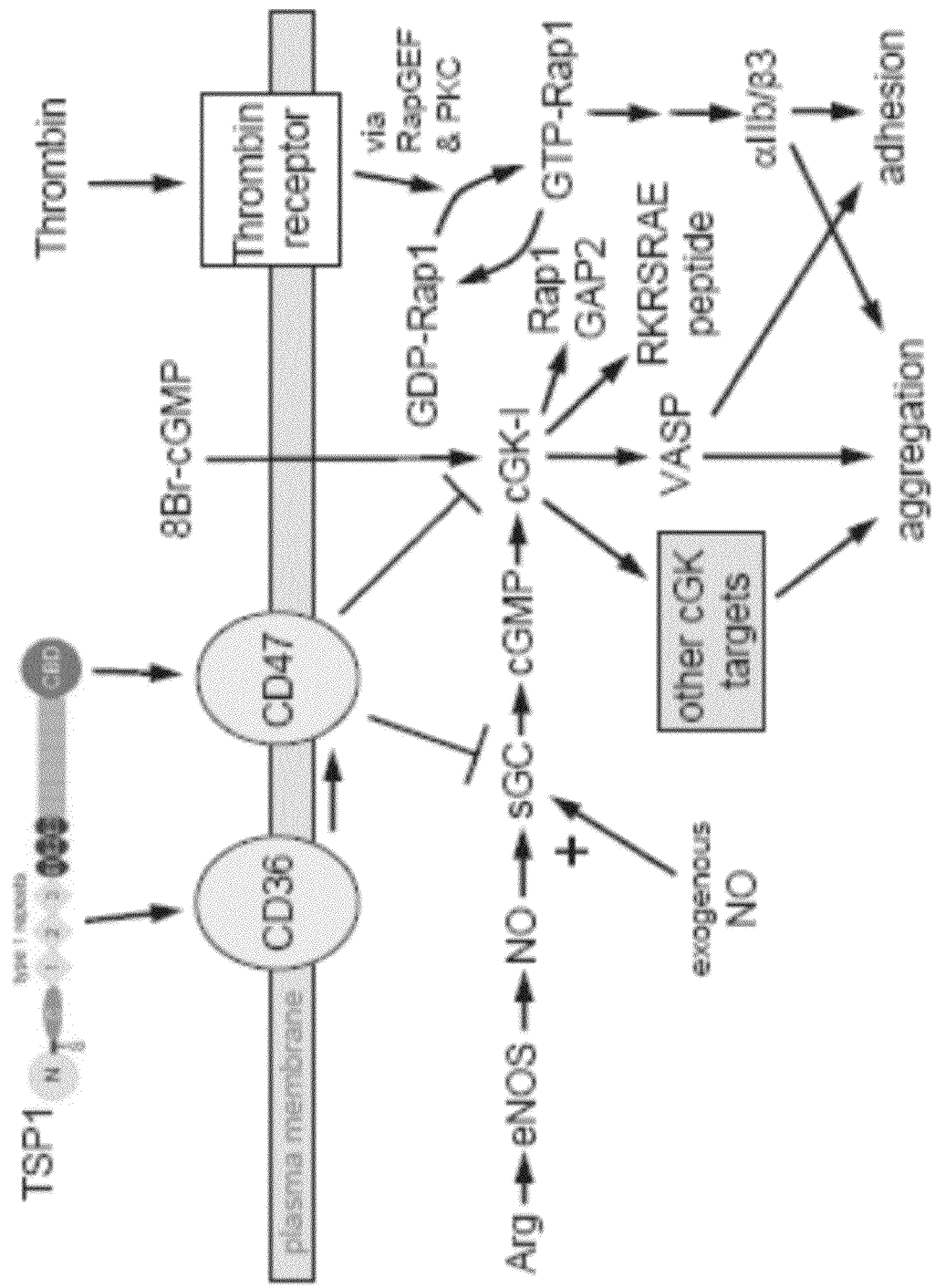

FIG. 42. Proposed mechanism for TSP1 antagonism of NO/cGMP signaling in platelets. Using recombinant domains and peptides of TSP1, we show that ligation of CD36 or CD47 is sufficient to block an NO-mediated delay in platelet aggregation. TSP1 blocks a delay mediated by either exogenous NO or NO synthesized by endogenous eNOS using Arg as substrate. The ability of TSP1 to prevent cGMP synthesis stimulated by exogenous NO identifies sGC as one target of TSP1 signaling. The ability of TSP1 to inhibit cGK-1-mediated phosphorylation of VASP and a cGK-1-selective peptide (RKRSRAE; SEQ ID NO: 17) stimulated by a cell-permeable cGMP analog (8Br-cGMP) identifies cGK-I as a second target of TSP1 signaling in platelets. VASP is required for NO/cGMP-mediated inhibition of agonist-induced platelet aggregation as well as platelet adhesion. TSP1 prevents cGK-1-mediated phosphorylation of VASP at Ser239. NO also stimulates phosphorylation of the cGK-I target Rap1GAP2, so TSP1 inhibition of sGC and cGK-I also controls GTP loading of Rap1, which is required for thrombin-stimulated activation of the adhesion receptor αIIb/β3

FIG. 43A-43E. Morpholino suppression of CD47 modulates TSP1 inhibition of NO signaling in porcine VSMC. Comparison of the 5'-UTR sequences of human and porcine CD47 mRNA showing complementarity to the antisense and control morpholinos (FIG. 43A). VSMC from the femoral artery of white hairless Yucatan miniature pigs were plated at a density of $1\times10^5$ cells/well in 96-well plates pre-coated with type I collagen (3 µg/ml) and treated with TSP1 (0.022-2.2 nM)±DEA/NO (10 µM) and adhesion measured as described (FIG. 43B). VSMC from the femoral artery of white hairless Yucatan miniature pigs were plated at a density of $5\times10^5$ cells/well in 12-well culture plates (Nunc) in minimal growth medium and treated with TSP1 (2.2 nM)±DEA/NO (10 µM) for 5 minutes and cGMP measured via immunoassay (FIG. 43C). Porcine VSMC were treated for 48 with a CD47 morpholino or mismatch control (10 µM). Cells were then treated in minimal growth medium with TSP1 (2.2 nM)±DEA/NO (10 µM) for 5 minutes and cGMP measured via immunoassay (FIG. 43D). Porcine VSMC were pre-incubated with TSP1 (2.2 nM) and TSP1 antibody A6.1 (10 µg/ml) in basal medium (without serum) and an exogenous NO donor added (DEA/NO 10 µM) and cGMP determined (FIG. 43E). Results represent the mean±SD of three separate experiments.

FIG. 44A-44C. CD47 suppression increases random cutaneous flap survival. White hairless Yucatan miniature pigs underwent 2×10 cm dorsal random cutaneous flaps with treatments to flaps as indicated (FIG. 44A). At the time of surgery flaps were injected with vehicle, mismatched or CD47 antisense morpholino and flap survival was determined on post-operative day 7 (FIG. 44B). The degree of flap necrosis was determined at 72 hours post-operatively as described (FIG. 44C).

Figure 45:
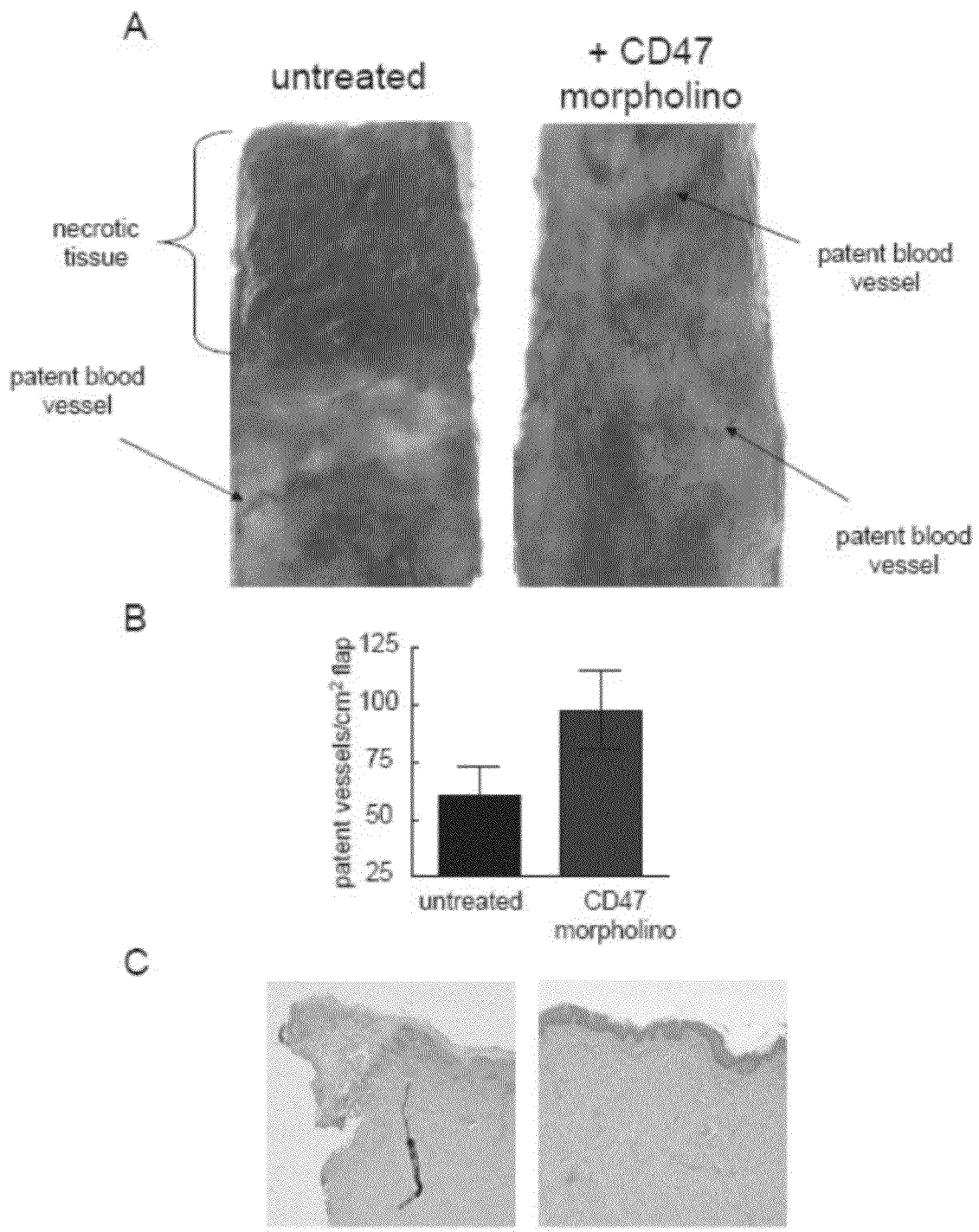

FIG. 45A-45C. CD47 suppression is associated with increased vascular patency in ischemic cutaneous units. Six month old white hairless Yucatan miniature pigs underwent random dorsal cutaneous flaps. On post-operative day 3 animals were euthanized and India ink injection of the central and peripheral vasculature performed as described. Flap vasculature in treated and untreated flaps was quantified (FIGS. 45A, 45B). Representative H & E staining of treated and untreated flaps.

FIG. 46A-46B. Antibody ligation of TSP1 increases ischemic tissue survival in a porcine model. White hairless Yucatan miniature pigs underwent 2×10 cm dorsal random cutaneous flaps. Flaps were treated with vehicle (normal saline) or a monoclonal TSP1 antibody (clone HB8432, n=2 or clone A6.1, n=16). Therapeutic agents were delivered via injection at the time of surgery directly to the flap (FIG. 46A). At 72 hours post-operatively flap viability was determined (FIG. 46B). Other random flaps were treated with the monoclonal TSP1 antibody ah-TSP1 and viability determined (FIG. 46C). Certain animals received intravenous fluorescein and flaps photographed under ultraviolet illumination.

Figure 47:
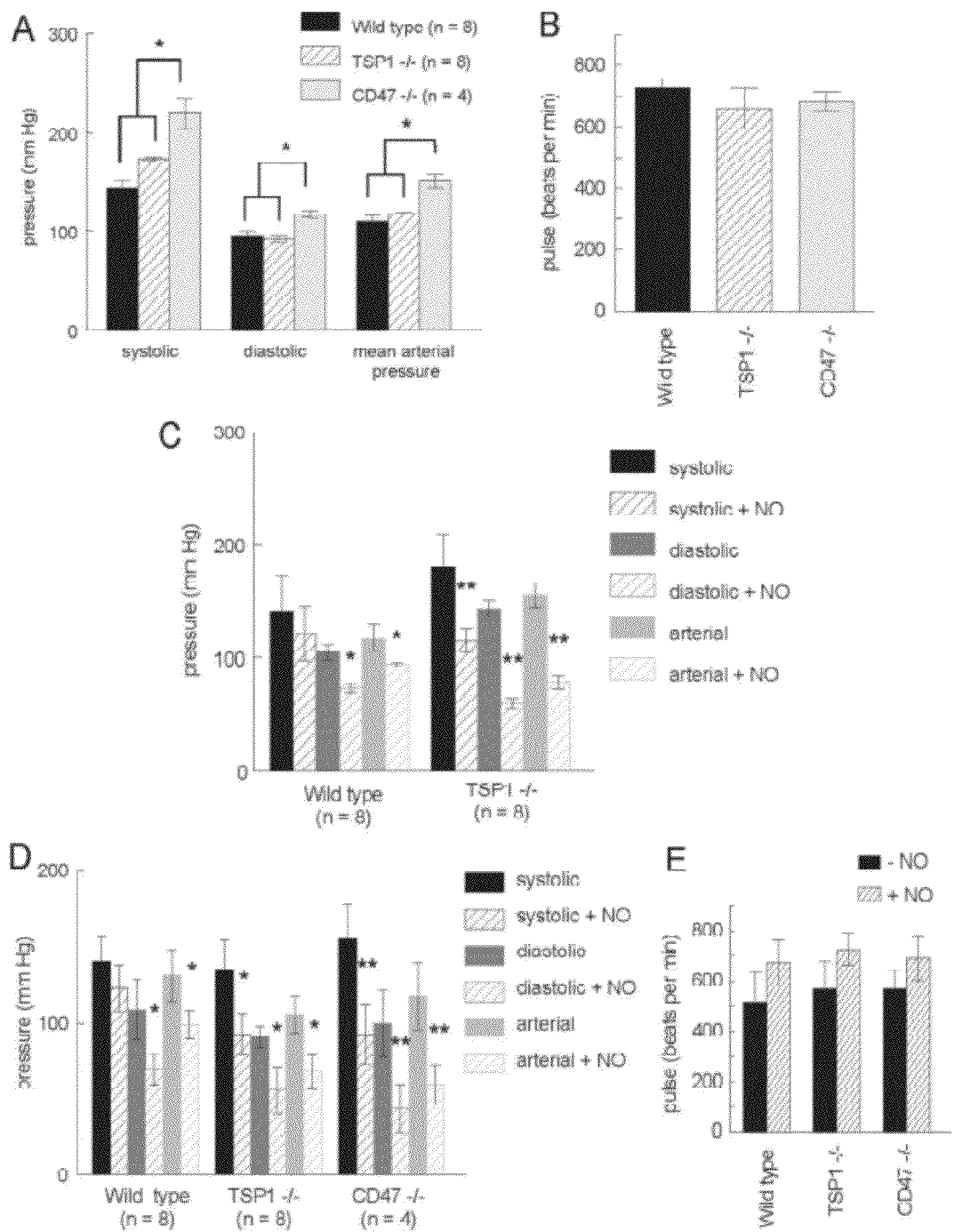

FIG. 47A-47E. TSP1 and CD47 limit blood pressure changes in response to NO. Age and sex matched wild type, TSP1, and CD47 null mice underwent analysis of resting blood pressure (FIG. 47A) and pulse (FIG. 47B). Wild type and TSP1 null matched for age and sex mice were treated with a rapid releasing NO-donor (DEA/NO 1 µl/gram body weight of 100 mM stock i.p.) and resting blood pressure measured (FIG. 47C). Wild type, TSP and CD47 null age and sex matched mice underwent treatment with an intermediate releasing NO-donor (PAPA/NO 1 µl/gram body weight of 100 mM stock i.p.) and resting blood pressure (FIG. 47D) and pulse (FIG. 47E) measurements obtained. Results are of the mean±SD of 8 animals each of wild type and TSP1 null and 4 CD47 null.

Figure 48:
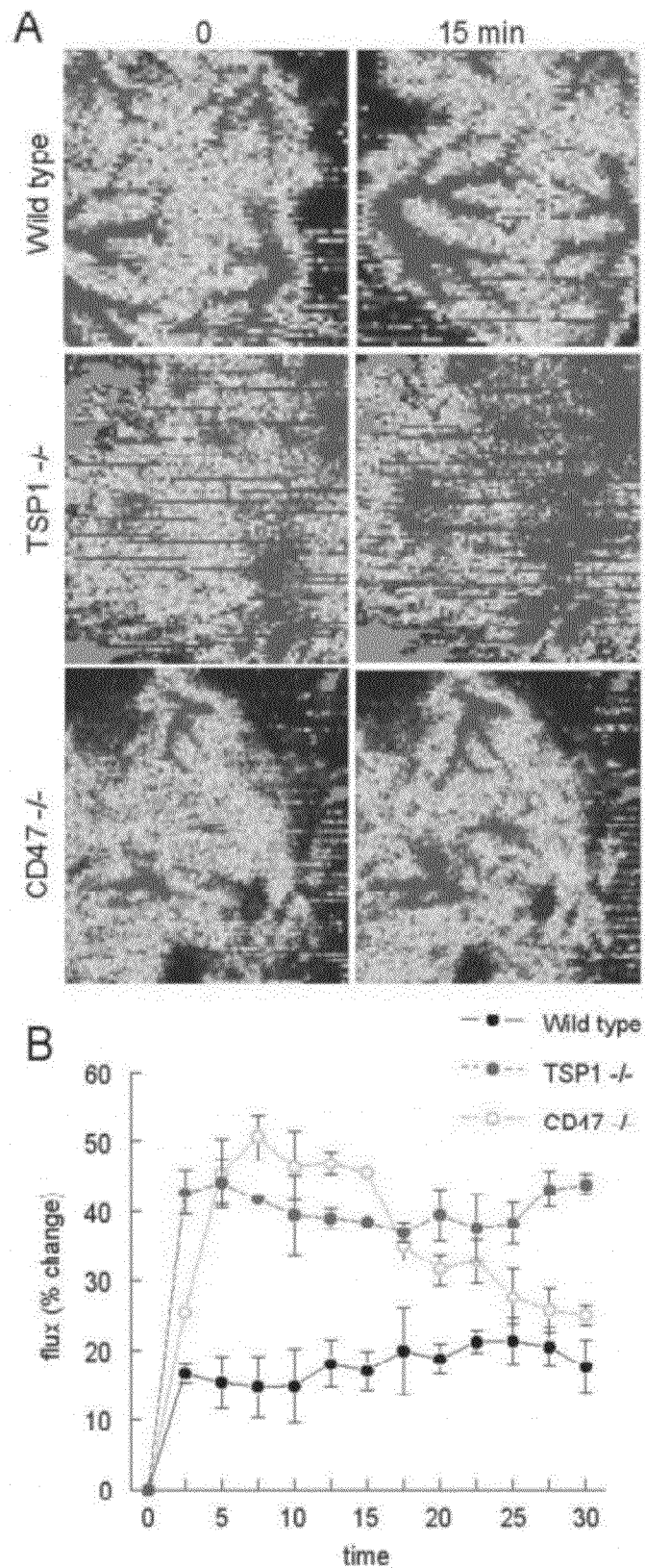

FIG. 48A-48B. TSP1 limits alterations in cutaneous perfusion by nitric oxide. (FIGS. 48A, 48B) Age and sex matched wild type, TSP1, and CD47 null mice were anesthetized with 1.5% isoflurane, core temperature maintained at 34.5° C. and cutaneous perfusion measured by laser Doppler (Moor Instruments). Animals were then treated with exogenous NO (DEA/NO 1 µl/gram weight of 100 mM stock) via rectal catheter bolus injection, and cutaneous perfusion was again measured. Results are of the mean±SD of 8 animals each of wild type, TSP1, and CD47 null.

Figure 49:
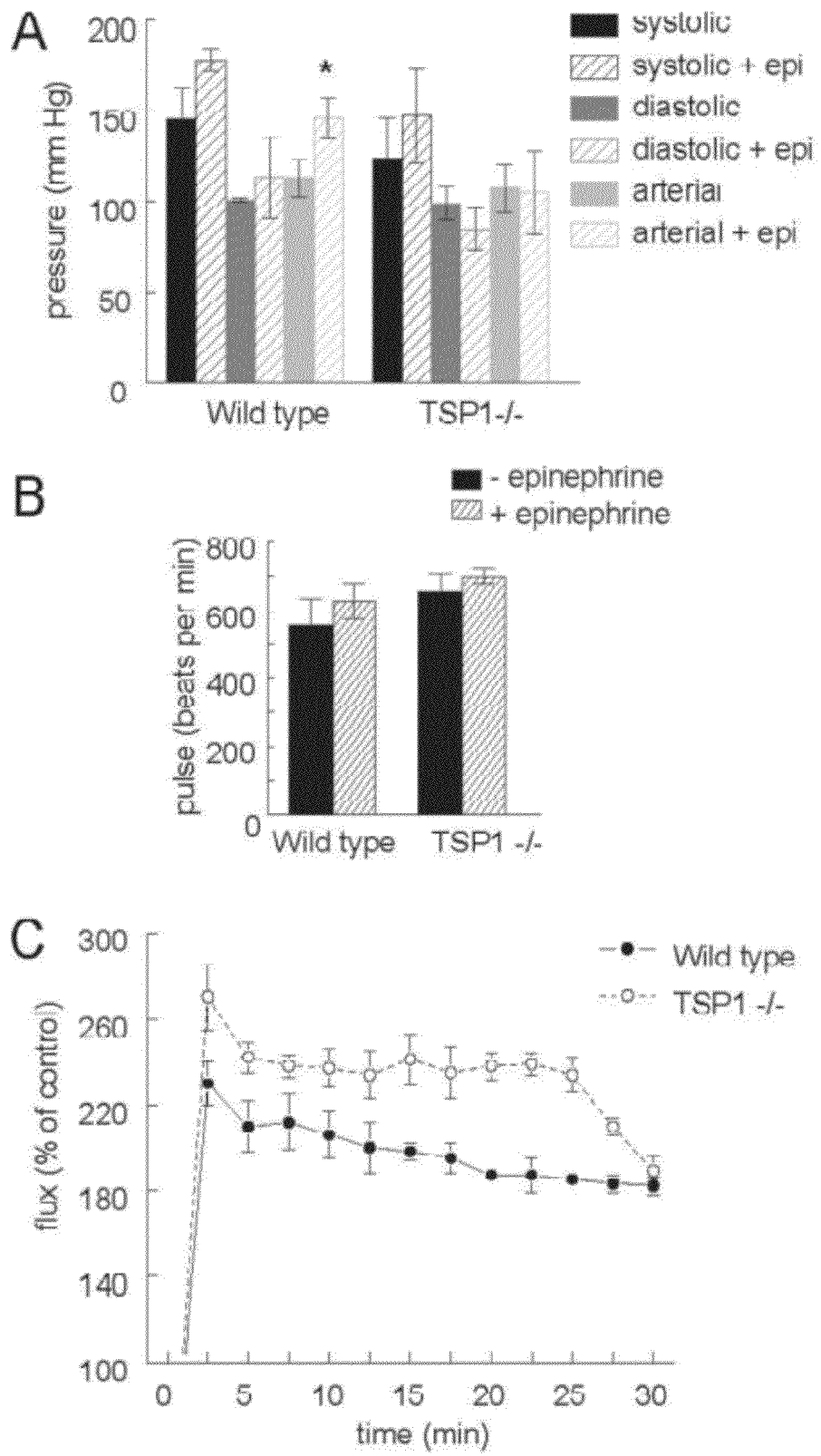

FIG. 49A-49C. TSP1 regulates blood pressure responses to vasoconstrictor stimulation. Wild type and TSP1 null age and sex matched mice underwent blood pressure (FIG. 49A) and pulse (FIG. 49B) analysis before and immediately after treatment with epinephrine (0.05 µg/animal i.p.). Under 1.5% general isoflurane anesthesia wild type and TSP1 null age and sex matched mice underwent laser Doppler analysis of cutaneous perfusion following treatment with epinephrine (0.05 µg/animal i.p.) (FIG. 49C). The core temperature of all animals was maintained at 35.5° C. throughout. Results are of the mean±SD of 8 animals each of wild type and TSP1 null.

Figure 50:
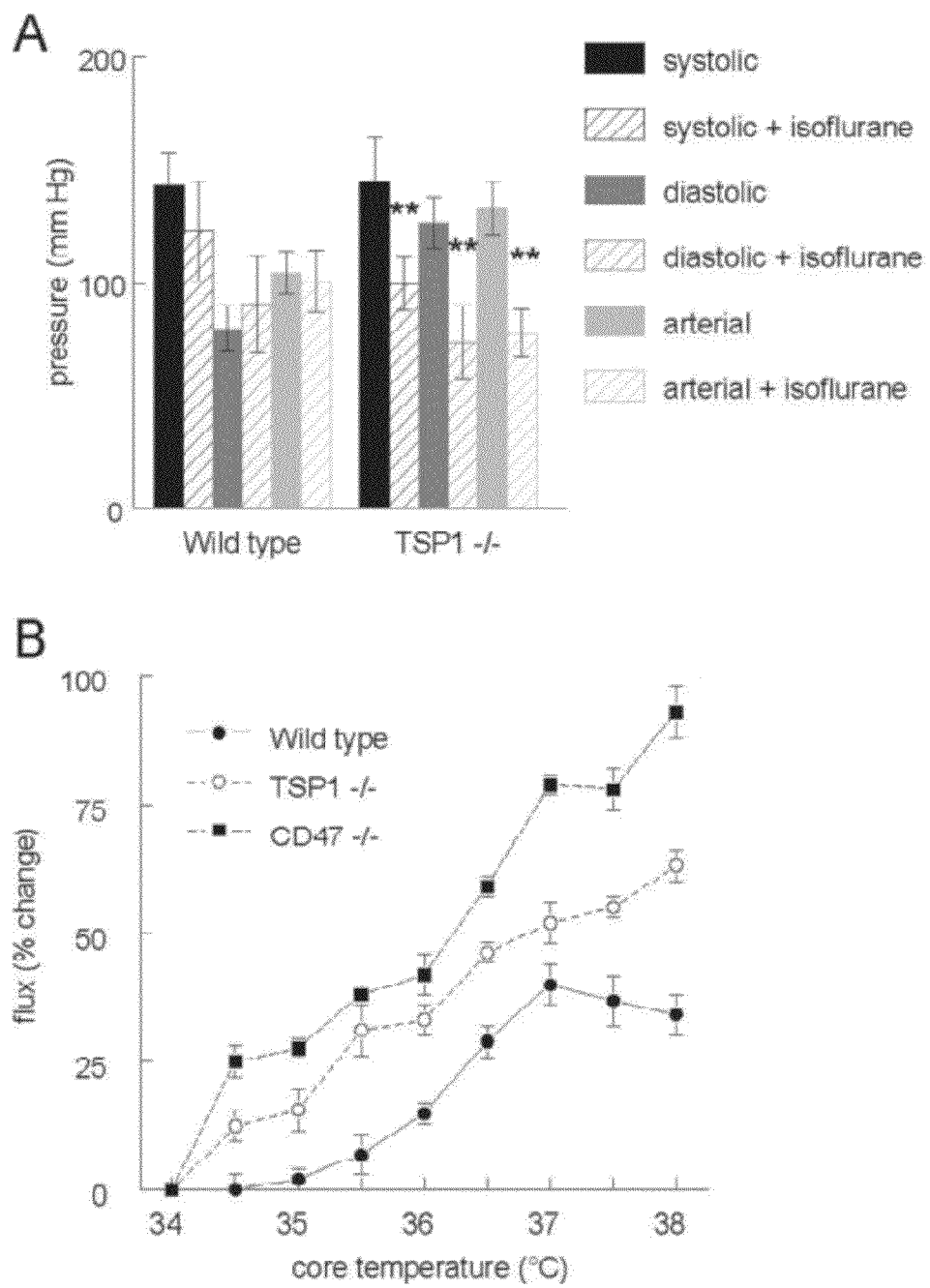

FIG. 50A-50B. TSP1 limits alterations in blood pressure in response to general anesthesia. (FIG. 50A) Wild type and TSP1 null age and sex matched mice were anesthetized with 1.5% isoflurane, core temperature maintained at 37° C. and blood pressure and pulse determined. Wild type TSP1 and CD47 null age and sex matched mice were anesthetized with 1.5% isoflurane and core temperature increased by 0.5° C. increments from 34-37° C. and cutaneous perfusion measured by laser Doppler (Moor Instruments) (FIG. 50B). Results are of the mean±SD of 8 animals each of wild type, TSP1, and CD47 null.

Figure 51:
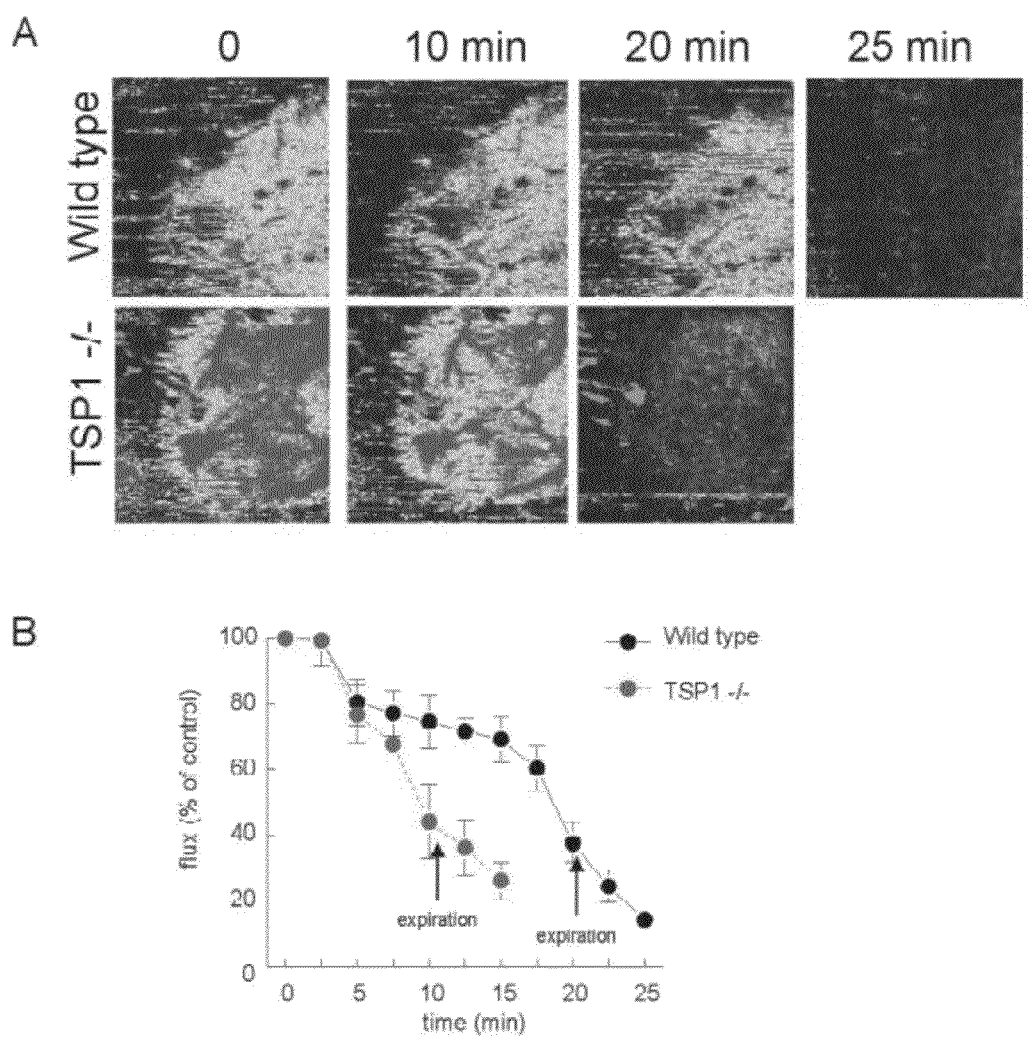

FIG. 51A-51B. TSP1 protects against cardiovascular collapse following autonomic blockade. (FIG. 551A) Wild type and TSP1 null age and sex matched mice were anesthetized with 1.5% isoflurane, and core temperature was maintained at 37° C. Baseline cutaneous perfusion was determined with laser Doppler Animals were then treated with the central autonomic ganglion blocking agent hexamethonium (30 µg/gram animal weight) given intravenously and cutaneous perfusion determined at 2.5 min intervals (FIG. 51B). Results are the mean±SD of 4 animals each of wild type and TSP1 null.

FIG. 52A-52E. TSP1 impairs ischemic tissue survival in aged animals. WT and TSP1-null (FIGS. 52A, 52B) mice 2-4 and 12-16 months of age underwent random dorsal myocutaneous flaps, and tissue survival determined. Results represent the mean±SD of 16 animals. Aged animals (FIG. 52C) underwent flap surgery and received ISDN or L-NAME in the drinking water post-operatively. Results represent the mean±SD of 16 animals. Skeletal muscle from young (12 weeks) and old (18 month) animals (FIG. 52D) or old animals±24 hours of ischemia (FIG. 52E) was processed for cGMP analysis. Results represent the mean±SD of 4 pairs of animals.

Figure 53:
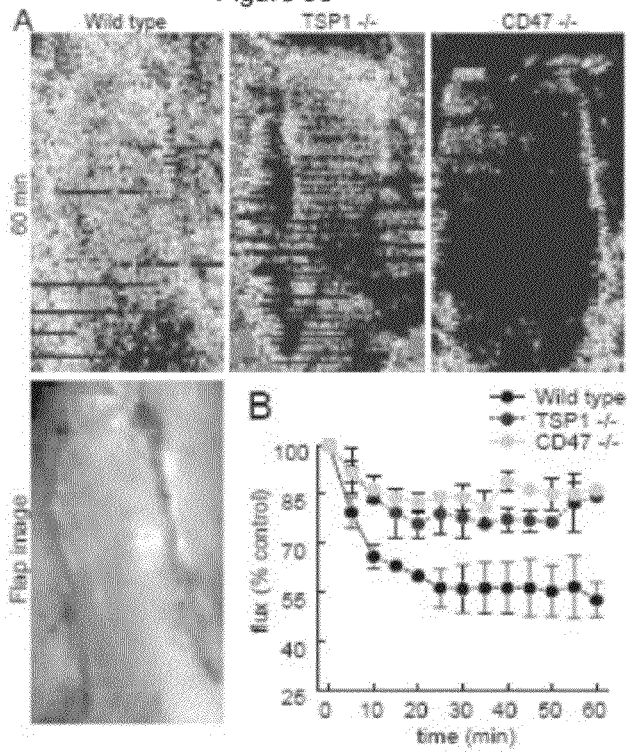

FIG. 53A-53B. Thrombospondin-1 limits immediate responses to ischemia in senescent animals. Mice 14-18 months of age underwent dorsal McFarlane flap surgery and perfusion was determined via laser Doppler (FIGS. 53A, 53B) Animals were maintained at 37° C. on a heated stage. Images and data are representative of 18 mice, 6 of each strain.

Figure 54:
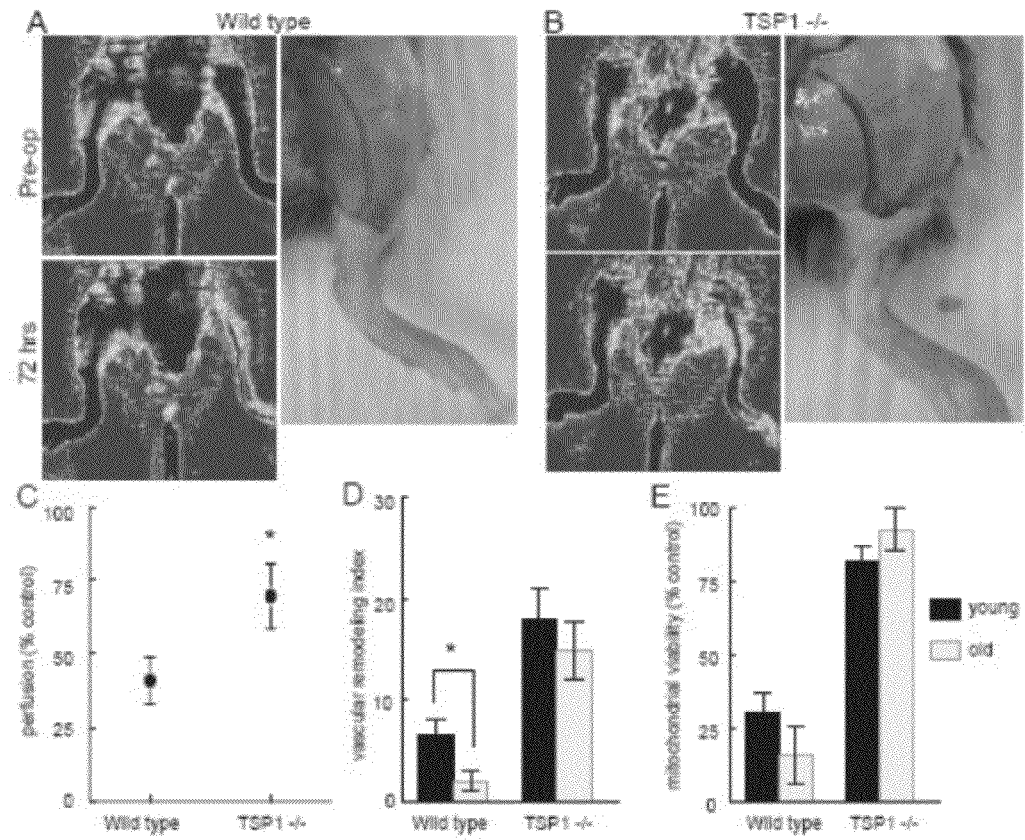

FIG. 54A-54E. Thrombospondin-1 limits hind limb survival to ischemia in aged animals. WT (FIG. 54A) and TSP1-null (FIG. 54B) mice 2-4 and 14-18 months in age underwent femoral artery ligation. Doppler analysis of limb perfusion was performed at 72 hours post-operatively (FIG. 54A-54C) (P>0.05). Images pictured are from representative aged animals. Under 5× magnification, visible vessels on the surface of the vastus medialis was quantified in both young and old animals (FIG. 54D). Mitochondrial viability of muscle from the tibialis anterior was determined and quantified (FIG. 54E). Results represent the mean±SD of 12 animals.

Figure 55:
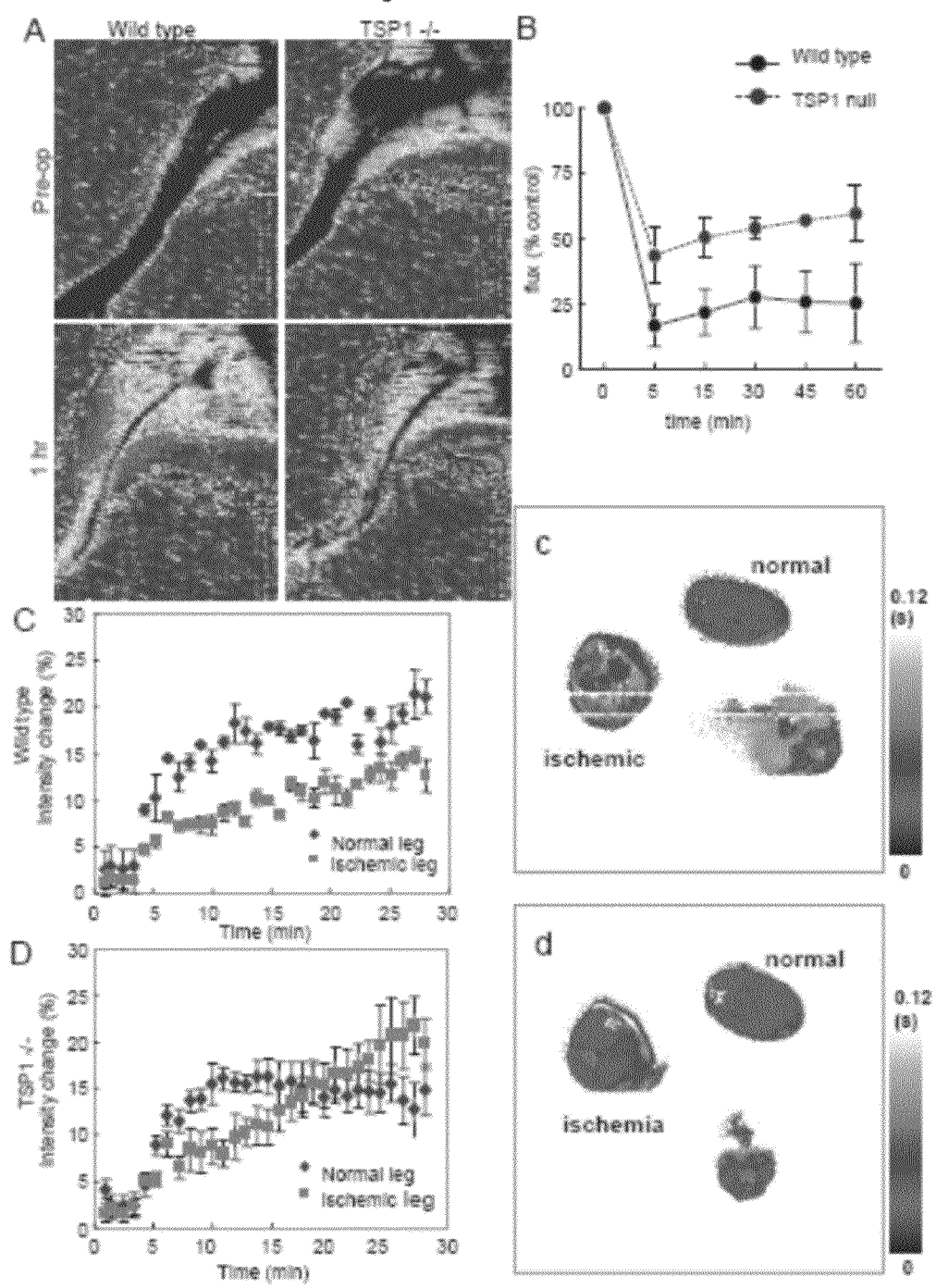

FIGS. 55A, 55B, 55C, 55D, 55c, 55d. Loss of TSP1 minimizes tissue loss following acute vascular interruption in aged animals. Mice aged 14-18 months underwent laser Doppler analysis of hind limb perfusion followed by ligation of the femoral artery and immediate analysis (FIGS. 55A, 55B). Results represent the mean±SD of 6 pairs of animals. Aged WT (FIG. 55C) and TSP1-null (FIG. 55D) mice underwent femoral artery ligation and BOLD MRI images were obtained from $T_2$* weighted gradient echo sequences. DEA/NO (100 nmol/g bodyweight) was administered 5 minutes after starting the scan. Values are presented as mean±SE of 4 and 5 experiments in wild type and TSP1-null mice respectively. $T_2$ maps of normal and ischemic hind limbs of aged WT (FIG. 55c) and TSP1-null (FIG. 55d) animals.

Figure 56:
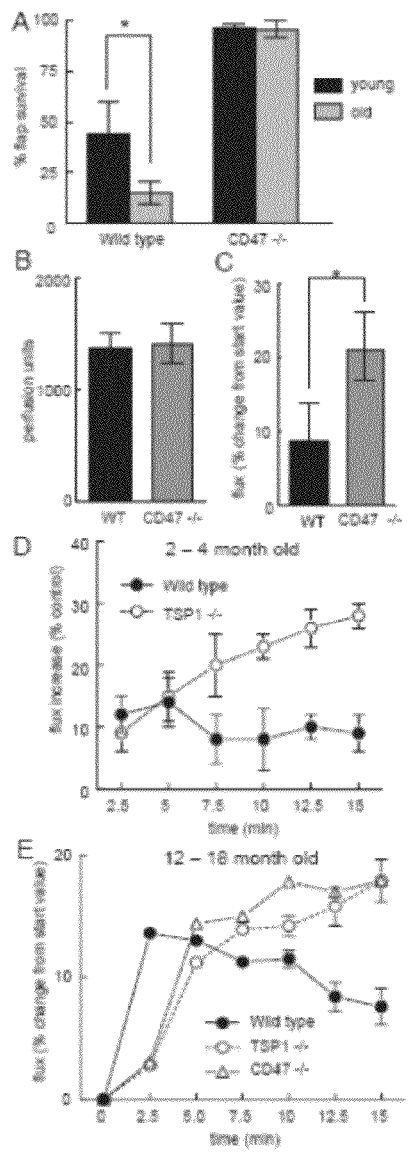

FIG. 56A-56E. TSP1 through CD47 limits ischemic tissue survival and NO-driven tissue perfusion in elderly animals. Mice aged 2-4 and 12-16 months underwent random dorsal flaps and tissue survival determined (FIG. 56A). Results represent the mean±SD of 18 animals (12 CD47-null and 6 WT). Mice 8-16 week old (FIGS. 56B, 56C, 56D) and 14-16 month old animals (FIG. 56E) underwent laser Doppler analysis of paw perfusion. Data were acquired pre-treatment (FIG. 56B) and at 5 minutes following application of 5% mustard oil (FIG. 56C) to the hind paw, or in young (FIG. 56D) or aged (FIG. 56E) WT, TSP1- and CD47-null mice. Results represent the mean±SD of 5 pair of WT, CD47-null and TSP1-null animals from each age group (FIGS. 56B, 56C) or the mean±SD of 24 mice, 8 of each strain (FIGS. 56D, 56E).

Figure 57:
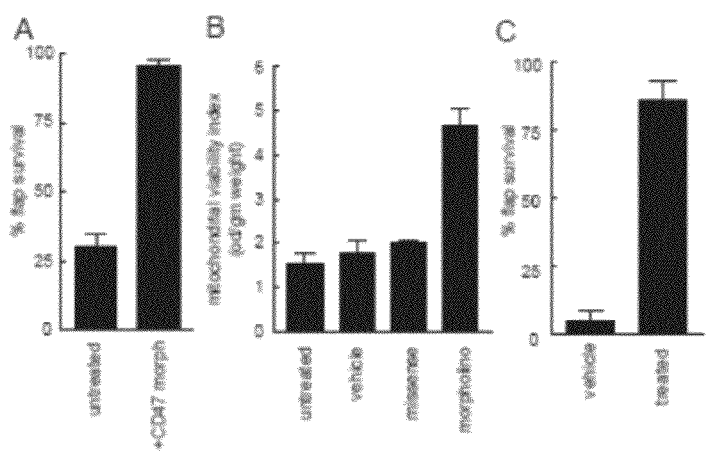

FIG. 57A-57C. Morpholino suppression of CD47 increases aged tissue survival to ischemia. WT mice 14-18 months of age underwent random dorsal flaps Animals were treated with control vehicle, missense control morpholino (data not shown) or a CD47 morpholino (FIG. 57A) (10 µM in PBS injected in the flap and wound bed) and flap survival determined. Results presented represent the mean±SD from 12 animals (6 treated with control vehicle and 6 treated with a CD47 morpholino). Mitochondrial viability of flaps was determined and quantified (FIG. 57B). ApoE-null mice on a high fat diet and of at least 12 months of age underwent random flaps Animals were treated with control vehicle or a CD47 morpholino and flap survival determined on post-operative day 7 (FIG. 57C). Results presented represent the mean±SD from 10 animals (5 treated with control vehicle and 5 treated with a CD47 morpholino).

FIG. 58a-58d. TSP1 impairs ischemic tissue survival in aged animals. Sections of random dorsal McFarlane flaps demonstrate near complete necrosis of wild type flaps with massive inflammatory infiltration and normal architecture with minimal inflammatory component in TSP1-null flaps. H&E sections under low (20× objective) (FIGS. 58a, 58b) and high magnification (40× objective) (FIGS. 58c, 58d).

FIG. 59A-59B. Thrombospondin-1 limits immediate responses to ischemia in senescent animals. WT, TSP1-null, and CD47-null mice 14-18 months of age 14-18 months of age underwent dorsal McFarlane flap surgery and perfusion was determined via laser Doppler every 5 minutes for the first post-operative hour (FIGS. 59A, 59B) Animals were maintained at 37° C. on a heated stage. Images and data are representative of 18 mice, 6 of each strain.

Figure 60:
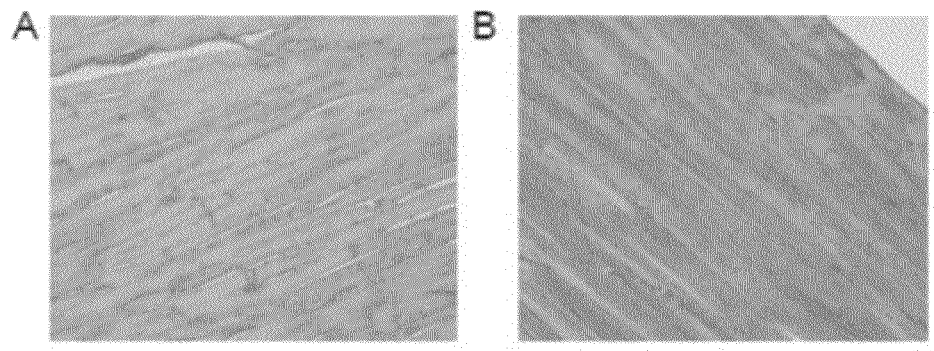

FIG. 60A-60B. Thrombospondin-1 limits hind limb survival to ischemia in aged animals. Sections from the tibialis anterior muscle of ischemic WT (FIG. 60A) and TSP1-null (FIG. 60B) hind limbs from aged animals are shown demonstrating hylinized degeneration and drop out of muscle fibers with mononuclear cell infiltration in wild type muscle compared to TSP1-null. H&E sections, 20× objective.

Figure 61:
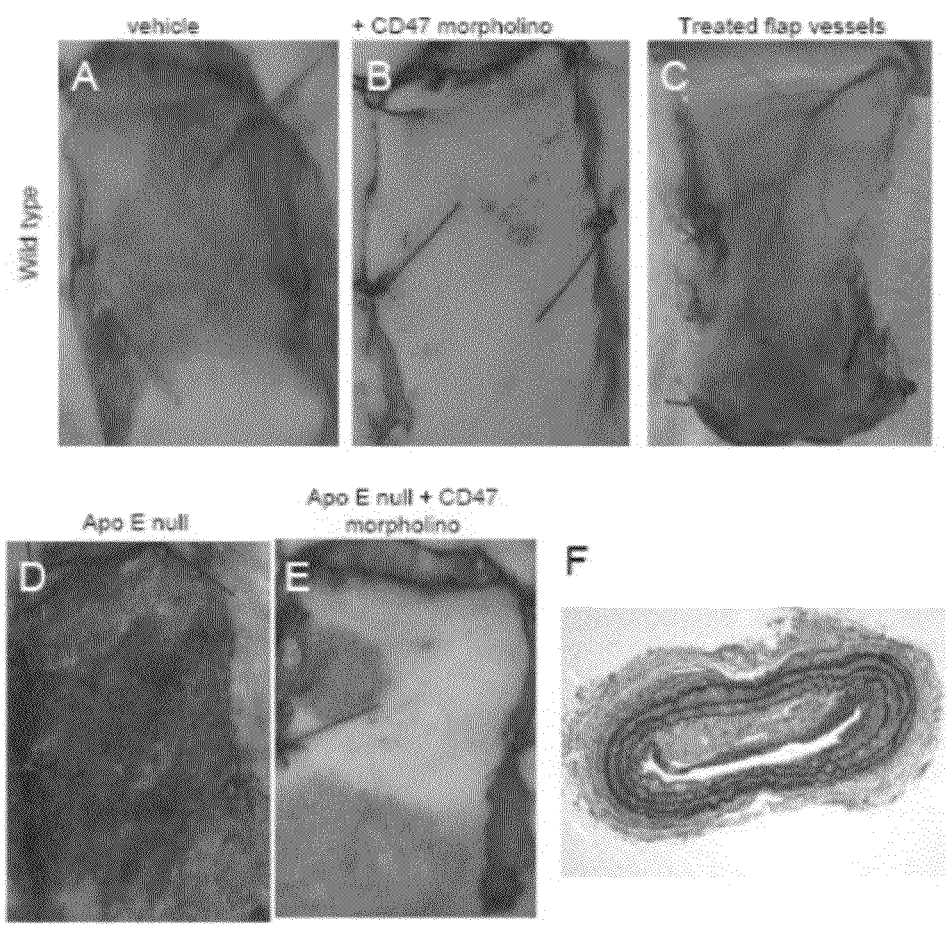

FIG. 61A-61F. Morpholino suppression of CD47 increases aged tissue survival to ischemia. WT mice 14-18 months of age underwent random dorsal flaps Animals were treated with control vehicle (61A), missense control morpholino (data not shown) or a CD47 morpholino (FIG. 61B). Representative image of flap vascular remodeling in WT flaps treated with a CD47 morpholino (FIG. 61C). ApoE-null mice on a high fat diet and of at least 12 months of age underwent random dorsal myocutaneous flaps. Animals received no treatment (FIG. 61D), a vehicle or a CD47 morpholino (FIG. 61E) and flap survival determined on post-operative day 7. Representative H&E section of artery from an aged apoE-null animal on a high-fat diet three weeks following soft tissue injury, 20× objective (FIG. 61F).

FIG. 62A-62F. NO/cGMP signaling in human platelets is limited by TSP1-derived peptides. Fresh human platelets were incubated in Tyrode's buffer in the presence of the indicated concentrations of peptides for 15 minutes and then 10 µM DEA/NO for 5 minutes, and cGMP was determined by immunoassay. Results are the mean±SD of at least three experiments.

FIG. 63A-63C. NO/cGMP signaling in HT-1080 cells is limited by several unique TSP1-derived peptides. HT-1080 cells previously transfected to over-express soluble guanylate cyclase were incubated in basal medium+0.1% BSA and the indicated concentrations of TSP1-derived peptides for 15 min, 10 µM DEA/NO added and cGMP determined via immunoassay.

FIG. 64. Fresh human platelets were suspended in Tyrode's buffer and under low shear conditions thrombin-stimulated aggregation measured. Platelets were then treated with peptide C6d (1 µM)±NO (10 µM DEA/NO) and thrombin and aggregation measure. Thrombin-stimulated aggregation under low shear conditions was markedly delayed by NO. Concurrent treatment with peptide C6d completely reversed the anti-coagulation effects on NO on thrombin-stimulated aggregation.

SEQUENCE LISTING

The disclosed nucleic and amino acid sequences are shown using standard letter abbreviations for nucleotide bases, and one or three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file named 75396-10_Sequences.txt, created on Jun. 5, 2012, ~8 KB, which is incorporated by reference herein. In the accompanying Sequence Listing:

SEQ ID NO: 1 is peptide IGWKDFTAYR

SEQ ID NO: 2 is peptide p37300 Ac-WKDFTAYR

SEQ ID NO: 3 is peptide biotin-IGWKDFTAYR

SEQ ID NO: 4 is peptide p37297 IGWKNFTAYR

SEQ ID NO: 5 is peptide p37299 IGWKDFAAYR

SEQ ID NO: 6 is peptide IGWKDETAYRWRLS

SEQ ID NO: 7 is peptide C6b HIGWKDFTAYRWRLS

SEQ ID NO: 8 is peptide p246 KRFKQDGGWSHWSPWSS

SEQ ID NO: 9 is peptide p245, VTCGGGVQKRSRL

SEQ ID NO: 10 is peptide p7N3 FIRVVMYEGKK

SEQ ID NO: 11 is peptide p604 FIRGGMYEGKK

SEQ ID NO: 12 is peptide p605 FIRVAIYEGKK

SEQ ID NO: 13 is peptide 4N1K KRFYVVMWKK

SEQ ID NO: 14 is peptide 4N1-1 RFYVVMWK

SEQ ID NO: 15 is peptide p761 RFYGGMWK

SEQ ID NO: 16 is peptide p37296 IGWKAFTAYR

SEQ ID NO: 17 is peptide RKRSRAE

SEQ ID NO: 18 is peptide p906 VTAGGGVQKRSRL

SEQ ID NO: 19 is peptide p907 GDGV(D-I)TRIR

SEQ ID NO: 20 is peptide p37298 IGWKDYTAYR

SEQ ID NO: 21 is morpholino

CGTCACAGGCAGGACCCACTGCCCA

SEQ ID NO: 22 is control morpholino

CGTgACAGcCAcGACCgACTGCgCA

SEQ ID NO: 23 is forward primer

CTGCTCCAGACACCTGAGG

SEQ ID NO: 24 is reverse primer

CGTCTTAGTACTCTCCAATC

SEQ ID NO: 25 is peptide C6e biotin-IGWKGFTAYR

SEQ ID NO: 26 is peptide C6s GAKDFTAYR

SEQ ID NO: 27 is peptide p37555 IGWKDFTAAR

SEQ ID NO: 28 is peptide p37554 IGWKDFTAYK

SEQ ID NO: 29 is peptide p37413 IGWADFTAYR

SEQ ID NO: 30 is peptide p37414 IGWHDFTAYR

SEQ ID NO: 31 is peptide p37415 IGWKEFTAYR

SEQ ID NO: 32 is peptide p37416 AGWKDFTAYR

SEQ ID NO: 33 is peptide p37417 IGYKDFTAYR

DETAILED DESCRIPTION

I. Abbreviations

3TSR type 1 repeats of TSP1
8-Br-cGMP 8-Bromo cyclic guanine monophosphate
ANOVA analysis of variance
BOLD MRI blood oxygen level dependent magnetic resonance imaging
cGMP cyclic guanine monophosphate
E3CaG1 C-terminal regions of TSP1
eNOS endothelial NO synthase
FTSG full thickness skin graft
HAVSMC human aortic vascular smooth muscle cells
HUVEC human vascular endothelial cells
I/R ischemia-reperfusion
L-NAME N-nitro-L-arginine methyl ester
NO nitric oxide
NoC1 N-terminal domains of TSP1
NOS nitric oxide synthase
PAD peripheral artery disease
PBS phosphate buffered saline
PVD peripheral vascular disease
SD standard deviation
sGC soluble guanylyl cyclase
TSP1 thrombospondin-1
VSMC vascular smooth muscle cells

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

Animal: Living multi-cellular vertebrate organisms, a category that includes, for example, mammals and birds. The term mammal includes both human and non-human mammals. Similarly, the term subject includes both human and veterinary subjects, for example, humans, non-human primates, dogs, cats, horses, and cows.

Angiogenesis: Biological process leading to the generation of new blood vessels through sprouting or growth from pre-existing blood vessels. The process involves the migration and proliferation of endothelial and vascular smooth muscle cells from preexisting vessels. Angiogenesis occurs during pre-natal development, post-natal development, and in the adult. In the adult, angiogenesis occurs during the normal cycle of the female reproductive system, wound healing, and during pathological processes such as cancer (for a review see Battegay, *J. Molec. Med.* 73(7): 333-346, 1995).

Administration: Administration of an active compound or composition can be by any route known to one of skill in the art. Administration can be local or systemic. Examples of local administration include, but are not limited to, topical administration, subcutaneous administration, intramuscular administration, intrathecal administration, intrapericardial administration, intra-ocular administration, topical ophthalmic administration, or administration to the nasal mucosa or lungs by inhalational administration. In addition, local administration includes routes of administration typically used for systemic administration, for example by directing intravascular administration to the arterial supply for a particular organ. Thus, in particular embodiments, local administration includes intra-arterial administration and intravenous administration when such administration is targeted to the vasculature supplying a particular organ. Local administration also includes the incorporation of active compounds and agents into implantable devices or constructs, such as vascular stents or other reservoirs, which release the active agents and compounds over extended time intervals for sustained treatment effects.

Systemic administration includes any route of administration designed to distribute an active compound or composition widely throughout the body via the circulatory system. Thus, systemic administration includes, but is not limited to intra-arterial and intravenous administration. Systemic administration also includes, but is not limited to, topical administration, subcutaneous administration, intramuscular administration, or administration by inhalation, when such administration is directed at absorption and distribution throughout the body by the circulatory system.

Altered expression: Expression of a biological molecule (for example, mRNA or protein) in a subject or biological sample from a subject that deviates from expression if the same biological molecule in a subject or biological sample from a subject having normal or unaltered characteristics for the biological condition associated with the molecule. Normal expression can be found in a control, a standard for a population, etc. Altered expression of a biological molecule may be associated with a disease. The term associated with includes an increased risk of developing the disease as well as the disease itself. Expression may be altered in such a manner as to be increased or decreased. The directed alteration in expression of mRNA or protein may be associated with therapeutic benefits.

Altered protein expression refers to expression of a protein that is in some manner different from expression of the protein in a normal (wild type) situation. This includes but is not necessarily limited to: (1) a mutation in the protein such that one or more of the amino acid residues is different; (2) a short deletion or addition of one or a few amino acid residues to the sequence of the protein; (3) a longer deletion or addition of amino acid residues, such that an entire protein domain or sub-domain is removed or added; (4) expression of an increased amount of the protein, compared to a control or standard amount; (5) expression of an decreased amount of the protein, compared to a control or standard amount; (6) alteration of the subcellular localization or targeting of the protein; (7) alteration of the temporally regulated expression of the protein (such that the protein is expressed when it normally would not be, or alternatively is not expressed when it normally would be); and (8) alteration of the localized (for example, organ or tissue specific) expression of the protein (such that the protein is not expressed where it would normally be expressed or is expressed where it normally would not be expressed), each compared to a control or standard.

Controls or standards appropriate for comparison to a sample, for the determination of altered expression, include samples believed to express normally as well as laboratory values, even though possibly arbitrarily set, keeping in mind that such values may vary from laboratory to laboratory. Laboratory standards and values may be set based on a known or determined population value and may be supplied in the format of a graph or table that permits easy comparison of measured, experimentally determined values.

Analog, derivative or mimetic: An analog is a molecule that differs in chemical structure from a parent compound, for example a homolog (differing by an increment in the chemical structure, such as a difference in the length of an alkyl chain), a molecular fragment, a structure that differs by one or more functional groups, a change in ionization. Structural analogs are often found using quantitative structure activity relationships (QSAR), with techniques such as those disclosed in Remington (*The Science and Practice of Pharmacology*, 19th Edition (1995), chapter 28). A derivative is a biologically active molecule derived from the base structure. A mimetic is a molecule that mimics the activity of another molecule, such as a biologically active molecule. Biologically active molecules can include chemical structures that mimic the biological activities of a compound. It is acknowledged that these terms may overlap in some circumstances.

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one light (about 25 kD) and one heavy chain (about 50-70 kD). The N-terminus of each chain defines a variable region of about 100 to 110 or more amino acids primarily responsible for antigen recognition. The terms variable light chain ($V_L$) and variable heavy chain ($V_H$) refer, respectively, to these light and heavy chains.

As used herein, the term antibody includes intact immunoglobulins as well as a number of well-characterized fragments produced by digestion with various peptidases, or genetically engineered artificial antibodies. Thus, for example, pepsin digests an antibody below the disulfide linkages in the hinge region to produce $F(ab)'_2$, a dimer of Fab which itself is a light chain joined to $V_H$-$C_H$1 by a disulfide bond. The $F(ab)'_2$ may be reduced under mild conditions to break the disulfide linkage in the hinge region thereby converting the $F(ab)'_2$ dimer into an Fab' monomer. The Fab' monomer is essentially a Fab with part of the hinge region (see, *Fundamental Immunology*, W. E. Paul, ed., Raven Press, N.Y., 1993). While various antibody fragments are defined in terms of the digestion of an intact antibody, it will be appreciated that Fab' fragments may be synthesized de novo either chemically or by utilizing recombinant DNA methodology. Thus, the term antibody as used herein also includes antibody fragments either produced by the modification of whole antibodies or synthesized de novo using recombinant DNA methodologies.

Antibodies for use in the methods, compositions, and systems of this disclosure can be monoclonal or polyclonal. Merely by way of example, monoclonal antibodies can be prepared from murine hybridomas according to the classical method of Kohler and Milstein (*Nature* 256:495-497, 1975) or derivative methods thereof. Detailed procedures for monoclonal antibody production are described in Harlow and Lane (*Antibodies, A Laboratory Manual*, CSHL, New York, 1988).

The terms bind specifically and specific binding refer to the ability of a specific binding agent (such as, an antibody) to bind to a target molecular species in preference to binding to other molecular species with which the specific binding agent and target molecular species are admixed. A specific binding agent is said specifically to recognize a target molecular species when it can bind specifically to that target.

A single-chain antibody (scFv) is a genetically engineered molecule containing the $V_H$ and $V_L$ domains of one or more antibody(ies) linked by a suitable polypeptide linker as a genetically fused single chain molecule (see, for example, Bird et al., *Science*, 242:423-426, 1988; Huston et al., *Proc. Natl. Acad. Sci.*, 85:5879-5883, 1988). Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., *Proc. Natl. Acad. Sci.*, 90:6444-6448, 1993; Poljak et al., *Structure*, 2:1121-1123, 1994). One or more CDRs may be incorporated into a molecule either covalently or noncovalently to make the resultant molecule an immunoadhesin. An immunoadhesin may incorporate the CDR(s) as part of a larger polypeptide chain, may covalently link the CDR(s) to another polypeptide chain, or may incorporate the CDR(s) noncovalently. The CDRs permit the immunoadhesin to specifically bind to a particular antigen of interest. A chimeric antibody is an antibody that contains one or more regions from one antibody and one or more regions from one or more other antibodies.

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

A neutralizing antibody or an inhibitory antibody is an antibody that inhibits at least one activity of a target—usually a polypeptide—such as by blocking the binding of the polypeptide to a ligand to which it normally binds, or by disrupting or otherwise interfering with a protein-protein interaction of the polypeptide with a second polypeptide. An activating antibody is an antibody that increases an activity of a polypeptide. Antibodies may function as mimics of a target protein activity, or as blockers of the target protein activity, with therapeutic effect derived therein.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens.

Antisense, Sense, and Antigene: Double-stranded DNA (dsDNA) has two strands, a 5'->3' strand, referred to as the plus strand, and a 3'->5' strand (the reverse compliment), referred to as the minus strand. Because RNA polymerase adds nucleic acids in a 5'->3' direction, the minus strand of the DNA serves as the template for the RNA during transcription. Thus, the RNA formed will have a sequence complementary to the minus strand and identical to the plus strand (except that U is substituted for T).

Antisense molecules are molecules that are specifically hybridizable or specifically complementary to either RNA or plus strand DNA. Sense molecules are molecules that are specifically hybridizable or specifically complementary to the minus strand of DNA. Antigene molecules are either antisense or sense molecules complimentary to a dsDNA target. In one embodiment, an antisense molecule specifically hybridizes to a target mRNA and inhibits transcription of the target mRNA.

Aptamer: A single-stranded nucleic acid molecule (such as DNA or RNA) that assumes a specific, sequence-dependent shape and binds to a target protein with high affinity and specificity. Aptamers generally comprise fewer than 100 nucleotides, fewer than 75 nucleotides, or fewer than 50 nucleotides. Mirror-image aptamer(s) (also called Spiegelmers™) are high-affinity L-enantiomeric nucleic acids (for example, L-ribose or L-2'-deoxyribose units) that display high resistance to enzymatic degradation compared with D-oligonucleotides (such as aptamers). The target binding properties of mirror-image aptamers are designed by an in vitro-selection process starting from a random pool of oligonucleotides, as described for example, in Wlotzka et al., *Proc. Natl. Acad. Sci.* 99(13):8898-8902, 2002. Applying this method, high affinity mirror-image aptamers specific for a polypeptide can be generated.

Arthritis: Arthritis is an inflammatory disease that affects the synovial membranes of one or more joints in the body. It is the most common type of joint disease, and it is characterized by the inflammation of the joint. The disease is usually oligoarticular (affects few joints), but may be generalized. The joints commonly involved include the hips, knees, lower lumbar and cervical vertebrae, proximal and distal interphangeal joints of the fingers, first carpometacarpal joints, and first tarsometatarsal joints of the feet.

Atherosclerosis: The progressive narrowing and hardening of a blood vessel over time. Atherosclerosis is a common form of arteriosclerosis in which deposits of yellowish plaques (atheromas) containing cholesterol, lipoid material and lipophages are formed within the intima and inner media of large and medium-sized arteries. Treatment of atherosclerosis includes reversing or slowing the progression of atherosclerosis, for example as measured by the presence of atherosclerotic lesions and/or functional signs of the disease, such as improvement in cardiovascular function as measured by signs (such as peripheral capillary refill), symptoms (such as chest pain and intermittent claudication), or laboratory evidence (such as that obtained by EKG, angiography, or other imaging techniques).

Binding affinity: A term that refers to the strength of binding of one molecule to another at a site on the molecule. If a particular molecule will bind to or specifically associate with another particular molecule, these two molecules are said to exhibit binding affinity for each other. Binding affinity is related to the association constant and dissociation constant for a pair of molecules, but it is not critical to the methods herein that these constants be measured or determined. Rather, affinities as used herein to describe interactions between molecules of the described methods are generally apparent affinities (unless otherwise specified) observed in empirical studies, which can be used to compare the relative strength with which one molecule (e.g., an antibody or other specific binding partner) will bind two other molecules (e.g., two versions or variants of a peptide). The concepts of binding affinity, association constant, and dissociation constant are well known.

Binding domain: The molecular structure associated with that portion of a receptor that binds ligand. More particularly, the binding domain may refer to a polypeptide, natural or synthetic, or nucleic acid encoding such a polypeptide, the amino acid sequence of which represents a specific region (binding domain) of a protein, which either alone or in combination with other domains, exhibits binding characteristics. Neither the specific sequences nor the specific boundaries of such domains are critical, so long as binding activity is exhibited. Likewise, used in this context, binding characteristics necessarily includes a range of affinities, avidities and specificities, and combinations thereof, so long as binding activity is exhibited.

Binding partner: Any molecule or composition capable of recognizing and binding to a specific structural aspect of another molecule or composition. Examples of such binding partners and corresponding molecule or composition include antigen/antibody, hapten/antibody, lectin/carbohydrate, apoprotein/cofactor and biotin/(strept)avidin.

cDNA (complementary DNA): A piece of DNA lacking internal, non-coding segments (introns) and transcriptional regulatory sequences. cDNA can also contain untranslated regions (UTRs) that are responsible for translational control in the corresponding RNA molecule. cDNA is synthesized in the laboratory by reverse transcription from messenger RNA extracted from cells.

Cerebral ischemia or ischemic stroke: A condition that occurs when an artery to the brain is partially or completely blocked such that the oxygen demand of the tissue exceeds the oxygen supplied. Deprived of oxygen and other nutrients following an ischemic stroke, the brain suffers damage and cell death as a result of the stroke.

Ischemic stroke can be caused by several different kinds of diseases. The most common problem is narrowing of the arteries in the neck or head. This is most often caused by atherosclerosis, or gradual cholesterol deposition. If the arteries become too narrow, blood cells may collect in them and form blood clots (thrombi). These blood clots can block the artery where they are formed (thrombosis), or can dislodge and become trapped in arteries closer to the brain (embolism). Also cerebral stroke can occur when atherosclerotic plaque separates away partially from the vessel wall and occludes the flow of blood through the blood vessel.

Another cause of stroke is blood clots in the heart, which can occur as a result of irregular heartbeat (for example, atrial fibrillation), heart attack, prior mural clot formation within a heart chamber and abnormalities of the heart valves such as occurs from rheumatic fever. While these are the most common causes of ischemic stroke, there are many other possible causes. Examples include use of street drugs, traumatic injury to the blood vessels of the neck, or disorders of blood clotting.

Ischemic stroke is by far the most common kind of stroke, accounting for about 80% of all strokes. Stroke can affect people of all ages, including children. Many people with ischemic strokes are older (60 or more years old, or 65 years or older), and the risk of stroke increases with older ages. At each age, stroke is more common in men than women, and it is more common among African-Americans than white Americans. Many people with stroke have other problems or conditions which put them at higher risk for stroke, such as high blood pressure (hypertension), heart disease, smoking, or diabetes. Subjects with cerebral ischemia can benefit from angiogenic therapy and therapies which prevents or reduces atherosclerotic plaque in the major arteries of the body.

Coronary Artery Disease: In coronary artery disease, the coronary arteries become narrowed (stenosed) or blocked (occluded) by a gradual build-up of fat (cholesterol) within or on the artery wall, which reduces blood flow to the heart muscle. This build-up is called atherosclerotic plaque or simply plaque.

If plaque narrows the lumen or channel of the artery, it may make it difficult for adequate quantities of blood to flow to the heart muscle. If the build-up reduces flow only mildly, there may be no noticeable symptoms at rest, but symptoms such as chest pressure may occur with increased activity or stress. Other symptoms include heartburn, nausea, vomiting, shortness of breath and heavy sweating.

When flow is significantly reduced and the heart muscle does not receive enough blood flow to meet its needs (cardiac ischemia), severe symptoms such as chest pain (angina pectoris), heart attack (myocardial infarction), or rhythm disturbances (arrhythmias) may occur. A heart attack usually is the result of a completely blocked artery, which may damage the heart muscle.

There are three conventional ways to treat atherosclerotic disease: medication, surgery, and minimally invasive interventional procedures such as stent implantation, percutaneous transluminal coronary angioplasty (PTCA), intravascular radiotherapy, atherectomy and excimer laser. The purpose of these treatments is to eliminate or reduce atherosclerotic narrowing of the coronary blood vessels and hence eliminate or reduce symptoms, and in the case of coronary artery disease, decrease the risk of heart attack.

DNA (deoxyribonucleic acid): A long chain polymer that comprises the genetic material of most living organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes a specific protein, or a fragment thereof, encompasses both the sense strand and its reverse complement. Thus, for instance, it is appropriate to generate probes or primers from the reverse complement sequence of the disclosed nucleic acid molecules.

Deletion: The removal of a sequence of DNA (which may be as short as a single nucleotide), the regions on either side being joined together.

Effective amount of a compound: A quantity of compound sufficient to achieve a desired effect in a subject being treated. An effective amount of a compound can be administered in a single dose, or in several doses, for example daily, during a course of treatment. However, the effective amount of the compound will be dependent on the compound applied, the subject being treated, the severity and type of the affliction, and the manner of administration of the compound.

Elderly: An aged subject, who has passed middle age. In one embodiment, an elderly mammalian subject is a subject that has survived more than two-thirds of the normal lifespan for that mammalian species. In a further embodiment, for humans, an aged or elderly subject is more than 65 years of age, such as a subject of more than 70, more than 75, more than 80 years of age. In yet another embodiment, for mice, an elderly mouse is from about 14 to about 18 months of age.

Encode: A polynucleotide is said to encode a polypeptide if, in its native state or when manipulated by methods well known to those skilled in the art, it can be transcribed and/or translated to produce the mRNA for and/or the polypeptide or a fragment thereof.

Epitope: An antigenic determinant. These are particular chemical groups or peptide sequences on a molecule that are antigenic, for instance, that elicit a specific immune response. An antibody binds a particular antigenic epitope, based on a 3-D structure of the antibody and the matching or cognate epitope. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or 8 to 10 amino acids in a unique spatial conformation. Methods of determining spatial conformation of epitopes include, for example, x-ray crystallography and 2-dimensional nuclear magnetic resonance. See, e.g., "Epitope Mapping Protocols" in *Methods in Molecular Biology*, Vol. 66, Glenn E. Morris, Ed (1996). In one embodiment, an epitope binds an MHC molecule, such an HLA molecule or a DR molecule. These molecules bind polypeptides having the correct anchor amino acids separated by about eight to about ten amino acids, such as nine amino acids.

Functionally equivalent sequence variant: Sequence alterations that yield the same results as described herein. Such sequence alterations can include, but are not limited to, deletions, base modifications, mutations, labeling, and insertions.

Fusion protein: A protein comprising two amino acid sequences that are not found joined together in nature.

Gene expression: The process by which the coded information of a nucleic acid transcriptional unit (including, for example, genomic DNA or cDNA) is converted into an operational, non-operational, or structural part of a cell, often including the synthesis of a protein. Gene expression can be influenced by external signals; for instance, exposure of a subject to an agent that inhibits gene expression. Expression of a gene also may be regulated anywhere in the pathway from DNA to RNA to protein. Regulation of gene expression occurs, for instance, through controls acting on transcription, translation, RNA transport and processing, degradation of intermediary molecules such as mRNA, or through activation, inactivation, compartmentalization or degradation of specific protein molecules after they have been made, or by combinations thereof. Gene expression may be measured at the RNA level or the protein level and by any method known in the art, including Northern blot, RT-PCR, Western blot, or in vitro, in situ, or in vivo protein activity assay(s).

The expression of a nucleic acid may be modulated compared to a control state, such as at a control time (for example, prior to administration of a substance or agent that affects regulation of the nucleic acid under observation) or in a control cell or subject, or as compared to another nucleic acid. Such modulation includes but is not necessarily limited to overexpression, underexpression, or suppression of expression. In addition, it is understood that modulation of nucleic acid expression may be associated with, and in fact may result in, a modulation in the expression of an encoded protein or even a protein that is not encoded by that nucleic acid.

Interfering with or inhibiting gene expression refers to the ability of an agent to measurably reduce the expression of a target gene. Expression of a target gene may be measured by any method known to those of skill in the art, including for example measuring mRNA or protein levels. It is understood that interfering with or inhibiting gene expression is relative, and does not require absolute suppression of the gene. Thus, in certain embodiments, interfering with or inhibiting gene expression of a target gene requires that, following application of an agent, the gene is expressed at least 5% less than prior to application, at least 10% less, at least 15% less, at least 20% less, at least 25% less, or even more reduced. Thus, in some particular embodiments, application of an agent reduces expression of the target gene by about 30%, about 40%, about 50%, about 60%, or more. In specific examples, where the agent is particularly effective, expression is reduced by 70%, 80%, 85%, 90%, 95%, or even more. Gene expression is substantially eliminated when expression of the gene is reduced by 90%, 95%, 98%, 99% or even 100%.

Graft: Material, especially living tissue or an organ, surgically attached to or inserted into a bodily part to replace a damaged part or compensate for a defect. Particular examples of grafts include organ grafts and skin grafts. Grafts can also include composite units of tissue composed of more than one tissue type, and may or may not be possessed of a dominant vascular supply. Such grafts may be applied to wounds and receive blood flow through angiogenesis or through immediate re-vascularization by microsurgical techniques. Grafts also may comprise a combination of living and a-cellular nonliving substrates that support a living cellular component, and may be artificially engineered in vitro for eventual in vivo implantation. Grafts may also be engineered to be capable of release of therapeutically active agents and compounds. For instance, grafts can include non-living tissue which may contain drugs and/or reagents for sustained release locally and/or systemically.

Heterologous: A type of sequence that is not normally (for example, in the wild-type sequence) found adjacent to a second sequence. In one embodiment, the sequence is from a different genetic source, such as a virus or other organism, than the second sequence.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as base pairing. More specifically, A will hydrogen bond to T or U, and G will bond to C. Complementary refers to the base pairing that occurs between to distinct nucleic acid sequences or two distinct regions of the same nucleic acid sequence.

Hypoxia: Deficiency in the amount of oxygen reaching body tissues. Hypoxia may occur concurrently with ischemia (lack of blood flow) due to loss of circulation to a specific tissue, organ or complete circulatory collapse; or without ischemia, as when secondary to a problem in ventilation alone.

Inflammation: A localized protective response elicited by injury to tissue that serves to sequester the inflammatory agent. Inflammation is characterized by the appearance in or migration into any tissue space, unit or region of any class of leukocyte in numbers that exceed the number of such cells found within such region of tissue under normal (healthy) circumstances. Inflammation is orchestrated by a complex biological response of vascular tissues to harmful stimuli, such as pathogens, damaged cells, or irritants. It is a protective attempt by the organism to remove the injurious stimuli as well as initiate the healing process for the tissue. An inflammatory response is an accumulation of white blood cells, either systemically or locally at the site of inflammation. The inflammatory response may be measured by many methods well known in the art, such as the number of white blood cells, the number of polymorphonuclear neutrophils (PMN), a measure of the degree of PMN activation, such as luminal enhanced-chemiluminescence, or a measure of the amount of cytokines present. Inflammation can lead to a host of inflammatory diseases, such as atherosclerosis, periodontitis and rheumatoid arthritis. Inflammation can be classified as either acute or chronic. Acute inflammation is the initial response of the body to harmful stimuli and is achieved by the increased movement of plasma and leukocytes from the blood into the injured tissues. A cascade of biochemical events propagates and matures the inflammatory response, involving the local vascular system, the immune system, and various cells within the injured tissue. Prolonged inflammation, known as chronic inflammation, leads to a progressive shift in the type of cells which are present at the site of inflammation and is characterized by simultaneous destruction and healing of the tissue from the inflammatory process.

Inhibiting protein activity: To decrease, limit, or block an action, function or expression of a protein. The phrase inhibit protein activity is not intended to be an absolute term. Instead, the phrase is intended to convey a wide-range of inhibitory effects that various agents may have on the normal (for example, uninhibited or control) protein activity. Inhibition of protein activity may, but need not, result in an increase in the level or activity of an indicator of the protein's activity. By way of example, this can happen when the protein of interest is acting as an inhibitor or suppressor of a downstream indicator. Thus, protein activity may be inhibited when the level or activity of any direct or indirect indicator of the protein's activity is changed (for example, increased or decreased) by at least 10%, at least 20%, at least 30%, at least 50%, at least 80%, at least 100% or at least 250% or more as compared to control measurements of the same indicator.

Inhibition of protein activity may also be effected, for example, by inhibiting expression of the gene encoding the protein or by decreasing the half-life of the mRNA encoding the protein.

Injectable composition: A pharmaceutically acceptable fluid composition comprising at least one active ingredient, for example, a protein, peptide, or antibody. The active ingredient is usually dissolved or suspended in a physiologically acceptable carrier, and the composition can additionally comprise minor amounts of one or more non-toxic auxiliary substances, such as emulsifying agents, preservatives, pH buffering agents and the like. Such injectable compositions that are useful for use with the compositions of this disclosure are conventional; appropriate formulations are well known in the art.

Ischemia: A vascular phenomenon in which a decrease in the blood supply to a bodily organ, tissue, or part is caused, for instance, by constriction or obstruction of one or more blood vessels. Ischemia sometimes results from vasoconstriction or thrombosis or embolism. Ischemia can lead to direct ischemic injury, tissue damage due to cell death caused by reduced oxygen supply. Ischemia can occur acutely, as during surgery, or from trauma to tissue incurred in accidents, injuries and war settings, for instance. It can also occur sub-acutely, as found in atherosclerotic peripheral vascular disease, where progressive narrowing of blood vessels leads to inadequate blood flow to tissues and organs.

Ischemia/reperfusion injury: In addition to the immediate injury that occurs during deprivation of blood flow, ischemic/reperfusion injury involves tissue injury that occurs after blood flow is restored. Current understanding is that much of this injury is caused by chemical products and free radicals released into the ischemic tissues.

When a tissue is subjected to ischemia, a sequence of chemical events is initiated that may ultimately lead to cellular dysfunction and necrosis. If ischemia is ended by the restoration of blood flow, a second series of injurious events ensue, producing additional injury. Thus, whenever there is a transient decrease or interruption of blood flow in a subject, the resultant injury involves two components—the direct injury occurring during the ischemic interval and the indirect or reperfusion injury that follows. When there is a long duration of ischemia, the direct ischemic damage, resulting from hypoxia, is predominant. For relatively short duration ischemia, the indirect or reperfusion mediated damage becomes increasingly important. In some instances, the injury produced by reperfusion can be more severe than the injury induced by ischemia per se. This pattern of relative contribution of injury from direct and indirect mechanisms has been shown to occur in all organs.

Isolated: An isolated biological component (such as a nucleic acid, peptide or protein) has been substantially separated, produced apart from, or purified away from other biological components in the cell of the organism in which the component naturally occurs, for instance, other chromosomal and extrachromosomal DNA and RNA, and proteins. Nucleic acids, peptides and proteins that have been isolated thus include nucleic acids and proteins purified by standard purification methods. The term also embraces nucleic acids, peptides and proteins prepared by recombinant expression in a host cell as well as chemically synthesized nucleic acids. The terms isolated and purified do not require absolute purity; rather, it is intended as a relative term. Thus, for example, an isolated peptide preparation is one in which the peptide or protein is more enriched than the peptide or protein is in its natural environment within a cell. Preferably, a preparation is purified such that the protein or peptide represents at least 50% of the total peptide or protein content of the preparation.

Label: A detectable compound or composition that is conjugated directly or indirectly to another molecule to facilitate detection of that molecule. Specific, non-limiting examples of labels include fluorescent tags, enzymatic linkages, and radioactive isotopes.

Mammal: This term includes both human and non-human mammals. Similarly, the term subject includes both human and veterinary subjects, for example, humans, non-human primates, mice, rats, dogs, cats, horses, and cows.

Modulator: An agent that increases or decreases (modulates) the activity of a protein or other bio-active compound, as measured by the change in an experimental biological parameter. A modulator can be essentially any compound or mixture (for example, two or more proteins), such as a NO donor, a polypeptide, a hormone, a nucleic acid, a sugar, a lipid and the like.

Morpholino: A morpholino oligo is structurally different from natural nucleic acids, with morpholino rings replacing the ribose or deoxyribose sugar moieties and non-ionic phosphorodiamidate linkages replacing the anionic phosphates of DNA and RNA. Each morpholino ring suitably positions one of the standard bases (A, G, C, T/U), so that a 25-base morpholino oligo strongly and specifically binds to its complementary 25-base target site in a strand of RNA via Watson-Crick pairing. Because the backbone of the morpholino oligo is not recognized by cellular enzymes of signaling proteins, it is stable to nucleases and does not trigger an innate immune response through the toll-like receptors. This avoids loss of oligo, inflammation or interferon induction. Morpholinos can be delivered by a number of techniques, including direct injection to tissues or via infusion pump and intravenous bolus.

Mutation: Any change of DNA sequence, for instance within a gene or chromosome. In some instances, a mutation will alter a characteristic or trait (phenotype), but this is not always the case. Types of mutations include base substitution point mutations (for example, transitions or transversions), deletions, and insertions. Missense mutations are those that introduce a different amino acid into the sequence of the encoded protein; nonsense mutations are those that introduce a new stop codon. In the case of insertions or deletions, mutations can be in-frame (not changing the frame of the overall sequence) or frame shift mutations, which may result in the misreading of a large number of codons (and often leads to abnormal termination of the encoded product due to the presence of a stop codon in the alternative frame).

This term specifically encompasses variations that arise through somatic mutation, for instance those that are found only in disease cells, but not constitutionally, in a given individual. Examples of such somatically-acquired variations include the point mutations that frequently result in altered function of various genes that are involved in development of cancers. This term also encompasses DNA alterations that are present constitutionally, that alter the function of the encoded protein in a readily demonstrable manner, and that can be inherited by the children of an affected individual. In this respect, the term overlaps with polymorphism, as defined below, but generally refers to the subset of constitutional alterations that have arisen within the past few generations in kindred and that are not widely disseminated in a population group. In particular embodiments, the term is directed to those constitutional alterations that have major impact on the health of affected individuals.

Neurodegenerative disorder: An abnormality in the nervous system of a subject, such as a mammal, in which neuronal integrity is threatened. Without being bound by theory, neuronal integrity can be threatened when neuronal cells display decreased survival or when the neurons can no longer propagate a signal. Specific, non-limiting examples of a neurodegenerative disorder are Alzheimer's disease, Pantothenate kinase associated neurodegeneration, Parkinson's disease, Huntington's disease (Dexter et al., *Brain* 114:1953-1975, 1991), HIV encephalopathy (Miszkziel et al., *Magnetic Res. Imag.* 15:1113-1119, 1997), and amyotrophic lateral sclerosis.

Alzheimer's disease manifests itself as pre-senile dementia. The disease is characterized by confusion, memory failure, disorientation, restlessness, speech disturbances, and hallucination in mammals (*Medical, Nursing, and Allied Health Dictionary*, 4th Ed., 1994, Editors: Anderson, Anderson, Glanze, St. Louis, Mosby).

Parkinson's disease is a slowly progressive, degenerative, neurologic disorder characterized by resting tremor, loss of postural reflexes, and muscle rigidity and weakness (*Medical, Nursing, and Allied Health Dictionary*, 4th Ed., 1994, Editors: Anderson, Anderson, Glanze, St. Louis, Mosby).

Nitric Oxide synthase: An enzyme that catalyzes conversion of 1-arginine, NADPH and oxygen to citrulline, nitric oxide and NADP+. Nitric oxide synthase catalyzes nitric oxide synthesis in the inner lining cells of blood vessels, as well as in macrophages and nerve cells. The generic nomenclature includes all three known isoforms of NOS designated in the literature as eNOS, iNOS and nNOS and alternatively as NOS-I, NOS-II and NOS-III.

Nucleic acid molecule: A polymeric form of nucleotides, which may include both sense and anti-sense strands of RNA, cDNA, genomic DNA, and synthetic forms and mixed polymers thereof. A nucleotide refers to a ribonucleotide, deoxynucleotide or a modified form of either type of nucleotide. A nucleic acid molecule as used herein is synonymous with nucleic acid and polynucleotide. A nucleic acid molecule is usually at least 10 bases in length, unless otherwise specified. The term includes single- and double-stranded forms. A polynucleotide may include either or both naturally occurring and modified nucleotides linked together by naturally occurring and/or non-naturally occurring nucleotide linkages.

Nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications, such as uncharged linkages (for example, methyl phosphonates, phosphotriesters, phosphoramidates, carbamates, etc.), charged linkages (for example, phosphorothioates, phosphorodithioates, etc.), pendent moieties (for example, polypeptides), intercalators (for example, acridine, psoralen, etc.), chelators, alkylators, and modified linkages (for example, alpha anomeric nucleic acids, etc.). The term nucleic acid molecule also includes any topological conformation, including single-stranded, double-stranded, partially duplexed, triplexed, hairpinned, circular and padlocked conformations. Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

Unless specified otherwise, the left hand end of a polynucleotide sequence written in the sense orientation is the 5' end and the right hand end of the sequence is the 3' end. In addition, the left hand direction of a polynucleotide sequence written in the sense orientation is referred to as the 5' direction, while the right hand direction of the polynucleotide sequence is referred to as the 3' direction. Further, unless otherwise indicated, each nucleotide sequence is set forth herein as a sequence of deoxyribonucleotides. It is intended, however, that the given sequence be interpreted as would be appropriate to the polynucleotide composition: for example, if the isolated nucleic acid is composed of RNA, the given sequence intends ribonucleotides, with uridine substituted for thymidine.

An anti-sense nucleic acid is a nucleic acid (such as, an RNA or DNA oligonucleotide) that has a sequence complementary to a second nucleic acid molecule (for example, an mRNA molecule). An anti-sense nucleic acid will specifically bind with high affinity to the second nucleic acid sequence. If the second nucleic acid sequence is an mRNA molecule, for example, the specific binding of an anti-sense nucleic acid to the mRNA molecule can prevent or reduce translation of the mRNA into the encoded protein or decrease the half life of the mRNA, and thereby inhibit the expression of the encoded protein.

Oligonucleotide: A plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules and morpholinos.

Particular oligonucleotides and oligonucleotide analogs can include linear sequences up to about 200 nucleotides in length, for example a sequence (such as DNA or RNA) that is at least 6 bases, for example at least 8, 10, 15, 20, 25, 30, 35, 40, 45, 50, 100 or even 200 bases long, or from about 6 to about 50 bases, for example about 10-25 bases, such as 12, 15 or 20 bases.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Open reading frame: A series of nucleotide triplets (codons) coding for amino acids without any internal termination codons. These sequences are usually translatable into a peptide.

Ortholog: Two nucleic acid or amino acid sequences are orthologs of each other if they share a common ancestral sequence and diverged when a species carrying that ancestral sequence split into two species. Orthologous sequences are also homologous sequences.

Parenteral: Administered outside of the intestine, for example, not via the alimentary tract. Generally, parenteral formulations are those that will be administered through any possible mode except ingestion. This term especially refers to injections, whether administered intravenously, intrathecally, intramuscularly, intraperitoneally, or subcutaneously, and various surface applications including intranasal, intradermal, and topical application, for instance.

Periodontal disease: An inflammatory disease affecting the tissues that surround and support the teeth. Periodontitis is an inflammation of the periodontium, or one of the four tissues that support the teeth in the mouth, such as the gingival (gum tissue), cementum (outer layer of the roots of teeth), alveolar bone (bone sockets into which the teeth are anchored), and the periodontal ligaments (connective tissue fibres that connect the cementum and the gingiva to the alveolar bone). Periodontitis involves progressive loss of bone around teeth which may lead to loosening and eventual loss of teeth.

Peripheral Vascular Disease (PVD): A condition in which the arteries and/or veins that carry blood to and from the arms, legs, soft tissues and vital organs of the body, including the heart and brain, become narrowed or occluded. This interferes with the normal flow of blood, sometimes causing pain but often causing no readily detectable symptoms. With progression of PVD, significant loss of blood flow to tissue and organs can lead to tissue death, necrosis and organ death.

The most common cause of PVD is atherosclerosis, a gradual process in which cholesterol and scar tissue build up, forming plaques that occlude the blood vessels. In some cases, PVD may be caused by blood clots that lodge in the arteries and restrict blood flow.

PVD affects about one in 20 people over the age of 50, or 8 million people in the United States. More than half the people with PVD experience leg pain, numbness or other symptoms, but many people dismiss these signs as a normal part of aging and do not seek medical help.

The most common symptom of PVD is painful cramping in the leg or hip, particularly when walking. This symptom, also known as claudication, occurs when there is not enough blood flowing to the leg muscles during exercise, such that ischemia occurs. The pain typically goes away when the muscles are rested.

Other symptoms may include numbness, tingling or weakness in the leg. In severe cases, people with PVD may experience a burning or aching pain in an extremity such as the foot or toes while resting, or may develop a sore on the leg or foot that does not heal. People with PVD also may experience a cooling or color change in the skin of the legs or feet, or loss of hair on the legs. In extreme cases, untreated PVD can lead to gangrene, a serious condition that may require amputation of a leg, foot or toes. People with PVD are also at higher risk for heart disease and stroke.

Typically most symptomatic PVD is ascribed to peripheral artery disease (PAD) denoting the above described pathology predominantly in arteries. The term PVD includes this symptomology and pathology in all classes of blood vessels.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of the compounds herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent: A chemical compound or composition capable of inducing a desired therapeutic or prophylactic effect when properly administered to a subject or a cell. Incubating includes exposing a target to an agent for a sufficient period of time for the agent to interact with a cell. Contacting includes incubating an agent in solid or in liquid form with a cell.

Polypeptide: A polymer in which the monomers are amino acid residues that are joined together through amide bonds. When the amino acids are alpha-amino acids, either the L-optical isomer or the D-optical isomer can be used, the L-isomers being preferred. The term polypeptide or protein as used herein encompasses any amino acid sequence and includes modified sequences such as glycoproteins. The term polypeptide is specifically intended to cover naturally occurring proteins, as well as those that are recombinantly or synthetically produced.

The term polypeptide fragment refers to a portion of a polypeptide that exhibits at least one useful epitope. The phrase "functional fragment(s) of a polypeptide" refers to all fragments of a polypeptide that retain an activity, or a measurable portion of an activity, of the polypeptide from which the fragment is derived. Fragments, for example, can vary in size from a polypeptide fragment as small as an epitope capable of binding an antibody molecule to a large polypeptide capable of participating in the characteristic induction or programming of phenotypic changes within a cell. An epitope is a region of a polypeptide capable of binding an immunoglobulin generated in response to contact with an antigen. Thus, smaller peptides containing the biological activity of insulin, or conservative variants of the insulin, are thus included as being of use.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

In some circumstances, variations in the cDNA sequence that result in amino acid changes, whether conservative or not, are minimized in order to preserve the functional and immunologic identity of the encoded protein. The immunologic identity of the protein may be assessed by determining whether it is recognized by an antibody; a variant that is recognized by such an antibody is immunologically conserved. Any cDNA sequence variant will preferably introduce no more than twenty, and preferably fewer than ten amino acid substitutions into the encoded polypeptide. Variant amino acid sequences may, for example, be 80%, 90%, or even 95% or 98% identical to the native amino acid sequence. Programs and algorithms for determining percentage identity can be found at the NCBI website.

Preventing or treating a disease: Preventing a disease refers to inhibiting the full development of a disease, for example inhibiting the development of myocardial infarction in a person who has coronary artery disease or inhibiting the progression or metastasis of a tumor in a subject with a neoplasm. Treatment refers to a therapeutic intervention that ameliorates a sign or symptom of a disease or pathological condition after it has begun to develop.

Purified: In a more pure form than is found in nature. The term purified does not require absolute purity; rather, it is intended as a relative term. Thus, for example, a purified protein preparation is one in which the protein referred to is more pure than the protein in its natural environment within a cell.

The term substantially purified as used herein refers to a molecule (for example, a nucleic acid, polypeptide, oligonucleotide, etc.) that is substantially free of other proteins, lipids, carbohydrates, or other materials with which it is naturally associated. In one embodiment, a substantially purified molecule is a polypeptide that is at least 50% free of other proteins, lipids, carbohydrates, or other materials with which it is naturally associated. In another embodiment, the polypeptide is at least at least 80% free of other proteins, lipids, carbohydrates, or other materials with which it is naturally associated. In yet other embodiments, the polypeptide is at least 90% or at least 95% free of other proteins, lipids, carbohydrates, or other materials with which it is naturally associated.

Recombinant: A nucleic acid that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques.

Reperfusion: Restoration of blood supply to tissue that is ischemic, due to decrease in blood supply. Reperfusion is a procedure for treating infarction or other ischemia, by enabling viable ischemic tissue to recover, thus limiting further necrosis. However, reperfusion can itself further damage the ischemic tissue, causing reperfusion injury.

Rheumatoid arthritis: A chronic, systemic, inflammatory disease that affects the synovial membranes of multiple joints in the body. Because the disease is systemic, there are many extra-articular features of the disease as well. For example, neuropathy, scleritis, lymphadenopathy, pericarditis, splenomegaly, arteritis, and rheumatoid nodules are frequent components of the disease. In most cases of rheumatoid arthritis, the subject has remissions and exacerbations of the symptoms. Rheumatoid arthritis is considered an autoimmune disease that is acquired and in which genetic factors appear to play a role.

Ribozyme: RNA molecules with enzyme-like properties, which can be designed to cleave specific RNA sequences. Ribozymes are also known as RNA enzymes or catalytic RNAs.

RNA interference (RNA silencing; RNAi): A gene-silencing mechanism whereby specific double-stranded RNA (dsRNA) trigger the degradation of homologous mRNA (also called target RNA). Double-stranded RNA is processed into small interfering RNAs (siRNA), which serve as a guide for cleavage of the homologous mRNA in the RNA-induced silencing complex (RISC). The remnants of the target RNA may then also act as siRNA; thus resulting in a cascade effect.

Senescence: The biological process(es) of aging and showing the effects of increased age. In one embodiment, a senescent cell does not divide and/or has a reduced capacity to divide.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith and Waterman (*Adv. Appl. Math.* 2: 482, 1981); Needleman and Wunsch (*J. Mol. Biol.* 48: 443, 1970); Pearson and Lipman (*PNAS. USA* 85: 2444, 1988); Higgins and Sharp (*Gene,* 73: 237-244, 1988); Higgins and Sharp (*CABIOS* 5: 151-153, 1989); Corpet et al. (*Nuc. Acids Res.* 16: 10881-10890, 1988); Huang et al. (*Comp. Appls Biosci.* 8: 155-165, 1992); and Pearson et al. (*Meth. Mol. Biol.* 24: 307-31, 1994). Altschul et al. (*Nature Genet.,* 6: 119-129, 1994) presents a detailed consideration of sequence alignment methods and homology calculations.

The alignment tools ALIGN (Myers and Miller, *CABIOS* 4:11-17, 1989) or LFASTA (Pearson and Lipman, 1988) may be used to perform sequence comparisons (Internet Program©1996, W. R. Pearson and the University of Virginia, fasta20u63 version 2.0u63, release date December 1996). ALIGN compares entire sequences against one another, while LFASTA compares regions of local similarity. These alignment tools and their respective tutorials are available on the Internet at the NCSA Website. Alternatively, for comparisons of amino acid sequences of greater than about 30 amino acids, the Blast 2 sequences function can be employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). The BLAST sequence comparison system is available, for instance, from the NCBI web site; see also Altschul et al., *J. Mol. Biol.* 215:403-410, 1990; Gish. & States, *Nature Genet.* 3:266-272, 1993; Madden et al. *Meth. Enzymol.* 266:131-141, 1996; Altschul et al., *Nucleic Acids Res.* 25:3389-3402, 1997; and Zhang & Madden, *Genome Res.* 7:649-656, 1997.

Orthologs of proteins are typically characterized by possession of greater than 75% sequence identity counted over the full-length alignment with the amino acid sequence of specific protein using ALIGN set to default parameters. Proteins with even greater similarity to a reference sequence will show increasing percentage identities when assessed by this method, such as at least 80%, at least 85%, at least 90%, at least 92%, at least 95%, or at least 98% sequence identity. In addition, sequence identity can be compared over the full length of particular domains of the disclosed peptides.

When significantly less than the entire sequence is being compared for sequence identity, homologous sequences will typically possess at least 80% sequence identity over short windows of 10-20 amino acids, and may possess sequence identities of at least 85%, at least 90%, at least 95%, or at least 99% depending on their similarity to the reference sequence. Sequence identity over such short windows can be determined using LFASTA; methods are described at the NCSA Website. One of skill in the art will appreciate that these sequence identity ranges are provided for guidance only; it is entirely possible that strongly significant homologs could be obtained that fall outside of the ranges provided.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found in Sambrook et al. (In *Molecular Cloning: A Laboratory Manual*, Cold Spring Harbor, N.Y., 1989) and Tijssen (*Laboratory Techniques in Biochemistry and Molecular Biology Part I, Ch.* 2, Elsevier, New York, 1993).

Hybridization conditions resulting in particular degrees of stringency will vary depending upon the nature of the hybridization method of choice and the composition and length of the hybridizing nucleic acid sequences. Generally, the temperature of hybridization and the ionic strength (especially the Na+ concentration) of the hybridization buffer will determine the stringency of hybridization, though waste times also influence stringency. Calculations regarding hybridization conditions required for attaining particular degrees of stringency are discussed by Sambrook et al. (ed.), *Molecular Cloning: A Laboratory Manual, 2nd ed., vol.* 1-3, Cold Spring Harbor Laboratory Press, Cold Spring Harbor, N.Y., 1989, chapters 9 and 11, herein incorporated by reference. The following is an exemplary set of hybridization conditions:

Very High Stringency (detects sequences that share 90% identity)
  Hybridization: 5×SSC at 65° C. for 16 hours
  Wash twice: 2×SSC at room temperature (RT) for 15 minutes each
  Wash twice: 0.5×SSC at 65° C. for 20 minutes each
High Stringency (detects sequences that share 80% identity or greater)
  Hybridization: 5×-6×SSC at 65° C.-70° C. for 16-20 hours
  Wash twice: 2×SSC at RT for 5-20 minutes each
  Wash twice: 1×SSC at 55° C.-70° C. for 30 minutes each
Low Stringency (detects sequences that share greater than 50% identity)
  Hybridization: 6×SSC at RT to 55° C. for 16-20 hours
  Wash at least twice: 2×-3×SSC at RT to 55° C. for 20-30 minutes each.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequences that each encode substantially the same protein.

Specifically hybridizable and specifically complementary are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

Small interfering RNAs: Synthetic or naturally-produced small double stranded RNAs (dsRNAs) that can induce gene-specific inhibition of expression in invertebrate and vertebrate species are provided. These RNAs are suitable for interference or inhibition of expression of a target gene and comprise double stranded RNAs of about 15 to about 40 nucleotides containing a 3' and/or 5' overhang on each strand having a length of 0- to about 5-nucleotides, wherein the sequence of the double stranded RNAs is essentially identical to a portion of a coding region of the target gene for which interference or inhibition of expression is desired. The double stranded RNAs can be formed from complementary ssRNAs or from a single stranded RNA that forms a hairpin or from expression from a DNA vector.

Small molecule inhibitor: A molecule, typically with a molecular weight less than 1000, or in some embodiments, less than about 500 Daltons, wherein the molecule is capable of inhibiting, to some measurable extent, an activity of some target molecule.

Subject: Living multi-cellular organisms, including vertebrate organisms, a category that includes both human and non-human mammals.

Target sequence: A target sequence is a portion of ssDNA, dsDNA, or RNA that, upon hybridization to a therapeutically effective oligonucleotide or oligonucleotide analog (e.g., a morpholino), results in the inhibition of expression of the target. Either an antisense or a sense molecule can be used to target a portion of dsDNA, as both will interfere with the expression of that portion of the dsDNA. The antisense molecule can bind to the plus strand, and the sense molecule can bind to the minus strand. Thus, target sequences can be ssDNA, dsDNA, and RNA.

Test compound: A compound used in a test or screen, and which can be essentially any compound, such as a small molecule, a chemotherapeutic, a polypeptide, a hormone, a nucleic acid, a modified nucleic acid, a sugar, a lipid and the like. Test compounds are used, for example, when screening for compounds that block the activity of TSP1 and/or CD47, or for compounds that affect TSP1 binding to CD47, and alternatively that mimic the activity of TSP1. Test compound may also function to suppress TSP1 and/or CD47 expression and/or production. They may also interfere in the action of nitric oxide (NO) on cells and tissues, both by blocking NO-driven stimulation of sGC and by blocking targets of NO downstream of sGC.

Therapeutic: A generic term that includes both diagnosis and treatment.

Therapeutically effective amount: A quantity of compound sufficient to achieve a desired effect in a subject being treated. An effective amount of a compound may be administered in a single dose, or in several doses, for example daily, during a course of treatment. However, the effective amount will be dependent on the compound applied, the subject being treated, the severity and type of the affliction, and the manner of administration of the compound. For example, a therapeutically effective amount of an active ingredient can be measured as the concentration (moles per liter or molar-M) of the active ingredient (such as a small molecule, peptide, protein, or antibody) in blood (in vivo) or a buffer (in vitro) that produces an effect.

Therapeutically effective dosages of morpholino are generally in the range of 1-10 µM concentrations. By way of example, as used herein total delivered morpholino to 1×2 cm flaps or hind limbs was approximately 1 to 10 µg of morpholino oligonucleotide. Antibodies to TSP1 or CD47 were therapeutically efficacious at 40 µg per flap diluted to a concentration of approximately 0.4 µg/µl. Exact dosage amounts will vary by the size of the subject being treated, the duration of the treatment, the mode of administration, and so forth.

Treating a disease: Includes inhibiting or preventing the partial or full development or progression of a disease, for example in a person who is known to have a predisposition to a disease. Furthermore, treating a disease refers to a therapeutic intervention that ameliorates at least one sign or symptom of a disease or pathological condition, or interferes with a pathophysiological process, after the disease or pathological condition has begun to develop.

Under conditions sufficient for: A phrase that is used to describe any environment that permits the desired activity. In one example, includes administering a therapeutically effective amount of a composition that includes a peptide, antibody, or oligonucleotide (e.g., morpholino), sufficient to enable the desired activity.

Vasculopathy: A disease of the blood vessels. An "age-related vasculopathy" is a disease of the blood vessels that is associated with advanced age. One specific, non-limiting vasculopathy is atherosclerosis. Other vasculopathies include, but are not limited to, diabetic associated vasculopathy, hypertension associated vasculopathy, Burger's disease associated vasculopathy and scleroderma associated vasculopathy. It is understood that "endothelial dysfunction" typically refers to an insufficiency in the production or response to nitric oxide.

Vasoconstriction. The diminution of the caliber or cross-sectional area of a blood vessel, for instance constriction of arterioles leading to decreased blood flow to a body part. This can be caused by a specific vasoconstrictor, an agent (for instance a chemical or biochemical compound) that causes, directly or indirectly, constriction of blood vessels. Such an agent can also be referred to as a vasohypertonic agent, and is said to have vasoconstrictive activity. A representative category of vasoconstrictors is the vasopressor (from the term pressor, tending to increase blood pressure), which term is generally used to refer to an agent that stimulates contraction of the muscular tissue of the capillaries and arteries.

Vasoconstriction also can be due to vasospasm, inadequate vasodilatation, thickening of the vessel wall, or the accumulation of flow-restricting materials on the internal wall surfaces or within the wall itself. Vasoconstriction is a major presumptive or proven factor in aging and in various clinical conditions including progressive generalized atherogenesis, myocardial infarction, stroke, hypertension, glaucoma, macular degeneration, migraine, hypertension and diabetes mellitus, among others.

Vasodilation. A state of increased caliber of the blood vessels, or the act of dilation of a blood vessel, for instance dilation of arterioles leading to increased blood flow to a body part. This can be caused by a specific vasodilator, an agent (for instance a chemical or biochemical compound) that causes, directly or indirectly, dilation of blood vessels. Such an agent can also be referred to as a vasohypotonic agent, and is said to have vasodilative activity.

Unless otherwise explained, all technical and scientific terms used herein have the same meaning as commonly understood by one of ordinary skill in the art to which this invention belongs.

The singular terms a, an, and the include plural referents unless context clearly indicates otherwise. Similarly, the word or is intended to include and unless the context clearly indicates otherwise. Hence comprising A or B means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Thrombospondin and CD47

Thrombospondin 1 (TSP1) is an extracellular protein that is involved in a myriad of cellular processes, including platelet aggregation, neurite outgrowth, and cellular proliferation. Among TSP1's best-characterized functions is inhibition of angiogenesis. Angiogenesis ameliorates the poor oxygenation of damaged tissue that is a limiting factor for patient recovery in a variety of clinical settings, including surgery, burn wound healing, organ transplantation and recovery, amputation, peripheral vascular disease and myocardial infarction. Because it is desirable to promote angiogenesis within these contexts, antagonizing TSP1's activity has been a valuable research objective. Additionally, tumors require vascularization for growth. Agents that mimic the ability of TSP1 to inhibit angiogenesis are therefore considered possible therapies for cancer. In vitro studies have shown the ability of this agent to block tumor driven angiogenesis. In vivo results in animals have also been encouraging and have led to clinical trials in people. See Rusk et al., *Clin Cancer Res* 12:7456-7464, 2006; Markovic et al., *Am J Clin Oncol* 30:303-309, 2007.

TSP1 contains three type 1 repeat structural domains and a carboxy-terminal domain that were identified as the loci of the full-length protein's anti-angiogenic functionality (Lawler, *Curr. Opin. Cell Biol.* 12(5): 634-640, 2000). Overexpression of TSP1 has been observed in ischemic tissue, and is proposed to regulate angiogenesis within ischemic tissue (Favier et al., *J. Pathol.* 207(3): 358-366, 2005), since TSP1 preferentially interferes with wound healing-associated angiogenesis (Streit et al., *EMBO J.* 19(13): 3272-3282, 2000) and limits revascularization in a model of hind limb ischemia similar to that employed by the current inventors (Kopp et al., *J. Clin. Invest.* 116(12): 3277-3291, 2006). Peptides derived from the type 1 repeats inhibit angiogenesis (Shafiee et al., *IOVS* 41(8): 2378-2388, 2000; Yee et al., *Am J. Pathol.* 165(2): 541-552, 2004; Tolsma et al., *J. Cell Biol.* 122: 497-511, 1993; Armstrong and Bornstein, *Mat. Biol.* 22(1): 63-71, 2003; Guo et al., *Cancer Res.* 58(14): 3154-3162, 1998). Additional TSP1 peptides (e.g., 4N1 and 7N3 classes) have previously been described; see, e.g., U.S. Pat. Nos. 5,399,667; 5,627,265; and 6,469,138.

TSP1 acts through several cellular receptors, including CD36 and integrin-associated protein (IAP)/CD47. It was originally thought that TSP1 exerted its anti-angiogenic effects by acting through CD36 (Quesada et al., *Cell Death and Diff.* 12: 649-658, 2005; Jiménez et al., *Nat. Med.* 6(1): 41-48, 2000; de Fraipon et al., *Trends Mol. Med.* 7(9): 401-407, 2001). Some evidence had indicated that CD36 was not solely responsible for the action of TSP1. For example, short peptides comprised of the TSP1 type 1 repeat can inhibit VEGF-induced migration of human endothelial cells that lack CD36 (Short et al., *J. Cell Biol.* 168(4): 643-653, 2005). A sequence in the carboxy-terminal domain of TSP1 was hypothesized to mediate at least part of the protein's anti-angiogenic effects through an interaction with CD47 (Bornstein, *J. Clin. Inv.* 107(8): 929-934, 2001). In contrast with the results from TSP1-derived peptides, the use of oligonucleotides to inhibit production of TSP1 suggested a contributory role of TSP1 in optimal wound healing (DiPietro et al., *Am J. Pathol.* 148(6): 1851-1860, 1996).

CD47 is an atypical member of the immunoglobulin and the G protein-coupled receptor superfamilies. It consists of an N-terminal extracellular IgV set domain, 5 transmembrane segments and an alternatively spliced cytoplasmic tail (Brown and Frazier, *Trends Cell Biol.* 11(3): 130-135, 2001). Although identified earlier as "integrin associated protein (IAP), CD47 was discovered to be a receptor for the C-terminal domain of TSP1 in 1996 (Gao et al., *J. Biol. Chem.* 271: 21-24, 1996). Two members of the signal inhibitory receptor protein family, SIRPα (also known as BIT, SHPS-1 and p84) and SIRPγ are cell-bound counter receptors for CD47 (van Beek et al., *J. Immunol.* 175:7781-87, 2005). CD47 is expressed on many or not all normal cells, and signals primarily through coupling to G proteins of the Gi heterotrimeric class (Frazier et al., *J. Biol. Chem.* 274:8554-8560, 1999).

It was recently discovered that TSP1 exerts anti-vasorelaxive effects on smooth muscle by antagonizing the ability of nitric oxide (NO) to stimulate cGMP synthesis (Isenberg et al., *Proc Natl Acad Sci USA*. 102(37): 13141-13146, 2005; E-pub Sep. 6, 2005). This pathway can proceed through either of two receptors, CD36 or CD47; but recent work demonstrated that only CD47 is necessary (Isenberg et al., *J Biol. Chem.* 281(36):26069-26080, 2006; E-pub Jul. 11, 2006).

The structure and function of CD47 has been explored using anti-CD47 antibodies and peptide ligands of the receptor. Anti-CD47 and TSP1-derived CD47 ligands initiate cell death in breast cancer cell lines (Manna and Frazier, *Cancer Res.* 64: 1026-1036, 2004) and Jurkat T cells (Manna and Frazier, *J Immunol.* 170(7): 3544-3553, 2003). These, and similar experiments, led to the hypothesis that CD47 is necessary for FAS-mediated apoptosis of Jurkat T cells (Manna et al., *J Biol. Chem.* 280(33): 29637-29644, 2005). Synthetic peptides derived from the full-length sequence of CD47 have been used to probe its structure (Rebres et al., *J. Biol. Chem.* 276(37): 34607-34616, 2001). Ligation of CD47 induces actin polymerization (Rebres et al., *J. Biol. Chem.* 276(10): 7672-7680, 2001); and its ligation by peptides derived from the carboxy-terminus of TSP1 stimulates the adhesion of melanoma cells to specific substrates (Barazi et al., *J. Biol. Chem.* 277(45): 42859-42866, 2002; Gao et al., *J. Cell Biol.* 135(2): 533-544, 1996).

Fundamental to all mammalian life is the ability to regulate blood flow. Acute and chronic responses to injury require precise control of blood flow. Lack of adequate regulation of blood flow is associated with significant morbidity and mortality. Blood flow can be regulated in the short term by alterations in vascular resistance which is determined by controlling the diameter of blood vessels. To increase flow, blood vessels dilate and increase in diameter. To decrease flow, the same vessels constrict and decrease their diameter. The control of vessel diameter is found within the vascular smooth muscle cells (VSMC) which make up the wall of all blood vessels other than capillaries. VSMC have the ability to lengthen (relax) or shorten (constrict) in response to various stimuli.

Over the long term blood flow can be regulated by increasing the total number of blood vessels in a particular tissue, a process called angiogenesis. One of the primary means by which blood vessel diameter is regulated is through the bioactive gas nitric oxide (NO). All vascular cells produce NO. Once formed NO signals the blood vessel to relax by uncoupling the contractile mechanism within vascular smooth muscle cells.

The inherent ability of NO to dilate and relax blood vessels is altered with age. A majority of elderly people (>65 years of age) show decreased ability to relax their blood vessels. Varying degrees of pathology in blood vessels at the histologic level and in response to stress can be found in a majority of older people in Western countries.

Described herein are means of maximizing the ability of NO to dilate blood vessels and increase blood flow in response to traumatic interruption of the same and, more importantly for elderly individuals, to increase blood flow in the face of peripheral vascular disease associated with aging. This allows for enhance blood flow around acute and chronic points of flow obstruction. Our identified therapeutics can be delivered precisely and will allow for the selective alteration in regional blood flow to vital organs as required and will avoid systemic side effects which have rendered other methods of limited use to date.

IV. Nitric Oxide, Ischemia, and Thrombospondin

Nitric oxide (NO) plays a central role in angiogenesis both through its direct activity on cells and tissue and through functioning as a mediator of signaling by vascular endothelial growth factor and other angiogenic factors. The pro-angiogenic activity of NO is mediated by activation of soluble guanylyl cyclase (sGC), leading to cGMP accumulation and activation of its target kinases and ion channels. New research has identified this pathway as the primary target of the endogenous angiogenesis inhibitor thrombospondin-1 (TSP1) and shown that circulating levels of thrombospondin-1 are sufficient to limit multiple activities of nitric oxide including NO-driven angiogenic responses and NO-stimulated effects on blood vessel diameter and blood flow. By blocking the ability of TSP1 to inhibit NO activity it is possible to selectively increase angiogenesis and/or blood flow and tissue/organ perfusion. This provides new insights into the significance of the widespread loss of thrombospondin-1 expression during malignant progression and the increased expression of TSP1 in peripheral vascular disease and atherosclerosis.

Mammalian cells express three isoforms of NOS that are regulated by different molecular mechanisms. These isoforms differ in their quantitative and temporal contributions to NO profiles associated with pro- or anti-angiogenic processes. Under physiological conditions, eNOS generates short bursts of NO (10-30 nM), causing relaxation of smooth muscle cells. Phosphorylation of eNOS at serine-1179 leads to sustained low fluxes of NO (estimated to be 1-10 nM) that stimulate pro-survival responses in endothelial cells and relaxation of VSMC.

TSP1 is a potent endogenous inhibitor of both physiologic and pathologic angiogenesis. TSP1 is a large trimeric glycoprotein that interacts with extracellular matrix components and with several cell surface receptors. Normally found at low concentrations in the circulation and soft tissues, TSP1 expression increases significantly following wounding, and its expression is altered in a number of pathologic diseases. In cancer, TSP1 expression generally decreases with malignant progression, resulting from regulation of its expression by a number of oncogene and tumor suppressor gene products, although stromal TSP1 expression in some cases masks this decrease. While some tumor cells produce large amounts of TSP1, these tumors accomplish angiogenesis by producing overwhelming levels of pro-angiogenic factors. Experimental tumors with decreased TSP1 expression show significantly increased growth and metastasis. In contrast TSP1 over-expressing tumors typically grow slower, exhibit less angiogenesis, and have fewer metastases. Recently, we reported that TSP1 blocks NO-driven pro-angiogenic responses in both endothelial and vascular smooth muscle cells by inhibiting NO-driven stimulation of sGC. Inhibition of NO signaling is mediated through TSP1 interactions with its receptors CD36 and CD47. More importantly, in the presence of physiologic levels of NO, vascular cells become hypersensitive to the inhibitory effects of TSP1. Under these conditions concentrations of TSP1 a thousand-fold less than normally effective completely block pro-angiogenic responses in vascular cells. These results suggest that low doses of NO donors could synergize with anti-angiogenic therapies utilizing TSP1 or drugs targeting its CD36 receptor.

The dramatic enhancement of the potency of TSP1 as an angiogenesis inhibitor in the presence of NO suggests that a major role of TSP1 is to antagonize the NO/cGMP pathway. Targeting downstream from eNOS may confer advantages for blocking angiogenesis in that endothelial cell signaling due to NO produced by other cells, such as iNOS from leukocytes, can also be blocked by TSP1. Furthermore, unlike Avastin and Lucentis, TSP1 can inhibit downstream signals resulting from angiogenic factors other than VEGF.

TSP1 is a major component of platelet α-granules and is released from platelets upon activation, where it modulates platelet adhesion and the properties of fibrin clots formed following acute vascular injury. TSP1 released from platelets or produced locally in response to cytokines and growth factors also plays an important role in recruitment of mononuclear cells during the early phases of wound repair, and the absence of TSP1 delays excisional wound repair in mice.

TSP1 also accumulates in the neointima of atherosclerotic lesions, where it may stimulate vascular smooth muscle cell proliferation and migration by enhancing responsiveness to platelet-derived growth factor. Antibody blocking of TSP1 can reverse this response and enhance the re-endothelialization of an injured artery. An N700S coding sequence polymorphism in TSP1 that alters its conformation is associated with increased risk of premature familial myocardial infarction.

TSP1 is also a potent modulator of angiogenesis. The N-terminal domain of TSP1 stimulates angiogenesis through its interactions with $\alpha_3\beta_1$ and $\alpha_4\beta_1$ integrins, but the central type 1 repeats contain sequences that potently inhibit angiogenesis via CD36 and/or heparin sulfate proteoglycan receptors. Under most circumstances, the net activity of intact TSP1 is anti-angiogenic. Thus, the absence of TSP1 enhances experimental and tumor-induced angiogenic responses.

Vascular effects of TSP1 are mediated by its binding to receptors on both endothelial and vascular smooth muscle cells (VSMC). Endothelial cells express at least eight TSP1 receptors, and several of these are shared on VSMC. Based on the activity of CD36 antibody FA6-152 to block the inhibitory effect of TSP1 on FGF2-induced microvascular endothelial cell motility and the failure of TSP1 to inhibit corneal angiogenesis induced by FGF2 in CD36−/− mice, CD36 is considered to be the primary TSP1 receptor that mediates this anti-angiogenic activity. Some evidence indicates that TSP1 also inhibits angiogenesis through $\beta_1$ integrins, CD47, LRP/calreticulin, and heparin sulfate proteoglycans, but the necessity of these receptors for TSP1 to inhibit angiogenesis has not been confirmed in the respective receptor null mice. To develop effective angiogenesis inhibitors based on TSP1, it is important to establish whether additional signaling pathways may allow TSP1 to inhibit angiogenesis in a CD36-independent manner.

Discoveries by the current inventors have also proven that the inhibitory activity of TSP1 on NO-driven angiogenesis and blood flow requires the cell surface receptor CD47. Targeting either TSP1 or CD47 allows for dramatic increases in tissue/organ blood flow and perfusion, and prevents tissue loss and necrosis from ischemia secondary (but not limited) to peripheral vascular disease, atherosclerosis, stroke, coronary artery disease, trauma, surgery and burn injury. Under conditions of both acute and chronic decrease in blood flow targeting TSP1-CD47 greatly increases blood flow through maximizing NO-stimulated vaso-relaxation. Even more stunning aged 18 month old TSP1-null mice demonstrate more dynamic blood flow increases to vasodilators than young 10 week old wild type mice. Then blocking TSP1 signaling renders the aged vasculature hyper-dynamic. Under a vasoactive challenge such a vasculature out performs the young vasculature. Therapeutic agents targeting TSP1-CD47 has the potential of ameliorating the deleterious effects of aging on blood flow. This will have profound impact since 85% of individuals over the age of 65 have varying degrees of peripheral vascular disease.

V. Overview of Several Embodiments

This disclosure demonstrates that CD47 ligation by TSP1 represents the means by which endogenous TSP1 tempers vascular responses to NO and in so doing alters tissue oxygen in the face of both ischemia and NO challenge. Findings reported herein suggest that TSP1 is a global regulator of tissue perfusion and blood flow through a CD47-dependent pathway, and suggests therapeutic modalities for tissue preservation in the presence of ischemia. These therapeutic modalities are described herein.

Provided herein are methods and compositions useful in exploiting the discoveries that TSP1 and CD47 influence and control tissue survival in response to ischemia. Included are the use of therapeutic compounds and compositions that block TSP1 action via CD47 either exclusively or in combination with other identified or yet to be identified receptors for TSP1 that may augment and/or focus the effect of TSP1 in certain tissues or to certain purposes. Such compounds and compositions thereby increase tissue survival to ischemia, as well as use of therapeutic compounds and compositions that block CD47 and thereby increase tissue survival to ischemia. Also included are compositions (including for instance nucleic acid and protein/peptide compositions) useful in such methods. Specific examples of compounds useful as therapeutics include anti-CD47 antibodies (or binding fragments thereof), including but not limited to the following: Ab miap301 (Chang et al., *Neuroscience* 102(2):289-296, 2001; commercially available for instance from RDI Division of Fitzgerald Industries Intl., as catalog number RDI-MCD47-301); Ab B6H12, Ab 2D3, Ab 1F7, Ab 3G3, Ab 2E11, or Ab 2B7 (described in Gresham et al., *J. Cell Biol.* 108:1935-1943, 1989, and Brown et al., *J. Cell Biol.* 111:2785-2794, 1990, for instance), Ab 3E9 (Weerasighe et al., *J. Cell Biol.*, 142(2):595-607, 1998), Ab 10G2 (Hermann et al., *J. Cell Biol.*, 144(4): 767-775, 1999), Ab C1KM1 (Barazi et al., *J.*

*Biol. Chem.*, 277(45):42859-42866, 2002), Ab 1G11 (Fleming et al. *J Pathol* 161:189, 1990), Ab Ad22 (Lamy et al., *J. Biol. Chem.*, 278(26):23915-23921, 2003; Pettersen et al., *Tissue Antigens* 45:203, 1995) (all mouse anti-human CD47); and additional anti-CD47 or anti-TSP1 antibodies that have similar effect on the interaction between CD47 and TSP1, as well as morpholinos (e.g., CD47 or TSP1 morpholinos), and peptides derived from CD47 or TSP1.

Thus, there is provided herein in one embodiment a peptide comprising the amino acid sequence HIGWKDFTAYR-WRLS (SEQ ID NO: 7), or comprising at least the amino acid sequence IGWKDFTAYR contained therein (SEQ ID NO: 1), or comprising an amino acid sequence derived therefrom that inhibits ligand binding to CD47, or another peptide recited herein, or an equivalent thereof. Also described are pharmaceutical compositions that contain such peptides or one or more derivatives thereof formulated to improve stability and/or bioavailability of the peptide.

Also described are oligonucleotides comprising at least about 15 contiguous nucleotides that hybridize to the mRNA of CD47 (e.g., accession number NM 001777 *Homo sapiens* CD47 mRNA) under high stringency conditions. In certain embodiments, the oligonucleotide is a morpholino.

Yet another embodiment is a pharmaceutical composition comprising an antisense oligonucleotide of at least 20 contiguous nucleotides complementary to human CD47 mRNA, and a suitable delivery vehicle, which composition limits tissue expression of CD47. By way of example, the antisense oligonucleotide in some cases is a morpholino. For instance, there is provided a pharmaceutical composition, in which the morpholino comprises an antisense oligonucleotide to CD47 having the sequence CGTCACAGGCAGGACCCACTGC-CCA (SEQ ID NO: 21), or another sequence from CD47 or a sequence from TSP1. Other representative sequences are described.

Also provided is a method to improve tissue survival during integument and soft tissue and composite tissue surgery, the method comprising one or more of: decreasing CD47 expression in the tissue; inhibiting ligand binding to CD47 in the tissue; inhibiting ligand binding to CD47 in tissue using the peptide of claim 1; inhibiting ligand binding to CD47 in tissue using CD47 binding peptide C6b or 7N3 or 4N1/4N1K; and inhibiting ligand binding to CD47 in tissue using a CD47 binding antibody.

Another provided method is a method to prevent or reduce ischemic tissue damage or necrosis, which method comprises any one or more of: decreasing CD47 expression in the tissue; inhibiting ligand binding to CD47 in the tissue; inhibiting ligand binding to CD47 in tissue using the peptide of claim 1; inhibiting ligand binding to CD47 in tissue using CD47 binding peptide C6b or 7N3; and inhibiting ligand binding to CD47 in tissue using a CD47 binding antibody.

Additional methods include a method to increase skin graft survival, which comprises decreasing CD47 expression in the graft and/or inhibiting ligand binding to CD47 in the tissue. There are also provides in various embodiments methods of use of antibodies and peptides, for instance antibodies (such as monoclonal antibodies, and humanized antibodies) to CD47 and peptides derived from CD47. For instance, there is provided use of an antibody to CD47 or a peptide derived from CD47 to prevent or reduce tissue necrosis and/or to increase skin graft survival and/or improve organ transplant success. Also provided is use of an isolated CD47 molecule, or molecule that binds thereto, to influence blood vessel flow and alter tissue perfusion.

Additionally, included is a method or methods to increase tissue and skin graft survival through blocking of the action of TSP1 directly with monoclonal antibodies, such as clone A6.1, and other antibodies which block the action of TSP1 on CD47 and thus increase tissue blood vessel diameter, blood flow and tissue perfusion.

Yet another embodiment is a method comprising selective application to a subject of one or more agents that inhibit function or expression of CD47, which method: improves tissue or organ survival in the subject; treats or ameliorates peripheral vascular disease or myocardial ischemia in the subject; improves blood flow in the subject; improves transplant organ or tissue survival in the subject; and/or improves skin graft survive in the subject. Without limitation, the subject to which such a method is applied may be a subject suffering from one or more diseases or conditions that have as a component or side effect a defect in circulation or vascular regulation or ischemia. For instance, in some examples the subject has diabetes, peripheral vascular disease, atherosclerotic vascular disease and/or other chronic vascular pathology (e.g., associated with macular degeneration), or is undergoing tissue or organ grafting or transplantation, or has suffered an injury or stroke or other event resulting in ischemia.

Another embodiment is a method to inhibit blood flow (for instance, to tumors) by application of an agent that mimics TSP-1 and binds to CD47. For instance, the agent in some cases is a CD47 antibody, such as a monoclonal antibody or humanized antibody, or a derivative molecule that maintains the ability to bind to an epitope. In other examples, the agent is a peptide, such as for instance a peptide comprising the amino acid IGWKDFTAYR (SEQ ID NO: 1), or another peptide that can bind or block the binding between TSP-1 and CD47.

Further, described herein are methods of increasing tissue perfusion in an elderly subject, examples of which include selecting an elderly subject in need of increased tissue perfusion; and administering to the subject a therapeutically effective amount of an agent that inhibits the interaction of thrombospondin-1 (TSP-1) and CD47, thereby increasing tissue perfusion in the elderly subject. By way of example, in some embodiments, the subject is a human, for instance a human of about 65 years of age or more.

In various embodiments, a surgical procedure has been (or is being, or will be) performed on the subject; the subject has a myocardial infarction, and wherein the tissue is the heart; and/or the subject has atherosclerosis.

Also contemplated herein are methods of treating tissue necrosis resulting from ischemia in an elderly subject with atherosclerotic vascular disease or age-related vasculopathy, which methods involve selecting an elderly subject with necrosis in a tissue, wherein the subject has atherosclerotic disease or age-related vasculopathy; and administering to the subject a therapeutically effective amount of an agent that inhibits the interaction of TSP1 and CD47, thereby treating the tissue necrosis. In specific examples of such methods, the age-related vasculopathy is peripheral vascular disease. By way of example, in some embodiments the subject is a human, for instance a human of about 65 years of age or more.

In various embodiments, a surgical procedure has been (or is being, or will be) performed on the subject, or specifically the tissue being treated in the method; the subject has a myocardial infarction, and wherein the tissue is the heart; and/or the subject has atherosclerosis. In other embodiments, the subject has diabetes, such as adult onset diabetes.

Additional embodiments provide use of an agent that decreases the expression of CD47, a CD47 antagonist, an antibody that specifically binds TSP-1, or an antibody that specifically binds CD47 for the treatment of an elderly subject with ischemia resulting from atherosclerosis or a vasculopathy.

Also provided are pharmaceutical compositions comprising an agent that decreases the expression of CD47, a CD47 antagonist, an antibody that specifically binds TSP-1, or an antibody that specifically binds CD47 for use in the treatment of ischemia in an elderly subject with atherosclerosis or a vasculopathy.

Yet another embodiment provides methods to improve tissue survival in an elderly subject in need thereof, the method comprising one or more of decreasing CD47 expression in the tissue; and inhibiting ligand binding to CD47 in the tissue, thereby improving tissue survival in the elderly subject. Optionally, the elderly subject has atherosclerosis, has PVD/PAD, has a graft; has had a myocardial infarction; has a vasculopathy, and/or has Alzheimer's or dementia, or a combination of any two or more thereof.

Still another embodiment provides methods for enhancing blood clotting and preventing bleeding. Data from peptides including C6d, C6b and other peptides described herein teaches that they agents enhance platelet aggregation and hence would be useful in applications to minimize, reduce, or slow bleeding. Such agents are therapeutically beneficial at controlling bleeding from many sources including trauma, elective and required surgery, and acquired or congenital bleeding disorders.

VI. Therapeutic Uses

Methods are disclosed herein for promoting blood flow in an area in a subject who has or is at risk for developing ischemia, for instance during or following surgery, burn injury, a graft, peripheral vascular disease, amputation, coronary artery disease, stroke, thrombosis, a clot, chronic vascular obstruction or vasculopathy (e.g., secondary to diabetes, hypertension, or peripheral vascular disease), cerebral ischemia, a wound, and so forth. Provided methods are useful in the treatment of various diseases and conditions, including but not limited to treatment of donor organs before and after transplantation; reattachment of severed extremities, body parts or soft tissues; pulmonary hypertension (adult or neonate); sickle cell disease; neointimal hyperplasia or restenosis (following angioplasty or stenting); primary burn care (before skin grafting); kidney disease (for instance, to increase kidney circulation); preeclampsia; erectile dysfunction; asthma or adult respiratory distress syndrome; Alzheimer's and other dementias secondary to compromised cranial blood flow. Methods are also disclosed herein for promoting blood flow and increasing tissue perfusion in a tissue, such as in an elderly subject with a degenerative disorder, such as in the brain of an elderly subject with dementia or Alzheimer's disease. The methods include introducing a therapeutically effective amount of a CD47 or TSP1 peptide, antibody, oligonucleotide, or other agent (such as those described herein) to the area being treated, thereby promoting blood flow in the subject. In some embodiments, the agent is administered as naked DNA encoding an inhibitory peptide, for instance using for instance protocols used for delivering VEGF to ischemic tissues (see, for example, Isner, et al., *J. Vasc. Surg.*, 1998; 28:964-975; Losardo et al., *Circulation*, 1998; 98:2800-2804). In other embodiments, the inhibitory oligonucleotide (e.g., a CD47-targeted or TSP1-targeted morpholino) is administered.

In some embodiments, a therapeutic antibody or antibody fragment, nucleic acid, or inhibitory oligonucleotide (e.g., morpholino), is administered locally to the affected area, for example by direct topical administration to a wound or other lesion in which neovascularization is desired, or is incorporated in to a vascular stent or other implant device and placed directly in a diseased blood vessel, or is placed directly in a blood vessel, or is parenterally directed to an affected area, such as an ischemic extremity. For subjects with peripheral vascular disease, administration is, for example, by direct topical administration to a wound, or by intra-arterial, intravenous, subcutaneous, or intramuscular injection into the affected limb. Efficacy of the treatment is shown, for example, by a regression of symptoms, for example, a lessening of cramping in the leg or arm, or a lessening of claudication, numbness, tingling, weakness, or pain, or healing of skin ulcers on the limb. An improvement in vascular function is also demonstrated, for example, by increased skin temperature or a color change in the skin of the limbs.

Also contemplated are uses of provided therapeutic compounds and compositions in ameliorating reperfusion injury following cardiac ischemia (MI/heart attack), or extracorporeal oxygenation (bypass) during heart surgery, heart transplant lung or heart-lung transplants.

For subjects with cerebral ischemia, administration is, for example, by intra-arterial or intrathecal injection, or by direct injection of ischemic brain areas. Intra-arterial injection can be directed to ischemic regions, for example, by injection into the basilar artery to administer the agent to the occipital cortex. In some embodiments, administration is by intravenous or intra-arterial injection following osmotic disruption of the blood brain barrier (see, for example, U.S. Pat. No. 5,124,146). In some embodiments, administration is, for example, by injection into the basilar, carotid, or cerebral arteries. A therapeutic agent can also be administered by intra-ventricular injection for degenerative disease of the brain, such as to an elderly subject with Alzheimer's disease or dementia. Efficacy of the treatment is indicated, for example, by an abatement of symptoms, for example, a lessening of numbness or weakness of the face, arm or leg, lessening of confusion, improvement in speaking, visual improvement, or improvement in walking, balance, or coordination.

Additionally, in some embodiments the therapeutic agents may be incorporated in implantable devices, such as vascular stents placed directly in diseased blood vessels in the coronary, cerebral or peripheral circulation, for instance to provide slow release of the compound, thereby providing regional sustained release of the therapeutic agents.

For subjects with peripheral artery disease (and other systemic and arterial diseases), administration is, for example, by intra-arterial (particularly intracoronary), or intrapericardial injection. In some embodiments, the therapeutic agent is administered systemically, such as by intravenous injection. Additionally, in some embodiments the therapeutic agents may be incorporated into or on an implantable device, such as vascular stents placed directly in diseased blood vessels in the coronary or cerebral circulation, and undergo slow release providing regional sustained release of the therapeutic agents. Efficacy of treatment is demonstrated, for example, by a regression of symptoms, for example chest pressure or pain.

For subjects with a wound such as a burn or a graft, administration is, for example, by subcutaneous or intravenous injection, by direct injection of the wound or burn or graft bed, or by topical application. Efficacy of the treatment is determined, for example, by an improvement in wound healing.

Administration may begin whenever a subject has developed, or is at risk for developing ischemia, when a wound, burn, graft, transplant or the like has occurred, or when symptoms of reduced blood flow to the brain, heart, or one or more limbs are present, such as chest or limb pain, or neurological symptoms, such as dizziness, confusion, loss of speech, or loss of mobility.

Combinations of blood flow enhancing factors are also of use. For example, a therapeutic peptide, peptide-encoding DNA, oligonucleotide, or other therapeutic agent is administered in conjunction with a nitric oxide (NO) donor or precursor, such as isosorbide dinitrate, Bidil or L-arginine, or NO generating topical agents. Such therapeutic agents also may be administered in conjunction with agents that act upon soluble guanylyl cyclase to activate the enzyme and with agents that act to inhibit cyclic nucleotide phosphodiesterases (Viagra®, Levitra®, Clalis®, for instance).

An effective amount of a therapeutic TSP1 or CD47 inhibitor peptide, inhibitor peptide-encoding DNA, or oligonucleotide (e.g., morpholino) can be administered in a single dose, or in multiple doses, for example daily, weekly, every two weeks, or monthly during a course of treatment. Additionally, the therapeutic agents may be incorporated into or on implantable constructs or devices, such as vascular stents, for sustained regional or local release.

Alternatively, peptides, antibodies or morpholinos targeting TSP1 and CD47 can be administered directly at the time of surgery and or wound reconstruction, for instance in the form of topical applied liquids or creams or via direct injection into tissues. Additionally, such agents can be incorporated into the irrigation fluid such as that routinely used to wash wound beds prior to closure. In this form, the therapeutic agents would be placed specifically were needed to maximize blood flow, angiogenesis and wound healing. The direct application of a TSP1 and CD47 blocking agent would also provide therapeutic benefit for burn patients undergoing skin grafts, by insuring improved blood flow to the healing graft.

The therapeutic agents described herein can also play a role in decreasing the overall size of the burn wound. Direct injection into the margins of the burn wound would encourage blood flow to the ischemic wound areas and maximize tissue survival.

In the case of surgery where controlling bleeding is of concern, agents which mimic TSP1 and TSP1 actions through CD47, including antibodies, peptides or small molecules (rather than those which block it), could be applied in irrigation liquids or other delivery vehicle and applied directly to the bleeding tissue surface to promote blood clot formation.

In the case of skin grafts and burn wounds, controlled release of any of the described compounds over extended periods of time may be of significant benefit in healing Methods are provided herein for increasing tissue perfusion in elderly subjects. Thus, the disclosed methods are of use in any subject, such as a mammalian subject, who has passed middle age. In one embodiment, an elderly mammalian subject is a subject that has survived more than two-thirds of the normal lifespan for that mammalian species. In a further embodiment, for humans, an aged or elderly subject is more than about 65 years of age, such as a subject of more than about 70 years of age, more than about 75 years of age, or more than about 80 years of age. In yet another embodiment, for mice, the disclosed methods are of use in animals that are from about 14 to about 18 months of age. One of skill in the art can readily distinguish the elderly subject for a specific mammalian species, based on the average lifespan for that species.

By way of example, mice mature rapidly (reaching puberty by 6 weeks) and loose breeding capabilities by one year or age. Current strains of mice employed in biomedical research have average life expectancies of from 1 to 2 years. Hence mice beyond 1 year of age are past middle age and can be considered elderly. Mice over 14-16 months are then reasonably considered senescent (Wordern, *The Care and Management of Laboratory Animals*, Williams and Wilkins, Baltimore, 1947).

It will be recognized that methods disclosed herein will also be effective in increasing blood flow secondary to tissue trauma or vascular disease regardless of the age of the subject.

Methods also are provided for the use of TSP1-based peptides such as C6d, C6b and other peptides described herein, or antibodies and small molecules having similar effect (in that they block or reduce the ability of NO to prevent platelet aggregation and blood clotting). Such agents can be used to treat subjects with bleeding, including bleeding disorders of diverse cause. These peptides and agents can be applied directly to bleeding wounds, both internal and external, and as such will function as topical hemostatic therapies. They may be incorporated into dressings and bandages, or combined with other available hemostatic agents. Representative immediate application for these treatments is in treating battle field wounds, accident trauma, and other injuries, where minimizing bleeding saves lives.

VII. Combination Therapies

In several embodiments, providing a nitric oxide source at the same time one eliminates or reduces effects of TSP1 can enhance tissue survival to ischemia. The therapeutic application of combination therapy employing an exogenous source of nitric oxide (such as isosorbide dinitrate) and TSP1 or CD47 blockade or suppression (e.g., with antibody or morpholino or small molecule inhibitors) can be used to enhance blood flow and angiogenesis to ischemic tissue and increase blood flow, tissue survival and blood flow.

Generally, it is believed that NO donors (or enhancers of nitric oxide availability or action, such as L-arginine) are effective when combined with administration of an agent that blocks or suppresses CD47 or TSP1, or the interaction between these proteins. For instance, in tissue flap models of ischemia, NO donors are shown to increase tissue survival. In experiments described herein, the use of one such agent (isosorbide dinitrate) dramatically increased tissue survival alone. When TSP1 was removed from the tissue, as in the null animals, these results were further improved.

Alternatively, the agent that blocks or suppresses CD47 or TSP1, or the interaction between these proteins, may be used in combinations with drugs and agents that limit the elimination rate of nitric oxide, or augment the action of nitric oxide. This combination could serve to increase the strength of responses to administered compounds for influencing blood flow.

Furthermore, the therapeutic agents that blocks or suppresses CD47 or TSP1, or the interaction between these proteins (e.g., peptides and oligos, such as morpholinos), may also be used in combination with other therapeutic agents, for example, pain relievers, anti-inflammatory agents, antihistamines, and the like, whether for the conditions described or some other condition. By way of example, the additional agent is one or more selected from the list consisting of an antibiotic (e.g., penicillin), hydroxyurea, butyrate, clotrimazole, arginine, or a phosphodiesterase inhibitor (such as sildenafil). The therapeutic agents that suppress CD47 or TSP-1, or the interactions between these proteins, can be used in combination with any pharmaceutical composition of use to treat a disorder.

Other specific combinations of therapeutic treatments are discussed herein.

VIII. Production of Antibodies

Optimally, antibodies raised against a target protein (such as TSP1 or CD47) would specifically detect that peptide/ protein, and optimally would inhibit the interaction between TSP1 and CD47. Antibodies that specifically detect a target protein would recognize and bind that protein (and peptides derived therefrom) and would not substantially recognize or bind to other proteins or peptides found in a biological sample. The determination that an antibody specifically detects its target protein is made by any one of a number of standard immunoassay methods; for instance, the Western blotting technique (Sambrook et al., In *Molecular Cloning: A Laboratory Manual*, CSHL, New York, 1989).

To determine by Western blotting that a given antibody preparation (such as one produced in a mouse or rabbit) specifically detects the target peptide, the peptide of interest is synthesized and transferred to a membrane (for example, nitrocellulose) by Western blotting, and the test antibody preparation is incubated with the membrane. After washing the membrane to remove non-specifically bound antibodies, the presence of specifically bound antibodies is detected by the use of an anti-mouse or anti-rabbit antibody conjugated to an enzyme such as alkaline phosphatase.

Application of an alkaline phosphatase substrate 5-bromo-4-chloro-3-indolyl phosphate/nitro blue tetrazolium results in the production of a dense blue compound by immunolocalized alkaline phosphatase. Antibodies that specifically detect the target peptide will, by this technique, be shown to bind to the target peptide band (which will be localized at a given position on the gel determined by its molecular weight). Non-specific binding of the antibody to other proteins may occur and may be detectable as a weak signal on the Western blot. The non-specific nature of this binding will be recognized by one skilled in the art by the weak signal obtained on the Western blot relative to the strong primary signal arising from the specific antibody-target peptide binding.

The determination that an antibody inhibits the association between TSP1 and CD47, or the ability of TSP1 or CD47 to modulate tissue survival in ischemia or blood clot formation, may be made, for example, using any one of the assays described herein, including for instance the flap model. For instance, the determination that an antibody inhibits TSP1 binding to purified or recombinant CD47 can be made by comparing the binding activity alone with the binding activity in the presence of the antibody using a solid phase ligand binding assay. An antibody that inhibits the activity of TSP1 to signal through CD47 on cells will reduce the activity of a cGMP-dependent reporter in a suitable transfected cell assay by a certain amount, for example, by 20%, 30%, 40%, 50%, 60%, 70%, 80%, 90%, or even by 100%.

A. Monoclonal Antibody Production by Hybridoma Fusion

Monoclonal antibody to epitopes of a target peptide (e.g., from TSP1 or CD47) can be prepared from murine hybridomas according to the classical method of Kohler and Milstein (*Nature* 256:495, 1975) or derivative methods thereof. Briefly, a mouse is repetitively inoculated with a few micrograms of the selected protein over a period of a few weeks. The mouse is then sacrificed, and the antibody-producing cells of the spleen are isolated. The spleen cells are fused by means of polyethylene glycol with mouse myeloma cells, and the excess un-fused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (*Enzymol.* 70:419, 1980), and derivative methods thereof. Selected positive clones can be expanded and their monoclonal antibody product harvested for use. Detailed procedures for monoclonal antibody production are described in Harlow and Lane (*Antibodies, A Laboratory Manual*, CSHL, New York, 1988).

B. Polyclonal Antibody Production by Immunization

Polyclonal antiserum containing antibodies to heterogeneous epitopes of a single protein can be prepared by immunizing suitable animals with the expressed protein, which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with either inadequate or excessive doses of antigen resulting in low titer antisera. Small doses (ng level) of antigen administered at multiple intradermal sites appear to be most reliable. An effective immunization protocol for rabbits can be found in Vaitukaitis et al. (*J. Clin. Endocrinol. Metab.* 33:988-991, 1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony et al. (In *Handbook of Experimental Immunology*, Wier, D. (ed.) chapter 19. Blackwell, 1973). Plateau concentration of antibody is usually in the range of about 0.1 to 0.2 mg/ml of serum (about 12 µM). Affinity of the antisera for the antigen is determined by preparing competitive binding curves, as described, for example, by Fisher (*Manual of Clinical Immunology*, Ch. 42, 1980).

C. Antibodies Raised Against Synthetic Peptides

A third approach to raising antibodies against a target peptide is to use synthetic peptides synthesized on a commercially available peptide synthesizer based upon the amino acid sequence of the native protein (e.g., TSP1 or CD47).

By way of example only, polyclonal antibodies to a CD47 or TSP1 peptide can be generated through well-known techniques by injecting rabbits with chemically synthesized peptide.

D. Antibodies Raised by Injection of a Peptide-Encoding Sequence

Antibodies may be raised against a target peptide by subcutaneous injection of a DNA vector that expresses that peptide into laboratory animals, such as mice. Delivery of the recombinant vector into the animals may be achieved using a hand-held form of the Biolistic system (Sanford et al., *Particulate Sci. Technol.* 5:27-37, 1987) as described by Tang et al. (*Nature* 356:152-154, 1992). Expression vectors suitable for this purpose may include those that express the desired peptide-encoding sequence under the transcriptional control of either the human β-actin promoter or the cytomegalovirus (CMV) promoter.

E. Humanized Antibodies

Also contemplated are humanized antibodies, for instance humanized equivalents of the described murine monoclonal antibodies. A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, such as at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

The use of antibody components derived from humanized monoclonal antibodies obviates potential problems associated with the immunogenicity of the constant regions of the donor antibody. Techniques for producing humanized monoclonal antibodies are described, for example, by Jones et al., *Nature* 321:522, 1986; Riechmann et al., *Nature* 332:323, 1988; Verhoeyen et al., *Science* 239:1534, 1988; Carter et al., *Proc. Natl. Acad. Sci. U.S.A.* 89:4285, 1992; Sandhu, *Crit. Rev. Biotech.* 12:437, 1992; and Singer et al., *J. Immunol.* 150:2844, 1993. The antibody may be of any isotype, but in several embodiments the antibody is an IgM or an IgG, including but not limited to, $IgG_1$, $IgG_2$, $IgG_3$ and $IgG_4$.

Humanized monoclonal antibodies can be produced by transferring donor complementarity determining regions (CDRs) from heavy and light variable chains of the donor mouse (or other animal) immunoglobulin. The production of chimeric antibodies, which include a framework region from one antibody and the CDRs from a different antibody, is well known in the art. For example, humanized antibodies can be routinely produced. The antibody or antibody fragment can be a humanized immunoglobulin having complementarity determining regions (CDRs) from a donor monoclonal antibody that binds a cell surface antigen of pancreatic cells (such as endocrine, exocrine or ductal cells) and immunoglobulin and heavy and light chain variable region frameworks from human acceptor immunoglobulin heavy and light chain frameworks. Generally, the humanized immunoglobulin specifically binds to the cell surface antigen (or cells expressing the antigen) with an affinity constant of at least $10^7 M^{-1}$, such as at least $10^8 M^{-1}$ at least $5 \times 10^8 M^{-1}$ or at least $10^9 M^{-1}$.

In one embodiment, the sequence of the humanized immunoglobulin heavy chain variable region framework can be at least about 65% identical to the sequence of the donor immunoglobulin heavy chain variable region framework. Thus, the sequence of the humanized immunoglobulin heavy chain variable region framework can be at least about 75%, at least about 85%, at least about 95%, or at least about 99% identical to the sequence of the donor murine immunoglobulin heavy chain variable region framework. Human framework regions, and mutations that can be made in a humanized antibody framework regions, are known in the art (see, for example, in U.S. Pat. No. 5,585,089, which is incorporated herein by reference). One of skill in the art can readily select a human framework region of use.

Also contemplated are fully human antibodies. Mice have been generated that express only human immunoglobulin genes, instead of mouse genes. These mice are immunized with the antigen, such as TSP1 or CD47, and resultant antibodies that are raised are selected for the activity desired. In the current instance, it is contemplated that this technique can be used to generate antibodies (including monoclonal antibodies) useful for blocking TSP-CD47 interactions. These procedures are substantially similar just those used to select a mouse anti-human Ab, but result in a fully human antibody since the mouse only has human Ig genes.

IX. Peptides and Peptide Variants

The peptides disclosed herein can be chemically synthesized by standard methods, or can be produced recombinantly. The synthesis of the presently disclosed compounds can be accomplished using standard chemical reactions known to be useful for preparing a variety of analogous compounds. Indeed, exemplary techniques known to those of ordinary skill in the art of peptide synthesis are taught by Bodanszky & Bodanszky (The Practice of Peptide Synthesis; Springer Verlag, New York, 1994) and by Jones (Amino Acid and Peptide Synthesis; 2nd ed.; Oxford University Press, 2002), both of which are incorporated herein by reference. The Bodanszky and Jones references detail the parameters and techniques for activating and coupling amino acids and amino acid derivatives. Moreover, the references teach how to select, use and remove various useful protecting groups. An exemplary specific process for (poly)peptide production is described in Lu et al. (*Fed. Europ Biochem Societies Lett.* 429:31-35, 1998).

Polynucleotides encoding the peptides disclosed herein are also provided. These polynucleotides include DNA, cDNA and RNA sequences that encode the peptide of interest. Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (e.g., L. Stryer, 1988, Biochemistry, $3^{rd}$ Edition, W.H. 5 Freeman and Co., NY).

A nucleic acid encoding a peptide can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the peptide (or a longer polypeptide, such as an expression fusion polypeptide, containing the peptide) can be isolated by polymerase chain reaction of cDNA using primers based on the DNA sequence of the molecule. A wide variety of cloning and in vitro amplification methodologies are well known to persons skilled in the art. PCR methods are described in, for example, U.S. Pat. No. 4,683,195; Mullis et al., *Cold Spring Harbor Symp. Quant. Biol.* 51:263, 1987; and Erlich, ed., *PCR Technology*, (Stockton Press, NY, 1989). Polynucleotides also can be isolated by screening genomic or cDNA libraries with probes selected from the sequences of the desired polynucleotide under stringent hybridization conditions.

The polynucleotides encoding a peptide (e.g., a peptide from or derived from TSP1 or CD47) include a recombinant DNA which is incorporated into a vector into an autonomously replicating plasmid or virus or into the genomic DNA of a prokaryote or eukaryote, or which exists as a separate molecule (such as a cDNA) independent of other sequences. The nucleotides of the invention can be ribonucleotides, deoxyribonucleotides, or modified forms of either nucleotide. The term includes single and double forms of DNA.

In one embodiment, vectors are used for expression in yeast such as *S. cerevisiae* or *Kluyveromyces lactis*. Several promoters are known to be of use in yeast expression systems such as the constitutive promoters plasma membrane H+-ATPase (PMA1), glyceraldehyde-3-phosphate dehydrogenase (GPD), phosphoglycerate kinase-1 (PGK1), alcohol dehydrogenase-1 (ADH1), and pleiotropic drug-resistant pump (PDR5). In addition, may inducible promoters are of use, such as GAL1-10 (induced by galactose), PHO5 (induced by low extracellular inorganic phosphate), and tandem heat shock HSE elements (induced by temperature elevation to 37° C.). Promoters that direct variable expression in response to a titratable inducer include the methionine-responsive MET3 and MET25 promoters and copper-dependent CUP1 promoters. Any of these promoters may be cloned into multicopy (2μ) or single copy (CEN) plasmids to give an additional level of control in expression level. The plasmids can include nutritional markers (such as URA3, ADE3, HIS1, and others) for selection in yeast and antibiotic resistance (AMP) for propagation in bacteria. Plasmids for expression on *K. lactis* are known, such as pKLAC1. Thus, in one example, after amplification in bacteria, plasmids can be introduced into the corresponding yeast auxotrophs by methods similar to bacterial transformation.

The peptides can be expressed in a variety of yeast strains. For example, seven pleiotropic drug-resistant transporters, YOR1, SNQ2, PDR5, YCF1, PDR10, PDR11, and PDR15, together with their activating transcription factors, PDR1 and PDR3, have been simultaneously deleted in yeast host cells, rendering the resultant strain sensitive to drugs. Yeast strains with altered lipid composition of the plasma membrane, such as the erg6 mutant defective in ergosterol biosynthesis, can also be utilized. Proteins that are highly sensitive to proteolysis can be expressed in a yeast lacking the master vacuolar endopeptidase Pep4, which controls the activation of other vacuolar hydrolases. Heterologous expression in strains carrying temperature-sensitive (ts) alleles of genes can be employed if the corresponding null mutant is inviable.

Viral vectors can also be prepared encoding the peptides disclosed herein. Myriad viral vectors have been constructed and are known to those of skill in the art, including but not limited to polyoma, SV40 (Madzak et al., *J. Gen. Virol.* 73:153311536, 1992), adenovirus (Berkner, *Cur. Top. Microbiol. Immunol.*, 158:39-36, 1992; Berliner et al., *BioTechniques*, 6:616-629, 1988; Gorziglia et al., *J. Virol.* 66:4407-4412, 1992; Quantin et al., *Proc. Nad. Acad. Sci. USA* 89:2581-2584, 1992; Rosenfeld et al., *Cell*, 68:143-155, 1992; Wilkinson et al., *Nucl. Acids Res.* 20:2233-2239, 1992; Stratford-Perricaudet et al., *Hum. Gene Ther.*, 1:241-256), vaccinia virus (Mackett et al., *Biotechnology*, 24:495-499, 1992), adeno-associated virus (Muzyczka, *Curr. Top. Microbiol. Immunol.* 158:91-123, 1992; On et al., 1990, *Gene*, 89:279-282), herpes viruses including HSV and EBV (Margolskee, *Curr. Top. Microbiol. Immunol.*, 158:67-90, 1992; Johnson et al., *J. Virol.* 66:2952-2965, 1992; Fink et al., *Hum. Gene Ther.* 3:11-19, 1992; Breakfield et al., *Mol. Neurobiol.*, 1:337-371, 1987; Fresse et al., *Biochem. Pharmacol.* 40:2189-2199, 1990), Sindbis viruses (Herweijer et al., *Human Gene Therapy* 6:1161-1167, 1995; U.S. Pat. No. 5,091,309), alphaviruses (Schlesinger, *Trends Biotechnol.* 11:18-22, 1993; Frolov et al., *Proc. Natl. Acad. Sci. USA* 93:11371-11377, 1996) and retroviruses of avian (Brandyopadhyay et al., *Mol. Cell. Biol.* 4:749-754, 1984; Petropoulos et al., *J. Virol.* 66:3391-3397, 1992), murine (Miller, *Curr. Top. Microbiol. Immunol.*, 158:1-24, 1992; Miller et al., 1985, Mol. Cell. Biol., 5:431-437; Sorge et al., *Mol. Cell. Biol.* 4:1730-1737, 1984; Mann et al., *J. Virol.* 54:401-407, 1985), and human origin (Page et al., *J. Virol.* 64:5370-5276, 1990; Buchschalcher et al., *J. Virol.* 66:2731-2739, 1992). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

Sequence Variants

Based on their activities for modulating vascular cell adhesion, platelet aggregation, and cellular cGMP levels, several residues in SEQ ID NO: 3 (C6d) are believed to influence or govern biological activity. At position 1, substituting Ile with Ala decreased activity at least 10-fold, indicating that a hydrophobic side chain is required. It is believed that conservative substitutions with other nonpolar amino acids would be tolerated. The Gly at position 2 might function to permit rotation about the phi and psi bonds, but other short chain residues such as Ala may be tolerated at this position as well. At position 3, substituting Trp with Tyr preserves activity; other nonpolar residues at this position could potentially also preserve activity.

Based on the inactivity of Ala and His substitutions at position 4, it is currently believed that Lys is required at this position. Similarly, Asp appears to be required at position 5, although substitution with Glu at this position preserved partial activity and is less preferred. At position 6, substituting the Phe with Tyr preserves activity, which leads us to predict that any aromatic amino acid can be present at this position, although other nonpolar residues also may be tolerated.

At position 7, substituting the Thr with Ala decreased activity approximately 100-fold indicating that the Thr is required. Position 8 was not substituted, so any aliphatic amino acid may be tolerated.

Substituting the Tyr at position 9 with Ala decreased activity approximately 100-fold, indicting that this residue is required, although conservative substitutions with other aromatic or nonpolar residues may be tolerated. At position 10 conservative substitution of the Arg with Lys abolished all activity. Therefore, the Arg is required.

The requirements for specific residues at positions 1 and 10 combined, with diminished or lack of activity for truncated peptides, appear to indicate that 10 residues is a minimal length for preferred peptide activities.

The following table provides a summary of biological activities of several TSP1-based peptides:

| ID | Sequence | Functional assays* | cGMP signaling IC50** | SEQ ID NO |
|---|---|---|---|---|
| C6b | HIGWKDFTAYRWRLS | +++ | ~0.1 μM | 7 |
| C6d | biotin-IGWKDFTAYR | ++ | ~0.1 μM | 3 |
| C6e | biotin-IGWKGFTAYR | 0 | inactive | 25 |
| C6s | GAKDFTAYR | 0 | inactive | 26 |
| 37300 | Ac-WKDFTAYR | + | ~1 μM | 2 |
| 37416 | AGWKDFTAYR | ND* | ~1 | 32 |
| 37417 | IGYKDFTAYR | ND | ~0.1 | 33 |

-continued

| ID | Sequence | Functional signaling assays* | cGMP IC50** | SEQ ID NO |
|---|---|---|---|---|
| 37413 | IGWADFTAYR | 0 | >10 | 29 |
| 37414 | IGWHDFTAYR | 0 | >10 | 30 |
| 37296 | IGWKAFTAYR | 0 | inactive | 16 |
| 37297 | IGWKNFTAYR | + | >10 µM | 4 |
| 37415 | IGWKEFTAYR | ++ | 1 µM | 31 |
| 37298 | IGWKDYTAYR | ++ | ~0.1 µM | 20 |
| 37299 | IGWKDFAAYR | + | >10 µM | 5 |
| 37555 | IGWKDFTAAR | ND | ~10 µM | 27 |
| 37554 | IGWKDFTAYK | ND | inactive | 28 |

*ND-no data
**IC50-concentration for 50% inhibition of effect

*ND—no data
**$IC_{50}$—concentration for 50% inhibition of effect

The characteristics of the peptides disclosed herein lie not in their precise and entire amino acid sequence, but rather in the three-dimensional structure inherent in the amino acid sequences encoded by the DNA sequences. It is possible to recreate the binding characteristics of any of these peptides, for instance the binding characteristics of any one of the specific peptides described herein, by recreating the three-dimensional structure, without necessarily recreating the exact amino acid sequence. Production of variations is enabled particularly in view of the guidance provided for the tolerance of variations at various positions within the core peptide. Such modifications and variations can be achieved for instance by designing a nucleic acid sequence that encodes for the three-dimensional structure, but which differs, for instance by reason of the redundancy of the genetic code or the substitution of one or more specific amino acids. Similarly, the DNA sequence may also be varied, while still producing a functional peptide.

Variant therapeutic peptides include peptides that differ in amino acid sequence from the disclosed sequence, but that share structurally significant sequence homology with any of the provided peptides. Such variants may be produced by manipulating the nucleotide sequence of the encoding sequence, using standard procedures, including site-directed mutagenesis or PCR. The simplest modifications involve the substitution of one or more amino acids for amino acids having similar biochemical properties. These so-called conservative substitutions are likely to have minimal impact on the activity of the resultant peptide, especially when made outside of the binding site of the peptide. One of ordinary skill in the art will be able to predict or empirically determine (particularly in view of the provided teachings) amino acids that may be substituted for an original amino acid in a peptide.

More substantial changes in peptide structure may be obtained by selecting amino acid substitutions that are less conservative than those listed in the above table. Such changes include changing residues that differ more significantly in their effect on maintaining polypeptide backbone structure (for example, sheet or helical conformation) near the substitution, charge or hydrophobicity of the molecule at the target site, or bulk of a specific side chain. The following substitutions are generally expected to produce the greatest changes in protein properties: (a) a hydrophilic residue (for example, seryl or threonyl) is substituted for (or by) a hydrophobic residue (for example, leucyl, isoleucyl, phenylalanyl, valyl or alanyl); (b) a cysteine or proline is substituted for (or by) any other residue; (c) a residue having an electropositive side chain (for example, lysyl, arginyl, or histadyl) is substituted for (or by) an electronegative residue (for example, glutamyl or aspartyl); or (d) a residue having a bulky side chain (for example, phenylalanine) is substituted for (or by) one lacking a side chain (for example, glycine).

Variant peptide-encoding sequences may be produced by standard DNA mutagenesis techniques, for example, M13 primer mutagenesis. Details of these techniques are provided in Sambrook (In *Molecular Cloning: A Laboratory Manual*, Cold Spring Harbor, N.Y., 1989), Ch. 15. By the use of such techniques, variants may be created which differ in minor ways from the angiogenic and anti-angiogenic-encoding sequences disclosed. DNA molecules and nucleotide sequences which are derivatives of those specifically disclosed herein and that differ from those disclosed by the deletion, addition, or substitution of nucleotides while still encoding a peptide that promotes or inhibits angiogenesis, are comprehended by this disclosure. In their most simple form, such variants may differ from the disclosed sequences by alteration of the coding region to fit the codon usage bias of the particular organism into which the molecule is to be introduced.

Alternatively, the coding region may be altered by taking advantage of the degeneracy of the genetic code to alter the coding sequence such that, while the nucleotide sequence is substantially altered, it nevertheless encodes a peptide having an amino acid sequence substantially similar to the disclosed peptide sequences. For example, one nucleotide codon triplet GCT encodes alanine. Because of the degeneracy of the genetic code, three other nucleotide codon triplets—(GCG, GCC and GCA)—also code for alanine. Thus, a nucleotide sequence containing GCT for alanine could be changed at the same position to any of the three alternative codons without affecting the amino acid composition or characteristics of the encoded peptide. Based upon the degeneracy of the genetic code, variant DNA molecules may be derived from the cDNA and gene sequences disclosed herein using standard DNA mutagenesis techniques as described above, or by synthesis of DNA sequences. Thus, this disclosure also encompasses nucleic acid sequences which encode the subject peptides, but which vary from the disclosed nucleic acid sequences by virtue of the degeneracy of the genetic code.

Peptide Modifications

The present disclosure includes biologically active molecules that mimic the action of the inhibitor/blockade peptides of the present disclosure. The peptides of the disclosure include synthetic embodiments of naturally-occurring peptides described herein, as well as analogues (non-peptide organic molecules), derivatives (chemically functionalized protein molecules obtained starting with the disclosed peptide sequences) and variants (homologs) of these peptides that specifically bind TSP1 or CD47, or that block the interaction there between. Each peptide of the disclosure is comprised of a sequence of amino acids, which may be either L- and/or D-amino acids, naturally occurring and otherwise.

Peptides may be modified by a variety of chemical techniques to produce derivatives having essentially the same activity as the unmodified peptides, and optionally having other desirable properties. For example, carboxylic acid groups of the peptides, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and R$_2$ are each independently H or C$_1$-C$_{16}$ alkyl, or combined to form a heterocyclic ring, such as a 5- or 6-membered ring. Amino groups of the peptides, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to C$_1$-C$_{16}$ alkyl or dialkyl amino or further converted to an amide.

Hydroxyl groups of the peptide side chains may be converted to C$_1$-C$_{16}$ alkoxy or to a C$_1$-C$_{16}$ ester using well-recognized techniques. Phenyl and phenolic rings of the peptide side chains may be substituted with one or more halogen atoms, such as fluorine, chlorine, bromine or iodine, or with C$_1$-C$_{16}$ alkyl, C$_1$-C$_{16}$ alkoxy, carboxylic acids and esters thereof, or amides of such carboxylic acids. Methylene groups of the peptide side chains can be extended to homologous C$_2$-C$_4$ alkylenes. Thiols can be protected with any one of a number of well-recognized protecting groups, such as acetamide groups. Those skilled in the art will also recognize methods for introducing cyclic structures into the peptides of this disclosure to select and provide conformational constraints to the structure that result in enhanced stability.

Peptidomimetic and organomimetic embodiments are also within the scope of the present disclosure, whereby the three-dimensional arrangement of the chemical constituents of such peptido- and organomimetics mimic the three-dimensional arrangement of the peptide backbone and component amino acid side chains in the described inhibitor peptides, resulting in such peptido- and organomimetics of the peptides of this disclosure having measurable or enhanced angiogenic or anti-angiogenic activity. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, Computer-Assisted Modeling of Drugs, in Klegerman & Groves, eds., 1993, *Pharmaceutical Biotechnology*, Interpharm Press: Buffalo Grove, Ill., pp. 165-174 and *Principles of Pharmacology* Munson (ed.) 1995, Ch. 102, for descriptions of techniques used in CADD. Also included within the scope of the disclosure are mimetics prepared using such techniques that produce angiogenic or anti-angiogenic peptides.

D. Additional Peptides

SIRP-alpha (Signal Inhibitory Regulatory Protein Alpha; SIRPα) and the closely related SIRP-gamma (SIRPγ formerly called SIRP-beta) are two ligands of CD47. They consist of an N-terminal IgV set domain and variable numbers of 1 g domains followed by a transmembrane segment and variously spliced cytoplasmic tails, some of which contain phosphorylatable tyrosines that constitute docking sites for tyrosine phosphatases such as SHP-1 and SHP-2. The IgV domain of SIRP-alpha and -gamma are high affinity ligands of CD47 with species specificity thought to allow self vs. non-self discrimination by phagocytes. The binding of the IgV domain of SIRPα to the IgV domain of CD47 can be measured in a simple ELISA assay using recombinant versions of each protein. For this purpose we have employed Fc-fusions of SIRP IgV domain and alkaline phosphatase fusions of the CD47 IgV domain. The Fc-IgV protein is adsorbed to well plates coated with protein A to which the Fc binds. Potential inhibitors are added and the binding of alkaline phosphatase-conjugated CD47 IgV domain is measured by routine procedures. Using this assay we have obtained data indicating that TSP1 G1 domain-derived peptides such as SEQ ID NO: 20 (IGWKDYTAYR), can inhibit the binding of the SIRP IgV domain to CD47. Conversely this suggests that the much larger G1 domain and the SIRP IgV domain should be mutually competitive for binding to CD47. Results with the ECaG1 construct suggest that this is the case.

Kato et al. (*J Thrombosis Haemostasis* 3:763-774, 2005) reported that an Fc-SIRP (also called SHPS-1) fusion binds to human platelets in a CD47-dependent manner. The SIRP IgV construct inhibits the aggregation of human platelets stimulated with submaximal doses of ADP, collagen and thrombin, and inhibits platelet spreading on immobilized fibrinogen, These effects are all precisely opposite to the effects of TSP1 and its CD47 ligand peptides, suggesting that the SIRPα IgV domain is blocking the action of endogenous TSP1 in this context. Further results include inhibition by the IgV domain of ADP-stimulated aIIbb3 integrin activation and surface expression of P-selecting (CD62P) and tyrosine phosphorylation of several platelet proteins was blocked in the presence of the SIRP IgV domain. All of these results are consistent with the idea that the SIRP IgV domain binds to platelet CD47 and thus prevents endogenous TSP1 from acting via CD47 to relieve NO inhibition of platelet activation and aggregation.

The binding of the IgV domains of CD47 and SIRPα to one another is well described in Liu et al., *J. Mol. Biol.* 365:680-693. They also describe mutants of the SIRPα IgV domain that modify the binding to CD47.

X. Pharmaceutical Compositions

The therapeutic compounds described herein may be formulated in a variety of ways depending on the location and type of disease to be treated or prevented in the subject. Pharmaceutical compositions are thus provided for both local use at or near an affected area and for systemic use (in which the agent is administered in a manner that is widely disseminated via the cardiovascular system). This disclosure includes within its scope pharmaceutical compositions including at least one peptide (for example, peptides IGWKDETAYR-WRLS (SEQ ID NO: 6), biotin-IGWKDFTAYR (SEQ ID NO: 3), IGWKNFTAYR (SEQ ID NO: 4), IGWKDYTAYR (SEQ ID NO: 20), IGWKDFAAYR (SEQ ID NO: 5), Ac-WKDFTAYR (SEQ ID NO: 2)), or another inhibitor of TSP1 or CD47 action or interaction (e.g., ab 301 or a CD47-directed morpholino), formulated for use in human or veterinary medicine. While the peptides and inhibitors typically will be used to treat human subjects, they may also be used to treat similar or identical diseases in other vertebrates, such other primates, dogs, cats, horses, and cows.

Pharmaceutical compositions that include at least one peptide or other inhibitor or therapeutic compound as described herein as an active ingredient, or that include both a therapeutic peptide or inhibitor/blockade agent and an additional agent as active ingredients, or that include both an ischemia-influencing peptide or inhibitor and an additional therapeutic agent, may be formulated with an appropriate solid or liquid carrier, depending upon the particular mode of administration chosen. Additional active ingredients include, for example, nitric oxide donors, nitrovasodilators, activators of the enzyme soluble guanylyl cyclase, or cGMP phosphodiesterase inhibitors.

A suitable administration format may best be determined by a medical practitioner for each subject individually. Various pharmaceutically acceptable carriers and their formulation are described in standard formulation treatises, for example, *Remington's Pharmaceutical Sciences* by E. W. Martin. See also Wang and Hanson, *J. Parenteral Sci. Technol.*, Technical Report No. 10, Supp. 42: 2S, 1988.

The dosage form of the pharmaceutical composition will be determined by the mode of administration chosen. For instance, in addition to injectable fluids, inhalational, topical, opthalmic, peritoneal, and oral formulations can be employed. Inhalational preparations can include aerosols, particulates, and the like. In general, the goal for particle size for inhalation is about 1 µm or less in order that the pharmaceutical reach the alveolar region of the lung for absorption. Oral formulations may be liquid (for example, syrups, solutions, or suspensions), or solid (for example, powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those of ordinary skill in the art.

The compositions or pharmaceutical compositions can be administered by any route, including parenteral administration, for example, intravenous, intramuscular, intraperitoneal, intrasternal, or intra-articular injection or infusion, or by sublingual, oral, topical, intra-nasal, ophthalmic, or transmucosal administration, or by pulmonary inhalation. When the active compounds are provided as parenteral compositions, for example, for injection or infusion, they are generally suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate/acetic acid buffers. A form of repository or depot slow release preparation may be used so that therapeutically effective amounts of the preparation are delivered into the bloodstream over many hours or days following transdermal injection or delivery.

Active compounds (e.g., peptides, proteins, oligos, and so forth) are also suitably administered by sustained-release systems. Suitable examples of sustained-release formulations include suitable polymeric materials (such as, for example, semi-permeable polymer matrices in the form of shaped articles, for example, films, or mirocapsules), suitable hydrophobic materials (for example as an emulsion in an acceptable oil) or ion exchange resins, and sparingly soluble derivatives (such as, for example, a sparingly soluble salt). Sustained-release compounds may be administered by intravascular, intravenous, intra-arterial, intramuscular, subcutaneous, intrapericardial, or intra-coronary injection. Administration can also be oral, rectal, parenteral, intracisternal, intravaginal, intraperitoneal, topical (as by powders, ointments, gels, drops or transdermal patch), buccal, or as an oral or nasal spray.

Preparations for administration can be suitably formulated to give controlled release of the therapeutic agent(s) (e.g., peptides, antibodies, oligonucleotides or other compounds that block CD47 and/or TSP1 activity or interaction). For example, the pharmaceutical compositions may be in the form of particles comprising a biodegradable polymer and/or a polysaccharide jellifying and/or bioadhesive polymer, an amphiphilic polymer, an agent modifying the interface properties of the particles and a pharmacologically active substance. These compositions exhibit certain biocompatibility features that allow a controlled release of the active substance. See, for example, U.S. Pat. No. 5,700,486.

In some embodiments, therapeutic agent(s) are delivered by way of a pump (see Sefton, CRC Crit. Ref. Biomed. Eng. 14:201, 1987; Buchwald et al., Surgery 88:507, 1980; Saudek et al., N. Engl. J. Med. 321:574, 1989) or by continuous subcutaneous infusions, for example, using a mini-pump. An intravenous bag solution may also be employed. The key factor in selecting an appropriate dose is the result obtained, as measured by increases or decreases in angiogenesis, or by other criteria for measuring control or prevention of disease, as are deemed appropriate by the practitioner. Other controlled release systems are discussed in the review by Langer (Science 249:1527-1533, 1990).

In another aspect of the disclosure, therapeutic agent(s) are delivered by way of an implanted pump, described, for example, in U.S. Pat. No. 6,436,091; U.S. Pat. No. 5,939,380; and U.S. Pat. No. 5,993,414. Implantable drug infusion devices are used to provide subjects with a constant and long term dosage or infusion of a drug or any other therapeutic agent. Essentially, such device may be categorized as either active or passive.

Active drug or programmable infusion devices feature a pump or a metering system to deliver the drug into the patient's system. An example of such an active drug infusion device currently available is the Medtronic SynchroMed™ programmable pump. Such pumps typically include a drug reservoir, a peristaltic pump to pump the drug out from the reservoir, and a catheter port to transport the pumped out drug from the reservoir via the pump to a patient's anatomy. Such devices also typically include a battery to power the pump, as well as an electronic module to control the flow rate of the pump. The Medtronic SynchroMed™ pump further includes an antenna to permit the remote programming of the pump.

Passive drug infusion devices, in contrast, do not feature a pump, but rather rely upon a pressurized drug reservoir to deliver the drug. Thus, such devices tend to be both smaller as well as cheaper as compared to active devices. An example of such a device includes the Medtronic IsoMed™. This device delivers the drug into the patient through the force provided by a pressurized reservoir applied across a flow control unit.

The implanted pump can be completely implanted under the skin of a subject, thereby negating the need for a percutaneous catheter. These implanted pumps can provide the patient with therapeutic agent(s) at a constant or a programmed delivery rate. Constant rate or programmable rate pumps are based on either phase-change or peristaltic technology. When a constant, unchanging delivery rate is required, a constant-rate pump is well suited for long-term implanted drug delivery. If changes to the infusion rate are expected, a programmable pump may be used in place of the constant rate pump system. Osmotic pumps may be much smaller than other constant rate or programmable pumps, because their infusion rate can be very low. An example of such a pump is described listed in U.S. Pat. No. 5,728,396.

The therapeutic agents may also be delivered passively and in sustained fashion as part of and incorporated into implantable devices, such as vascular stents which can be placed directly into diseased blood vessels through several standard approaches, including direct surgical insertion or percutaneously with angiographic control.

For oral administration, the pharmaceutical compositions can take the form of, for example, tablets or capsules prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates or sorbic acid). The preparations can also contain buffer salts, flavoring, coloring, and sweetening agents as appropriate.

For administration by inhalation, the compounds for use according to the present disclosure are conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges for use in an inhaler or insufflator can be formulated containing a powder mix of the compound and a suitable powder base such as lactose or starch.

For topical administration, the compounds can be, for example, mixed with a liquid delivery agent for administration locally. The agents used therapeutically (such as peptides, antibodies and morpholinos) are readily soluble or suspendable in water and saline, and as such these would be useful for delivery since water or saline do not cause adverse biological tissue effects. This allows sufficiently high doses to be administered locally or systemically, without secondary toxicity from the delivery vehicle.

By way of example, in the treatment of burns agents can be given by direct injection into the wound bed or topically dissolved in saline as a spray to the burn area, to skin grafts and/or to graft wound beds. They may also be mixed directly into antibiotic creams used to treat burns, such as bacitracin or silver sulfadine, or incorporated in a manner allowing release into dressing and bandaging materials applied to wounds, grafts or burns.

Pharmaceutical compositions that comprise at least one therapeutic agent as described herein as an active ingredient will normally be formulated with an appropriate solid or liquid carrier, depending upon the particular mode of administration chosen. The pharmaceutically acceptable carriers and excipients useful in this disclosure are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate. Actual methods of preparing such dosage forms are known, or will be apparent, to those skilled in the art.

For example, for parenteral administration, therapeutic agent(s) can be formulated generally by mixing them at the desired degree of purity, in a unit dosage injectable form (solution, suspension, or emulsion), with a pharmaceutically acceptable carrier, for instance, one that is non-toxic to recipients at the dosages and concentrations employed and is compatible with other ingredients of the formulation. A pharmaceutically acceptable carrier is a non-toxic solid, semisolid or liquid filler, diluent, encapsulating material or formulation auxiliary of any type.

Generally, the formulations are prepared by contacting the therapeutic agent(s) each uniformly and intimately with liquid carriers or finely divided solid carriers or both. Then, if necessary, the product is shaped into the desired formulation. Optionally, the carrier is a parenteral carrier, and in some embodiments it is a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The pharmaceutical compositions that comprise at least one therapeutic agent, in some embodiments, will be formulated in unit dosage form, suitable for individual administration of precise dosages. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

The therapeutically effective amount of therapeutic agent, such as a peptide, antibody, or oligonucleotide (e.g., morpholino or other antisense molecule) will be dependent on the peptide or inhibitor utilized, the subject being treated, the severity and type of the affliction, and the manner of administration. The exact dose is readily determined by one of skill in the art based on the potency of the specific compound, the age, weight, sex and physiological condition of the subject.

The peptides/proteins of the present disclosure (for example, CD47 or TSP1 peptides, or a peptide that inhibits or alters binding between TSP1 and CD47) also can be administered as naked DNA encoding the peptide. To simplify the manipulation and handling of the nucleic acid encoding the peptide, the nucleic acid is generally inserted into a cassette, where it is operably linked to a promoter. Preferably, the promoter is capable of driving expression of the protein in cells of the desired target tissue. The selection of appropriate promoters can readily be accomplished. Preferably, the promoter is a high expression promoter, for example the 763-base-pair cytomegalovirus (CMV) promoter, the Rous sarcoma virus (RSV) promoter (Davis, et al., *Hum. Gene. Ther.* 4:151, 1993), or the MMT promoter.

Other elements that enhance expression also can be included, such as an enhancer or a system that results in high levels of expression, such as a tat gene or tar element. This cassette is inserted into a vector, for example, a plasmid vector such as pUC118, pBR322, or other known plasmid vector, that includes, for example, an *E. coli* origin of replication. See, Sambrook, et al., *Molecular Cloning: A Laboratory Manual*, Cold Spring Harbor Laboratory Press (1989). The plasmid vector may also include a selectable marker such as the β-lactamase gene for ampicillin resistance, provided that the marker polypeptide does not adversely affect the metabolism of the organism being treated. The cassette also can be bound to a nucleic acid binding moiety in a synthetic delivery system, such as the system disclosed in PCT publication WO 95/22618.

Optionally, the DNA may be used with a microdelivery vehicle such as cationic liposomes and adenoviral vectors. (For a review of the procedures for liposome preparation, targeting and delivery of contents, see Mannino and Gould-Fogerite, *BioTechniques,* 6:682, 1988); Feigner and Holm, *Bethesda Res. Lab. Focus,* 11(2):21, 1989); and Maurer, *Bethesda Res. Lab. Focus,* 11(2):25, 1989). Replication-defective recombinant adenoviral vectors can be produced in accordance with known techniques. (See Quantin, et al., Proc. Natl. Acad. Sci. USA, 89:2581-2584, 1992; Stratford-Perricadet, et al., J. Clin. Invest., 90:626-630, 1992; and Rosenfeld, et al., Cell, 68:143-155, 1992).

The effective dose of the nucleic acid will be a function of the particular expressed protein, the target tissue, the subject, and his or her clinical condition. Effective amounts of DNA are between about 1 and 4000 µg, or about 1000 and 2000, or between about 2000 and 4000. In certain situations, it is desirable to use nucleic acids encoding two or more different proteins in order to optimize the therapeutic outcome. For example, DNA encoding a therapeutic peptide, such as a CD47 or TSP1 peptide (e.g., peptides IGWKDETAYRWRLS (SEQ ID NO: 6), biotin-IGWKDFTAYR (SEQ ID NO: 3), IGWKNFTAYR (SEQ ID NO: 4), IGWKDYTAYR (SEQ ID NO: 20), IGWKDFAAYR (SEQ ID NO: 5), Ac-WKDFTAYR (SEQ ID NO: 2)), can be used. Alternatively, DNA encoding a CD47 or TSP1 peptide can be combined with other genes or their encoded gene products to enhance the activity of targeted cells.

In order to facilitate injection, the nucleic acid is formulated with a pharmaceutically acceptable carrier. Examples of suitable carriers include, but are not limited to, saline, albumin, dextrose and sterile water. The nucleic acid is injected into the ischemic tissue using standard injection techniques by use of, for example, a hypodermic needle, for example a hypodermic needle size between No. 29 and No. 16. The nucleic acid also may be injected by an externally applied local injection apparatus, such as that used to inject antigens for allergy testing; or a transcutaneous patch capable of delivery to subcutaneous muscle. The nucleic acid is injected at one site, or at multiple sites throughout the ischemic tissue.

Once injected, the nucleic acid capable of expressing the desired angiogenic protein is taken up and expressed by the cells of the tissue. Because the vectors containing the nucleic acid of interest are not normally incorporated into the genome of the cells, expression of the protein of interest takes place for only a limited time. Typically, the angiogenic protein is only expressed in therapeutic levels for about two days to several weeks, preferably for about one to two weeks. Reinjection of the DNA can be utilized to provide additional periods of expression of the angiogenic protein. If desired, use of a retrovirus vector to incorporate the heterologous DNA into the genome of the cells will increase the length of time during which the therapeutic polypeptide is expressed, from several weeks to indefinitely.

The therapeutic agents can also be administered directly as part of a surgical procedure, or at the bedside by a treating physician. Drug quality product (e.g., peptide, antibody or morpholino) can be diluted for instance in sterile saline and given by injection using sterile 1 cc syringes and small bore needles (25 gauge and less) to ischemic soft tissue units. Alternatively, a wound bed can be irrigated for instance with a saline or other therapeutically effective solution containing a known concentration (dosage) of drug or compound, or a combination thereof. Precise control and localization of therapeutic effects can thus be obtained.

Controlled release parenteral formulations can be made as implants, oily injections, or as particulate systems. For a broad overview of protein delivery systems, see Banga, Therapeutic Peptides and Proteins: Formulation, Processing, and Delivery Systems, Technomic Publishing Company, Inc., Lancaster, Pa., 1995. Particulate systems include microspheres, microparticles, microcapsules, nanocapsules, nanospheres, and nanoparticles. Microcapsules contain the therapeutic peptide as a central core. In microspheres, the therapeutic agent is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly (see Kreuter, Colloidal Drug Delivery Systems, J. Kreuter, ed., Marcel Dekker, Inc., New York, N.Y., pp. 219-342, 1994; Tice & Tabibi, Treatise on Controlled Drug Delivery, A. Kydonieus, ed., Marcel Dekker, Inc. New York, N.Y., pp. 315-339, 1992).

Also contemplated is the use of nanoparticles as delivery agents, which can be targeted to specific cells, tissues or organ for instance by incorporation on their surface ligands of receptors specific in their expression to the targeted cells, tissues or organs, The targeting entity can be the same or different than the therapeutically active agent carried by the nanoparticle. Further, distribution of nanoparticles to certain tissues spaces (e.g. the blood versus the central nervous system protected by the blood-brain barrier) can be determined by altering the size of the nanoparticles thereby allowing or preventing their transit of such barriers between tissue compartments.

Polymers can be used for ion-controlled release. Various degradable and nondegradable polymeric matrices for use in controlled drug delivery are known in the art (Langer, Accounts Chem. Res. 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., Pharm. Res. 9:425, 1992; Pec, J. Parent. Sci. Tech. 44(2):58, 1990). Alternatively, hydroxyapatite has been used as a microcarrier for controlled release of proteins (Ijntema et al., Int. J. Pharm. 112:215, 1994). In yet another aspect, liposomes are used for controlled release as well as drug targeting of lipid-capsulated compounds (Betageri et al., Liposome Drug Delivery Systems, Technomic Publishing Co., Inc., Lancaster, Pa., 1993). Numerous additional systems for controlled delivery of therapeutic proteins are known (e.g., U.S. Pat. No. 5,055,303; U.S. Pat. No. 5,188,837; U.S. Pat. No. 4,235,871; U.S. Pat. No. 4,501,728; U.S. Pat. No. 4,837,028; U.S. Pat. No. 4,957,735; and U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254,342; and U.S. Pat. No. 5,534,496).

XI. Suppression of Protein Expression

In some embodiments, it is desirable to reduce or suppress TSP1 or CD47 protein expression, for example in various experimental conditions or in the treatment of an ischemic condition such as those exemplified herein.

Although the exact mechanism by which antisense RNA molecules interfere with gene expression has not been elucidated, it is believed that antisense RNA molecules bind to the endogenous mRNA molecules and thereby inhibit translation of the endogenous mRNA. A reduction of protein expression in a cell may be obtained by introducing into cells an antisense construct based on the TSP1 (or CD47) encoding sequence, including the human TSP1 cDNA or human CD47 cDNA or gene sequence or flanking regions thereof. For antisense suppression, a nucleotide sequence from a TSP1-encoding sequence, for example all or a portion of the TSP1 cDNA or gene, is arranged in reverse orientation relative to the promoter sequence in the transformation vector. One of ordinary skill in the art will understand how other aspects of the vector may be chosen.

The introduced sequence need not be the full length the cDNA or gene, or reverse complement thereof, and need not be exactly homologous to the equivalent sequence found in the cell type to be transformed. Generally, however, where the introduced sequence is of shorter length, a higher degree of homology to the native target sequence will be needed for effective antisense suppression. The introduced antisense sequence in the vector may be at least 20 nucleotides in length, and improved antisense suppression will typically be observed as the length of the antisense sequence increases. The length of the antisense sequence in the vector advantageously may be greater than about 30 nucleotides, or great than about 100 nucleotides. For suppression of the TSP1 gene itself, transcription of an antisense construct results in the production of RNA molecules that are the reverse complement of mRNA molecules transcribed from the endogenous TSP1 gene in the cell.

Suppression of endogenous TSP1 or CD47 expression can also be achieved using ribozymes. Ribozymes are synthetic molecules that possess highly specific endoribonuclease activity. The production and use of ribozymes are disclosed in U.S. Pat. No. 4,987,071 and U.S. Pat. No. 5,543,508. The inclusion of ribozyme sequences within antisense RNAs may be used to confer RNA cleaving activity on the antisense RNA, such that endogenous mRNA molecules that bind to the antisense RNA are cleaved, which in turn leads to an enhanced antisense inhibition of endogenous gene expression.

Suppression can also be achieved using RNA interference, using known and previously disclosed methods. Several models have been put forward to explain RNAi, in particular the mechanisms by which the cleavage derived small dsRNAs or siRNAs interact with the target mRNA and thus facilitate its degradation (Hamilton et al., *Science* 286, 950, 1999; Zamore et al., *Cell* 101, 25, 2000; Hammond et al., *Nature* 404, 293, 2000; Yang et al., *Curr. Biol.* 10, 1191, 2000; Elbashir et al., *Genes Dev.* 15, 188, 2001; Bass *Cell* 101, 235, 2000). It has been proposed that the cleavage derived small dsRNAs or siRNAs act as a guide for the enzymatic complex required for the sequence specific cleavage of the target mRNA. Evidence for this includes cleavage of the target mRNA at regular intervals of ~21-23 nts in the region corresponding to the input dsRNA (Zamore et al., *Cell* 101, 25, 2000), with the exact cleavage sites corresponding to the middle of sequences covered by individual 21- or 22 nt small dsRNAS or siRNAs (Elbashir et al., *Genes Dev.* 15, 188, 2001). Although mammals and lower organisms appear to share dsRNA-triggered responses that involve a related intermediate (small dsRNAs), it is likely that there will be differences as well as similarities in the underlying mechanism. dsRNAs can be formed from RNA oligomers produced synthetically (for technical details see material from the companies Xeragon and Dharmacon, both available on the internet). Small dsRNAs and siRNAs can also be manufactured using standard methods of in vitro RNA production. In addition, the Silencer™ siRNA Construction kit (and components thereof) available from Ambion (Catalog #1620; Austin, Tex.), which employs a T7 promoter and other well known genetic engineering techniques to produce dsRNAs. Double stranded RNA triggers could also be expressed from DNA based vector systems.

Inhibition also can be accomplished using morpholino oligonucleotides, as described herein. The herein described discoveries and therapeutics find immediate application through implanted devices in the management and treatment, for instance, of coronary artery and peripheral vascular disease. Implantation of vascular stents is routine in the treatment of peripheral vascular and coronary arterial disease. Morpholinos targeting CD47 or TSP1 can be incorporated into (or onto) such implanted stents for sustained local release directly to enhance vascular blood flow and prevent tissue death and heart attack. The therapeutic agents (morpholino, TSP1 antibody) could be then targeted specifically to areas of maximum benefit throughout the body including the carotid vascular network, the heart and other peripheral arterial networks. In more general applications, various implantable scaffolds or synthetics can serve the same means by allowing for controlled and extended release of the therapeutic agent. The agents could be incorporated into engineered tissue constructs and as such stimulate the growth of blood vessels into the construct and at the same time maximize blood flow to the same. The therapeutics would enhance blood flow and tissue healing in both the young and elderly and may greatly increase chronic wound healing. To this end the therapeutics can be incorporated directly into wound dressing and gels and applied directly to the wound surface. In localizing the therapeutic to the area needed we will essentially eliminate and potential negative side effects derived from the other nonspecific roles TSP1 and CD47 have.

XII. Screening for Agents that Affect TSP1/CD47 Activity and/or Interaction

In various embodiments, it may be useful to treat a subject with an ischemic or clotting condition with an agent that mimics or augments TSP1 or CD47 activity, or with an agent that inhibits a TSP1 or CD47 activity. Examples of such methods are described herein, along with example compounds and compositions useful in such methods. However, equivalents of the specifically described compounds are also useful in these methods. Thus, here described are methods for identifying agents with TSP1 or CD47 inhibitory activity, methods of identifying agents that interfere with an interaction between a TSP1 polypeptide and a CD47 polypeptide, and methods for the identification of agents that mimic TSP1's CD47-binding activity.

The compounds which may be screened in accordance with this disclosure include, but are not limited to peptides, antibodies and fragments thereof, and other organic compounds (for example, peptidomimetics, small molecules) that inhibit TSP1 and/or CD47 activity as described herein or interfere with an interaction between TSP1 and CD47. Such compounds may include, but are not limited to, peptides such as, for example, soluble peptides, including but not limited to members of random peptide libraries; (see, for example, Lam et al., *Nature,* 354:82-84, 1991; Houghten et al., *Nature,* 354:84-86, 1991), and combinatorial chemistry-derived molecular library made of D- and/or L-configuration amino acids, phosphopeptides (including, but not limited to, members of random or partially degenerate, directed phosphopeptide libraries; see, for example, Songyang et al., *Cell,* 72:767-778, 1993), antibodies (including, but not limited to, polyclonal, monoclonal, humanized, anti-idiotypic, chimeric or single chain antibodies, and Fab, F(ab')$_2$ and Fab expression library fragments, and epitope-binding fragments thereof), and small organic or inorganic molecules.

Other compounds which can be screened in accordance with this disclosure include but are not limited to small organic molecules that are able to gain entry into an appropriate cell and affect the expression of TSP1 gene or some other gene involved in a TSP1-mediated pathway (for example, by interacting with the regulatory region or transcription factors involved in TSP1 gene expression); or such compounds that affect an activity of a TSP1 isoform or the activity of some other intracellular factor involved in a TSP1-mediated pathway, such as CD47.

Computer modeling and searching technologies permit identification of compounds, or the improvement of already identified compounds that can modulate expression or activity of TSP1. Examples of molecular modeling systems are the CHARMM (Chemistry at HARvard Molecular Mechanics) and QUANTA programs (Polygen Corporation, Waltham, Mass.). CHARMM performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific-proteins, such as Rotivinen et al., *Acta Pharmaceutical Fennica* 97:159-166, 1988; Ripka, *New Scientist* 54-57, 1988; McKinaly and Rossmann, *Annu Rev Pharmacol Toxicol* 29:111-122, 1989; Perry and Davies, OSAR: *Quantitative Structure-Activity Relationships in Drug Design pp.* 189-193, 1989, (Alan R. Liss, Inc.); Lewis and Dean, *Proc R Soc Lond* 236:125-140 and 141-162, 1989; and, with respect to a model receptor for nucleic acid components, Askew et al., *J Am Chem Soc* 111:1082-1090, 1989. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to regions of DNA or RNA, once that region is identified.

Screening for TSP1 (or CD47) Inhibitory Agents

Disclosed herein are methods of identifying agents with potential for inhibition of TSP1 or CD47, and particularly the activity of either of these proteins in influencing tissue survival to ischemia, platelet function, or tissue response to aging. Any agent capable of inhibiting (to a measurable degree) at least one biological activity of TSP1 or CD47 is contemplated. In some embodiments, a TSP1 (or CD47) inhibitory agent interferes with an interaction between TSP1 and CD47, which is discussed below.

Screening assays may be conducted in a variety of ways. For example, one method would involve transiently transfecting CD47-expressing cells with expression vector encoding sGC and a suitable cGMP-inducible reporter plasmid and screening for, inhibitory agents that either directly regulate reporter activity in the absence or presence of nitric oxide or prevent exogenous TSP1 from inhibiting a nitric oxide signal. Any eukaryotic cells or cell line may be used for transfections, such as 293T, NIH373, Wehi 7.2, 293F, or Cos7 cell lines. In one embodiment, vascular cells may be transfected with an the two expression vectors and an EGFP vector, in which case transfectants could be identified by EGFP fluorescence and, optionally, could be separated or analyzed by fluorescence activated cell sorting (FACS; also called flow cytometry). Test compounds would be applied to the transfected cells and cGMP-dependent reporter activity evaluated using an assay. TSP1 inhibitory compounds would be identified by a decrease in cGMP-dependent reporter activity, as compared to control. Animal models, for instance based on transgenic animals such as transgenic mice, are also contemplated.

Screening for Compounds that Affect TSP1/CD47 Interaction

In vitro systems may be designed to identify compounds capable of affecting an interaction between TSP1 and CD47. Compounds identified may be useful, for example, in modulating an activity of TSP1 or CD47, or increasing or decreasing a binding affinity between TSP1 and CD47, thereby treating an ischemic or other described condition.

Representative assays used to identify compounds that affect an interaction between TSP1 and CD47 involves preparing a reaction mixture of a TSP1 polypeptide, fragment, or functional variant and a CD47 polypeptide, fragment, or functional variant under conditions and for a time sufficient to allow the two components to interact and form a complex. Thereafter, a test compound is added to the reaction mixture and various means are used to determine if the TSP1/CD47 complex is affected by the test compound. Alternatively, the two components are brought into contact in the presence of as test compound, and the impact of that compound is determined compared to a mixture without the test compound.

Screening assays can be conducted in a variety of ways. For example, one method to conduct such an assay would involve anchoring a TSP1 polypeptide, peptide, or fusion protein onto a solid surface or a soluble support, adding a CD47 polypeptide, peptide, or fusion protein to the reaction vessel, and adding the test substance and detecting TSP1/CD47 complexes anchored on the solid phase or soluble support at the end of the reaction. In one embodiment of such a method, TSP1 may be anchored onto a solid surface, and the CD47 component, which is not anchored, may be labeled, either directly or indirectly. It will be clear that the reverse system (anchored CD47, free and labeled TSP1) is also contemplated.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein (or peptide or variant) to be immobilized may be used to anchor the protein to the solid surface. The surfaces may be prepared in advance and stored.

In order to conduct the assay, the non-immobilized component and test compound are added to the coated surface containing the anchored component. After the reaction is complete, unreacted components are removed (for example, by washing) under conditions such that any TSP1/CD47 complexes formed (or a substantial portion thereof) will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; for example, using a labeled antibody specific for the previously non-immobilized component (the antibody, in turn, may be directly labeled or indirectly labeled with a labeled anti-Ig antibody).

Alternatively, the solid phase can be a bead composed of a material such as latex (either fluorescent or not), such that beads coated with a component of TSP1 or CD47 can be interacted with cells expressing either CD47 components or cell anchored TSP1 components. Such interaction is conveniently assayed by flow cytometric (FACS) analysis.

Alternatively, a screening reaction can be conducted in a liquid phase, the reaction products separated from unreacted components, and complexes detected; for example, using an immobilized antibody specific for a TSP1 protein, polypeptide, peptide, or fusion protein or a CD47 protein, polypeptide, peptide, or fusion protein to anchor any complexes formed in solution, and a labeled antibody specific for the other component of the possible complex to detect anchored complexes.

Screening for Mimics or Enhancing Agents

Other methods contemplated herein include identifying agents that mimic or enhance TSP1 (or CD47) activity, for example to increase its activity in altering survival in ischemia, or influencing platelet function and/or blood clotting.

Agents that mimic or enhance activity can include, for example, agents that induce or increase TSP1 expression (or CD47 expression) in one or more cells; or agents that interact with TSP1 (or CD47) and enhance its activity; or TSP1 (or CD47) peptides having a desired activity; or molecules designed to have a TSP1 (or CD47) structure that mediates a particular activity.

In some embodiments, agents that induce or increase TSP1 or CD47 expression in one or more cells may be identified by contacting a biological system (such as a cell) that expresses or is capable of expressing that protein with an agent. Protein expression or activity in the biological system (e.g., expression or activity of TSP1 or CD47, or both) may be measured in response to contact with the agent by methods well known in the art. For instance, trans-acting coactivators of the TSP1 gene regulatory region may be expected to increase TSP1 activity. In other embodiments, agents may increase the half-life of the TSP1 protein or its mRNA and thereby increase TSP1 activity.

In other embodiments, agents that interact with TSP1 (or CD47) and enhance its activity in at least one of the described systems are contemplated. These agents may be identified, for example, by first identifying agents that interact with TSP1 or CD47. Biophysical methods of accomplishing this step are well known in the art and include, for example, co-immunoprecipitation, yeast two-hybrid system, and GST pulldown assay, cross-linking of small molecules to the target protein, among other methods. Agents that interact with TSP1 (or CD47) are then screened for enhancement of the desired biological or biochemical activity. In some embodiments, TSP1 activity may be increased by agents that enhance an interaction between TSP1 and CD47.

In other embodiments, molecules can be designed to have a TSP1-like or CD47-like structure that mediates a particular activity using modeling analyses. Candidate agents designed, for example in silico, to assume a selected structure may then be screened for desired biological activity, for example binding to TSP1 (or CD47, respectively), or increasing activity in a biological system. Agents with such activity may then be used to influence ischemia, alter blood clotting, or otherwise influence one or more of the systems described herein.

XIII. Increasing Blood Flow and Tissue Healing in the Elderly

Also provided herein are methods for the treatment of elderly subjects using agents that affect TSP1 and/or CD47.

People over the age of 65 represent the fastest growing segment of the United States population and are estimated to comprise 20% of the country's population by 2030. Complications from peripheral vascular disease including coronary artery disease and myocardial infarction, stroke and ischemic vascular disease affect some 80% of people over the age of 65. Age is a recognized risk factor for complications following surgical procedures, including delayed and incomplete wound healing and tissue loss, and accounts for significant morbidity and mortality in this group (Gohel et al., *Eur J Vasc Endovasc Surg.* 29(1):74-77, 2005; Gosain et al., *World J. Surg.* 28(3):321-326, 2004; Brem et al. *Surg Technol Int.* 11:161-167, 2003; Crooks *J Wound Care.* 14(5):222-223, 2005). The elderly have significant alterations in vascular anatomy including loss of vascular networks and capillary loops (Lamah et al., *Int J Microcirc Clin Exp.* 16(5):271-276, 1996) and alterations in vascular response to injury (Ryan, *Micron.* 35(3):161-171, 2004). Animal studies have confirmed the impact of ageing upon wound healing (Ashcroft et al., *Biogerontology.* 3(6):337-345, 2002). Blood flow and wound healing are delayed from 20 to 60% in aged animals compared to young animals (Ashcroft et al., *J Anat.* 187 (Pt 1):1-26, 1995; Kivirikko et al., *Med. Biol.* 54(3):159-186, 1976). Capillary growth rates decline in older animals. These changes have been associated with altered levels of growth factors production in response to injury in older animals (Wagatsuma, *Exp Gerontol.* 41(1):49-54, 2006). Stimulated macrophages from old animals produce less vascular endothelial growth factor (VEGF), and VEGF treatment in aged animals has less impact on tissue perfusion (Yu et al., *Faseb J.* 20(3):479-48, 2006). The body depends upon adequate blood flow. At the same time, vascular response to growth factors is muted in aged animals. Additionally, aged animals demonstrate alterations in immune responses (Brown, *J Wound Care.* 13(3):94-96, 2004) and the ability of vessels to respond to stress is decreased.

Tissue perfusion is regulated through the control of blood vessel diameter, which itself level of organs and tissue, blood flow is controlled by the contractile state of vascular smooth muscle cells (VSMC). Though a number of factors can impact VSMC contractility and vessel size, nitric oxide (NO) is a primary and ubiquitous dilator of blood vessels (Ignarro, *J Physiol Pharmacol.* 53(4 Pt 1):503-514, 2002). Nitric oxide is constitutively produced by blood vessels by the enzyme endothelial nitric oxide synthase (eNOS). NO activates soluble guanylate cyclase (sGC) leading to cGMP production and GMP-dependent protein kinas activation, which ultimately prevents phosphorylation of the contractile protein myosin light chain 2 (MLC2) in VMSC, preventing cell contraction (Murad, *Adv Pharmacol.* 26:1-5, 1994). In aged vascular cells (Bernardini et al., *Biochim Biophys Acta.* 1745: 265-272, 2005), animals and people, both eNOS expression (Woodman et al., *J Appl Physiol.* 95(5):2164-2170, 2003) and NO production (Qian et al., *J Cardiovasc Pharmacol.* 47(4): 587-593, 2006) are decreased. These cells line every blood vessel of the body. The contraction of these cells determines the amount of blood that flow through a certain vessel and on to organs and tissues. The contraction (and relaxation) of vascular smooth muscle cells is in turn controlled by the bioactive gas nitric oxide (NO) which is constantly produced by blood vessels. NO causes blood vessels to dilate and increases blood flow to tissues and organs. Disruption of this process leads to significant diseases, morbidity and mortality including peripheral vascular disease, ischemic heart disease, stroke and diabetes. Additionally, lack of blood flow causes tissue death and wound healing problems both during and after surgery.

There are many complications that occur in elderly subjects resulting from decreased tissue perfusion. Acute loss of blood flow can occur secondary to accidental or elective trauma (surgery), as a consequence of acute vascular obstruction and clotting both alone and in combination with diffuse peripheral vascular disease or as the end results of progressive but chronic vascular disease. Thus, there is a need for methods to increase tissue perfusion for treatment of ischemia, atherosclerosis, wound healing and other conditions relating to reduced blood flow in these subjects. The therapeutic benefits obtained by the discoveries described herein will have multiple applications in the elderly for both acute and chronic alterations in blood flow. Immediate benefits under conditions of acute blood loss would be both local/regional and systemic.

The elderly are particularly vulnerable to stress and have decreased reserve capacity. Hence, what might be a small area of tissue loss associated with decreased blood flow in a young person can lead to tremendous tissue/organ death in the elderly. Any agent that minimizes or prevents blood loss will have substantial benefit acutely. Long term benefits of maximizing NO-effects on blood vessel health and blood flow will include a decrease in chronic tissue ischemia associated with peripheral vascular disease, tissue preservation, enhanced energy and exercise capacity and increased responses of other vital organs.

Provided herein are methods for the treatment of elderly subjects using agents that affect TSP1 and CD47, in order to affect tissue perfusion. Included are the use of therapeutic compounds and compositions that block TSP1 action via CD47 either exclusively or in combination with other identified or yet to be identified receptors for TSP1 that may augment and/or focus the effect of TSP1 in certain tissues or to certain purposes. Such compounds and compositions thereby increase tissue survival to ischemia in the elderly subject. Specific examples of compounds of use in these methods include anti-CD47 antibodies (or binding fragments thereof), including but not limited to the following: Ab miap301 (Chang et al., *Neuroscience* 102(2):289-296, 2001; commercially available for instance from RDI Division of Fitzgerald Industries Intl., as catalog number RDI-MCD47-301); Ab B6H12, Ab 2D3, Ab 1F7, Ab 3G3, Ab 2E11, or Ab 2B7 (described in Gresham et al., *J. Cell Biol.* 108:1935-1943, 1989, and Brown et al., *J. Cell Biol.* 111:2785-2794, 1990, for instance), Ab 3E9 (Weerasighe et al., *J. Cell Biol.*, 142(2): 595-607, 1998), Ab 10G2 (Hermann et al., *J. Cell Biol.*, 144(4): 767-775, 1999), Ab C1KM1 (Barazi et al., *J. Biol. Chem.*, 277(45):42859-42866, 2002), Ab 1G11 (Fleming et al. *J Pathol* 161:189, 1990), Ab Ad22 (Lamy et al., *J. Biol. Chem.*, 278(26):23915-23921, 2003; Pettersen et al., *Tissue Antigens* 45:203, 1995) (all mouse anti-human CD47); and additional anti-CD47 or anti-TSP1 antibodies that have similar effect on the interaction between CD47 and TSP1, as well as morpholinos (e.g., CD47 or TSP1 morpholinos), and peptides derived from CD47 or TSP1.

Also of use in the disclosed methods is a peptide comprising the amino acid sequence HIGWKDFTAYRWRLS (SEQ ID NO: 7), or comprising at least the amino acid sequence IGWKDFTAYR contained therein (SEQ ID NO: 1), or comprising an amino acid sequence derived therefrom that inhibits ligand binding to CD47, or another peptide recited herein, or an equivalent thereof. Also of use in the disclosed methods are pharmaceutical compositions that contain such peptides or one or more derivatives thereof formulated to improve stability and/or bioavailability of the peptide.

Also of use in the disclosed methods are oligonucleotides comprising at least about 20 contiguous nucleotides that hybridize to the mRNA of CD47 (e.g., accession number NM 001777 *Homo sapiens* CD47 mRNA) under high stringency conditions. In certain embodiments, the oligonucleotide is a morpholino. Yet another embodiment is the use of a pharmaceutical composition comprising an antisense oligonucleotide of at least 20 contiguous nucleotides complementary to human CD47 mRNA, and a suitable delivery vehicle, which composition limits tissue expression of CD47. By way of example, the antisense oligonucleotide in some cases is a morpholino. For instance, in some embodiments, the methods include the use of a morpholino comprising an antisense oligonucleotide to CD47 having the sequence CGTCACAG-GCAGGACCCACTGCCCA (SEQ ID NO: 21), or another sequence from CD47 or a sequence from TSP1. Other oligonucleotides are also of use in the disclosed methods.

Also provided is a method to improve tissue survival during integument and soft tissue and composite tissue surgery in an elderly subject, the method comprising one or more of: decreasing CD47 expression in the tissue; inhibiting ligand binding to CD47 in the tissue using a peptide or small molecule inhibitor, or decreasing ligand binding to CD47 in tissue using an antibody that specifically binds CD47. Another provided method is a method to prevent or reduce ischemic tissue damage or necrosis in an elderly subject, which method comprises any one or more of: decreasing CD47 expression in the tissue; inhibiting ligand binding to CD47 in the tissue using a peptide or small molecule inhibitor of CD47; and inhibiting ligand binding to CD47 in tissue using an antibody that specifically binds CD47. Additional methods include a method to increase skin graft survival in an elderly subject, which comprises decreasing CD47 expression in the graft and/or inhibiting ligand binding to CD47 in the tissue. There are also provides in various embodiments methods of use of antibodies and peptides, for instance antibodies (such as monoclonal antibodies, and humanized antibodies) to CD47 and peptides derived from CD47. For instance, there is provided use of an antibody to CD47 or a peptide derived from CD47 to prevent or reduce tissue necrosis and/or to increase skin graft survival and/or improve organ transplant success in elderly subjects. Also provided is use of an isolated CD47 molecule, or molecule that binds thereto, to influence blood vessel flow and alter tissue perfusion in the elderly subject.

Additionally, included the use of agents that block the action of TSP1 directly, such as with monoclonal antibodies, for example clone A6.1, and other antibodies which block the action of TSP1 on CD47 and thus increase tissue blood vessel diameter, blood flow and tissue perfusion.

Yet another embodiment is a method comprising selective application to an elderly subject of one or more agents that inhibit function or expression of CD47, which method: improves tissue or organ survival in the elderly subject; treats or ameliorates peripheral vascular disease or myocardial ischemia in the elderly subject; improves blood flow in the elderly subject; improves transplant organ or tissue survival in the elderly subject; and/or improves skin graft survival in the elderly subject. Without limitation, the elderly subject to whom such a method is applied may be a subject suffering from one or more diseases or conditions that have as a component or side effect a defect in circulation or vascular regulation or ischemia. For instance, in some examples the subject has diabetes, a vasculopathy, peripheral vascular disease, atherosclerotic vascular disease and/or other chronic vascular pathology (e.g., associated with macular degeneration), or is undergoing tissue or organ grafting or transplantation, or has suffered an injury, cardiac arrest or stroke or other event resulting in ischemia. The subject can also have a condition associated with advanced age, such as dementia, Alzheimer's disease, a stroke, or another condition wherein increased tissue perfusion would result in alleviating a symptom of the condition.

XIV. Influencing Blood Clotting

Results presented herein demonstrate that peptides based on the sequences of C6d, including C6b (SEQ ID NO: 7) and other peptides described herein, can promote platelet aggregation and blood clotting. These peptides and similar peptides can be used to stop bleeding from congenital bleeding disorders and acquired bleeding disorders. The will also be effective as topically applied hemostatic agents and may be used directly or incorporated into wound dressings and bandages for use in emergency situations and in treating victims of trauma. They can be used in the operating room to achieve bleeding control from large wound surfaces such as found during burn or liver surgery. The provided compositions also are useful in the control or modulation of thrombocytopenia and congenital bleeding disorders.

Being amenable to direct topical application these agents function as topical hemostatic therapies. As such they avoid systemic side effects and maximize therapeutic benefits. Such agents can be applied as sprays, ointments or in sustained release forms that are part of the dressings and bandages placed on the bleeding wound or tissue site. They would especially beneficial under emergency conditions both civilian and military. They would also be useful for individuals with congenital or acquired bleeding disorders. Local applications may also reduce blood loss during elective surgical procedures in which hemorrhage is usually extensive.

Such therapeutics also are useful beyond trauma wounds, for instance in cases in which a subject has been extensively anti-coagulated as immediately after a heart attack, and then must undergo a surgical procedure such as an angioplasty, bypass surgery, or perhaps other surgery unrelated to the heart attack, as a victim of trauma (car accident, etc) that has a heart attack coincident with the trauma. To prevent excessive bleeding, the patient can be treated with a coagulant peptide or its analogs locally or systemically to promote clotting thus avoiding life threatening hemorrhage.

The following examples are provided to illustrate certain particular features and/or embodiments. These examples should not be construed to limit the invention to the particular features or embodiments described.

EXAMPLES

Example 1

CD47 is Necessary in Inhibition of Nitric Oxide-Stimulated Vascular Cell Responses by Thrombospondin-1

The anti-angiogenic activity of TSP1 is dramatically potentiated in the presence of low concentrations of nitric oxide (NO) donors. This activity is mediated at least in part through inhibition by TSP1 of cGMP signaling via NO-mediated activation of soluble guanylyl cyclase in both endothelial cells and VSMC. Moreover, TSP1 null vascular cells exhibit elevated basal cGMP levels and enhanced cGMP and phenotypic responses to exogenous NO. The inhibitory activity of TSP1 on NO signaling was replicated by an agonist CD36 antibody and by a recombinant CD36-binding region of TSP1. This example demonstrates that a second TSP1 receptor, CD47, plays the primary role in mediating the inhibitory activities of TSP1 for vascular cells. Remarkably, CD47 is also necessary for inhibition of NO signaling by CD36 ligands. At least portions of this example were published in Isenberg et al., *J. Biol. Chem.* 281(36):26069-26080, 2006.

Materials and Methods

Cells and Reagents

Human umbilical vein endothelial cells (HUVEC, Cambrex, Walkersville, Md.) were maintained in endothelial cell growth medium (Cambrex) with 5% FCS in 5% $CO_2$ at 37° C. Cells were utilized at passages 4-8. Purity of cultures was monitored by immunochemical staining with monoclonal human anti-CD31 antibody and monoclonal anti-α smooth muscle actin from Sigma (St. Louis, Mo.). Human aortic smooth muscle cells (HASMC) (Cambrex) were maintained in smooth muscle cell growth medium with the manufacturer's additives (SM-GM, Clonetics) and 5% fetal calf serum (FCS) in 5% $CO_2$ at 37° C. Cells utilized were within passages 4 through 9. Purity of primary cultures was monitored by immunochemical staining with monoclonal human anti-CD31 antibody and a smooth muscle actin (Sigma). DEA/NO and DETA/NO were kindly provided by Dr. Larry Keefer (National Cancer Institute, Frederick). TSP1 was prepared from human platelets obtained from the NIH blood bank as previously described (Roberts et al., *J Tissue Cult Methods* 16:217-222, 1994). Recombinant proteins expressed in insect cells containing the N-terminal domains (NoC1), type 1 repeats (3TSR), or C-terminal regions of TSP1 (E3CaG1) were generously provided by Dr. Deane Mosher (University of Wisconsin) and Dr. Jack Lawler, Harvard Medical School (Misenheimer et al., *J Biol Chem* 275:40938-40945, 2000; Tan et al., *J Cell Biol* 159:373-382, 2002). The recombinant C-terminal cell-binding domain (CBD) was prepared as previously described (McDonald et al., *Biochemistry* 42:10001-10011, 2003). Murine anti-human CD36 antibody (clone SMΦ) was purchased from Chemicon International (Temecula, Calif.). CD36 antibody clone FA6-152 was purchased from Immunotech (Beckman Coulter). CD36 antibody clone 185-1G2 was purchased from Neomarkers (Fremont, Calif.). Anti-cyclin D1 ($IgG_1$) and estrogen receptor-α ($IgG_{2a}$) monoclonal antibodies were purchased from Santa Cruz Biotechnology (Santa Cruz, Calif.). Anti-HSP-60 monoclonal antibody (IgM) was purchased from Affinity Bioreagents Inc. (Golden, Colo.). Anti-CD47 antibody (clone CIKm1) was from ICN (Costa Mesa, Calif.). Type I collagen (Vitrogen) was from Cohesion Technologies (Palo Alto, Calif.). Peptides 246 (KRFKQDGGWSHWSPWSS; SEQ ID NO: 8), 245 (VTCGGGVQKRSRL; SEQ ID NO: 9), 7N3 (FIRVVMYEGKK; SEQ ID NO: 10), 4N1-1 (RFYVVMWK; SEQ ID NO: 14) and 761 (RFYGGMWK; SEQ ID NO: 15) were prepared as described (Barazi et al., *J Biol Chem* 277:42859-42866, 2002). Peptides 906 (VTAGGGVQKRSRL; SEQ ID NO: 18) and 907 (GDGV(D-I)TRIR; SEQ ID NO: 19) were prepared by Peptides International (Louisville, Ky.). B6H12 (anti-CD47) (American Type Culture Collection HB-9771) was purified by protein G affinity chromatography (Pierce) from conditioned media of the respective hybridoma.

Murine Cell Cultures

Murine ASMC were obtained from aortic segments harvested sterilely from C57B1/6 CD47 null or CD36 null mice as described (Ray et al., *Methods Cell Sci* 23:185-188, 2001) and cultured in SM-GM (Cambrex)+20% FCS. In the case of CD36 null cells, culture flasks were pre-coated with 1% gelatin prior to cell plating. Wild type C57B1/6 ASMC cultures were prepared as previously described (Isenberg et al., *Matrix Biol* 24:110-123, 2005). Cell culture purity was determined by immunohistochemistry staining for α-smooth muscle actin. Cells were used within passage 1 to 4 to minimize overgrowth of other cell types.

Animals

C57B1/6 WT and TSP1 null (Lawler et al., *J Clin Invest* 101:982-992, 1998) CD47 null (Lindberg et al., *Science* 274: 795-798, 1996) and CD36 null mice (Moore et al., *J Biol Chem* 277:47373-47379, 2002) were all extensively backcrossed on the C57B1/6 background and were housed in a pathogen free environment. Handling and care of animals was in compliance with the guidelines established by the Animal Care and Use Committees of the National Cancer Institute and of Washington University School of Medicine.

Explant Invasion Assay

Muscle biopsies from the pectoralis major muscle of 8 to 12 week old wild type or transgenic mice were harvested and explanted into 100 µl of type I collagen gel in 96-well tissue culture plates as described (Isenberg et al., Matrix Biol 24:110-123, 2005). Following gelation, the embedded explants were overlayed with 75 µl of EGM+2% FCS in the presence or absence of a dose range of DETA/NO (0.01-1000 µM) and other indicated treatments and then incubated at 37° C. and 5% $CO_2$ for 7 days, at which time maximum vascular cell migration through the matrix was measured.

Cell Proliferation

Proliferation of vascular cells was measured with a non-radioactive colorimetric assay (CellTiter 96, Promega, Madison, Wis.). Briefly, to each well of a 96-well culture plate (Nunc, Denmark) $5 \times 10^3$ cells were suspended in 100 µl of culture medium with indicated treatments and incubated for 72 hours at 37° C. in a 5% $CO_2$ atmosphere. Following incubation 20 µl of tetrazolium compound/solubilization agent was added and incubation continued for 4 hours under the same conditions. The plate was then read on a MR580 Microelisa Auto Reader (Dynatech) at a wavelength of 490 nm. Appropriate zero time controls were run for all assays and the optical density readings obtained then subtracted from those obtained at 72 hours.

Cell Adhesion Assay

Cell adhesion was carried out in 96-well culture plates. After pre-coating wells with type I collagen (3 µg/ml in DPBS) harvested cells were plated at a density of $1 \times 10^4$ cells/well in medium plus 0.1% BSA and treatment agents and incubated in 5% $CO_2$ for 1 h. Wells were washed with PBS and cells fixed with 1% glutaraldehyde for 10 min., washed and stained with 1% crystal violet for 20 min. Excess stain was rinsed away, adherent cells treated with 10% acetic acid, and plates read at 570 nm.

Intracellular cGMP Measurement

HUVEC ($10^4$ cells/well) grown overnight in 96-well culture plates containing full growth medium with 2% FCS and weaned in growth medium without additives and 1% FCS over 24 hrs before treatment with NO donors and other agents in SM-GM without additives+0.1% BSA. Intracellular cGMP levels were determined according to the manufacturer's instructions using an enzyme immunoassay kit (Amersham Biosciences). In other experiments ASMC from wild type and CD36 or CD47 null mice were plated onto 96-well culture plates and incubated overnight in full growth medium. They were then weaned off serum as described to SM-GM+ 0.1% BSA and treated with NO donor and other agents as indicated. Intracellular cyclic nucleotides were determined via immunoassay.

Statistics

All studies were repeated in triplicate and results presented as the mean±SD, with analysis of significance done using the Student's t test and a p<0.05 taken as significant.

Results

Peptide Ligands of Three TSP1 Receptors Inhibit Explant Angiogenic Responses

As previously reported (Isenberg et al., Proc Natl Acad Sci USA 102:13141-13146, 2005), sustained exposure to exogenous NO released by the donor DETA/NO stimulated vascular outgrowth from muscle explants in 3D collagen cultures to a greater extent in those from TSP1 null when compared to WT mice (FIG. 2A controls). Consistent with their reported affects on endothelial cells in vitro and angiogenesis in vivo (Iruela-Arispe et al., Circulation 100:1423-1431, 1999; Kanda et al., Exp Cell Res 252:262-272, 1999), a CD36-binding peptide from the third type 1 repeat of TSP1 (p245, VTCGGGVQKRSRL; SEQ ID NO: 9), a CD47 binding peptide from the C-terminal module of TSP1 (p7N3, FIRVVMY-EGKK; SEQ ID NO: 10), and to a lesser extent a heparin- and TGFβ-binding peptide from the second type 1 repeat (p246, KRFKQDGGWSHWSPWSS; SEQ ID NO: 8) inhibited vascular cell outgrowth from both wild type and TSP1 null explants stimulated by NO (FIG. 2). Conversely, the described pro-angiogenic activities of the N-terminal region of TSP1 (Calzada et al., Circ Res 94:462-470, 2004; Chandrasekaran et al., Mol Biol Cell 11:2885-2900, 2000) were reflected by enhanced vascular outgrowth from explants in the presence of recombinant NoC1. Assuming that these peptides act as agonists of their respective receptors, this indicates that ligating CD36, heparin sulfate proteoglycans, or CD47 is sufficient to inhibit NO-stimulated vascular outgrowth, whereas ligating $β_1$ integrins or other TSP1 N-module receptors enhances vascular outgrowth under the same conditions.

Figure 3:
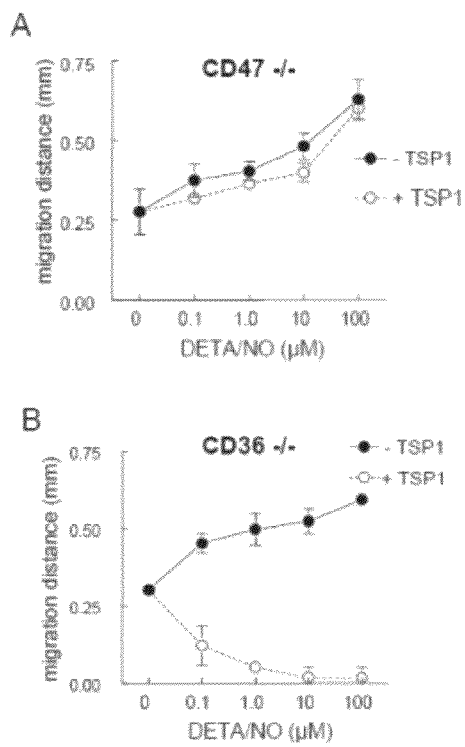
FIG. 3A-3B. CD47 but not CD36 is necessary for TSP1 inhibition of ex vivo angiogenesis.

CD47 but not CD36 is Necessary for Inhibition by TSP1 of Explant Angiogenic Responses Although the former data show that ligating CD36 or CD47 is sufficient to inhibit explant angiogenesis stimulated by NO, they do not prove that the respective receptors are necessary for activities of the peptide ligands or of intact TSP1. Furthermore, although these peptides clearly bind to the indicated receptors, structural studies have raised concerns that VVM peptides may not represent the true CD47 binding site in the C-terminal domain of TSP1 (Kvansakul et al., Embo J 23:1223-1233, 2004). To directly address the roles of CD36 and CD47 in the inhibitory activity of TSP1, muscle explants from mice lacking the respective receptors were placed into 3D collagen cultures (FIG. 3). Similar to wild type explants, NO dose-dependently stimulated vascular outgrowth in CD36- or CD47-null explants. Remarkably, the ability of exogenous TSP1 to antagonize this response was preserved in CD36-null explants (FIG. 3B) but lost in CD47-null explants (FIG. 3A). Thus, CD47 is necessary for the anti-angiogenic activity of TSP1 in this assay, but CD36 is not. This result was unexpected given that a recombinant CD36-binding domain of TSP1 (3TSR) and a CD36 antibody (SM4) described to be an agonist based on its ability to mimic TSP1 (Dawson et al., J Cell Biol 138:707-717, 1997)) were shown previously to inhibit endothelial cell adhesion on type I collagen stimulated by acute NO exposure (Isenberg et al., Proc Natl Acad Sci USA 102:13141-13146, 2005). This prompted us to reexamine the role of CD36 in this activity of TSP1. CD36 ligation is sufficient but not necessary for inhibition of NO responses by TSP1

Figure 4:
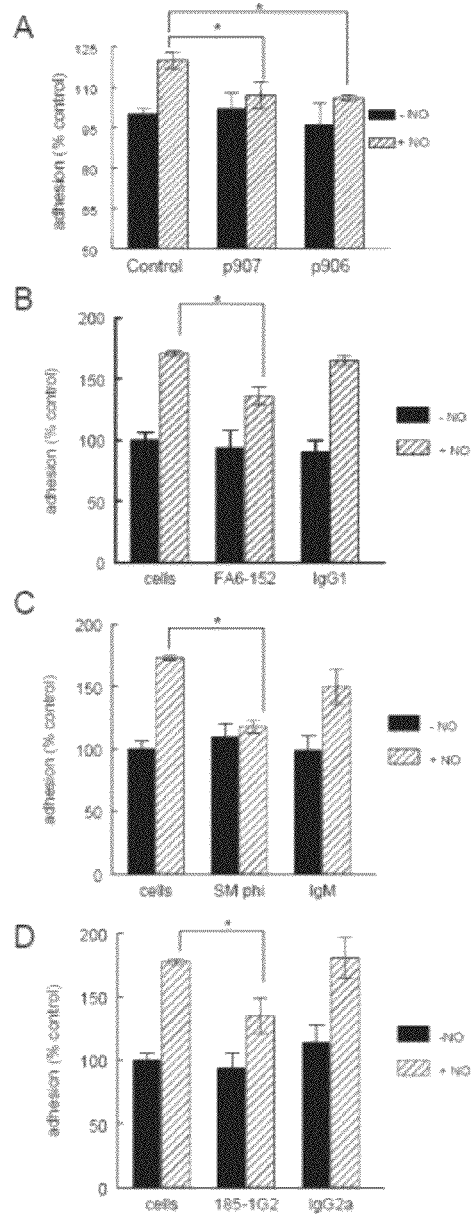
FIG. 4A-4D. Agonist or antagonist antibody ligation of CD36 inhibits NO-driven endothelial cell adhesion.

A CD36-binding peptide derived from the third type 1 repeat (p906, VTAGGGVQKRSRL; SEQ ID NO: 18) and a derivative of the second type 1 repeat with enhanced CD36-binding and anti-angiogenic activity (p907, GDGV(D-I)TRIR; SEQ ID NO: 19; Dawson et al., Mol Pharmacol 55:332-338, 1999) similarly inhibited NO-stimulated endothelial cell adhesion (FIG. 4A). As previously reported, the CD36 agonist antibody SMΦ inhibited NO-stimulated cell adhesion, whereas a control IgM was inactive (FIG. 4C). However, two CD36 antibodies that were reported to antagonize inhibition by TSP1, FA6-152 (Dawson et al., J Cell Biol 138:707-717, 1997) and 185-1G2 (Short et al., J Cell Biol 168:643-653, 2005) also inhibited NO-stimulated adhesion (FIGS. 4B and 4D). Isotype-matched control antibodies did not inhibit NO stimulated cell adhesion, demonstrating the specificity of these CD36 antibodies for blocking an NO response. Thus, various CD36 ligands are sufficient to inhibit NO-stimulated endothelial cell responses, but their mechanism of action may differ from the previously described TSP1 responses that were antagonized by the CD36 antibody FA6-152 (Dawson et al., *J Cell Biol* 138:707-717, 1997).

Figure 5:
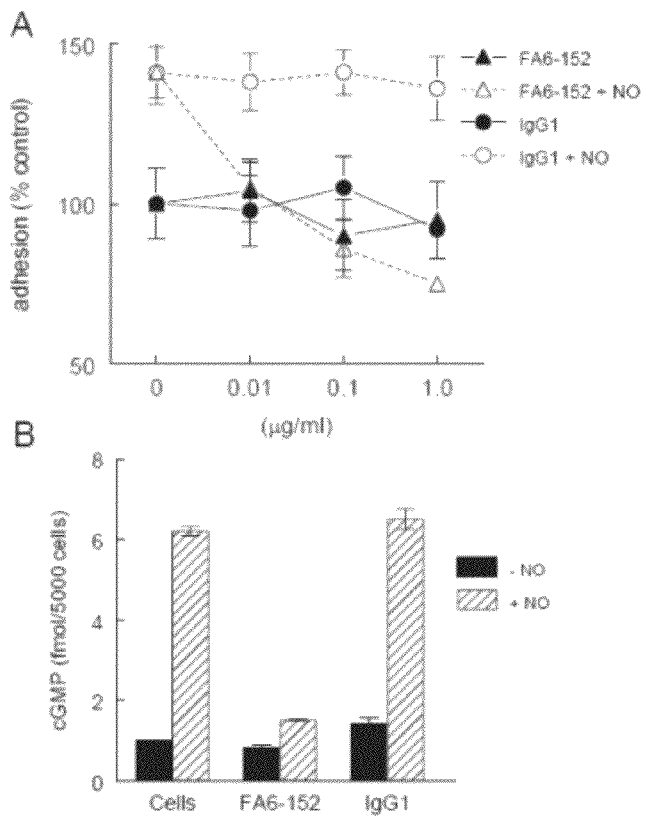
FIG. 5A-5B. Antagonist CD36 ligation inhibits HASMC NO signaling.

Antagonism of NO signaling by TSP1 is conserved in VSMC (Isenberg et al., *Cardiovasc Res* 71(4):785-793, 2006). Consistent with the data for endothelial cells in FIG. 4, the CD36 antagonist antibodies FA6-152 and 185-1G2 but not isotype-matched control antibodies were dose-dependent inhibitors of NO-stimulated HASMC adhesion (FIG. 5A). The FA6-152 antibody also prevented NO-induced accumulation of cGMP in HASMC (FIG. 5B), consistent with its effects on NO-stimulated adhesion but not with its reported activity as a TSP1 antagonist (Dawson et al., *J Cell Biol* 138:707-717, 1997; Jimenez et al., *Nat Med* 6:41-48, 2000). Therefore, inhibition of NO signaling by CD36 ligation is conserved in both types of vascular cells but is independent of the ability of CD36 ligands to mimic or inhibit TSP1 activity in other angiogenesis assays.

Figure 6:
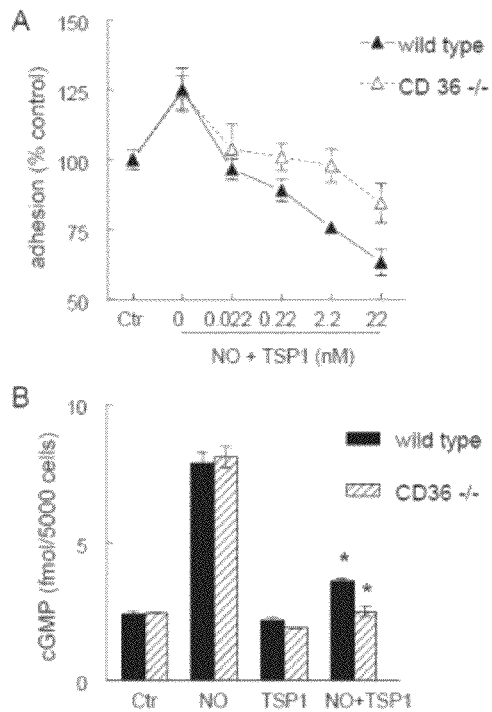
FIG. 6A-6B. CD36 is not necessary for TSP1 inhibition of NO-stimulated vascular cell adhesion and cGMP accumulation.

To clarify the role of CD36 in inhibition by TSP1 of NO-stimulated responses, we used MASMC derived from WT and CD36 null mice (FIG. 6). Low dose NO significantly stimulated adhesion of WT MASMC on type I collagen, and TSP1 at 22 μM inhibited this response to control levels (FIG. 6A). Higher doses of TSP1 further inhibited adhesion below baseline. Remarkably, 22 μM TSP1 inhibited NO-stimulated adhesion of CD36 null MASMC to the same extent as in WT cells. Although higher concentrations of TSP1 further suppressed NO-induced adhesion of WT cells to levels below the basal level of the untreated controls, in the CD36 null cells further inhibition by TSP1 was only seen at 22 nM.

These data established that CD36 is not necessary for picomolar concentrations of TSP1 to inhibit an NO-stimulated response, although a secondary inhibitory response at nanomolar concentrations of TSP1 does require CD36. We have shown that picomolar concentrations of TSP1 inhibit NO signaling at the level of cGMP (Isenberg et al., *Proc Natl Acad Sci USA* 102:13141-13146, 2005; Isenberg et al., *Cardiovasc Res* 71(4):785-793, 2006). To establish whether inhibition by TSP1 of NO signaling through cGMP requires CD36, cGMP levels were analyzed in the WT and CD36 null MASMC (FIG. 6B). As shown previously (Isenberg et al., *Cardiovasc Res* 71(4):785-793, 2006), NO-stimulated cGMP levels in WT cells were inhibited by exogenous TSP1. This activity of TSP1 does not require CD36, however, because the cGMP response was also completely inhibited by TSP1 in CD36 null MASMC (FIG. 6B). Notably, basal cGMP levels were similar in WT and CD36 null cells, suggesting that the previously reported effects of endogenous TSP1 on basal cGMP levels in vascular cells (Isenberg et al., *Proc Natl Acad Sci USA* 102:13141-13146, 2005; Isenberg et al., *Cardiovasc Res* 71(4):785-793, 2006) do not require CD36.

CD47 Ligation Inhibits NO Responses

The explant data in FIG. 3 suggested that CD47 could mediate the CD36-independent regulation of NO signaling by TSP1. To further examine the role of CD47, we tested two CD47-binding sequences identified in the C-terminal domain (CBD) of TSP1 (Gao et al., *J Biol Chem* 271:21-24, 1996). Peptides containing the first (4N1-1, FIG. 7A) or second VVM motifs from this domain (7N3, FIG. 7B) inhibited NO-stimulated endothelial cell adhesion on type I collagen. Inhibition by peptide 7N3 was dose dependent and maximal at 10 μM. Specificity was confirmed using a control peptide in which the first VVM motif was substituted by GGM (p4N1G, RFYGGMWK; SEQ ID NO: 15), which at 10 μM did not significantly inhibit NO-stimulated adhesion.

Figure 8:
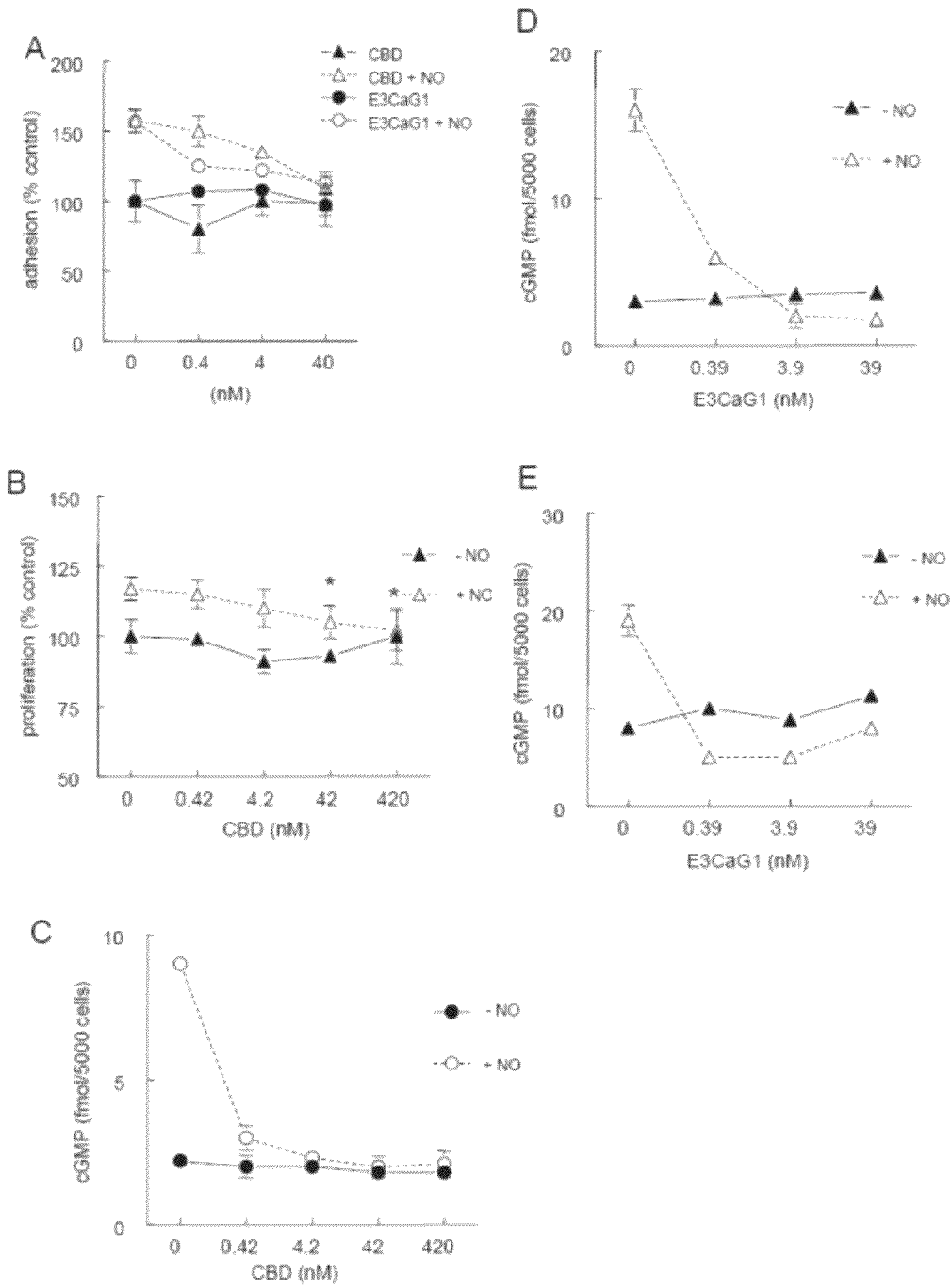
FIG. 8A-8E. The C-terminal binding domain of TSP1 is sufficient to inhibit NO-stimulated responses in vascular smooth muscle cells.

Although the VVM peptides clearly bind to CD47 (Gao et al., *J Biol Chem* 271:21-24, 1996; Frazier et al., *J Biol Chem* 274:8554-8560, 1999), crystal structures of recombinant C-terminal regions of TSP1 and TSP2 have raised doubts about the exposure of the VVM motifs in native TSP1 (Kvansakul et al., *Embo J* 23:1223-1233, 2004; Carlson et al., *Nat Struct Mol Biol* 12:910-914, 2005). Based on a crystal structure for this domain of the paralog TSP2 (Carlson et al., *Nat Struct Mol Biol* 12:910-914, 2005), the third type 2 repeat, the Ca-binding repeats, and the G module fold together to form the C-terminal globular domain of TSP1. A recombinant construct containing these elements of TSP1 (E3CaG1, FIG. 2B) at >0.4 nM inhibited NO-driven but not basal HASMC adhesion to collagen (FIG. 8A). Recombinant G module (CBD), which is also documented to interact with CD47 and to signal through that receptor (McDonald et al., *Biochemistry* 42:10001-10011, 2003), was slightly less active but also dose-dependently inhibited NO-stimulated HASMC adhesion on type I collagen but not basal adhesion on the same substrate (FIG. 8A). CBD also inhibited NO-stimulated HASMC proliferation, but required much higher concentrations to reach basal levels (FIG. 8B). Consistent with their effects on NO-stimulated adhesion, CBD and E3CaG1 were equipotent dose-dependent inhibitors of NO-stimulated cGMP levels in HASMC (FIGS. 8C, 8D). E3CaG1 also potently inhibited NO-driven cGMP production in HUVEC, demonstrating that this function of CD47 is conserved in both endothelial and VSMC (FIG. 8E)

Figure 9:
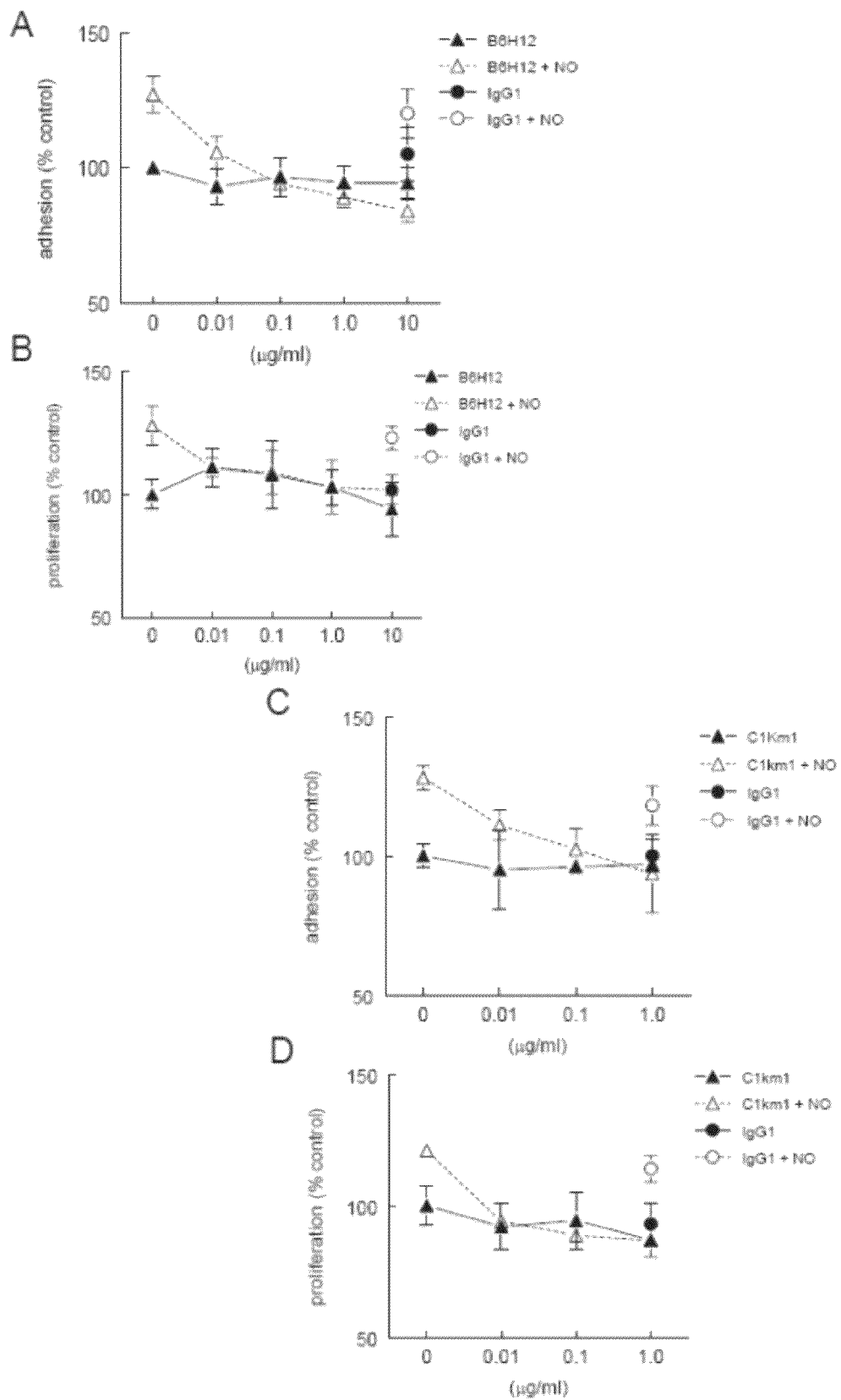
FIG. 9A-9D. Antibody ligation of CD47 inhibits NO-stimulated endothelial cell adhesion and proliferation. HUVEC ($1\times10^4$ cell/well) were plated in 96-well culture dishes pre-coated with type I collagen (5 µg/ml) and incubated in EGM+0.1% BSA±B6H12 (0.01-10 µg/ml) (FIG. 9A) or C1K1m1 (0.01-1 µg/ml) (FIG. 9C). An isotype matched control antibody ($IgG_1$) was also tested at comparable doses. Following incubation for 1 hour at 37° C. plates were washed and cells fixed, stained, developed and read at 570 nm. HUVEC ($5\times10^3$ cells/well) were plated on 96-well culture plates and incubated for 72 hours in EGM+1% FCS±DETA/NO (10 µM) and antibodies B6H12 (0.01-10 µg/ml) (FIG. 9B) or C1Km1 (0.01-1 µg/ml) (FIG. 9D). An isotype matched control antibody ($IgG_1$) was also tested at comparable doses. Cell proliferation was assayed via the colorimetric change obtained after incubation with MTS reagent at 490 nm. Results are expressed as percent of control and represent the mean±SD of at least three separate experiments.

Because E3CaG1 also contains an integrin binding site, we used two CD47 antibodies to independently verify that CD47 ligation is sufficient to inhibit NO-stimulated responses (FIG. 9). B6H12 inhibits CD47-dependent endothelial and T cell chemotaxis, $\alpha_v\beta_3$ integrin activation, and calcium mobilization (Gao et al., *J Biol Chem* 271:21-24, 1996; Gao et al., *J Cell Biol* 135:533-544, 1996; Tsao and Mousa, *J Biol Chem* 270:23747-23753, 1995; Li et al., *J Cell Biol* 157:509-519, 2002; Li et al., *J Immunol* 166:2427-2436, 2001) but stimulates CD47-dependent activation of $\alpha_4\beta_1$ integrin (Barazi et al., *J Biol Chem* 277:42859-42866, 2002). B6H12 was a dose-dependent inhibitor of NO-stimulated HUVEC adhesion on type I collagen (FIG. 9A). B6H12 also prevented stimulation of HUVEC proliferation by sustained exposure to NO (FIG. 9B). CIKm1 is a nonblocking CD47 antibody for integrin function (Barazi et al., *J Biol Chem* 277:42859-42866, 2002) and an activating antibody for T cell receptor signaling (Li et al., *J Immunol* 166:2427-2436, 2001). CIKm1 treatment also inhibited HUVEC adhesion and proliferation (FIGS. 9C, 9D). Non-specific isotype-matched antibodies did not block the NO-driven increase in cell adhesion or proliferation (FIG. 9A-9D). The activities of these antibodies confirm that CD47 ligation is sufficient to inhibit NO signaling.

CD47 is Necessary for Inhibition of NO Responses by TSP1 in Vascular Cells

Figure 10:
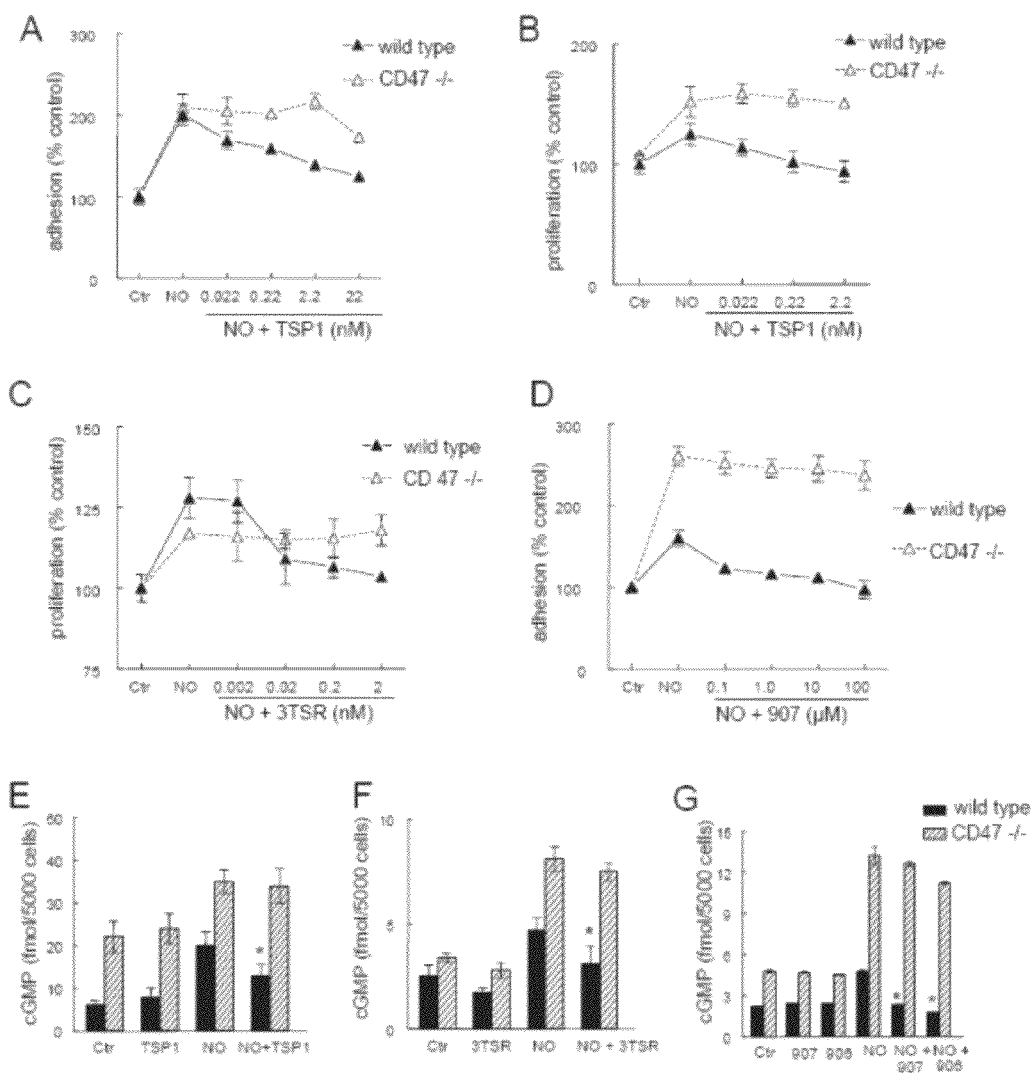
FIG. 10A-10G. CD47 is necessary for TSP1 inhibition of NO-driven vascular cell responses.

In contrast to CD36, CD47 is required for inhibition of NO-stimulated MASMC responses by exogenous TSP1 (FIG. 10). Exogenous TSP1 had no effect on NO-stimulated adhesion of CD47 null MASMC at concentrations up to 2.2 nM and only moderately inhibited the response at 22 nM (FIG. 10A). Similarly, TSP1 did not inhibit NO-stimulated proliferation in CD47 null MASMC (FIG. 10B). Remarkably, recombinant type 1 repeats of TSP1 that bind to CD36 also failed to inhibit NO-stimulated proliferation in CD47 null cells (FIG. 10C), and a CD36-binding peptide analog derived from the second type 1 repeat failed to inhibit NO-stimulated adhesion in CD47 null cells (FIG. 10D).

The inability of CD47 null cells to respond to exogenous TSP1 extended to NO-stimulated cGMP signaling. As reported previously for TSP1 null endothelial cells and MASMC (Isenberg et al., *Proc Natl Acad Sci USA* 102: 13141-13146, 2005; Isenberg et al., *Cardiovasc Res* 71(4): 785-793, 2006), basal cGMP levels were significantly higher in CD47 null MASMC (FIG. 10E). Addition of NO elevated these levels, but exogenous TSP1 did not significantly inhibit the basal or NO-stimulated cGMP levels in the CD47 null MASMC (FIG. 10E). Similar results were obtained using recombinant type 1 repeats and peptide 907, which bind to CD36 and inhibited NO-stimulated cGMP responses in WT but not in CD47 null MASMC (FIGS. 10F, 10G). NO-stimulated cGMP was slightly inhibited by a CD36-binding peptide from the $3^{rd}$ type 1 repeat (p907, FIG. 10G).

Figure 11:
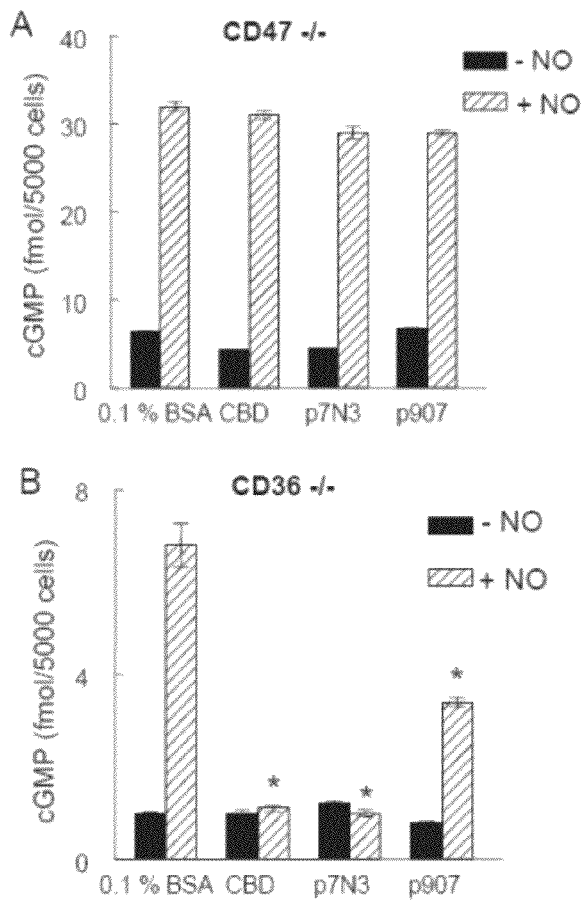
FIG. 11A-11B. CD47 is necessary for inhibition of NO signaling by both CD36- and CD47 binding sequences of TSP1.

To further define the roles of CD36 and CD47, we compared cGMP responses of VSMC from the respective null mice to peptide and recombinant protein ligands (FIG. 11). Two CD47 ligands (CBD and peptide 7N3) and a CD36 ligand (peptide 907) did not significantly inhibit NO-stimulated cGMP accumulation in CD47 null MASMC (FIG. 11A). In contrast, CBD and its derived peptide 7N3 completely inhibited NO-stimulated cGMP in CD36 null MASMC (FIG. 11B). Therefore, CD47 is necessary for inhibition of cGMP signaling and downstream SMC responses to NO by either CD36 or CD47 ligands, but CD36 is not necessary for inhibition by a CD47 ligand. Remarkably, peptide 907, a reported CD36 ligand (Dawson et al., *Mol Pharmacol* 55:332-338, 1999), partially inhibited NO-stimulated cGMP in CD36 null cells (FIG. 11B). The mechanism by which peptide 907 inhibits NO-induced cGMP formation in the CD36 null cells is unknown, but possibilities include binding to another member of the class B scavenger receptor family expressed on these cells (Crombie and Silverstein, *J Biol Chem* 273:4855-4863, 1998) or interaction of peptide 907 with CD47.

Although the inability of TSP1 to inhibit angiogenesis in corneas of CD36 null mice is strong evidence that CD36 is a necessary TSP1 receptor in the context of FGF2-driven corneal angiogenesis (Jimenez et al., *Nat Med* 6:41-48, 2000), ligation of several other TSP1 receptors is sufficient to inhibit angiogenic responses in vitro and in vivo. TSP1-derived peptides or recombinant regions of TSP1 that bind to heparin sulfate proteoglycans (Iruela-Arispe et al., *Circulation* 100: 1423-1431, 1999; Vogel et al., *J Cell Biochem* 53:74-84, 1993) or CD47 (Kanda et al., *Exp Cell Res* 252:262-272, 1999) each have such activities. However, these previous studies did not determine whether the respective receptors are necessary for the activity of native TSP1. The present data provides genetic evidence that CD47 but not CD36 is essential the anti-angiogenic activity of TSP1 in the context of NO, a key mediator of signaling for several major angiogenic factors (Ziche et al., *J Clin Invest* 99:2625-2634, 1997; Fukumura et al., *Proc Natl Acad Sci USA* 98:2604-2609, 2001; Namkoong et al., *Exp Mol Med* 37:588-600, 2005; Cooke, *Atheroscler Suppl* 4:53-60, 2003). CD47-binding recombinant domains of TSP1 lacking its CD36 binding sites are sufficient to inhibit cGMP signaling downstream of NO. Although CD36 is not necessary and, therefore, does not mediate this activity of TSP1, we found that various CD36 ligands are sufficient to inhibit the same NO-stimulated responses, provided that CD47 is expressed. This activity, however, is independent of the ability of a given CD36 ligand to block TSP1 interaction with CD36.

Figure 12:
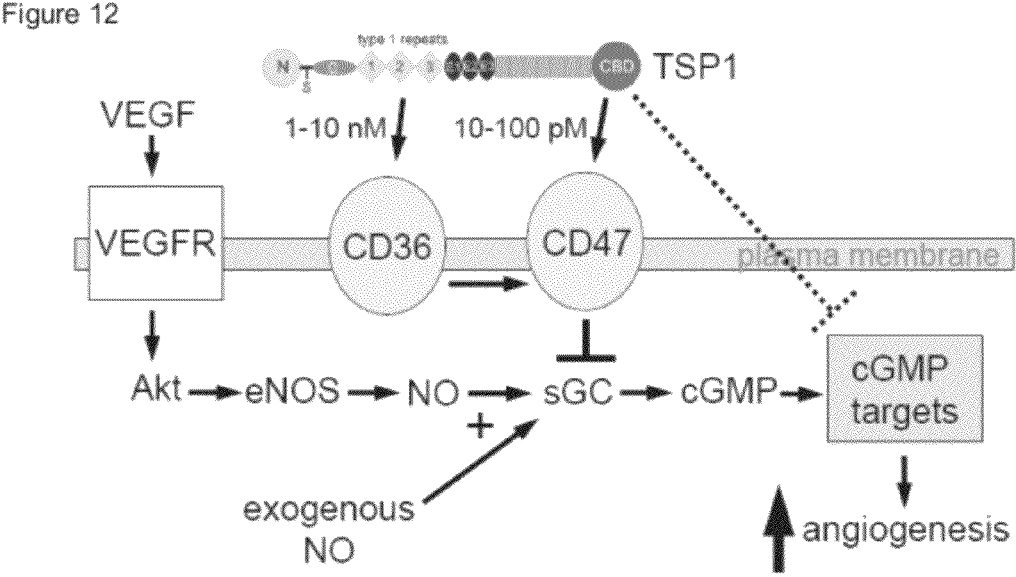
FIG. 12. Regulation of NO signaling by TSP1 via CD36 and CD47. Endogenous NO synthesis is stimulated via Akt-mediated phosphorylation of endothelial nitric oxide synthase (eNOS) downstream of VEGF receptor (Dimmeler et al, *FEBS Lett,* 477:258-262, 2000). Ligation of either CD36 or CD47 is sufficient to inhibit activation of soluble guanylyl cyclase (sGC) mediated by endogenous or exogenous NO. CD47 is downstream of CD36 because ligation on CD36 can not inhibit signaling in the absence of CD47. The requirement for CD47 is consistent with lateral interactions with CD36 or with CD36 signaling requiring a convergent CD47 signal at some point upstream of sGC. The mechanism by which CD47 ligation regulates sGC is not known. TSP1 also inhibits NO signaling downstream of cGMP (Isenberg et al, *PNAS,* 102: 13141-13146, 2005), but the receptors mediating this second signal have not been defined.

The CD36-binding type 1 repeats of TSP1 were previously shown to inhibit NO signaling, but we now demonstrate that this activity also requires CD47. This should not be interpreted to show that CD47 is a receptor for the type 1 repeat sequences, although that can not be excluded. Our data indicates that, in the context of NO-stimulation, CD47 is the essential inhibitory receptor for TSP1, and CD36 ligation is sufficient to mediate a secondary inhibitory response that also requires CD47 (FIG. 12). Basal cGMP levels are elevated in CD47 null and in TSP1 null vascular cells, but this is not observed in CD36 null MASMC. Therefore, the ability of endogenous TSP1 to suppress basal cGMP levels also requires CD47 but not CD36.

In vitro studies have shown that CD36 mediates only a subset of endothelial cell interactions with TSP1 (Magnetto et al., *Cell Biochem Funct* 16:211-221, 1998; Calzada et al., *J Biol Chem* 279:41734-41743, 2004), and CD36 now appears to be necessary only for a subset of the anti-angiogenic activities of TSP1. Antibody blockade of CD36 prevented the inhibitory effects of TSP1 and peptides derived from its type 1 repeats on FGF2-driven endothelial cell migration (Dawson et al., *J Cell Biol* 138:707-717, 1997), and exogenous TSP1 could not inhibit FGF2-driven angiogenesis in the mouse cornea in the absence of CD36 (Jimenez et al., *Nat Med* 6:41-48, 2000). However, we now show that CD36 antibodies that block TSP1 inhibition in the cornea can themselves inhibit angiogenic responses stimulated by NO. The basis for a differential requirement of CD36 in FGF2-versus NO-dependent angiogenic responses remains to be determined. However, it is notable that NO signaling is required for angiogenic responses to VEGF but not to FGF2 (Fukumura et al., *Proc Natl Acad Sci USA* 98:2604-2609, 2001; Shizukuda et al., *Circ Res* 85:247-256, 1999; Papapetropoulos et al., *J Clin Invest* 100:3131-3139, 1997).

Low to moderate concentrations of NO (<1 to 30 nM) elicit pro-survival and pro-angiogenic responses from vascular cells (Isenberg et al., *Proc Natl Acad Sci USA* 102:13141-13146, 2005; Isenberg et al., *Cardiovasc Res* 71(4):785-793, 2006; Cooke, *Atheroscler Suppl* 4:53-60, 2003). Bi-directional crosstalk with TSP1 potently regulates this angiogenic activity of NO (Isenberg et al., *Proc Natl Acad Sci USA* 102:13141-13146, 2005; Ridnour et al., *Proc Natl Acad Sci USA* 102:13147-13152, 2005). Consistent with previous publications, we find that CD36 ligation is sufficient to block pro-angiogenic responses, but only if CD47 is also expressed. As with exogenous TSP1, CD36 antibodies effectively block several NO-stimulated vascular cell responses including cell proliferation, adhesion, migration, and cGMP accumulation. However, agonist (SMΦ) and antagonist antibody (FA6 152 and 185 1 G2) ligation of CD36 equally inhibited NO signaling. These results contrast with previous reports that have classified these CD36 antibodies on the basis of their abilities to mimic or block the inhibitory activity of TSP1. Therefore, we propose that both agonist and antagonist antibodies elicit signaling through CD36 that is independent of TSP1.

Activation of CD47 has been described to inhibit (Wang et al., *J Cell Biol* 147:389-400, 1999) or stimulate ERK phosphorylation (Wilson et al., *J Immunol* 163:3621-3628, 1999). We found that NO-stimulated ERK phosphorylation in endothelial cells was inhibited by exogenous TSP1 (Ridnour et al., *Proc Natl Acad Sci USA* 102:13147-13152, 2005), consistent with the evidence that CD47 mediates inhibition of angiogenic responses by TSP1. This was supported by the ability of CD47 antibodies, peptide ligands, and two forms of the C-terminal CD47-binding domain of TSP1 to inhibit NO-stimulated vascular cell responses. Moreover, neither NO-stimulated VSMC adhesion on collagen nor NO-stimulated cGMP levels could be blocked by pretreatment with TSP1 in CD47 null cells. Taken together these results demonstrate that either CD36 or CD47 ligation is sufficient to mimic TSP1 inhibition of NO-driven pro-angiogenic cell responses, but only CD47 expression is absolutely required for TSP1 inhibition of these angiogenic responses.

Given that CD47 is necessary for some responses to both CD36 and CD47 ligands, we must reconsider the roles of these two receptors in vascular cell responses to TSP1. It has been generally assumed that if TSP1 binds to a receptor and genetic evidence shows that receptor to be necessary for a specific response, one can infer that TSP1 binds to the same receptor to mediate that response. This may not be valid logic for a protein such as TSP1 that engages multiple receptors on vascular cells. Convergent signaling downstream of CD36 and CD47 may mediate a single response even if TSP1 binds only to CD47. Alternatively, the cross talk between CD36 and CD47 may occur at the plasma membrane (FIG. 12). CD36 and CD47 both associate with lipid rafts and with certain integrins that themselves bind TSP1 (Barazi et al., *J Biol Chem* 277:42859-42866, 2002; McDonald et al., *J Biol Chem* 279:17301-17311, 2004; Zeng et al., *J Biol Chem* 278:45931-45936, 2003). The physical proximity of CD47, its associated integrins, or one of its cytoplasmic binding partners may be necessary for signal transduction through CD36. Such cooperative signaling by a CD36/$\beta_1$ integrin/CD47 complex has been proposed for another CD36 ligand, β-amyloid (Bamberger et al., *J Neurosci* 23:2665-2674, 2003) and may explain the recent evidence that $\beta_1$ integrins are also necessary for some inhibitory responses of vascular cell to TSP1 (Short et al., *J Cell Biol* 168:643-653, 2005).

Together, these considerations suggest that multiprotein complexes containing two or more TSP1 receptors could mediate its actions on vascular cells. Further, since other TSP family members bind to different subsets of these receptors, the potential exists for finely tuned spatial or temporal regulation during development, wound healing and pathological states.

Example 2

Thrombospondin-1 Limits Ischemic Tissue Survival by Inhibiting Nitric Oxide-Mediated Vascular Smooth Muscle Relaxation NO is a key signaling molecule in ischemia. NO stimulates vascular smooth muscle cell (VSMC) relaxation to increase blood flow and tissue perfusion. Low dose NO also has pro-angiogenic and anti-inflammatory activities. Consistent with these activities, elevating NO levels increases tissue survival in situations of ischemic insult.

This example demonstrates that TSP1 antagonizes NO signals to regulate the actin/myosin cytoskeleton and contraction of VSMC in vitro. Endogenous TSP1 modulates acute effects of NO in vivo on tissue perfusion and blood oxygen levels in healthy muscle and in ischemic tissues following surgery. Furthermore, soft tissue survival in ischemic myocutaneous flaps is increased in the absence of endogenous TSP1, and this negative effect of endogenous TSP1 upon tissue survival is NO dependent. At least portions of this example were also published in Isenberg et al., Blood First Edition Paper, prepublished online Nov. 2, 2006; DOI 10.1182/blood-2006-08-041368 (Blood, 109(5):1945-1952, 1 Mar. 2007).

Methods

Animals:

C57/B16 wild type (WT) and TSP1 null mice were housed in a pathogen free environment and had ad libitum access to filtered water and standard rat chow. Handling and care of animals was in compliance with the guidelines established by the Animal Care and Use Committee of the National Cancer Institute and the National Institutes of Health.

Cells and Reagents:

Aortic-derived VSMCs were isolated from WT and TSP1 null mice as previously described (Napoli et al., *Proc Natl Acad Sci USA* 102:17202-17206, 2005) and cultured in smooth muscle growth medium. HAVSMC (Cambrex, Walkersville, Md.) were maintained in smooth muscle cell growth medium supplemented with the manufacturer's additives (SM-GM, Cambrex) and 2% FCS in 5% $CO_2$ at 37° C. Cells were utilized within passages 4-9. Monomeric type I collagen was obtained from Inamed (Fremont, Calif.). L-NAME and ISDN were purchased from Sigma (St. Louis, Mo.). LiPc crystals were prepared as previously described (Krishna et al., *Proc Natl Acad Sci USA* 99:2216-2221, 2002; Hammond et al., *Plast Reconstr Surg* 91:316-321, 1993). DEA/NO and DETA/NO were kindly provided by Dr. Larry Keefer (National Cancer Institute, Frederick). TSP1 was prepared from human platelets obtained from the NIH blood bank as previously described (Knox et al., *Microsurgery* 17:425-427, 1996).

Actin Cytoskeleton Staining:

VSMC were grown on glass well slides (Lab-Tek, Nunc) under standard growth conditions. Cells were incubated at 37° C. for 1 hour in serum and additive deficient growth medium and the indicated treatment agents, after which the media was removed and the cells were fixed in 4% paraformaldehyde in PBS (pH 7.4, Fisher Scientific) for 15 minutes at room temperature. After washing with DPBS, cells were permeabilized for 5 minutes in 0.1% Triton X-100 in PBS and then blocked in M199E/2% BSA for 30 min at room temperature. Cells were stained for F-actin with 1 unit/200 μl medium/1% BSA of Oregon Green 488 phalloidin (Molecular Probes). Slides were imaged using an Olympus IX70 microscope and photographed at constant exposure and gain. In other experiments VSMC were plated on 24-well culture plates (Nunc, Denmark) in smooth muscle growth medium (50,000 cells/well) and weaned from serum and additives over 24 hours. Cell treatment was performed with the indicated agents in plain medium with 0.1% BSA for 5 minutes. Wells were processed as described above. Following staining with phalloidin cells were incubated in methanol for 30 minutes, samples aliquoted to 96-well black plates and fluorescence read at 520 nm (excitation 495 nm). Data was normalized to total protein. Results represent the mean±SD of at least three separate experiments.

3D Matrix Contraction Assay:

Type I collagen gel (3 mg/ml) with 10×M199 (Gibco, Grand Island, N.Y.) at a 10:1 ratio of collagen to medium was prepared, pH balanced with NaOH and seeded with either HAVSMC or VSMC harvested from aortic segments from C57B16 WT or TSP1 null mice (50,000 cells in 75 μl of gel/well) and aliquoted to 96-well plates (Nunc, Denmark). Plates were incubated for 12 h 37° C. and 5% $CO_2$ allowing for gelation and cell spreading, gently released from the well walls and incubated in serum and additive deficient growth medium with 0.1% BSA in the presence of the indicated treatment agents for 10 h. Contraction was determined by measuring the diameter in perpendicular planes (x, y) of each disk, an average obtained and surface area calculated as $(d/2)^2 \pi$. Experiments were performed in triplicate. Results represent the mean±SD of at least three separate experiments.

Myosin Light Chain Phosphorylation:

VSMC were plated at 90% confluence and grown in smooth muscle growth media containing 2% FBS overnight. To stimulate MLC phosphorylation, sphingosine-1-phosphate (SIP; Biomol International, Plymouth, Pa.) was added at a final concentration of 100 nM. The nitric oxide donor DEA/NO was added at a final concentration of 10 µM. For TSP1 pretreatment, cells were incubated with 2.2 nM TSP1 before addition of SIP or DEA/NO. Cells were subsequently washed twice with PBS and lysed immediately in 1×SDS sample buffer containing 10 µg/mL leupeptin, 10 µg/mL aprotinin, 1 mM $Na_3VO_4$, and 40 mM NaF. Lysates prepared in the SDS sample buffer described above were electrophoresed in 4-12% BisTris NuPAGE gels and transferred to PVDF membranes prior to immunoblotting with rabbit polyclonal antibodies against myosin light chain-2 (MLC) and phospho-MLC2 (T18/S19, Cell Signaling Technology, Danvers, Mass.).

Flap Model:

WT and TSP1 null mice were matched for sex and age. Under isoflurane inhalation anesthesia 1×2 cm random myocutaneous flaps were raised. Where indicated, animals received either L-NAME (0.5 mg/ml) or ISDN (1 mg/ml) ad libitum in drinking water during the post-operative period. On postoperative day 7, the animals were again anesthetized with inhalation isoflurane and flaps evaluated. Viable and necrotic areas of the flaps were determined by color, refill, eschar, and the pin-prick test. Outlines of viable and nonviable areas were traced using transparent film and the area of flap necrosis versus total flap area determined as described (Yu et al., *Proc Natl Acad Sci USA* 102:10999-11004, 2005).

Histology.

Sections of excised wounds were cut parallel to the long axis of each flap including the entire length of the tissue sample, fixed in 10% buffered formaldehyde, paraffin embedded and sectioned at a thickness of 5 µm. Sections were then stained with hematoxylin and eosin (H+E) according to standard procedures. Review of each slide was performed by an independent pathologist blinded to the origin of each tissue slide.

Immunohistochemistry:

Immunohistochemical studies were performed on 5 m-thick paraffin-embedded tissues sections from flaps harvested at 4 and 72 hrs. Sections were deparaffinized in xylene and rehydrated in graded alcohol (100%, 95% and 70%). Sections were subjected to antigen retrieval solution in a pressure cooker containing 1.5 liters of antigen retrieval solution, pH 6.1 (Dako Corporation, Carpinteria, Calif.) for 10 min., cooled down in the same solution for 20 minutes at room temperature, and then washed with PBS 1×. Block activity of endogenous peroxidase and secondary antibody were performed using EnVision plus System-HRP (DAB) antimouse (Dako Corporation), 5 and 30 minutes respectively at room temperature. A blocking step was performed using Protein Block Serum-Free (Dako Corporation) for 10 minutes. The TSP1 primary antibody (clone A6.1, NeoMarkers, Fremont, Calif.) was applied for 1 hr at room temperature and the working dilution was 1:25. The peroxidase reaction was developed with 3,3-diaminobenzidine chromogen solution (Dako Corporation) for 5 min. As negative control we used slides that excluded the primary antibody. Only cytoplasmic and extracellular matrix immunoreactivity was considered positive for TSP1. Inflammatory cells were considered as an internal positive control.

Blood Oxygen Level Dependent (BOLD) MRI Imaging:

MRI images were acquired using a Bruker Biospin 4.7 T scanner and isoflurane anesthesia. Muscle tissue scanned was at rest, so alterations in oxygenation reflected changes in perfusion rather than in oxygen consumption (Krishna et al., *Ilar J* 42:209-218, 2001; Watterson et al., *Cell Signal* 17:289-298, 2005). MR measurements were started after the mouse's body temperature reached 37° C. Prior to the experiments, gradient echo based $T_1$ sequence was used to determine the target slice location. A series of $T_2^*$ weighted gradient echo blood oxygenation level dependent (BOLD) image data sets at transverse to the midpoint of the femur were repeatedly acquired for 30 min to monitor temporal changes in blood oxygenation and blood flow. DEA/NO (100 nmol/g body weight) was injected with saline via the rectal cannula 5.0 min after starting the scan. Imaging parameters used were: TR=450 ms, Flip angle=45, Nex=1, slice thickness=2 mm, matrix size=64×64, total imaging time for the series was 29 min.

Implantation of LiPc Crystals:

WT or TSP1 null mice matched for age and sex were anesthetized by administering 1.5-2% isoflurane in medical air (flow rate was 700 mL/min). The fur of the back was removed by shaving and depilatory cream. A portion of LiPc crystals (5-10 mg) was suspended with an appropriate volume (10-20 µL) of corn oil and kneaded until a slurry paste was obtained (Hammond et al., *Plast Reconstr Surg* 91:316-321, 1993). Then, the LiPc slurry was placed in the 2-3 mm tip of a 20-gauge injection needle. The needle was injected into the desired region of the animal, and the LiPc crystals were pushed out using a smooth-fitting piston. The average weight of the LiPc injected was 0.8 mg. Implantation of LiPc crystal slurry was done to the following three locations on the back of the mouse—to the distal and proximal regions of the flap and to an area 1 cm from the flap base.

EPR Measurement of Tissue Oxygen In Vivo:

Dorsal modified McFarlane flaps bearing LiPc crystals implanted 7 days prior were created as described above and EPR measurements carried out at 3, 6, 24, 48, and 72 hr post-surgical procedure. Again mice were anesthetized with 1.5-2% isoflurane in medical air flow (700 mL/min) and placed in a special mouse holder. The surface coil (7.3 mm i.d.) was placed on the region where the LiPc crystal was implanted. The EPR signal was measured by CW EPR at 700 MHz using a single loop surface coil resonator (7.3 mm i.d.). The 300 MHz CW EPR system, which was previously described (Hammond et al., *Plast Reconstr Surg* 91:316-321, 1993; Sorbera and Bayes, *Drugs of the Future* 30:1081-1086, 2005), was equipped with a 700 MHz bridge and the surface coil type resonator, instead of a 300 MHz bridge and a parallel coil type resonator. The experimental settings were as follows: microwave frequency=700 MHz, scan rate=0.5 Gauss/sec, and time constant=0.003 sec, field modulation frequency=13.5 kHz. The microwave power (0.08-0.3 mW) and field modulation width (0.01-0.2 Gauss) were adjusted to avoid saturation and line broadening. The core body temperature (sampled continuously from the rectum) was monitored by a nonmagnetic probe (FISO technologies Inc., Quebec, CANADA), and was kept at 37±0.5° C. using a hot air heater during EPR measurements. Tissue $pO_2$ values were calculated from a calibration curve obtained previously for each batch of LiPc crystals used in the experiment.

Statistics:

All experiments were replicated at least three times. Results are presented as the mean±SD with analysis of significance done by the Student's t test or one-way or two way ANOVA with Tukey post hoc test where indicated using Origin software (version 7, OriginLabs Corp., Northampton, Mass.), with significance taken at p values <0.05.

Results

TSP1 Inhibits NO-Induced Actin Disassembly in VSMC

Figure 13:
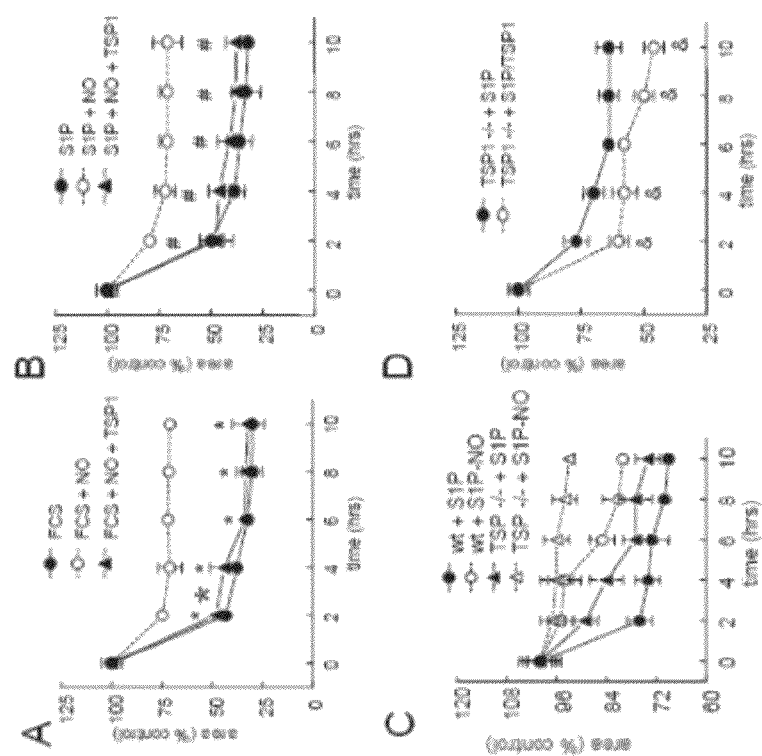
FIG. 13A-13F. TSP1 antagonizes NO-dependent alterations in F-actin and dephosphorylation of MLC in VSMC. HAVSMC plated on glass chamber slides were incubated in basal medium with 0.1% BSA (FIGS. 13A, 13B) or 2.2 nM TSP1 (FIGS. 13C, 13D)±DEA/NO (10 µM). Cells were then fixed, permeabilized, and stained with Oregon Green-phalloidin to visualize F-actin. Photomicrographs representative of three separate experiments are presented. Scale bar=50 µm. HAVSMC in 96 well plates were similarly treated, stained as above, and the fluorescent signal quantified (FIG. 13E). * $P<0.05$ vs. BSA−NO, Student's t test. # $P<0.05$ vs. BSA+NO, \$ $P<0.05$ vs BSA−NO, two-way ANOVA. & $P<0.05$ vs. S1P−NO, one-way ANOVA. Lysates of HAVSMC in growth medium with 2% serum and treated with the indicated combinations of 100 nM S1P, 10 M DEA/NO, and 2.2 nM TSP1 for 5 minutes were separated by SDS-PAGE and analyzed by western blot to determine the levels of MLC phosphorylation and total MLC (FIG. 13F). The blot shown is representative of four independent experiments.
Figure 19:
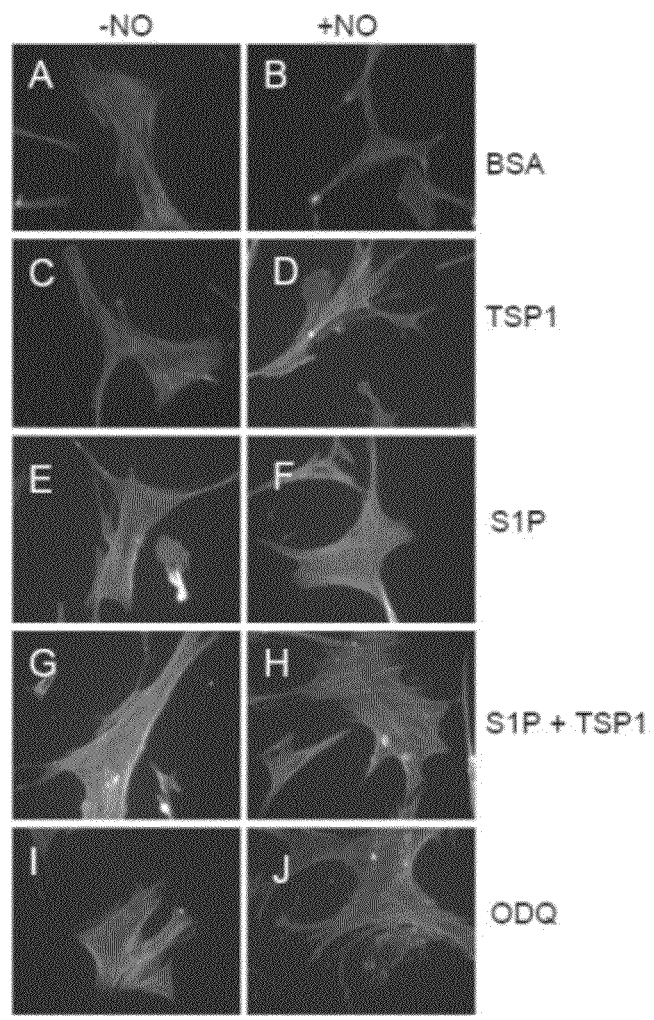
FIG. 19A-19J. HAVSMC were plated on glass chamber slides and incubated in basal medium with 0.1% BSA (FIGS. 19A, 19B), 2.2 nM TSP1 (FIGS. 19C, 19D), 100 nM S1P (FIGS. 19E-19H), or 10 µM 1H-[1,2,4]oxadiazole[4,3-a]quinoxalin-1-one (FIGS. 19I, 19J)±10 µM DEA/NO for 5 minutes. Cells were then fixed, permeabilized, and stained with phalloidin to visualize F-actin. Photomicrographs representative of three separate experiments are presented.
Figure 20:
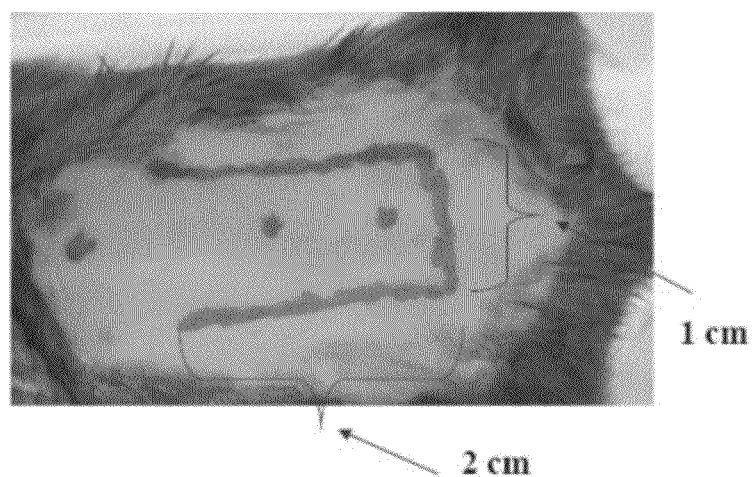
FIG. 20. Random myocutaneous murine flap model. Random flaps (1×2 cm) were developed sharply along the dorsal midline of C57B16 mice (WT and TSP1-null) as indicated and secured with several simple 5-0 nylon sutures. The undersurface of each flap was inspected following mobilization to insure the absence of an identifiable axial vessel prior to flap inset.

Actin cytoskeletal reorganization and actin-myosin interactions control the contractile state of VSMC (Isenberg et al., *Matrix Biol* 24:110-123, 2005). Treatment of human aortic VSMC(HAVSMC) with exogenous NO resulted in dissolution of organized actin bundles and decreased total cellular F-actin (FIGS. 13A, 13B, 13E). Based on inhibition of actin disassembly by NO in the presence of 1H-[1,2,4]oxadiazole [4,3-a]quinoxalin-1-one, this activity of NO requires soluble guanylyl cyclase. TSP1 blocks NO-induced changes in actin organization in endothelial cells (Isenberg et al., *Proc Natl Acad Sci USA* 102:13141-13146, 2005). Similarly, addition of TSP1 alone to VSMC slightly increased F-actin levels (FIGS. 13C, 13E) and completely prevented actin disassembly by NO (FIGS. 13D, 13E). Sphingosine 1-phosphate (SIP), a lipid known to regulate VSMC contractility (reviewed in Afeworki et al., *Free Radic Biol Med* 25:72-78, 1998), also increased F-actin, which was disassembled upon addition of NO (FIG. 13E and FIG. 19E-19F). Addition of TSP1 further increased F-actin in the presence of S1P. However, disassembly of S1P-induced F actin by NO was attenuated in the presence of TSP1 (FIG. 13E and FIGS. 19G-19H).

Myosin Light Chain-2 (MLC) Dephosphorylation Induced by NO is Blocked by TSP1

MLC phosphorylation is a critical step in VSMC contraction (Isenberg et al., *Matrix Biol* 24:110-123, 2005). S1P inhibits MLC phosphatase via Rho and thereby increases phosphorylation of MLC (Matsumoto et al., *Magn Reson Med* 54:1530-1535, 2005). This response to S1P was reversed by exogenous NO (FIG. 13F). Concurrent treatment with exogenous TSP1 prevented this activity of NO and partially restored MLC phosphorylation.

Exogenous and Endogenous TSP1 Inhibit NO-Stimulated VSMC Relaxation

Figure 14:
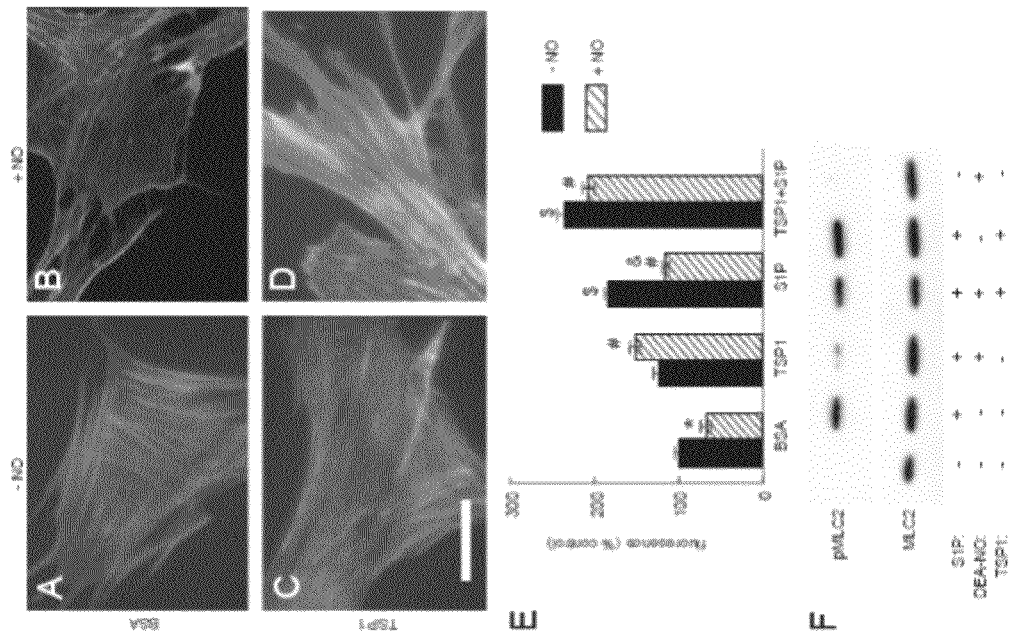
FIG. 14A-14D. NO-stimulated VSMC contraction is blocked in the presence of exogenous and endogenous TSP1 and SIP. Type I collagen gels (3 mg/ml) were prepared and seeded with either HAVSMC (FIGS. 14A, 14B) (50,000 cells in 75 µl gel/well) or VSMC harvested from aortic segments from WT or TSP1 null mice (FIGS. 14C, 14D) (75,000 cells in 75 µl gel/well) and aliquoted to 96-well plates (Nunc, Denmark) and incubated overnight. Wells treated with TSP1 were pre-incubated overnight with 2.2 nM TSP1. Following release of the gels, contraction was initiated with either 10% FCS or 100 nM S1P±10 µM DETA/NO and contraction determined. * $P<0.05$ vs. FCS+NO, # $P<0.05$ vs. S1P+NO, \$ $P<0.05$ vs. WT S1P−NO, & $P<0.05$ vs. TSP−/−+S1P, Student's t test.

Blood flow is controlled by vascular resistance, which depends upon blood vessel diameter regulated by contraction and relaxation of VSMC. The effects of TSP1 on NO-mediated changes in F actin and MLC phosphorylation suggested that TSP1 may regulate VSMC contraction. Using a well characterized assay of VSMC contraction in 3D type I collagen gels (Roberts et al., *J Tissue Cult Methods* 16:217-222, 1994), HAVSMC demonstrated significant contraction in response to either 10% FCS or 100 nM S1P, a component of serum and stimulator of VSMC contraction (Li S et al., *J Vasc Res* 40:378-388, 2003) (FIG. 14A-14B). Treatment with a slow releasing NO donor (DETA/NO) inhibited gel contraction by both agonists, but addition of 2.2 nM TSP1 completely abrogated this inhibitory activity of NO (FIG. 14A-14B). Conversely, aortic-derived TSP1 null murine VSMC demonstrated reduced contraction to S1P compared to WT cells, although both were relaxed by NO (FIG. 14C). A positive effect of TSP1 on the contractile response to S1P was confirmed by adding exogenous TSP1, which increased the contractile response of TSP1 null cells to S1P (FIG. 14D). A more modest enhancement of S1P-induced contraction was observed for WT cells. The direct effect of TSP1 on S1P-induced contraction may result from cGMP-dependent activation of the MLC phosphatase (Matsumoto et al., *Magn Reson Med* 54:1530-1535, 2005), which should be higher in TSP1 null cells due to their elevated basal cGMP levels (Isenberg et al., *Cardiovasc Res* 71(4):785-793, 2006).

Endogenous TSP1 Limits NO-Stimulated Soft Tissue Perfusion

Figure 15:
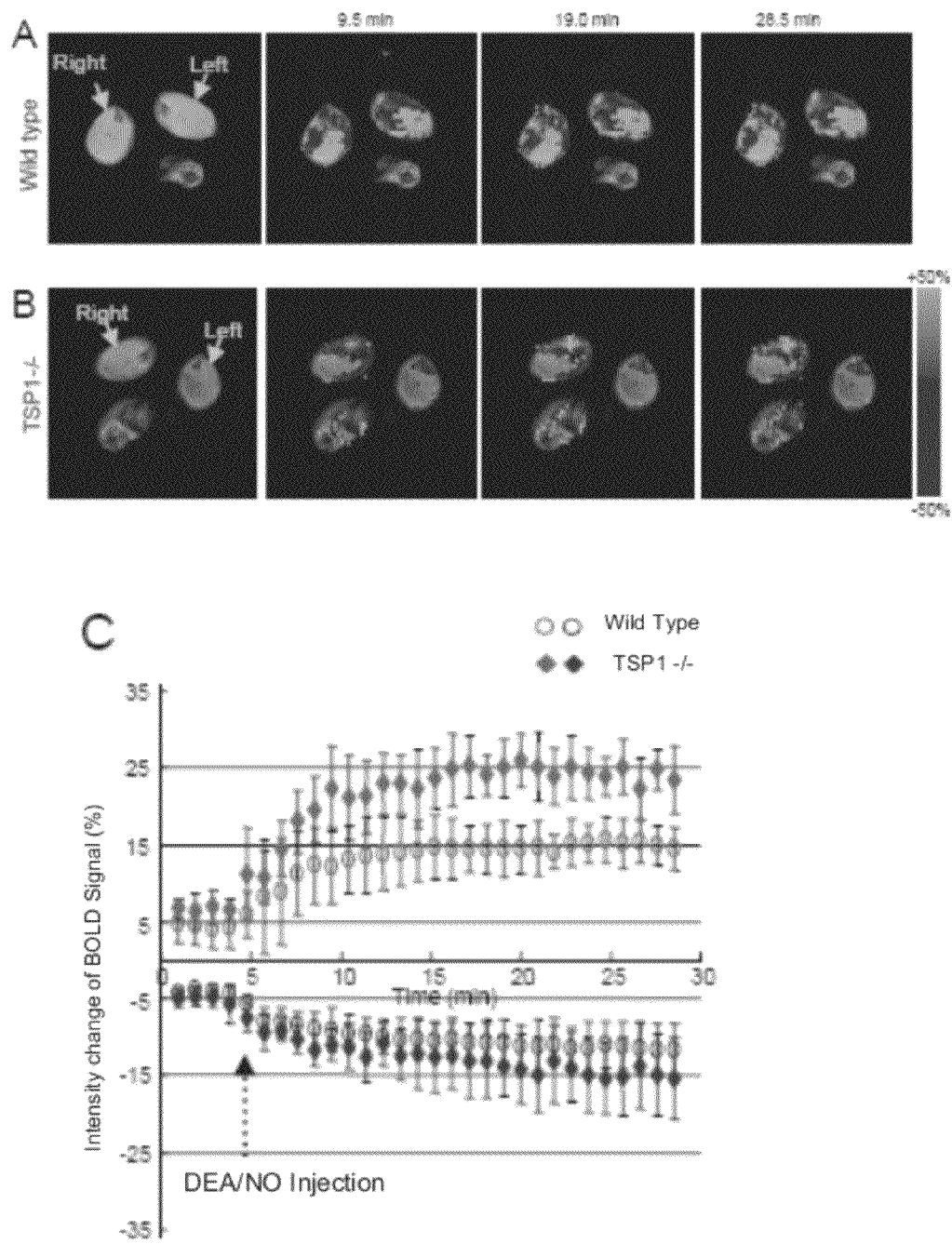
FIG. 15A-15C. Endogenous TSP1 limits tissue perfusion responses to NO in vivo. BOLD MRI images for (FIG. 15A) WT and (FIG. 15B) TSP1 null mice were obtained from $T_2^8$ weighted sequences. DEA/NO (100 nmol/g body weight)

A major physiological function of NO is to control tissue perfusion by regulating vascular smooth muscle tone (Ignarro, *J Physiol Pharmacol* 53:503-514, 2002). To investigate whether endogenous TSP1 regulates this vascular response to exogenous NO, we used BOLD MRI (Ueda et al., *J Surg Res* 10:200-204, 1998; Krishna et al., *Ilar J* 42:209-218, 2001) for real-time imaging of blood oxygenation in WT and TSP1 null C57B16 mice (FIG. 15). Intrarectal injection of the rapidly releasing NO donor diethylamine NONOate (DEA/NO, $t_{1/2}$~2 minutes) induced rapid focal increases in the BOLD MRI signal in lateral thigh sections of both TSP1 null and WT mice (FIGS. 15A, B). Notably, the magnitude of this signal in areas showing a positive response to NO was significantly greater in TSP1 null mice (25%) than in WT mice (15%, FIG. 15C, p<0.05). Furthermore, the rate of signal change was greater in the null animals versus WT. In contrast, areas with decreased BOLD signal did not differ significantly (TSP null—14%, WT—11%). Therefore, endogenous TSP1 significantly limits the acute vasodilator response to NO in skeletal muscle tissue.

Endogenous TSP1 Limits Random Myocutaneous Flap Survival

Tissue survival following a fixed ischemic insult requires restoration of regional perfusion and blood flow. We used a well characterized model of soft tissue ischemic responses (Noseworthy et al., *Semin Musculoskelet Radiol* 7:307-315, 2003) to assess the role of endogenous TSP1 in tissue survival under ischemic stress. WT and TSP1 null mice matched for sex and age underwent random dorsal modified McFarlane flap elevation and suturing under inhalation anesthesia (supplemental FIG. 14). Changes in flap perfusion and viability were noticeable immediately after surgical elevation in WT animals, with the distal aspects of flaps appearing pale and hypo-perfused. On post-operative day 7, flaps in WT animals demonstrated 38% less tissue survival compared to flaps in TSP1 null animals (59±6% versus 96±2%, p<0.05, FIGS. 16A, D). Flap survival was not gender dependent. Older WT mice (>6 months) tended to experience greater tissue loss compared to younger animals (10-16 weeks), but this difference was not statistically significant.

Post-Operative Inhibition of Nitric Oxide Synthase (NOS) Increases Tissue Necrosis To address the role of NO signaling in random soft tissue flap survival, WT and TSP1 null mice were given ad libitum access to drinking water containing L-NAME (0.5 mg/ml) during the post-operative period. In WT animals, NOS inhibition by L-NAME significantly decreased mean flap survival (46±2%) compared to flaps in animals that did not receive L-NAME (FIG. 16B, D, p<0.05). In contrast, NOS inhibition by L-NAME moderately increased tissue necrosis in TSP1 null animals (82±4% survival) but did not reach statistical significance.

An NO Donor Decreases Tissue Necrosis in Random Soft Tissue Flaps in WT Mice

To increase tissue NO levels, animals were provided isosorbide dinitrate (ISDN, 1 mg/ml) in their drinking water during the post-operative period. Flap survival was increased significantly in the treated WT animals compared to untreated WT animals (79±4% vs. 59±6%, p<0.05, FIGS. 16C, 16D). ISDN treatment resulted in essentially complete flap survival in TSP1 null animals compared to untreated animals, but the increase was not significant (100±3% vs. 97±2%). Therefore, exogenous NO can partially overcome the inhibitory effect of endogenous TSP1 on ischemic tissue survival.

TSP1 Null Flaps Exhibit Increased Granulation Tissue

Histologic examination of excised flaps demonstrated that granulation tissue formation at the necrotic tissue sites and the interface between viable and necrotic tissue was significantly higher in the flaps of time-matched TSP1 null versus WT mice (FIGS. 17A, 17B). Consistent with the known anti-angiogenic activity of TSP1, the granulation tissue in the TSP1 null flaps contained a larger number of newly formed capillaries when compared to that of the WT mice (FIGS. 17C, 17D).

Immunohistochemical staining with a TSP1 antibody of sections from wild type McFarlane flaps at 4 hours post-operatively showed diffuse TSP1 staining including the epidermis, subcutaneous blood vessels, extracellular matrix, striated muscle and inflammatory cells (FIG. 17E). By 72 hours, TSP1 staining had localized to the margins of the striated muscle cell component of the flap and surrounding extracellular matrix (FIG. 17F). Differences in the degree of TSP1 staining in proximal versus distal regions of flaps could not be discerned.

Endogenous TSP1 Acutely and Chronically Alters Post-Surgery Tissue $PO_2$

Recovery and maintenance of tissue oxygenation are critical for tissue survival following ischemic injury. EPR was used to determine tissue $pO_2$, sensed by line broadening of lithium phthalocyanine (LiPc) crystals preimplanted in proximal and distal regions of dorsal flaps and in a unit of soft tissue adjacent to the flap (control, FIG. 18A). Pre-operative tissue $pO_2$ values obtained 1 hour prior to flap elevation were essentially identical in WT and TSP1 null mice (FIG. 18B). Immediately following surgery, tissue $pO_2$ in the control area adjacent to the flap increased rapidly in WT mice, presumably due to acute inflammatory responses associated with the adjacent injury. The elevated $pO_2$ in the control area was maintained for at least 3 days. Remarkably, this acute response was initially absent in the control areas of TSP1 null mice, but their $pO_2$ gradually increased to match the WT control $pO_2$ at 48 hours.

As expected, $pO_2$ values within the flaps decreased immediately following surgery to similar levels for TSP1 null and WT mice (FIG. 18B). In WT animals, tissue $pO_2$ in the distal and proximal flap areas remained low 3 days following surgery, being 4.5±1.6 and 4.2±1.7 mm Hg, respectively. Conversely, $pO_2$ values in distal and proximal area of flaps for TSP1 null mice showed a progressive recovery of tissue $pO_2$ with time. The $pO_2$ values of distal and proximal flap areas in TSP1 null animals 3 days after surgery were significantly greater (11.1±3.4 and 17.5±3.2 mm Hg, respectively, p<0.05) than $pO_2$ found in WT flaps.

TSP1 potently antagonizes the adhesive, migratory and proliferative responses of endothelial and VSMC to NO by limiting cGMP signaling (Isenberg et al., Proc Natl Acad Sci USA 102:13141-13146, 2005; Isenberg et al., Cardiovasc Res 71(4):785-793, 2006). The same NO signaling pathway is important for maintaining vascular patency through relaxing VSMC, which causes blood vessel dilation and increased tissue perfusion (Yamada et al., J Magn Reson 154:287-297, 2002). We now identify TSP1 as a potent physiological antagonist of NO signaling to regulate VSMC cytoskeletal and contractile responses in vitro and tissue perfusion in vivo.

Calcium binding to calmodulin activates MLC kinase to phosphorylate MLC. Phosphorylated MLC stimulates interactions between myosin and actin, cross-bridge cycling, and ultimately cell contraction. S1P induces VSMC contraction via several S1P receptors, which in turn signal to inhibit MLC phosphatase activity (Matsumoto et al., Magn Reson Med 54:1530-1535, 2005). NO/cGMP signaling relaxes VSMC via cGMP dependent protein kinase, which enhances intracellular calcium $[Ca^{2+}]_i$ sequestration and also regulates MLC phosphatase (Matsumoto et al., Magn Reson Med 54:1530-1535, 2005). Consistent with these signaling pathways, MLC phosphorylation in VSMC is increased by S1P, and NO blocks this response. Significantly, TSP1 prevents the NO-driven dephosphorylation of MLC in S1P-treated VSMC. The activity of TSP1 to antagonize NO-driven actin disassembly is also important because F-actin-containing cytoskeletal stress fibers interact with the contractile protein myosin to mediate VSMC contraction. These results predicted that TSP1 should block NO-driven relaxation of VSMC, which was confirmed using in vitro assays of VSMC contraction mediated by serum or S1P in 3D collagen gels.

The differential effects of an NO donor on blood flow in WT and TSP1 null mice confirm the physiological significance of TSP1 as an antagonist of NO-mediated vasorelaxation. In resting animals, the changes in blood oxygen levels detected by BOLD MRI directly reflect alterations in tissue blood flow. Using this technique, we found that endogenous TSP1 limits the increase in peripheral blood oxygenation following an acute NO challenge. The speed of this response supports our hypothesis that preexisting endogenous TSP1 limits soft tissue perfusion by inhibiting NO-mediated vasorelaxation.

Results from the ischemic flap model indicate a clinically important role for TSP1 in modulating tissue perfusion. Tissue survival following a fixed ischemic insult was markedly increased in the absence of endogenous TSP1. Importantly, the negative effect of endogenous TSP1 on tissue survival could be partially overcome by providing exogenous NO. Recent clinical reports suggest immediate relevance of the above findings to human disease. Increased TSP1 expression in ischemic lower extremities correlates with limb amputation rates (Favier et al., J Pathol 207:358-366, 2005). Additionally, TSP1 has been ascribed a role in myocardial infarct size, though the mechanism behind its effects remains debated (Sezaki et al., Exp Biol Med (Maywood) 230:621-630, 2005; Frangogiannis et al., Circulation 111:2935-2942, 2005). In the absence of TSP1, inflammatory responses were increased and associated with greater infarct remodeling, although total infarct size did not differ between control and TSP1 null animals (Frangogiannis et al., Circulation 111: 2935-2942, 2005). Furthermore, TSP1 expression was rapidly induced following reperfusion after ischemic injury in the kidney, and exogenous TSP1 induced proximal tubule injury (Thakar et al., J Clin Invest 115:3451-3459, 2005). These reports provide evidence that TSP1 influences tissue preservation under ischemic conditions through different, though not mutually exclusive, mechanisms.

Conversely, NO clearly plays an important role in modulating tissue ischemia secondary to vascular insufficiency. In both random flap and ischemia/reperfusion models, exogenous NO and L-arginine, the substrate of NOS, are tissue protective (van Nieuw Amerongen and van Hinsbergh, Arterioscler Thromb Vasc Biol 21:300-311, 2001). Treatment with L-arginine in the drinking water and autologous bone marrow cells increased perfusion in a hind-limb ischemia model (Watterson et al., Cell Signal 17:289-298, 2005). Non-selectively inhibiting NOS using L-NAME decreased tissue preservation under ischemic conditions (Bolz et al., Circulation 107:3081-3087, 2003), and eNOS null mice have defective recovery of blood flow following hindlimb ischemia (Coussin et al., Circ Res 91:151-157, 2002). These results are consistent with the effects of L-NAME to decrease and ISDN to increase tissue survival in our ischemic flap model.

LiPc EPR provides a complementary assessment of pO$_2$ in ischemic soft tissue flaps (Krishna et al., *Proc Natl Acad Sci USA* 99:2216-2221, 2002; Hammond et al., *Plast Reconstr Surg* 91:316-321, 1993). At two anatomic locations, tissue pO$_2$ after 3 days was greater in TSP1 null flaps as compared to WT flaps. These results correlate with the significantly greater tissue survival under fixed ischemic stress in TSP1 null flaps. Limiting NO production by inhibiting NOS increased whereas supplementing NO using ISDN decreased tissue necrosis only in WT mice, further supporting a role for TSP1 in limiting the alteration of tissue perfusion by NO.

The immediate divergence in pO$_2$ following surgery in areas adjacent to null versus WT flaps indicates that endogenous TSP1 also acutely regulates tissue pO$_2$ under ischemic stress. This positive effect of endogenous TSP1 on pO$_2$ can not be directly explained by the negative effect of TSP1 on vasodilation reported here. However, the delayed increase in TSP1 null mice might result from the reported defect in monocyte recruitment noted previously in excisional skin wounds (Mullen et al., *Circ Res* 88:145-151, 2001). In this case, the immediate increase in pO$_2$ in the WT mice could result from inflammatory cytokine release by macrophages recruited to the area adjacent to the flap in a TSP1-dependent manner.

The present studies extend the known activity of TSP1 as a potent antagonist of NO-induced vascular cell adhesion, proliferation, and migration (Isenberg et al., *Proc Natl Acad Sci USA* 102:13141-13146, 2005; Isenberg et al., *Cardiovasc Res.* 71(4):785-793, 2006) to modulation of NO-dependent VSMC contractility and MLC phosphorylation. Endogenous TSP1 thereby directly limits NO-mediated increases in perfusion of healthy and injured tissues. Thus, TSP1 plays a broader role in regulating vascular physiology than previously known, and drugs developed to mimic the anti-angiogenic activity of TSP1 (Khiabani and Kerrigan, *Plast Reconstr Surg* 110:169-176, 2002) may likewise have anti-vasodilator activities that impact their clinical use. Conversely, inhibiting TSP1 expression or function could improve clinical outcome for surgical procedures that result in ischemic stress.

Example 3

Blockade of Thrombospondin-1-CD47 Interactions Prevents Necrosis of Full Thickness Skin Grafts Skin graft survival and healing requires rapid restoration of blood flow to the avascular graft. Failure or delay in the process of graft vascularization is a significant source of morbidity and mortality. One of the primary regulators of blood flow and vessel growth is nitric oxide (NO). The secreted protein thrombospondin-1 (TSP1) limits NO-stimulated blood flow and growth and composite tissue survival to ischemia. We herein demonstrate a role for TSP1 in regulating full thickness skin graft survival.

Full thickness skin grafts (FTSG) consistently fail in wild type C57 B1/6 mice but survive in mice lacking TSP1 or its receptor CD47. Ablation of the TSP1 receptor CD36, however, did not improve FTSG survival. Remarkably, wild type FTSG survived on TSP1 null or CD47 null mice, indicating that TSP1 expression in the wound bed is the primary determinant of graft survival. FTSG survival in wild type mice could be moderately improved by increasing NO flux, but graft survival was increased significantly through antibody blocking of TSP1 binding to CD47 or antisense morpholino oligonucleotide suppression of CD47.

TSP1 through CD47 limits skin graft survival. Blocking TSP1 binding or suppressing CD47 expression drastically increased graft survival. The therapeutic applications of this approach could include burn patients and the broader group of people requiring grafts or tissue flaps for closure and reconstruction of complex wounds of diverse etiologies.

Introduction

Burn injuries constitute a major source of mortality and morbidity (Wong & Munster, *Surg Clin North Am* 73(2):363-371, 1993). Among people aged 5-29 years, burns rank among the top 15 causes of morbidity and mortality worldwide (International Association for the Study of Insurance Economics. World fire statistics: information bulletin of the world fire statistics. Geneva: The Geneva Association, 2003). Over 2 million burn injuries are reported each year in the United States alone (Finkelstein & Miller, Incidence and Economic Burden of Injuries in the United States. New York: Oxford University Press, 2006; Quinney et al., *J Burn Care Rehabil* 23(5):305-310, 2002). Survival from major burns has improved over the last century as a result of improved management of the cardiovascular collapse attendant to major burns and aggressive management of the burn wound and subsequent infection (Atiyeh et al., *World J Surg* 29(2):131-148, 2005; Nolan, *Ann Plast Surg* 7(3):243-251, 1981; Shuck, *Clin Plast Surg* 1(4):577-590, 1974). As a source of damaged and/or dead tissue, the burn injury requires aggressive debridement (Makepeace, *Burns Incl Therm Inj* 9(3):153-157, 1983; Quinby et al., *Intensive Care Med* 7(2):71-6, 1981). However, this invariably creates massive open wounds, often with vital underlying structures exposed. Increasingly, aggressive surgical approaches with early tangential excision and wound closure are being applied (Shuck, *Surg Clin North Am* 50(6):1325-1335, 1970; Oshima et al., *Hum Cell* 15(3):118-128, 2002). Such therapeutic approaches represent a significant change in burn wound care and have lead to improvement in mortality rates of burn victims at a substantially lower cost (Zhu et al., *Burns* 29(1):65-72, 2003). These approaches can also decrease the severity of hypertrophic scarring, joint contractures and stiffness, and promote faster rehabilitation (Pruitt, *Curr Probl Surg* 16(5):1-95, 1979). Irrespective of any other consideration, early healing is paramount for good aesthetic and functional recovery. Disruption of epidermal-mesenchymal communication due to a delay in epithelialization increases the frequency of developing fibrotic conditions such as scar hypertrophy and contractures. Autografts from uninjured skin remain the mainstay of treatment for the majority of patients (Boyce & Warden, *Am J Surg* 183(4):445-456, 2002). Skin grafting is also a primary approach to the management of complex and non-healing wounds of diverse etiology (Snyder, *Clin Dermatol* 23(4):388-395, 2005; Hierner et al., *Clin Dermatol* 23(4):343-352, 2005).

Maximizing skin graft survival and take is paramount to successful wound reconstruction. Numerous techniques and agents have been utilized in an attempt to maximize skin graft survival. These include special dressings and splints to prevent movement of the skin graft-wound bed interface (Danikas et al., *Plast Reconstr Surg* 111(1):489, 2003). Growth factors and clotting related products, such as fibrin, have been placed in the interface between the skin graft and the wound bed (Sierra et al., *J Biomed Mater Res* 59(1):1-11, 2002). Yet substantial complications in healing remain, with significant numbers of patients requiring additional intervention due to skin graft failure and loss, and non-healing of burn wounds (Subrahmanyam, *Burns* 25(8):729-731, 1999; Unal et al., *Ann Plast Surg* 55(1):102-106, 2005; McCampbell et al., *J Burn Care Rehabil* 23(3):157-166, 2002; Desai et al., *J Burn Care Rehabil* 12(5):482-484, 1991). Interventions to date have not addressed a fundamental problem, and determinant, of skin graft survival, namely the degree of vascularity within the wound bed. Following wounding, vascularity can increase by two primary methods: (1) the development of new blood vessels from an existing vascular network, a process termed angiogenesis; or (2) remodeling and recruitment of existing blood vessels within the wound bed. Control of angiogenesis represents a balance between factors that stimulate the process and inhibit the process. Recruitment and remodeling of an existing vascular network is an effect of vascular dilatation and alterations of regional perfusion.

Thrombospondin-1 (TSP1) was the first identified endogenous inhibitor of angiogenesis (Good et al., *Proc Natl Acad Sci USA* 87(17):6624-6628, 1990; Taraboletti et al., *J Cell Biol* 111(2):765-772, 1990). TSP1, a major secretory product of activated platelets, is over expressed in wound beds (Reed et al., *J Histochem Cytochem.* 41(10):1467-1477, 1993). TSP1 inhibits angiogenesis by modulating proliferation and migration of endothelial and vascular smooth muscle cells (VSMC) (Lawler, *Curr Opin Cell Biol* 12(5):634-640, 2000; Isenberg et al., *Matrix Biol* 24(2):110-123, 2005). Conversely, tumor driven angiogenesis has been found in several major cancers to be associated with decreased expression and production of TSP1 (Lawler & Detmar, *Int J Biochem Cell Biol* 36(6):1038-1045, 2004). Recently, the TSP1 status of endothelial progenitor cells has been linked to their ability to enhance angiogenic responses (Ii et al., *Circ Res.* 98(5):697-704 2006).

The bioactive gas nitric oxide (NO) is a major effector of vessel dilation and angiogenesis that was first identified as endothelial derived relaxing factor (EDRF) (Lawler, *Curr Opin Cell Biol* 12(5):634-640, 2000). NO functions in both paracrine and autocrine fashions to regulate a number of cell responses that occur on rather different time scales. NO regulates VSMC contractility and in so doing controls blood pressure and, by altering the caliber of resistance vessels, acutely regulates tissue perfusion (Isenberg, *Microsurgery* 24(5):385-391, 2004; Bolz et al., *Circulation.* 107(24):3081-3087, 2003). NO also modulates a number of processes that, in toto, contribute to the healthy status of the cardiovascular system over an individual's lifetime (McAllister & Laughlin, *Essays Biochem.* 42:119-131 2006; Rush et al., *Can J Appl Physiol.* 30(4):442-474, 2005).

Recently we reported that picomolar concentrations of TSP1 can effectively block the growth- and motility-promoting activities NO in endothelial and VSMC and that this inhibitory signal requires the TSP1 receptor CD47 (Isenberg et al., *Proc Natl Acad Sci USA* 102(37):13141-13146, 2005; Isenberg et al., *Cardiovasc Res* 71(4):785-793, 2006). Furthermore, endogenous TSP1 limits the vasodilator activity of NO, and thereby limits tissue survival under ischemic conditions by blocking NO-dependent restoration of vascular perfusion (Isenberg et al., *Blood* 2006; Example 2). In the absence of TSP1, NO-driven signaling is enhanced, increasing tissue oxygenation. As a result, tissue necrosis in ischemic dorsal skin flaps is virtually eliminated (Isenberg et al., *Circ Res.* Feb. 9, 2007). We now present evidence that TSP1 is limiting for full thickness skin graft (FTSG) survival. We further report that expression of TSP1 and its receptor CD47 within the wound bed, but not the skin graft, are major determinants of graft survival. Relevant to therapeutic applications, we show that functional blockade of TSP1 signaling at the wound bed-graft interface is sufficient to allow complete survival of FTSG.

Materials and Methods

Animals.

C57BL/6 wild type, TSP1-null, CD47-null, and CD36-null mice were housed and maintained in a pathogen free environment and had ad libitum access to filtered water and standard rat chow. Handling and care of animals was in compliance with the guidelines established by the Animal Care and Use Committee of the National Cancer Institute, National Institutes of Health and of Washington University.

Reagents and Cells.

Human umbilical vein endothelial cells (HUVEC, Cambrex, Walkersville, Md.) were maintained in endothelial cell growth medium (EM-GM) supplemented with the manufacturer's additives (Cambrex) and 2% fetal calf serum (FCS) in 5% $CO_2$ at 37° C. Cells were utilized within passages 4-9. Isosorbide dinitrate (ISDN), an exogenous NO donor, and N-nitro-L-arginine methyl ester (L-NAME), a competitive inhibitor of nitric oxide synthase (NOS), were purchased from Sigma (St. Louis, Mo.). A CD47 targeting morpholino oligonucleotide (5'-CGTCACAGGCAGGACCCACTGC-CCA3'; SEQ ID NO: 21) and control mismatch morpholino were purchased from GeneTools (Philomath, Oreg.). The CD47 targeting morpholino recognized a sequence conserved between the murine and human mRNAs. A rat monoclonal antibody to murine CD47, Ab 301, was prepared as described (Lindberg et al., *J Cell Biol* 123(2):485-496, 1993). An isotype matched IgG2a control antibody was purchased from Santa Cruz Biotechnology (Santa Cruz, Calif.). An antibody to CD47, B6H12, was purified by protein G affinity chromatography (Pierce) from conditioned media of the respective hybridoma (American Type Culture Collection).

Full Thickness Skin Graft Model:

Wild type, TSP1 null, CD47 null and CD36 null mice were matched for sex and age. Anesthesia was induced by and maintained with inhalation isoflurane. Body temperature was maintained at 37° C. with a heating pad during the procedure. The dorsal surface was clipped of hair and depilated with Nair®. The skin was then cleansed with surgical soap and alcohol and the animals draped. Using sterile technique, a 1×1 cm FTSG incorporating the panniculus carnosus, subcutaneous tissues and skin were raised. Graft dimensions were marked on the animal skin surface with the aid of a template to insure consistency in dimension. Grafts were in the midline of the animal and secured with four interrupted 5-0 nylon sutures. Sutures were so placed as to include the fascia of the dorsal musculature to provide increased immobilization of grafts to the underlying wound bed Animals were awakened and returned to individual cages and allowed ad libitum access to food and water. Trauma to FTSG was not encountered during the post-operative interval since grafts were located in the dorsal midline over the mid thoracic area and each animal was housed individually following surgery. On postoperative day three or seven, the animals were again anesthetized with inhalation isoflurane and skin graft survival evaluated.

Treatment Groups and Protocols.

Figure 21:
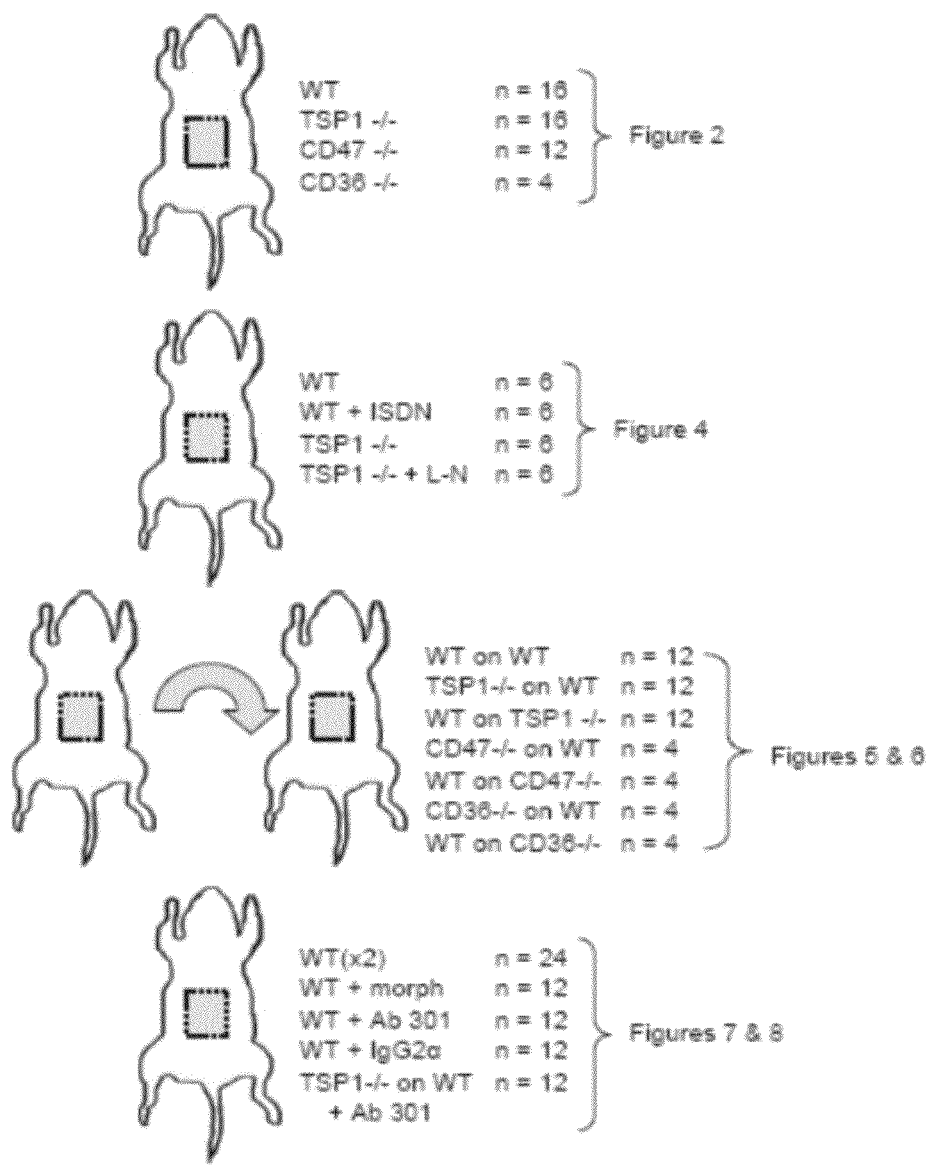
FIG. 21. Treatment and experimental groups. The indicated groups and numbers of animals on a C57BL/6 background were utilized and received treatments as indicated either at the time of skin grafting and/or during the post-operative interval. Treatments included isosorbide dinitrate (ISDN) or L-NAME (L-N) in the drinking water, or treatment of skin grafts and wound beds using a CD47 blocking antibody (Ab 301) or an isotype matched control antibody (IgG2a) or a CD47 oligonucleotide morpholino (morph). Additional control mice were included in experimental groups.

The groups of animals utilized and the treatments received as indicated either at the time of skin grafting and/or during the post-operative interval are summarized in FIG. 21. Animals treated with ISDN (1 mg/ml) or L-NAME (0.5 mg/ml) had ad libitum access to drinking water containing the given concentrations of agents during the post-operative interval. Animals treated with a CD47 monoclonal antibody (Ab clone 301) or an isotype matched control antibody (Ig2α) underwent injection of 40 μg delivered as 10 μl of a 4 mg/ml stock in 100 μl of PBS with equal volumes injected between the wound bed and graft prior to suturing the graft in place.

Animals treated with a CD47 morpholino oligonucleotide underwent injection of the FTSG and wound bed with 10 µmol/L in 250 µl of PBS with 125 µl volumes injected in the graft and wound bed, respectively prior to suturing the graft in place.

Estimation of Survival Area in FTSG.

The necrotic areas of the FTSG were determined by color, refill, eschar, and the pin-prick test. The outlines of viable and nonviable areas were traced using transparent film, and the area of necrosis cut from the template and the area of skin graft necrosis versus total skin graft area determined by comparison of the original template weight to the weight of the cut template utilizing the method described by Ueda (Ueda et al., *J Surg Res* 80(2):200-204, 1998). Skin graft survival area was presented as the ration of graft survival on post-operative day three or seven divided by the original graft area multiplied by 100%. Additionally, digital images were then acquired using an Olympus C5500 digital camera at a fixed distance (20 cm perpendicular to the animal) under standard room lighting with autoflash and macro settings engaged and uploaded for image analysis of tissue survival with a standard software program (Image-Pro Plus, Media Cybernetics, Inc., Silver Spring, Md.). Animals were euthanized and skin grafts and wound beds excised, fixed in 10% paraformaldehyde and processed for routine histology. Independent review of representative histologic sections from FTSG was performed to assess levels of tissue necrosis and inflammation providing another assessment of FTSG survival.

Laser Doppler Analysis of Tissue Perfusion.

Animals were secured supine as dictated by the anatomic area analyzed. Core temperature was monitored via rectal probe and maintained at 37° C. by a heated stage. Anesthesia was maintained with 1.5% isoflurane and a 50:50 mixture of room air and oxygen. The following scanner parameters were employed using a Moor Instruments LDI2-2λ imager: scan area—1.6×2.5 cm; scan speed—4 ms/pixel, scan time 1 min 54 sec, override distance 25 cm. Measurement of the flux of blood was determined by the formula flux=blood×area$^{-1}$× time$^{-1}$. Pre-operative baseline perfusion data was obtained, FTSG elevated and sutured in place and post-operative scanning initiated at the indicated time points.

Western Analysis of CD47.

HUVEC were plated in 12-well culture plates (5×10$^4$ cells/well) (Nunc, Denmark) in full growth medium and treated over 48 h with indicated doses of CD47 and control morpholino. Cells were subsequently washed twice with PBS and lysed immediately in 1×SDS sample buffer containing 10 g/mL leupeptin, 10 g/mL aprotinin, 1 mM Na$_3$VO$_4$, and 40 mM NaF. Lysates prepared in the SDS sample buffer described above were electrophoresed in 4-12% BisTris NuPAGE gels and transferred to PVDF membranes prior to immunoblotting with a monoclonal antibody to CD47 (clone B6H12, Lab Visions, Inc, Fremont, Calif.). The membrane was stripped and reprobed with a monoclonal antibody against β-actin (Sigma-Aldrich, St. Louis, Mo.).

Histology:

Full thickness skin grafts and graft wound beds were excised, fixed in 10% buffered formaldehyde, paraffin embedded and sectioned at a thickness of 5 µm. Sections were then stained with hematoxylin and eosin (H+E) according to standard procedures. Review of each slide was performed by an independent pathologist blinded to the origin of each tissue slide.

Wound Bed Vascular Index.

Skin graft wound beds were assessed at indicated time points (72 hours or 7 days post-operatively) for visible alterations in vascularity under 5× magnification. An arbitrary though strictly applied definition of countable vessels was employed to highlight both individual vessels and vascular ramifications. In any given vascular plexus visible by 5× magnification a vessel was defined as that segment traversing two branches. Visible vessels without ramifications and branches were counted once. Treatment status and genetic background of tissue images was not known by the reviewer. Results are expressed as vessels per cm$^2$.

Mitochondrial Viability Assay.

Mitochondrial viability of full thickness skin grafts as a correlate of tissue viability was assessed by the reduction of a tetrazolium salt to water insoluble colored formazan crystals through mitochondrial metabolism. Full thickness skin grafts from wild type and TSP1 null mice were weighed and incubated in 3 ml PBS supplemented 1:10 with 3-(4,5-dimethylthiazol-2-yl)-2,5 diphenyl tetrazolium (MTT, Promega) for 3 h in the dark at 37° C. Samples were removed, washed with distilled water and blotted dry. The formazan salt was extracted in 3 ml of 2-propranol for 6 h in the dark at 37° C. Absorbance for 200 µl aliquots was determined at 450 nm on a microplate reader. Samples were dried at 90° C. overnight and weighed again. Results were expressed as absorbance normalized to tissue dry weight.

Statistics:

Results are presented as the mean±SD of a total of 196 animals distributed as indicated above including the described treatments groups and controls (see also FIG. 21 and Figure Legends). Significance was calculated with Student's t test or where appropriate with one-way ANOVA using a standard soft ware package (Origin) with p values as indicated.

Results

Thrombospondin-1 Limits FTSG Survival.

Figure 22A:
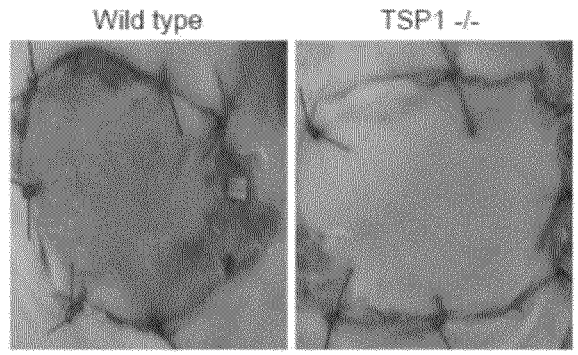
FIG. 22A-22G. Endogenous TSP1 is limiting for full thickness skin graft survival. Age and sex matched C57BL/6 wild type (FIGS. 22A, 22B), TSP1-null (FIGS. 22C, 22D), CD47-null and CD36-null mice (FIGS. 22F, 22G) underwent autologous FTSG to the dorsal back. Graft survival and wound bed vascularity was measured on post-operative day 3. Mitochondrial viability of wild type and TSP1-null FTSG units was determined at the indicated time points (FIG. 22E). Results represent the mean±SD. p=0.006 (FIG. 22B) and 0.004 (FIGS. 22D, 22G) and 0.004 versus wild type on day 1 and 3 respectively (FIG. 22E).
Figure 22C:
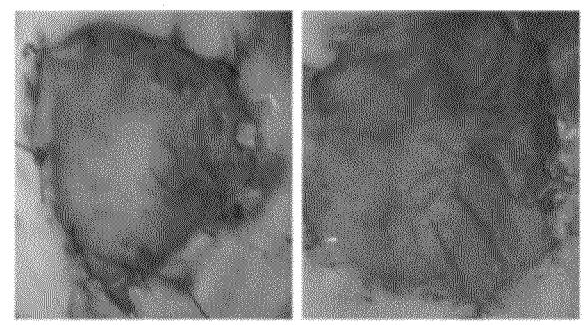
Figure 22F:
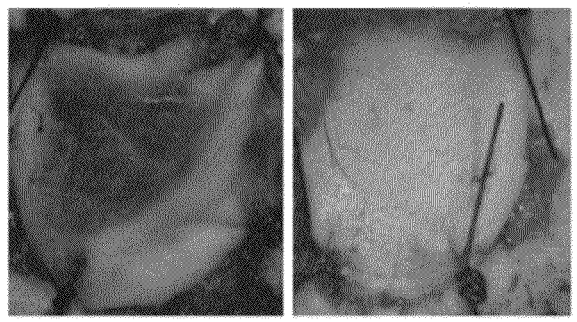
Figure 22B:
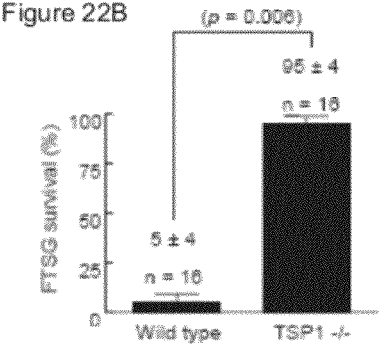
Figure 22D:
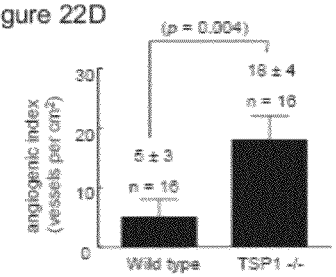
Figure 22E:
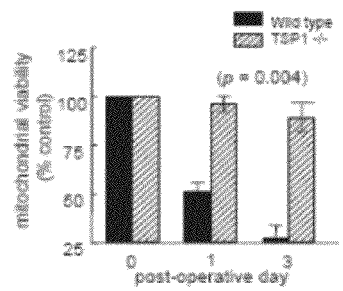
Figure 22G:
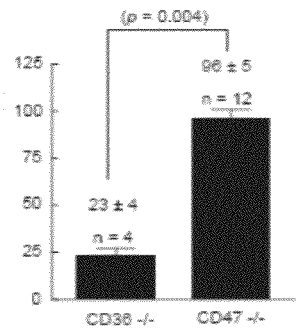
Figure 23:
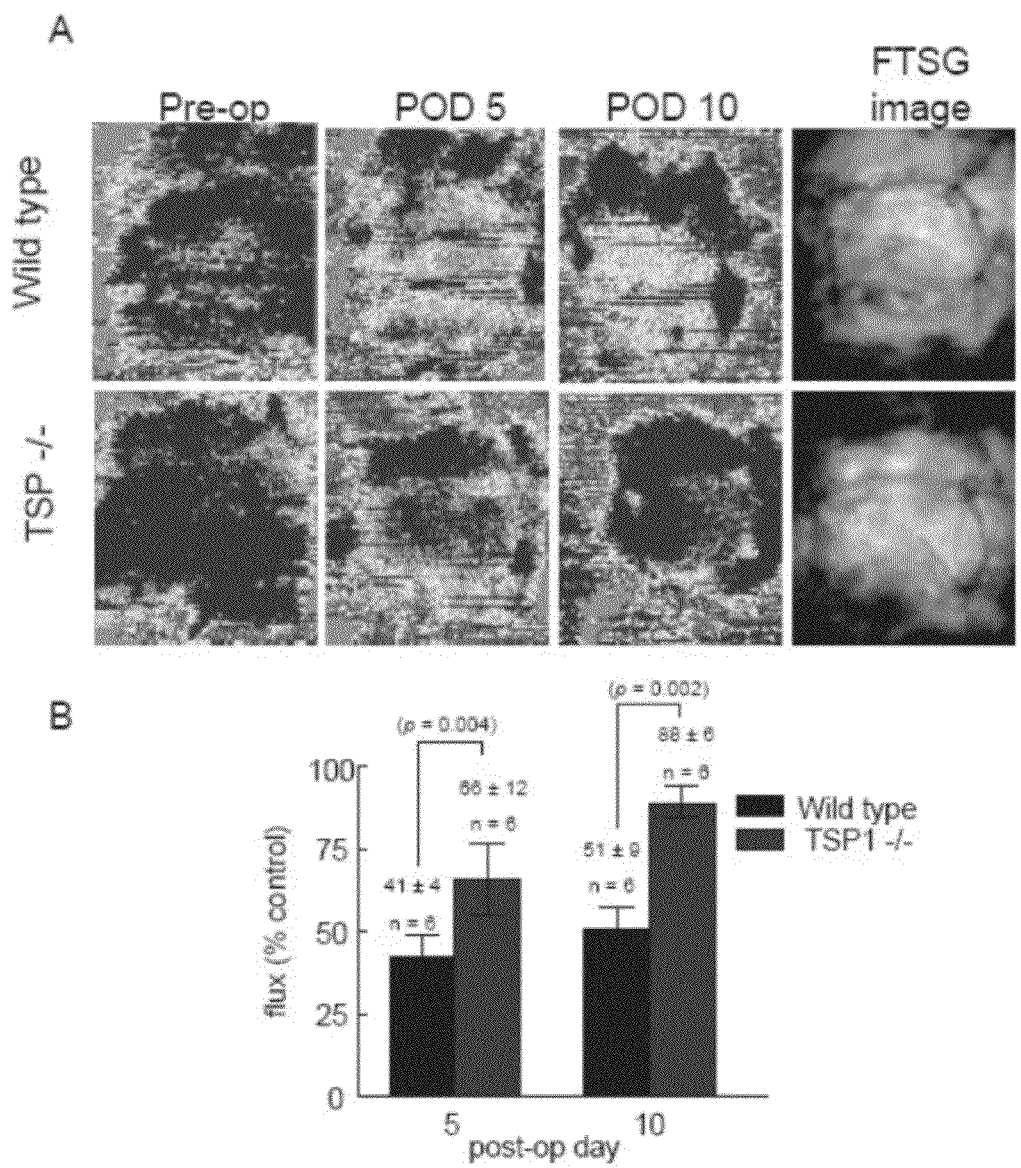
FIG. 23A-23B. Endogenous TSP1 limits reperfusion of FTSG. Age and sex matched C57BL/6 wild type and TSP1-null mice underwent FTSG and at the indicated post-operative time points laser Doppler analysis of tissue perfusion was performed (FIGS. 23A, 23B). The following scanner parameters were employed: scan area—1.6×2.5 cm; scan speed—4 ms/pixel, scan time 1 min 54 sec, override distance 25 cm. Measurement the flux of blood was determined by the formula flux=blood×area$^{-1}$×time$^{-1}$. Pre-operative baseline perfusion data was obtained, FTSG elevated and sutured in place and post-operative scanning initiated at the indicated time points. Results represent the mean±SD of 6 mice from each background. p=0.004 and 0.002 versus wild type on post-operative day 5 and 10 respectively.

FTSG in both wild type (FIGS. 22A, 22B) and CD36 null animals (FIGS. 22F, G) demonstrated 95±6 and 77±6% necrosis respectively. In contrast FTSG in TSP1 (FIGS. 23A, 23B) and CD47 null animals (FIGS. 22F, 22G) showed almost complete survival (95±4 and 96±12% respectively). Analysis of wound bed vascularity at 72 hours post skin grafting demonstrated significantly increased numbers of visible vessels in those wounds beds lacking endogenous TSP1 compared to wild type (FIGS. 22C, 22D). Similarly, wound bed analysis at 72 hours of CD47 null mice demonstrated increased vascularity compared to CD36 null wound beds. Consistent with increased graft survival and take, mitochondrial viability was found to be significantly greater in TSP1 null FTSG at 24 and 72 hours post-operatively compared to wild type (FIG. 22E) Laser Doppler analysis of FTSG survival was also performed in a series of wild type and TSP1-null animals on post-operative days 5 and 10 (FIGS. 23A, 23B). In the absence of TSP1 significant perfusion was found at both time points compared to wild type FTSG supporting clinical and histologic analysis of graft survival.

Modulation of FTSG Survival Through Nitric Oxide Regulation.

Wild type FTSG survival increased significantly (62±8%) on supplementation of the drinking water post-operatively with the NO releasing drug ISDN (FIGS. 24A, 24B). FTSG survival, already approaching 100%, in TSP1-null grafts was not substantially altered by ISDN. Conversely, inhibiting endogenous NO synthesis through L-NAME administration in the drinking water during the post-operative interval decreased TSP1-null graft survival (58±6%) (FIGS. 24C, 24D).

Wound Bed TSP1 or CD47 are Limiting for FTSG Survival.

Figure 25A:
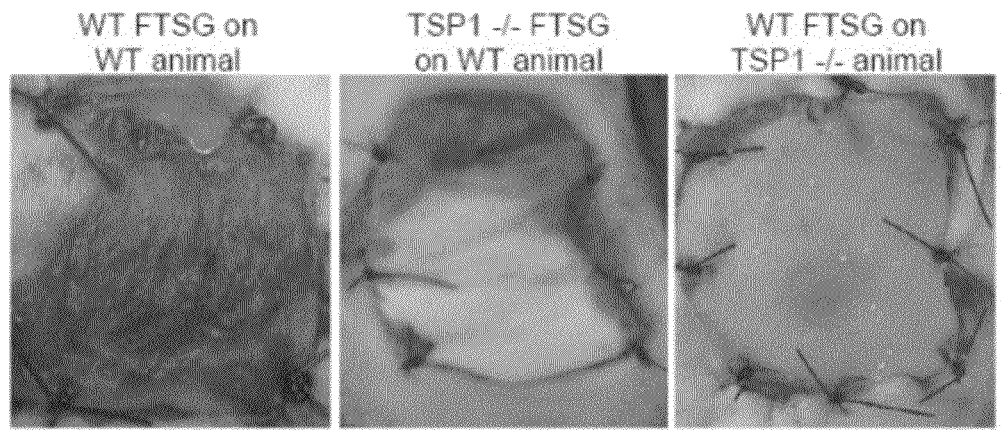
FIG. 25A-25B. Wound bed TSP1 determines FTSG survival. Age and sex matched wild type and TSP1-null mice underwent cross allograft FTSG to the dorsal back (FIGS. 25A, 25B). Graft survival was measured on post-operative day 7. Results represent the mean±SD of 12 pairs of animals. p=0.004 (B) versus wild type on wild type, one-way ANOVA.
Figure 25B:
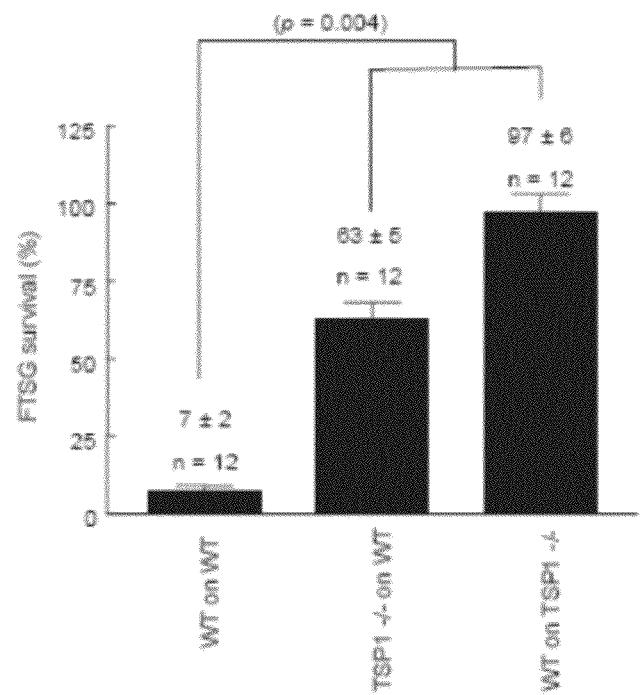
Figure 26A:
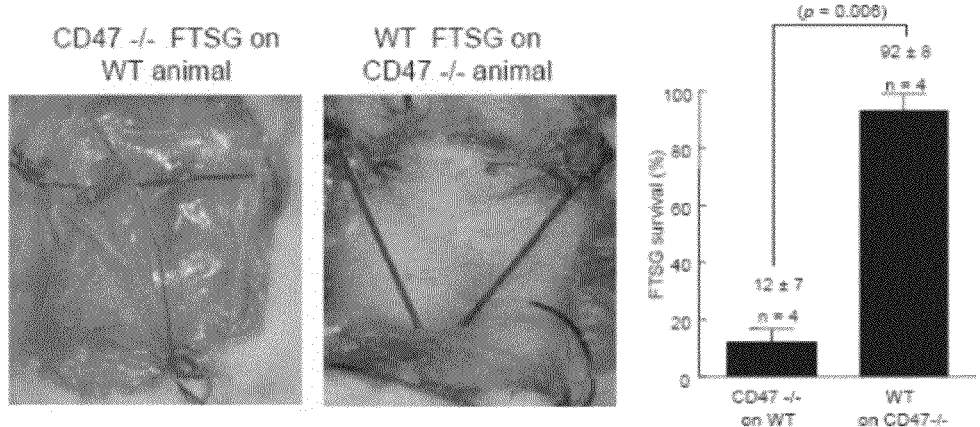
FIG. 26A-26C. Wound bed CD47 is limiting for FTSG survival. Age and sex matched CD47 and CD36-null mice underwent cross allograft FTSG to the dorsal back (FIGS. 26A, 26B). Graft survival was measured at 72 h. Results represent the mean±SD of 4 pairs of animals. Quantification of vascularity in wild type, TSP1-null, CD47-null and CD36-null wound beds was made on post-operative day 7 and expressed per cm sq of wound bed surface area (FIG. 26C).
Figure 26B:
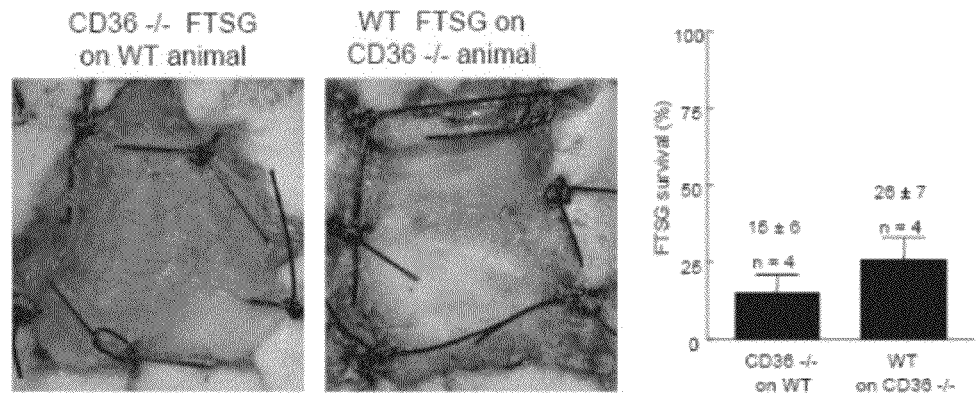
Figure 26C:
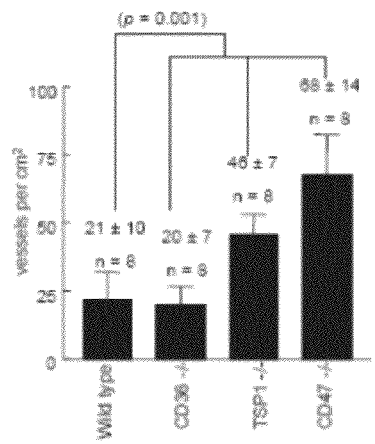

To examine the role in graft survival of TSP1 expression in the graft versus the wound bed, wild type skin grafts were transplanted onto TSP1-null wound beds (recipients), and TSP1-null grafts were transplanted onto wild type wounds. At 72 hours post-operatively, survival was significantly greater in wild type FTSG placed on TSP1-null wound beds (97±6%) (FIGS. 25A, 25B). Remarkably, TSP1-null FTSG placed on wild type wound beds all underwent significant necrosis at 72 hours (37±5%), as did a series of control wild type FTSG placed on wild type wound beds. These findings again correlated with wound bed vascularity. TSP1-null wound beds demonstrated increased vascularity despite the presence of wild type FTSG, whereas wild type wound beds showed minimal vascularity despite the presence of TSP1-null FTSG. In other experiments FTSG from wild type animals were transplanted to CD47-null wound beds and, as on TSP1-null wound beds, demonstrated dramatically increased graft survival (92±8%) (FIG. 26A). In contrast CD47-null FTSG placed on wild type wounds demonstrated nearly total necrosis, similar to TSP1-null grafts transplanted to wild type wounds. Wild type FTSG on CD36-null wound beds all showed substantial necrosis and not unexpectedly, CD36-null grafts on wild type wounds experienced substantial necrosis (85±4 and 74±3% respectively) (FIG. 26B). Analysis of wound bed vascularity at 7 days post grafting found significantly increased vascularity in both TSP1-null (47±7) and CD47-null (68±14) wound beds regardless of the genotype of the skin graft applied (FIG. 26C) as compared to wild type (21±10) and CD36-null (20±7) wound beds. Interestingly, extension of the post-operative interval at which wound bed analysis was performed from 72 hours to 7 days greatly enhanced the mean vessel count in TSP1-null but not wild type wound beds (see FIG. 22D versus FIG. 26C).

Suppression of CD47 Expression is Sufficient to Increase FTSG Survival.

Wild type FTSG and wound beds were treated with either a CD47 antisense morpholino oligonucleotide or a mismatched control morpholino (10 μM) at the time of graft elevation (10 μmol/L in 250 μl of PBS with 125 μl volumes injected in the graft and wound bed, respectively). All grafts treated with the CD47 morpholino demonstrated dramatically increased survival (79±5%) and were comparable to results obtained in TSP1 null and CD47 null animals (FIGS. 27A, 27B). Conversely, control morpholino treated grafts and grafts treated with delivery vehicle alone demonstrated significant graft necrosis and loss. Effective dose-dependent suppression of CD47 with the same morpholino was demonstrated in HUVEC (FIG. 27C) and previously in VSMC (Isenberg et al., *Circ Res* 2007; Example 4). Effective tissue suppression of CD47 through local delivery via syringe injection has also been demonstrated (Isenberg et al., *Circ Res* 100(5): 712-720, 2007). Control morpholino treated endothelial cells (and VSMC, see (Isenberg et al., *Circ Res* 2007; Example 4) did not show suppression of CD47. H & E staining of morpholino treated wild type FTSG found essentially normal tissue architecture without evidence of necrosis and increased vessel density (FIG. 27D). These histologic findings were paralleled in TSP1 null skin grafts (Isenberg et al., *Blood* 2006; Example 2) Conversely, untreated wild type FTSG showed loss of epidermis and hair follicles with ulceration, necrosis of dermal collagen, inflammatory cell infiltration, and decreased vascular density (FIG. 27E).

CD47 Blockade Increases Survival of FTSG.

A monoclonal antibody to murine CD47, Ab clone 301, (40 μg delivered as 10 μl of a 4 mg/ml stock in 100 μl of PBS delivered as 50 μl to the skin graft and wound bed, respectively) when infiltrated into wild type FTSG and wound beds increased survival of wild type FTSG from only 5±2% to 82±4% (FIGS. 28A, 28B). FTSG and wound beds infiltrated with vehicle (PBS) or an isotype matched control IgG2a antibody showed no increase in graft survival (8±5%). FTSG transplanted from TSP1-null animals were placed upon wild type wound beds pretreated with monoclonal antibody (Ab 301) and demonstrated increased graft survival (95±4%) as compared to grafts placed on untreated wound beds (FIG. 28B). H & E of antibody treated wild type FTSG demonstrated normal architecture without ulceration and minimal inflammatory cell infiltration (FIG. 28C).

Discussion

Skin consists of two tissue layers—a keratinized epidermis and a deeper layer of dermis. Appendages including hair and glands are derived from the epidermis and project into the dermis. Skin serves as a protective barrier, and any break in it must be rapidly and efficiently repaired. A temporary repair is achieved in the form of a clot. Inflammatory cells, fibroblasts and capillaries invade the clot and form granulation tissue while the epithelial edges migrate to cover the wound surface. The current standard for wound closure following excision of a deep partial or full thickness burn is the application of a skin graft. Recently skin substitutes and engineered products have been employed with some success to minimize the need for skin grafts (Wood et al., *Burns* 32(4):395-401, 2006; Atiyeh et al., *Burns* 31(8):944-956, 2005). These methods of wound closure all require rapid restoration of perfusion to the grafted elements. Restoration of tissue perfusion is important to wound healing and tissue survival under a range of conditions (Hochberg et al., *Int J Microcirc Clin Exp.* 14(1-2):67-72, 1994; Israeli et al., *Ann Plast Surg.* 32(3):305-309, 1994). L-arginine, the precursor for NO production, has been reported to be useful in resuscitation of burn wound patients (Yan et al., *Burns.* 33(2):179-184, 2007) and in increasing survival and re-perfusion of ischemic tissues (Komorowska-Timek et al. *Br J Plast Surg.* 57(4):317-325, 2004; Cordeiro et al., *Plast Reconstr Surg.* 100(5):1227-1233, 1997). NO has also been shown to enhance ischemic tissue survival (Gatti et al., *Ann Plast Surg.* 16(6):521-526, 1986; Gribbe et al., *J Plast Reconstr Aesthet Surg.* 60(3):287-293, 2007; Topp et al., *J Am Coll Surg.* 201(4):628-639, 2005).

The present report demonstrates for the first time a critical role for TSP1 in controlling survival of FTSG by limiting the beneficial effects of NO. In the absence of endogenous TSP1, or its receptor CD47, significant increases in survival of FTSG were achieved. These findings parallel our recent reports that TSP1 regulates soft tissue survival under ischemic conditions in a NO-dependent manner (Isenberg et al., *Blood* 2006; Example 2; and Isenberg et al., *Circ Res* 2007; Example 4). Random myocutaneous flaps were found to experience more than 50% increase in survival in the absence of endogenous TSP1 (Isenberg et al., *Blood* 2006; Example 2). Random myocutaneous flaps, though ischemic, retain partial perfusion through vascular networks at the base of the flap. In contrast FTSG initially lack any vascular connections. Therefore, FTSG survival requires rapid angiogenic and vascular remodeling responses. Analysis of wound beds at 72 hours and 7 days post-operatively in TSP1-null animals suggests that the absence of TSP1 results in rapid vascular remodeling of the wound bed. These findings are consistent with similar data obtained in wound beds of random ischemic myocutaneous flaps, and in muscle units of hind limbs following proximal vascular ligation (Isenberg et al., *Blood* 2006; Example 2; and Isenberg et al., *Circ Res* 2007; Example 4), supporting a role for TSP1 in regulating vascular remodeling to hypoxic/ischemic stress in addition to its known long term regulation of angiogenesis (Bornstein et al., *Int J Biochem Cell Biol* 36(6):1115-1125, 2004).

CD47 is the critical target for controlling vascular responses to ischemia. This concept is clearly demonstrated here and in our earlier study in less severe models of tissue ischemia (Isenberg et al., *Circ Res*. Feb. 9, 2007). Our results also demonstrate that the previously-identified anti-angiogenic TSP1 receptor, CD36, plays a minimal role in limiting FTSG survival. These results support our findings that ischemic composite tissue survival is also not limited by CD36 (Isenberg et al., *Circ Res* 100(5):712-720, 2007). These in vivo findings complement our recent findings that CD47 is necessary for TSP1 abrogation of the pro-angiogenic effects of NO in vitro, and that direct ligation of CD47 effectively blocks NO signaling (Isenberg et al., *J Biol Chem* 281(36): 26069-26080, 2006). Importantly for therapeutic application of these findings, antibody blockade of CD47 or morpholino suppression of CD47 increases survival of FTSG (and composite tissue units; Isenberg et al., *Circ Res* 100(5):712-720, 2007). Ab 301, a monoclonal antibody that recognizes murine CD47, and a CD47 morpholino, when infiltrated into wild type FTSG and wound beds promoted tissue survival to nearly the same extent as genetic deletion of CD47 or TSP1. Both the morpholino and Ab 301 are target specific (Isenberg et al., *Circ Res* 2007; Example 4), yet the ability to completely block or suppress CD47 with these agents in vivo is likely incomplete. Although we cannot determine the precise extent to which CD47 and CD47 signaling responses are neutralized by these agents, our results in animals clearly confirm they are efficacious within the specific models employed.

Our data show that it is the presence or absence of TSP1 and CD47 in the wound bed, not the graft, which ultimately dictates graft survival. Vascular index data from wild type wound beds treated with a morpholino or Ab 301 and wound beds from CD47- and TSP1-null animals found substantial increases in visible vasculature suggesting that the TSP1-CD47 interaction limits acute vascular remodeling. Additional support for the primacy of the wound bed in determining FTSG survival was provided by cross-allograft transplant experiments. Regardless of the TSP1 or CD47 status of the FTSG itself, improved graft survival occurred if the wound bed was either inherently TSP1- or CD47-null or rendered effectively so through antibody ligation of or morpholino suppression of CD47. Preliminary experiments with autograft transplants of wild type FTSG to wild type wound beds in which only the wound beds were treated with a CD47 monoclonal antibody or CD47 morpholino similarly demonstrated increased survival of skin grafts. Therefore, skin graft survival is primarily determined by the status of the wound bed vis a vis functioning CD47 and TSP1. Interfering with TSP1-CD47 interactions or decreasing the total number of such interactions through temporary receptor suppression is sufficient to significantly enhance skin graft survival and take. Since all animals were extensively backcrossed to the same C57B1/6 background, T cell rejection would not be expected to be a complicating factor.

TSP1 has also been found to be important in tumor growth and metastasis (Bornstein et al., *Int J Biochem Cell Biol* 36(6):1115-1125, 2004; Adams, *Int J Biochem Cell Biol;* 29(6):861-865, 1997). Over-expression of TSP1 in cancer cells has been found to slow their growth and spread (Weinstat-Saslow et al., *Cancer Res;* 54(24):6504-6511, 1994). Though TSP1-null animal do not demonstrate increased rates of tumor formation, crossing TSP1-null mice with tumor prone mice such as p53 nulls, enhances tumor progression (Lawler et al., *Am J Pathol;* 159(5):1949-5196, 2001; Ren et al., *Biochim Biophys Acta;* 1765(2):178-188, 2006). Targeting either TSP1 or CD47 for the brief intervals employed in the present studies would not be expected to increase rates of tumor formation in the treated tissues. Also, the protocols of this study were based on local-regional application of the therapeutic agents, making systemic side effects less likely. It remains to be seen if targeting TSP1 and CD47 for extended lengths of time increases tumor formation rates.

The clinical implications of the data presented herein are substantial. Skin graft necrosis and loss is a major source of morbidity and mortality worldwide. Though we found a modest increase in FTSG survival could be obtained by elevating tissue NO through orally administered ISDN, systemic delivery of such agents may have potential untoward side effects. More importantly, we demonstrate that engagement of CD47 with monoclonal antibody or suppression using a specific morpholino can dramatically improve FTSG survival. This again illustrates the underlying principle that TSP1-CD47 interactions limit the responsive range of NO whether it is produced endogenously or administered exogenously as a therapeutic agent. Because the morpholino we used was designed to hybridize with a sequence conserved in the human CD47 and was demonstrated to suppress CD47 in cultured human cells (Isenberg et al., *Blood* 2006; Example 2), this morpholino can be further tested for immediate clinical applications in improving skin graft survival and outcomes from burn wounds. A number of function modifying antibodies that recognize human CD47 are currently available and, with proper humanization, could also warrant clinical testing. Importantly, both therapeutic agents can be delivered directly to the wound bed, minimizing potential systemic side effects. Additionally, these therapeutic agents may have a role in the treatment of burns irrespective of skin grafting. A major impediment to proper healing of burn wounds is their initial ischemic state (Pruitt, *Curr Probl Surg.* 16(5):1-95, 1979; Foley, *Surg Clin North Am.* 50(6):1201-1210, 1970). Given the demonstrated benefit of anti-CD47 therapy on ischemic tissue survival, direct application to the ischemic burn wound may promote increased perfusion of the burn wound and thereby limit the extent of tissue death, decreasing the overall magnitude, duration and need for reconstruction of the burn injury (Pruitt, *Clin Plast Surg;* 1(4):667-691, 1974; Wang et al., *Br J Plast Surg;* 50(4):266-271, 1997).

Example 4

Increasing Survival of Ischemic Tissue by Targeting CD47

This example demonstrates that CD47 ligation by TSP1 represents the means by which endogenous TSP1 tempers vascular responses to NO and in so doing alters tissue oxygen in the face of both ischemia and NO challenge. In wild type VSMC, NO-induced changes in cytoskeleton organization and myosin light chain (MLC) phosphorylation were blocked by TSP1. In contrast, TSP1 did not block these NO-induced changes in CD47 null VSMC. Further, random flaps subject to acute ischemia demonstrated minimal tissue necrosis in CD47 null transgenic mice. In contradistinction, random flaps in CD36 null animals demonstrated a degree of tissue necrosis comparable and even slightly greater than that obtained in wild type animals. Further, treatment of random flaps with a CD47 blocking antibody or an inhibitory peptide in both wild type and CD36 null animals was sufficient to recapitulate tissue survival results obtained in TSP1 null flaps. CD47 null mice subject to partial hindlimb ischemia also showed less tissue necrosis and increased skeletal muscle mitochondrial viability as compared to wild type and CD36 null animals. Increases in tissue survival in CD47 null flaps correlated to increases in tissue oxygen as measured by EPR oximetry. These findings suggest that TSP1 is a global regulator of tissue perfusion through a CD47 dependent pathway and suggests novel therapeutic modalities for tissue preservation in the presence of ischemia.

Thrombospondin-1 (TSP1) limits the angiogenic and vasodilator activities of NO. This activity of TSP1 can be beneficial in some disease states, but endogenous TSP1 limits recovery of tissue perfusion following fixed ischemic injury in dorsal skin flaps in mice. Using mice lacking the TSP1 receptors CD36 or CD47, we show in this example that CD47 is the necessary receptor for limiting NO-mediated vascular smooth muscle relaxation and tissue survival following ischemic injury in skin flaps and hindlimbs. We further show that blocking CD47 or TSP1 using monoclonal antibodies and decreasing CD47 expression using an antisense morpholino oligonucleotide are effective therapeutic approaches to dramatically increase survival of soft tissue subjected to fixed ischemia. These treatments facilitate rapid vascular remodeling to restore tissue perfusion and increase skin and muscle viability. Thus, limiting CD47-dependent antagonism of NO-mediated vasodilation and vascular remodeling is a promising therapeutic modality to preserve tissues subject to ischemic stress.

Tissue viability requires continuous perfusion, which in turn depends on vascular tone, sufficient intravascular volume, and adequate blood oxygenation (Drexler *Prog Cardiovasc Dis*. 39:287-324, 1997; Hollenberg & Cunnion, *J Crit. Care* 9:262-280, 1994; Levenson et al., *J Cardiovasc Pharmacol*. 7(Suppl 2):5115-120, 1985). The contractile status of arterial smooth muscle is the major determinant of vascular tone, with venous tone playing a lesser role (Segal, *Microcirculation*. 12:33-45, 2005; Pohl et al., *Acta Physiol Scand*. 168:505-510, 2000). Underperfusion of soft tissues is the leading cause of tissue necrosis and secondary delayed wound healing in surgical patients (Athanasiou et al., *Eur J Cardiothorac Surg*. 26:1015-1026, 2004). The complications incurred can be substantial and life threatening (Raghunathan et al., *J Vasc Surg*. 43:1175-1182, 2006). Complications of inadequate tissue perfusion are multiplied in the elderly and patients with hypertension and diabetics due to the general vasculopathies associated with these disease processes (Nowygrod et al., *J Vasc Surg*. 43:205-216, 2006; Niezgoda & Mewissen, *Ostomy Wound Manage*. 50:1-11; quiz 12, 2004).

Current therapies to improve vascular perfusion combine surgical vessel manipulation/bypass with vasodilators that relax VSMC (Hankey et al., *JAMA*. 295:547-553, 2006; Antignani, *Curr Vasc Pharmacol*. 1:205-216, 2003). The bioactive gas NO is a potent vasodilator (Furchgott & Vanhoutte, *Faseb J*. 3:2007-2018, 1989) that activates soluble guanylate cyclase (sGC). The increased cGMP activates cGMP-dependent protein kinases and thereby decreases VSMC sensitivity to intracellular $Ca^{2+}$, leading to relaxation of contractile proteins (Ignarro, *J Physiol Pharmacol*. 53:503-514, 2002; Arnal et al., *Cell Mol Life Sci*. 55:1078-1087, 1999; Munzel et al., *Herz*. 22:158-172, 1997; Sauzeau et al., *J Biol. Chem*. 275: 21722-21729, 2000).

We recently reported that NO/cGMP signaling in VSMC and endothelial cells is potently inhibited by the secreted protein thrombospondin-1 (TSP1) (Isenberg et al., *Cardiovasc Res*. 71(4):785-793, 2006; Isenberg et al., *Matrix Biol*. 24:110-123, 2005; Ridnour et al., *Proc Natl Acad Sci USA*. 102:13147-13152, 2005). We further showed that endogenous TSP1 limits the ability of NO to increase skeletal muscle perfusion and blood oxygen levels in vivo (Isenberg et al., *Blood* 2006; Example 2). Following surgically induced acute ischemia in random dorsal skin flaps, endogenous TSP1 also limits tissue survival and recovery of tissue oxygenation. Ischemic tissue survival could be improved by increasing NO levels using isosorbide dinitrate, but the degree of tissue necrosis in treated wild type mice remained higher than in TSP1 null mice, which achieved essentially complete flap survival following this treatment.

To further improve survival of ischemic stress in wild type mice, we explored therapeutic approaches that target the TSP1 receptors mediating its antagonism of NO signaling. Although ligation of the anti-angiogenic TSP1 receptor CD36 (Dawson et al., *J Cell Biol*. 138:707-717, 1997) by antibodies or TSP1-derived peptides is sufficient to inhibit NO/cGMP signaling in endothelial and VSMC (Isenberg et al., *Cardiovasc Res*. 71(4):785-793, 2006; Dawson et al., *J Cell Biol*. 138:707-717, 1997), we recently found that CD36 is not necessary for this activity of TSP1 (Isenberg et al., *J Biol. Chem*. 281:26069-26080, 2006). Instead, engaging the TSP1 and SIRPα/SHPS1 receptor CD47 (Gardai et al., *J Leukoc Biol*. 79:896-903, 2006; Gao et al., *J Biol. Chem*. 271:21-24, 1996; Wang & Frazier, *Mol Biol Cell*. 9:865-874, 1998) is necessary and sufficient for TSP1 to inhibit NO-driven responses in both endothelial and VSMC (Isenberg et al., *J Biol. Chem*. 281:26069-26080, 2006).

We now show that CD47 is also the critical TSP1 receptor that regulates vascular responses to NO in skin and hindlimb ischemia models. We demonstrate that CD47 null but not CD36 null mice are protected from necrosis due to acute ischemia. We further show that suppressing CD47 expression by local application of an antisense CD47 morpholino oligonucleotide or locally applying CD47 or TSP1 blocking antibodies dramatically reduces tissue loss resulting from fixed ischemia. At least portions of this example were published as Isenberg et al. (*Circ. Res*., Feb. 9, 2007, e-pub ahead of print; 100(5):712-720, 2007).

Material and Methods

Animals:

C57BL6 wild type, TSP1-null (Guo et al., *Cancer Res*. 58:3154-3162, 1998), CD36-null (Febbraio et al., *J Biol. Chem*. 274:19055-19062, 1999), and CD47-null mice (Gao et al., *J Cell Biol*. 135:533-544, 1996) were allowed ad libitum access to water and standard chow and maintained in a pathogen free environment in accordance with guidelines established by Animal Care and Use Committees of the National Cancer Institute and Washington University, St. Louis.

Cell and Reagents:

Human aortic VSMC were obtained from Clonetics (Walkersville, Md.) and cultured in standard growth medium according to the manufacturer's recommendations. Wild type, TSP1 null and CD47 null aortic VSMC were prepared as described (Isenberg et al., *Cardiovasc Res*. 71(4):785-793, 2006). Rat anti-murine CD47 monoclonal antibody, Ab 301 was prepared as described (Lindberg et al., *J Cell Biol*. 123: 485-496, 1993). cGMP was measured using an immunoassay obtained from Amersham BioSciences (Piscataway, N.J.). TSP1 was prepared from human platelets obtained from the NIH blood bank as previously described (Roberts et al., *J Tissue Cult Methods*. 16:217-222, 1994). Diethylamine NONOate (DEA/NO) and diethyltriamine NONOate (DETA/NO) were provided by Dr. Larry Keefer (National Cancer Institute, Frederick, Md.). Type I collagen (Vitrogen) was from Inamed (Fremont, Calif.). The TSP1 monoclonal antibody clone A6.1 was purchased from Neomarkers/Lab Vision (Fremont, Calif.). An isotype-matched control IgG2a antibody was obtained from Santa Cruz Biotechnology (Santa Cruz, Calif.).

VSMC Contraction of Collagen Gels.

Collagen gel contraction assays were performed using murine derived VSMC ($7.5 \times 10^4$ cells/gel) as described (Isenberg et al., *Blood* 2006; Example 2). Wells receiving TSP1 were pre-incubated with the indicated concentrations of agent overnight. Contraction was initiated with either 10% FCS or sphingosine 1-phosphate (S1P, 100 nM).

Morpholino Suppression of CD47 in VSMC.

Human aortic VSMC were plated onto 12-well culture plates (Nunc) at a density of $5 \times 10^4$ cells/well in SM-GM+2% FCS and cultured until approximately 90% confluent. A translation-blocking antisense morpholino oligonucleotide complementary to human and murine CD47 (CGTCACAG-GCAGGACCCACTGCCCA; SEQ ID NO: 21) and a five-base mismatch control (CGTgACAGcCAcGACCgACT-GCgCA; SEQ ID NO: 22) were obtained from GeneTools (Philomath, Oreg.). Cultured cells were treated as per the manufacturer's recommendation with morpholinos (10 µM) and utilized within 48 hours of treatment.

Western Analysis of CD47.

Murine VSMC were plated in 12-well culture plates ($5 \times 10^4$ cells/well) (Nunc) in growth medium and weaned over 48 h of additives and serum and then treated in basic medium with 0.1% BSA. Cells were washed twice with PBS and lysed in 1×SDS sample buffer containing 10 µg/mL leupeptin, 10 µg/mL aprotinin, 1 mM $Na_3VO_4$, and 40 mM NaF. Lysates prepared in the SDS sample buffer described above were electrophoresed in 4-12% BisTris NuPAGE gels and transferred to PVDF membranes prior to immunoblotting using a mouse monoclonal CD47 antibody, clone B6H12 (Lab Visions, Fremont, Calif.).

Intracellular cGMP Measurement.

cGMP was determined in human aortic VSMC via immunoassay as described (Isenberg et al., *Blood* 2006; Example 2). In some situations cells were pretreated with a CD47 or control morpholino prior to assay.

Random Flap Model:

Wild type, TSP1 null, CD36 null and CD47 null mice were matched for sex and age underwent random dorsal myocutaneous flaps as described (Isenberg et al., *Blood* 2006; Example 2) and tissue harvested on postoperative day 7.

Estimation of Survival Area in Flaps.

The necrotic area of the flap was determined as described (Isenberg et al., *Blood*. Nov. 2, 2006) Animals were then euthanized and flaps excised, fixed in 10% paraformaldehyde and processed for histology.

Hindlimb Ischemia.

Wild type C57BL6, TSP1 null, CD47 null and CD36 null mice, age and sex matched, underwent ligation of the left external iliac and common femoral arteries. The right limb served as control. All animals underwent examination every 24 h to assess clinical ischemia based on a previously published index (Paek et al., *J Vasc Surg.* 36:172-179, 2002). At the end of 3 or 7 days animals were euthanized, and the tibialis anterior muscles from the right and left limbs were harvested, weighed and processed for mitochondrial viability.

Vascular Index Determination.

Random myocutaneous flap wound beds and/or ischemic hindlimb vastus medialis muscle was assessed at indicated time points (72 hours or 7 days post-operatively) for visible alterations in vascularity under 5× magnification. An arbitrary though strictly applied definition of countable vessels was employed to highlight both individual vessels and vascular ramifications. In any given vascular plexus visible by 5× magnification a vessel was defined as that segment traversing two branches. Visible vessels without ramifications and branches were counted once. Treatment status and genetic background of tissue images was not known by the reviewer.

Mitochondrial Viability Assay:

Mitochondrial viability of hindlimb muscle biopsies was assessed by the reduction of a tetrazolium salt to water insoluble formazan through mitochondrial oxidation as described (Bonheur et al., *J Surg Res.* 116:55-63, 2004). Tibialis anterior muscle biopsies were weighed and incubated in 3 ml of PBS supplemented 1:10 with 3-(4,5-dimethylthi-azol-2-yl)-2,5 diphenyl tetrazolium stock (MTT, Promega, Madison, Wis.) for 3 h in the dark at 37° C., washed with distilled water and blotted dry. The formazan salt was extracted in 3 ml of 2-propranol for 6 hours in the dark at 37° C. Absorbance for 200 µl aliquots was determined at 425 nm on a microplate reader. Muscle samples were dried at 90° C. and weighed again. Results were expressed as absorbance normalized to dry tissue weight.

Laser Doppler Imaging of Hindlimb Perfusion.

Laser Doppler blood-flow imaging was used to assess the extent of hindlimb perfusion following arterial ligation using a Doppler imager (Moor Instruments Inc., Wilmington, Del.), which measures the flux of blood (blood×area$^{-1}$×time$^{-1}$). Body temperature was maintained at 37° C. Mice were scanned immediately before and after surgery and 7 days after surgery. Equal areas of the control and ischemic limbs from the same anatomical region of the limbs were compared. To control for ambient light and temperature, calculated perfusion was expressed as the flux ratio between the ischemic and non-ischemic limbs.

Histology:

Sections of excised skin wounds were cut parallel to the long axis of each flap to include the entire length of the tissue sample, fixed in 10% buffered formaldehyde, paraffin embedded, sectioned at a thickness of 5 µm and stained with hematoxylin and eosin. Grading of inflammatory cell infiltrate and necrosis was also performed for each section. Immunohistology of morpholino and control tissue samples was performed as previously described with a primary monoclonal antibody to CD47 (clone B6H12, Lab Vision, Fremont, Calif.) (Isenberg et al., *Blood* 2006; Example 2).

Statistics:

Statistical significance was calculated with the Student's t test or one-way or two-way ANOVA as appropriate with a p value <0.05 taken as significant using a standard software package (Origin 7, Origin Labs, Northampton, Mass.). All in vitro experiments were repeated a minimum of three times.

Results

CD47 Null Mice Demonstrate Increased Soft Tissue Survival of Fixed Ischemia.

Dorsally located random myocutaneous McFarlane flaps in wild type mice demonstrated significant necrosis at 7 days (FIGS. 29A, 29B). In contrast, random flaps in CD47 null mice demonstrated minimal to no tissue necrosis to the same ischemic challenge. The response of CD47 null animals to ischemia resembled that of TSP1 null mice (Isenberg et al., *Blood* 2006; Example 2). In contrast, CD36 null flaps demonstrated areas of necrosis similar to, and in some instances greater than, wild type flaps.

CD47 is Necessary for Exogenous TSP1 to Limit NO-Stimulated VSMC Relaxation.

FCS-driven VSMC contraction of type I collagen gels was robust in both wild type and CD47 null VSMC, and exogenous NO comparably delayed contraction in both (FIG.

Figure 29C:
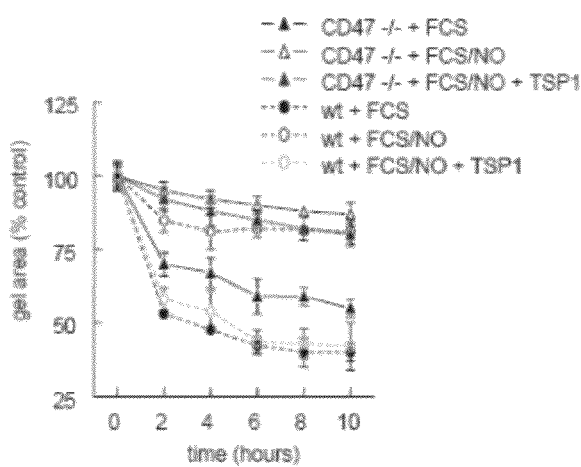
Figure 29D:
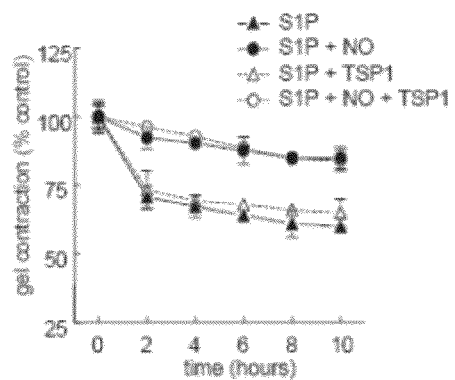

29C). As previously reported (Isenberg et al., *Blood* 2006; Example 2), relaxation of pre-contracted VSMC by NO was completely inhibited by addition of exogenous TSP1 in wild type cells, but this response to TSP1 was absent in CD47 null VSMC (FIG. 29C). Similar results were found for VSMC pre-contracted using S1P (FIG. 29D). Therefore, CD47 is the TSP1 receptor that mediates its inhibition of VSMC relaxation by NO.

Antibody Engagement of CD47 or Sequestration of TSP1 Increases Ischemic Tissue Survival Independent of CD36.

Treatment with the function blocking anti-murine CD47 antibody 301 (10 µl of 4 mg/ml stock in 90 µl PBS) but not with a control IgG2a resulted in essentially complete tissue survival in wild type myocutaneous flaps (FIGS. 30A, 30B). A similar increase in survival was observed using CD36 null mice, further indicating that this response is independent of CD36 (FIG. 30B). We also tested an anti-human TSP1 antibody known to recognize an epitope that is conserved in murine TSP1 (clone A6.1; Annis et al., *J Thromb Haemost.* 4:459-468, 2006) as a strategy to sequester endogenous TSP1. Tissue survival was enhanced in wild type flaps by treatment with this TSP1 antibody (FIG. 30C, p<0.05).

Antisense Knockdown of CD47 Prevents TSP1 Inhibition of NO-Stimulated VSMC Relaxation.

Figure 31A:
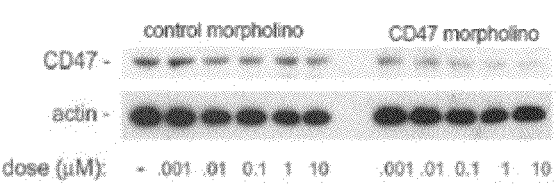
Figure 31B:
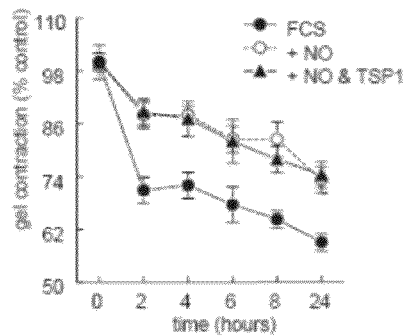

Because blocking the CD47 receptor preserved ischemic tissue, we examined the effectiveness of temporarily reducing CD47 expression to enhance tissue survival. To first validate this approach in vitro, human aortic VSMC were pre-treated with a CD47 morpholino oligonucleotide or a control morpholino. Western blotting showed a dose dependent decrease in CD47 protein following treatment with the CD47 morpholino but not in cells treated with the control morpholino (FIG. 31A). Based on these result, VSMC were pretreated with 10 µM of the CD47 morpholino, seeded into 3D collagen gels and the gel contraction measured (FIG. 31B). As in untreated cells, FCS-induced gel contraction of CD47 morpholino-treated VSMC was relaxed by exogenous NO, but TSP1 was not able to block this relaxation (FIG. 31B). Control morpholino-treated VSMC remained sensitive to TSP1 inhibition of NO-stimulated relaxation.

CD47 Knockdown Prevents TSP1 Inhibition of NO-Driven cGMP Accumulation.

Figure 31C:
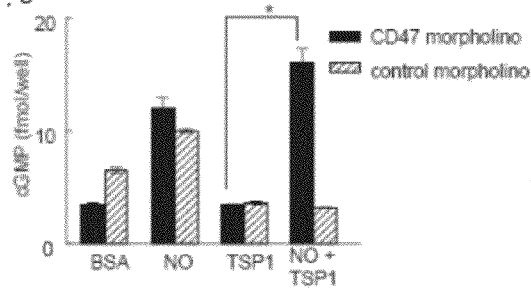

We further confirmed suppression of CD47 signaling by assessing cGMP levels in the morpholino treated cells. Human aortic VSMC were pre-treated with the CD47 or control morpholinos, and cGMP accumulation in response to NO±TSP1 determined. Knockdown of CD47 using the CD47 morpholino rendered the human aortic VSMC essentially blind to the inhibitory effects of TSP1 upon NO-driven cGMP accumulation (FIG. 31C). Conversely, control morpholino-treated cells retained sensitivity to inhibition of an NO-stimulated cGMP flux by TSP1. Control experiments with untreated VSMC demonstrated complete inhibition of an NO-driven cGMP flux by exogenous TSP1 and decreased basal and stimulated levels in the presence of CD47 as previously reported (Isenberg et al., *J Biol. Chem.* 281:26069-26080, 2006).

CD47 Knockdown Increases Tissue Survival of Ischemic Myocutaneous Flaps.

The CD47 morpholino was designed to complement a sequence in the CD47 mRNA that is conserved between the murine and human transcripts. Wild type C57BL6 mice undergoing mobilization of dorsal McFarlane flaps received either the CD47 morpholino (10 µM in 250 µl of PBS with 125 µl volumes injected in the flap and wound bed respectively) or the control morpholino. To validate CD47 knockdown in vivo, immunohistochemical staining of soft tissue flaps treated with the CD47 morpholino was done and demonstrated decreased protein staining compared to untreated controls (FIG. 31D). Remarkably, wild type flaps treated with the CD47 morpholino showed essentially 100% survival (FIG. 31D). In contrast, treatment of flaps with the control morpholino resulted in necrosis comparable to that for untreated wild type flaps. Treatment with vehicle alone or vehicle plus delivery agent (Endoporter®, GeneTools) did not alter tissue survival. Quantification of wound bed vascularity showed substantial increases in visible blood vessels following CD47 morpholino treatment relative to treatment with the control morpholino (FIG. 31E) or untreated wound beds.

CD47 Null Flaps Demonstrate Increased Numbers of Patent Blood Vessels Compared to Wild Type Flaps.

Figures 31F, 31G:
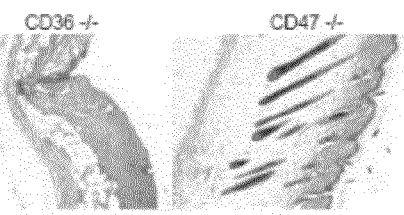
Figure 31D:
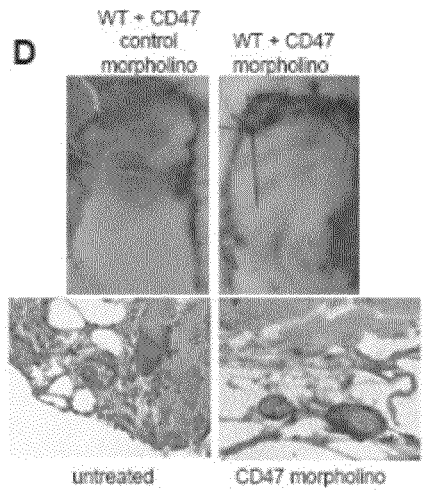

Histologic inspection of sections from CD36 null and CD47 null flaps harvested 72 hours post-operatively found evidence of early ischemic necrosis in CD36 null flaps with, epithelial loss, hair follicle drop out and thinning and coagulation of the dermis (FIGS. 31F, 31G). CD47 null flaps demonstrated normal cutaneous architecture with only a modest inflammatory cell infiltration at the inferior aspects of the flap units.

Endogenous TSP1 Limits Tissue Survival Under Fixed Hindlimb Ischemia.

Figure 32A:
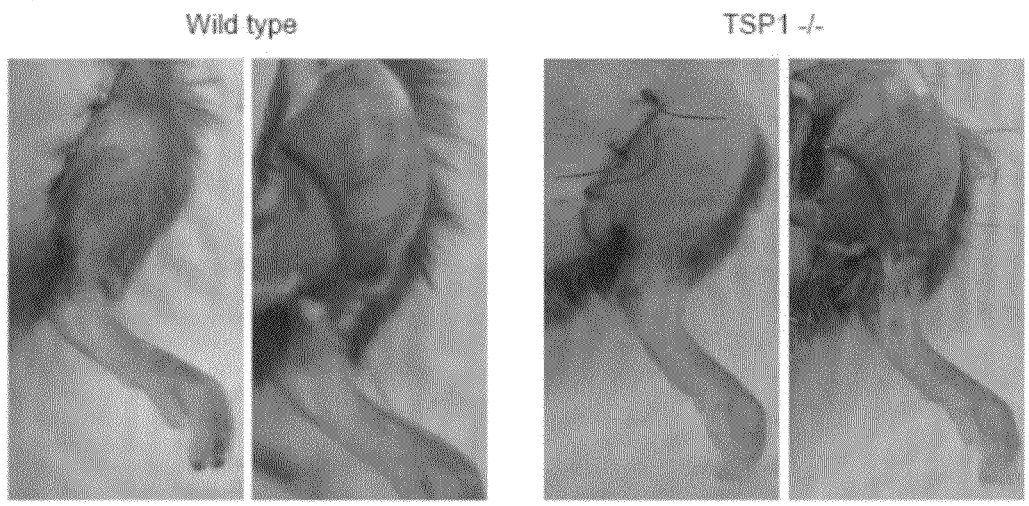

Although the random dorsal flap is a useful model of ischemic injury, the limited thickness of murine myocutaneous tissue may facilitate diffusion of oxygen from the wound bed into the ischemic flap. Therefore, large composite tissue units might not obtain similar tissue protection in the absence of TSP1 or CD47. To better model a complex 3-dimensional ischemic injury, we examined fixed ischemic insult secondary to proximal ligation of the external iliac and common femoral arteries in hindlimbs. Tissue survival was dramatically increased in the absence of TSP1 (FIG. 32A). The clinical findings in ischemic hindlimbs correlated with the increased muscle perfusion of TSP1 null limbs induced by an NO challenge (Isenberg et al., *Blood* 2006; Example 2).

Figure 32B:
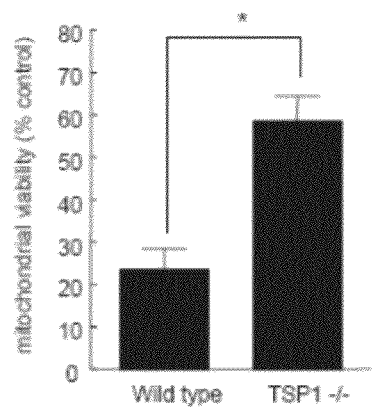
Figure 32C:
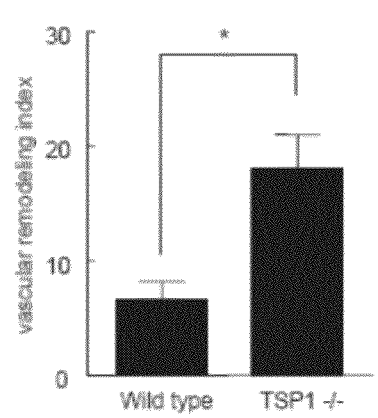
Figure 32D:
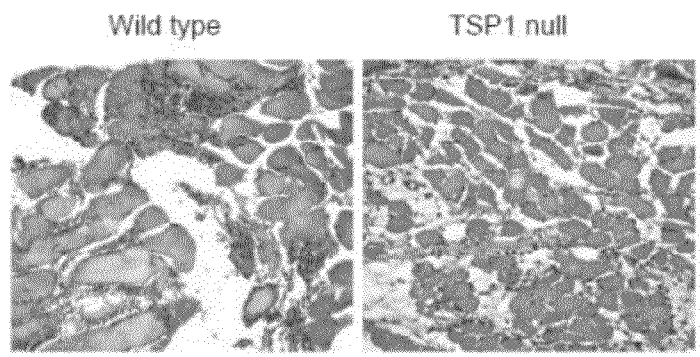

The clinical assessments of hindlimb survival were confirmed by quantifying mitochondrial viability in limb muscle using MTT reduction and normalizing to mitochondrial function in the untreated contralateral muscle (FIG. 32B). Mitochondrial function decreased to 23.5±5% of control in wild type ischemic hindlimb but remained at 58.5±6% of control in TSP1 null hindlimbs (p<0.05). Increased muscle viability was consistent with increased vascular remodeling in the treated TSP1 null hindlimbs (FIG. 32C). These findings correlated with histologic findings of muscle cell necrosis and inflammatory cell invasion of wild type hindlimbs as compared to TSP1 null limbs (FIG. 32D).

Consistent with the flap ischemia model, hindlimb ischemia was well tolerated in CD47 null mice as compared to wild type or CD36 nulls (FIG. 33A). Both CD47 null and TSP1 null animals showed minimal to no clinical evidence of tissue necrosis. In contrast, wild type and CD36 null hindlimbs demonstrated necrosis of skin, muscle and acral parts including the toes in response to vessel ligation. Similar to the TSP1 null mice, muscle mitochondrial viability was significantly increased under a fixed ischemic insult in CD47 null limbs (FIG. 33B) compared to wild type or CD36 null animals. Both CD47 and TSP1 null animals exhibited significantly increased vascular remodeling following vascular ligation as compared to wild type and CD36 null animals (FIG. 33C).

Most surprisingly, treatment of ischemic wild type hindlimbs with a CD47 morpholino recapitulated the TSP1/CD47 null phenotype with essentially no tissue necrosis and increased muscle mitochondrial viability (FIG. 33D). A control morpholino did not protect ischemic wild type hindlimbs from tissue necrosis.

Laser Doppler analysis of ischemic hindlimb perfusion was performed in wild type and transgenic mice. All animals demonstrated equal and profound decreases in hindlimb perfusion in the immediate postoperative interval. However, CD47 null animals demonstrated statistically greater levels of perfusion compared to wild type animals by the end of the first post-operative week (FIG. 34) Also in keeping with clinical findings, TSP1 null animals demonstrated increased perfusion compared to CD36 null.

Discussion

It was recently reported that NO-stimulated VSMC contraction in vitro and acute vasodilation in vivo are effectively blocked by TSP1 (Isenberg et al., *Blood* 2006; Example 2). VSMC express two TSP1 receptors that can mediate its inhibition of NO signaling: CD36 and CD47 (Isenberg et al., *Proc Natl Acad Sci USA*. 102:13141-13146, 2005; Isenberg et al., *J Biol. Chem.* 281:26069-26080, 2006). CD36 is necessary for inhibition of angiogenesis by TSP1 in the cornea (Jimenez et al., *Nat. Med.* 6:41-48, 2000), but inhibition of NO signaling by TSP1 in vascular cells requires CD47, not CD36 (Isenberg et al., *J Biol. Chem.* 281:26069-26080, 2006). The cell surface glycoprotein CD47 is expressed by all vascular cells and has been ascribed roles in regulating integrin-matrix protein interactions, self recognition and immunity (Oldenborg, *Leuk Lymphoma*. 45:1319-1327, 2004; Brown & Frazier, *Trends Cell Biol.* 11:130-135, 2001; Grimbert et al., *J Immunol.* 177:3534-3541, 2006).

Utilizing CD47 null cells and morpholino knockdown of CD47, we now show that CD47 is required for TSP1 to block NO-stimulated relaxation of VSMC. We further show that this pathway limits the ability of soft tissue to survive ischemic injury. Under conditions of soft tissue ischemia, CD47 null mice resemble TSP1 null mice in lacking significant tissue necrosis (Isenberg et al., *Blood* 2006; Example 2). Conversely, CD36 null flaps and ischemic hindlimbs, which express TSP1 and CD47, demonstrate tissue necrosis comparable to that of wild type mice. Thus, CD47 is the dominant receptor through which TSP1 limits survival of ischemic soft tissues, whereas CD36 does not play a significant role in this pathology.

The increased tissue survival in TSP1 null and CD47 null flaps correlated with increased blood vessel density in tissue sections as compared to wild type and CD36 null sections. Angiogenesis may contribute to revascularization under acute ischemic challenge (Simons, *Circulation*. 111:1556-1566, 2005). However, angiogenesis may not be rapid enough to account for the increased random flap and hindlimb survival of tissue ischemia in CD47 nulls or induced by CD47 blockade or suppression. Differences between wild type and CD47 mice could be detected based on clinical markers of viability and perfusion in ischemic flaps and hindlimbs immediately following surgery. EPR tissue oxygen measurement in ischemic flaps of CD47 null mice showed similar recovery rapid recovery as previous reported for TSP1 null mice (Isenberg et al., *Blood* 2006; Example 2). Combined with the ability of endogenous TSP1 to acutely limit an increase in muscle oxygenation stimulated by NO (Isenberg et al., *Blood* 2006; Example 2), the acute recovery of blood flow we observe by preventing TSP1/CD47 signaling may result from blood vessel remodeling in addition to angiogenesis. The increased number of visible vessels in treated flap wound beds and on the surface of the vastus medialis following proximal femoral ligation also suggests rapid adaptation by existing vascular networks. Such changes were found within 24 hours post-operatively. Angiogenic neo-vascularization and arteriogenesis, as opposed to vascular dilation, require time intervals from days to weeks (Chen & Walterscheid, *Circ Res.* 99:787-789, 2006). Such dramatic and immediate effects in tissue vascularity must arise through a process of dilation and remodeling of existing vascular networks, permitting increased flow across a preexisting vascular plexus rather than formation of new vessels. The dramatic increase in perfusion in response to fixed ischemia in the corresponding null mice reflects the central role TSP1 and CD47 play in controlling these vascular responses.

Ligation of the external iliac and common femoral arteries supplying the hindlimb creates fixed ischemia in a complex composite structure that includes cutaneous, muscle and osseous tissues and has greater metabolic needs than cutaneous flaps. TSP1 and CD47 null mice were protected from significant tissue loss and necrosis of acral parts relative to wild type and CD36 null animals, confirming that eliminating TSP1/CD47 signaling is sufficient to allow survival of fixed ischemia in a complex composite tissue as well as in skin flaps. Differences in tissue survival correlated with mitochondrial viability in biopsies taken from the tibialis anterior muscle. This muscle unit, by virtue of its distal location in the lower limb vascular runoff, provided a reliable barometer of limb perfusion. Analysis of limb perfusion with laser Doppler imaging further confirmed the clinical and muscle mitochondrial findings. Despite exhibiting comparable initial losses of limb perfusion following vascular ligation, recovery of perfusion was always greater in the TSP1 and CD47 null limbs compared to wild type and CD36 null.

These data from transgenic mice suggested that CD47 could be a useful therapeutic target for improving survival of ischemic tissues. We confirmed this by demonstrating that treating wild type mice with a CD47 blocking antibody or knockdown of CD47 using a morpholino dramatically increases tissue survival from ischemia. These results show that temporary suppression of TSP1/CD47 signaling is sufficient to prevent loss of ischemic tissue and suggest that similar approaches may be effective for treating patients subject to acute ischemic stress due to injury or surgical reconstruction. The CD47 antibody that we used is specific for murine CD47, but a number of anti-human CD47 antibodies exist that could be evaluated for preventing necrosis of ischemic tissues. The CD47 morpholino hybridizes to a sequence that is conserved between human and murine CD47, and we have verified that it suppresses CD47 expression in human VSMC and murine tissue. This morpholino is proposed to be an effective therapeutic.

The strategies we present to block TSP1/CD47 signaling are believed to have broad clinical relevance. The responses in cutaneous flaps show that CD47 morpholino and antibody treatments can effectively prevent tissue loss due to ischemia in skin. Despite the potential difficulties in delivering agents to composite tissues, treatment with the CD47 morpholino in the hindlimb ischemia model resulted in a similar degree of tissue protection. Treatment resulted in decreased limb necrosis manifest clinically as protection from necrosis of toes, skin and muscle ulceration and limb shrinkage. Muscle mitochondrial viability was significantly improved in treated limbs relative to the control limbs.

The results described herein establish an important pathophysiological role for TSP1/CD47 signaling to limit NO-driven responses in VSMC and tissue perfusion. In the absence of CD47, tissue subjected to a fixed ischemic insult can approach 100% survival suggesting that CD47 is the dominant TSP1 receptor for mediating its effects on survival of ischemic stress. The absence of CD47 relieves vascular beds from the inhibitory actions of TSP1 on NO-signaling. Therapeutic intervention targeting TSP1 or CD47 (including those discussed herein) can improve tissue survival with potential to circumvent the significant morbidity and mortality due to ischemic tissue necrosis. Therapeutic modalities based upon modulation of TSP1 and CD47 could have profound clinical utility for individuals through increasing tissue perfusion and eliminating ischemia as a limiting factor in wound healing and tissue reconstruction.

Example 5

Thrombospondin-1 Stimulates Platelet Aggregation by Blocking the Antithrombotic Activity of Nitric Oxide/cGMP Signaling Platelet α-granules constitute the major rapidly releasable reservoir of thrombospondin-1 in higher animals. Although some fragments and peptides derived from thrombospondin-1 stimulate or inhibit platelet aggregation, its physiological function in platelets has remained elusive. This example shows that endogenous thrombospondin-1 is necessary for platelet aggregation in vitro in the presence of physiological levels of nitric oxide (NO). Exogenous NO or elevation of cGMP delays thrombin-induced platelets aggregation under high shear and static conditions, and exogenous thrombospondin-1 reverses this delay. Thrombospondin-1 null murine platelets fail to aggregate in response to thrombin in the presence of exogenous NO or 8Br-cGMP. At physiological concentrations of the NO synthase substrate arginine, thrombospondin-1 null platelets have elevated basal cGMP. Ligation of CD36 or CD47 is sufficient to block NO induced cGMP accumulation and mimic the effect of thrombospondin-1 on aggregation. Exogenous thrombospondin-1 also reverses the suppression by NO of αIIb/β3 integrin-mediated platelet adhesion on immobilized fibrinogen, mediated in part by increased GTP loading of Rap1. Thrombospondin-1 also inhibits cGMP-mediated activation of cGMP-dependent protein kinase and thereby prevents phosphorylation of VASP. Thus, release of thrombospondin-1 from α-granules during activation provides positive feedback to promote efficient platelet aggregation and adhesion by overcoming the antithrombotic activity of physiological NO.

Introduction

Platelets play important roles in hemostasis and cancer metastasis and were the first source from which thrombospondin-1 (TSP1) was isolated (Jurasz et al., Br J Pharmacol. 143:819-826, 2004; Baenziger et al., J Biol. Chem. 247:2723-2731, 1972). TSP1 is a major protein component of platelet α-granules, from which it is rapidly released during platelet activation. The physiological function of TSP1 in platelets, however, remains controversial. Platelets from TSP1 null mice show normal aggregation in vitro (Lawler et al., J Clin Invest. 101:982-992, 1998; Bonnefoy et al., Blood. 107:955-964, 2006). However, exogenous TSP1 enhances thrombin-stimulated aggregation (Tuszynski et al., Blood. 72:109-115, 1988), and some monoclonal antibodies recognizing TSP1 inhibit thrombin and ionophore-stimulated platelet aggregation (Dixit et al., Proc Natl Acad Sci USA. 82:3472-3476, 1985; Leung, J Clin Invest. 74:1764-1772, 1984; Kasirer-Friede et al., Thromb Haemost. 86:653-659, 2001). Certain fragments of TSP1 inhibit platelet aggregation (Legrand et al., Arterioscler Thromb. 14:1784-1791, 1994), yet some monovalent TSP1 peptides promote aggregation (Chung et al., Blood. 94:642-648, 1999; Dorahy et al., J Biol. Chem. 272:1323-1330, 1997; Fujimoto et al., J Biol. Chem. 278:26655-26665, 2003). Because TSP1 interacts with fibrinogen, TSP1 was proposed to bridge platelets via binding to fibrinogen bound to the platelet integrin αIIbβ3 or by binding directly to this integrin (Bonnefoy et al., J. Biol. Chem. 276:5605-5612, 2001). Alternatively, TSP1 may regulate degradation of von Willebrand factor by ADAMTS13. (Bonnefoy et al., Blood. 107:955-964, 2006), which is consistent with the increased collagen- and von Willebrand factor-mediated aggregation of TSP1 null platelets (Pimanda et al., J Biol. Chem. 279:21439-21448, 2004). Functions of the several TSP1 receptors expressed on platelets have also been controversial. CD36 was the first such receptor identified (Asch et al., J Clin Invest. 79:1054-1061, 1987), but subsequent studies showed that TSP1 binding is normal to activated platelets from Naka-individuals who lack CD36 (Kehrel et al., Biochem Biophys Res Commun. 179:985-991, 1991; Tandon et al., Blood. 78:2809-2813, 1991). A proposed role for the platelet integrin αIIbβ3 as a TSP1 receptor was similarly put in doubt by normal TSP1 binding to thrombin-activated platelets from patients with Glanzmann's thrombasthenia that lack αIIbβ3 (Aiken et al., Clin Invest. 78:1713-1716, 1986; Boukerche et al., Eur J. Biochem. 171:383-392, 1988). The TSP1 receptor CD47 is highly expressed on platelets (Chung et al., Blood. 94:642-648, 1999). Despite some controversy about the role of CD47 as platelet receptor for native TSP1, several groups have confirmed that CD47-binding peptides derived from TSP1 stimulate platelet aggregation (Chung et al., Blood. 94:642-648, 1999; Dorahy et al., J Biol. Chem. 272:1323-1330, 1997; Fujimoto et al., J Biol. Chem. 278:26655-26665, 2003). Similarly, the TSP1 antibody C6.7, which inhibits TSP1 binding to CD47, inhibits platelet aggregation (Dixit et al., Proc Natl Acad Sci USA. 82:3472-3476, 1985). The relevance of the peptide data, however, has been questioned because some CD47-binding peptides appear to signal in platelets through FcRγ rather than CD47 (Tulasne et al., Blood. 98:3346-3352, 2001). Furthermore, the VVM sequences implicated in their binding to CD47 may not be accessible to mediate binding of native TSP1 to this receptor (Kvansakul et al., Embo J. 23:1223-1233, 2004). Nitric oxide (NO) is a well defined inhibitor of platelet activation (Radomski et al., Proc Natl Acad Sci USA. 87:5193-5197, 1990), although its effector cGMP also exerts some stimulatory effects on the early phases of activation (Li et al., Blood. 107:965-972, 2006). Recently, we demonstrated that TSP1 potently inhibits NO-driven responses in vascular smooth muscle and endothelial cells (Isenberg et al., Proc Natl Acad Sci USA. 102:13141-13146, 2005; Isenberg et al., Cardiovasc Res. 71:785-793, 2006). This activity of TSP1 involves inhibition of NO-stimulated synthesis of cGMP by soluble guanylyl cyclase (sGC) as well as inhibition of an unknown target downstream of cGMP. Engaging either CD36 or CD47 mimics the inhibitory actions of TSP1 on NO/cGMP signaling in vascular cells, although only CD47 is necessary for inhibition by TSP1 (Isenberg et al., J Biol. Chem. 281:26069-26080, 2006). Expression of CD36 and CD47 on platelets led us to propose that the potent antagonism of NO signaling we identified in vascular cells could extend to platelets and might clarify the role TSP1 plays in platelet aggregation. We report here that TSP1 is a physiological antagonist of NO to regulate platelet aggregation and adhesion. In the absence of TSP1, NO/cGMP signaling precludes thrombin-induced platelet aggregation.

Materials and Methods

Animals

Wild type (WT) and TSP1-null C57BL/6 mice were housed under pathogen free conditions with ad libitum access to filtered water and standard chow. Handling and care of animals was in compliance with the guidelines established by the Animal Care and Use Committees of the National Cancer Institute and Washington University.

Reagents

Thrombin was kindly provided by Dr. Jules Gladner (NIDDK). The nitric oxide donor diethylamine NONOate (DEA/NO) was kindly provided by Dr. Larry Keefer (NCI, Frederick, Md.) TSP1 was purified from fresh human platelets as described (Roberts et al., *J Tissue Cult Methods.* 16:217-222, 1994). TSP1-based peptides were synthesized as described (Barazi et al., *J Biol Chem.* 277:42859-42866, 2002) or purchased from Peptides International (Louisville, Ky.). Oxadiazole-[4,3-a]quinoxalin-1-one (ODQ) was from Sigma-Aldrich (St. Louis, Mo.). Recombinant domains of TSP1 were kindly provided by Dr. Deane Mosher (University of Wisconsin, Madison, Wis.) and Jack Lawler (Harvard). Platelet rich plasma (PRP) was provided by the blood bank of the Clinical Center of the National Institutes of Health. Fibronectin was purified from human plasma (Clinical Center of the National Institutes of Health) as described (Akiyama et al., *J Biol Chem.* 260:4492-4500, 1985). Type I collagen was purchased by Inamed (Fremont, Calif.). Fibrinogen was obtained from Calbiochem (La Jolla, Calif.).

Preparation of Human Platelets

Platelets were pelleted from platelet-rich plasma (PRP) by centrifugation for 10 minutes at 200 g. They were then washed with acid citrate dextrose (ACD) (85 mM citric acid, 65 mM sodium citrate, 100 mM glucose, pH 5.1) at a ratio of 1:7 at room temperature. After pelleting the platelets again and removing the supernatant, the platelets were resuspended in 5 mL of Tyrode's buffer (137 mM NaCl, 3 mM KCl, 12 mM NaHCO3, 0.3 mM NaHPO4, 2 mM $CaCl_2$, 1 mM $MgCl_2$, 5.5 mM glucose, 5 mM HEPES, 3.5 mg/mL BSA, pH 7.4). The final platelet number was adjusted to 200 platelets/μl in 500 μl/cuvette of Tyrode's buffer.

Preparation of Murine Platelets for cGMP Assay

After induction of general anesthesia with isoflurane 2%, age and sex matched C57BL/6 WT and TSP1-null mice underwent cardiac puncture. Blood was aspirated into 1 cc syringes with a 25 gauge needle containing 100 μl heparin (Heparin Lock Flush, Abbott, Chicago, Ill.), mixed with 100 μl 3% ACD and centrifuged in 1.2 ml S-Monovette separation tubes (Sarstedt, Germany). PRP was aspirated off, centrifuged, and the resulting platelet pellet was resuspended in 200 μl of Tyrode's buffer.

Platelet Aggregation Assay

Aggregation of human platelets under high shear conditions was assessed using a standard optical aggregometer (Lumi-Dual Aggregometer, Chrono-Log Corp., Havertown, Pa.) at 37° C. and 1200 rpm in a volume of 500 μl buffer with a final platelet concentration of $2 \times 10^5$ platelets/μl over a 5 minute interval. Pre-incubation with TSP1 and TSP1-based agents was for 15 minutes prior to addition of thrombin and/or the rapidly releasing nitric oxide donor DEA/NO. In some experiments platelets were pre-incubated with the Rap1 inhibitor GGTI-298 (10 μM) (Calbiochem, La Jolla, Calif.) for 30 minutes prior to initiating aggregation. In other high shear aggregation experiments murine platelets were prepared as above with the following modifications. Mouse blood was collected by retro-orbital bleeding of anesthetized mice using heparinized tubes. PRP was prepared and then diluted with 4 vol. of Tyrodes containing 5 mM EDTA to prevent activation. After collection by centrifugation, platelets were resuspended in 2× initial PRP volume and held at room temperature for less than 1 hour before use. Aggregation conditions consisted of 250 μL of washed platelets stirred at 1200 rpm in a Chronolog Optical aggregometer at 37° C. DEA/NO (10 μM) was added 30 seconds prior to activation and 8-BrcGMP added 15 min prior to activation with 0.2 U/ml human thrombin. Data was collected using Chronolog "Aggrolink" software. Platelet aggregation under static conditions was assessed using a spectrophotometer (Beckman DU 640, Beckman Coulter, Fullerton, Calif.) and determined as a change in absorbance at 400 nm with continuous observation over a five minute interval. The cuvette was inverted once every 60 seconds. Pre-incubation with TSP1 and TSP1-based agents was for 15 minutes prior to addition of thrombin and/or DEA/NO to minimize the formation of thrombin-serpinthrombospondin complexes (Chang & Detwiler, *Arch Biochem Biophys.* 299:100-104, 1992), which interfere with thrombin-platelet interactions.

Platelet Adhesion Assay

Bacteriological Petri dishes (35×10 mm, Becton Dickinson Labware) were pre-coated with collagen (3 μg/ml) or fibrinogen (15 μg/mL) overnight. Following aspiration of non-adherent matrix, dishes were blocked with 1% BSA. Fresh platelets were washed and suspended in Tyrode's buffer and allowed to adhere for 30 minutes. Plates were washed with PBS, fixed with 0.5% glutaraldehyde and stained with 0.02% toluidine blue. Adherent platelets were counted microscopically. In some experiments platelets were pre-incubated with the Rap1 geranylgeranyltransferase inhibitor GGTI-298 (10 μM) for 30 minutes prior to initiating adhesion.

Intracellular cGMP Assay

Fresh human platelets at $2 \times 10^5$ platelets/μl in Tyrode's buffer or PRP were pre-incubated with the indicated agents for 15 minutes and then challenged with DEA/NO for the indicated time interval at room temperature and total cGMP determined via immunoassay (Amersham, GE Healthcare, Buckinghamshire, UK). Murine WT and TSP1-null platelets were treated with DEA/NO and cGMP flux measured.

Rap1 Pulldown Assay

Platelets were diluted to $5 \times 10^8$ platelets/mL in Tyrode's buffer and treated with various reagents for the indicated times. Immediately following treatment, platelets were pelleted at 13,000 g for 30 seconds at 4° C. and resuspended in ice-cold lysis buffer containing 20 mM HEPES (pH 7.5), 100 mM NaCl, 10 mM EGTA, 20 mM $MgCl_2$, 8 mM α-glycerophosphate, 1% Triton X-100, 1 mM phenylmethylsulfonylfluoride, 40 mM NaF, 1 mM $Na_3VO_4$, 10 μg/mL aprotinin, and 10 μg/mL leupeptin. Lysates were centrifuged at 13,000 g for 5 minutes at 4° C. and the supernatants were incubated for 15 minutes on a tumbler at 4° C. with glutathione Sepharose 4B beads (Amersham) prebound with a GST-Ral GDS RBD fusion protein (kind gift of J. Silvio Gutkind, NIH, Bethesda, Md.). Bead complexes were washed by centrifugation at 6,000 g for 30 seconds at 4° C. followed by resuspension in 0.5 mL lysis buffer; 2 washes were performed for each sample. After the second wash, beads were resuspended in an equal volume of 2×SDS sample buffer and stored at −20° C. For Western analysis, bead-bound proteins in sample buffer were boiled for 10 minutes and subjected to electrophoresis on NuPAGE 10% Bis-Tris gels (Invitrogen, Carlsbad, Calif.), transferred to Immobilon-P PVDF membranes (Millipore, Billerica, Mass.), and blotted with rabbit polyclonal anti-Rap1 (sc-65; Santa Cruz Biotechnology, Santa Cruz, Calif.).

Phospho-Ser239 Vasodilator-Stimulated Phosphoprotein (VASP) Western Blotting

Washed human platelets (resuspended in Tyrode's buffer to $3 \times 10^8$ platelets/mL to a final volume of 0.5 mL) were incubated at 37° C. for 30 minutes before treatment. TSP1 was added 15 minutes prior to treatment. Immediately following treatment, platelets were pelleted at 13,000×g at 4° C. for 15 seconds and resuspended in 1 mL of a lysis buffer containing 10 mM Tris-HCl (pH 7.5), 150 mM NaCl, 1 mM EDTA, 1 mM Na$_3$VO4, 40 mM NaF, 1 µg/mL aprotinin, 1 µg/mL leupeptin, 1 mM phenylmethysulfonylfluoride and 1% Triton X-10. This suspension was placed at 4° C. with gentle agitation for 5 minutes before centrifugation at 13000×g for 5 minutes at 4° C. 5 µg lysates were electrophoresed on 4-12% Bis-Tris NuPAGE gels, transferred to Immobilon PVDF membranes and probed with a rabbit polyclonal antiserum against Serine 239-phosphorylated VASP (Santa Cruz Biotechnology, Santa Cruz, Calif.).

cGK In Vitro Kinase Assay

Platelets were washed as described above and resuspended in Tyrode's buffer (3×108 platelets/mL). Platelets were pre-incubated with TSP1 (2.2 nM) or Rp-8-pCPT-cGMP for 15 minutes prior to treatment with 8-Br-cGMP (100 µM) or NO (DEA/NO 10 µM) for 2 minutes. Treatment was stopped by placing the platelets on ice. Immediately following treatment, platelets were pelleted by centrifugation at 13,000×g at 4° C. for 15 seconds and resuspended in a lysis buffer containing 10 mM HEPES (pH 7.4), 1 mM EDTA, 1 mM 3-Isobutyl-1-methylxanthine, 125 mM KCl, 1 mM phenylmethysulfonylfluoride, 1 µg/ml aprotinin, and 1 µg/ml leupeptin. Resuspended platelets were sonicated on ice 3 times for 10 seconds each before centrifugation at 13,000×g for 5 minutes at 4° C. 100 µg lysate from each sample was incubated at 25° C. for 20 minutes with kinase buffer (150 µM Arg-Lys-Arg-Ser-Arg-Ala-Glu (SEQ ID NO: 17) peptide substrate (Bachem, King of Prussia, Pa.)), 10 mM HEPES pH 7.4, 35 mM β-glycerophosphate, 4 mM MgCl$_2$, 5 µM Rp-8 pCPT-cAMPS, 0.5 mM EDTA, 200 mM [γ-32P]ATPS (Sigma-Aldrich, St. Louis, Mo.)). Kinase assay reactions were terminated by spotting 50 µL of reaction mixture onto nitrocellulose. Nitrocellulose spots were washed 5 times each with 100 µL of 0.5% phosphoric acid before analysis with a scintillation counter.

Statistics.

All assays were repeated at least in triplicate and are presented as the mean±SD with significance being determined by the Students t test for a p>0.05. Where appropriate, significance was assessed with one-way ANOVA for an F value of 0.95.

Results

TSP1 Blocks the Ability of NO to Delay Thrombin-Stimulated Platelet Aggregation

Thrombin-induced aggregation of human platelets was significantly delayed in the presence of exogenous NO (10 µM DEA/NO) under high shear conditions, and this delay was reversed in a dose-dependent manner by TSP1 (FIG. 35A). The lowest concentration of TSP1 tested, 0.022 nM, was sufficient to accelerate platelet aggregation in the presence of NO, indicating that the physiological levels of TSP1 in normal plasma (0.1-0.2 nM) are sufficient to tonically regulate this response. This response was specific for TSP1 in that fibrinogen or fibronectin had no significant effect on the NO delay at the same concentrations (FIG. 35B). Because TSP1 has been reported to differentially affect platelet aggregation at high and low shear (Kasirer-Friede et al., Thromb Haemost. 86:653-659, 2001; Jurk et al., Faseb J. 17:1490-1492, 2003; Agbanyo et al., J Clin Invest. 92:288-296, 1993), we also examined the effect of TSP1 on static platelet aggregation in the presence of NO. Preincubation of platelets with exogenous TSP1 (2.2 nM) did not significantly alter aggregation in the presence of thrombin alone under these conditions, but TSP1 completely abrogated the NO-stimulated delay in aggregation (FIG. 35C). Therefore, TSP1 stimulates aggregation independent of shear rate.

TSP1 Prevents Activation by NO of sGC in Platelets sGC is the primary intracellular target of NO in platelets (Moro et al., Proc Natl Acad Sci USA. 93:1480-1485, 1996). Increased synthesis of cGMP induced by binding of NO to the heme of sGC activates cGMP-dependent protein kinase Iβ (cGK), which in turn phosphorylates several targets to delay platelet aggregation (Massberg et al., J Exp Med. 189:1255-1264, 1999). As previously demonstrated in vascular cells (Isenberg et al., Proc Natl Acad Sci USA. 102:13141-13146, 2005; Isenberg et al., Cardiovasc Res. 71:785-793, 2006), sGC is a target of TSP1 signaling in platelets. Both basal and NO stimulated cGMP levels were decreased following pre-treatment with TSP1 (FIG. 35D). The dose-dependence for TSP1 to inhibit NO-mediated sGC activation is consistent with that for accelerating platelet aggregation. Inhibition of cGMP accumulation is specific for TSP1 in that platelets pre-treated with fibronectin demonstrated no inhibition of an NO-stimulated cGMP flux (FIG. 35E). Even in PRP, which contains physiological levels of both fibrinogen and fibronectin, TSP1 continued to block NO-stimulated cGMP flux in platelets (FIG. 35F). Thus physiological levels of these known TSP1 ligands do not interfere with its activity.

Endogenous TSP1 Inhibits NO-Driven cGMP Accumulation in Murine Platelets

The preceding results establish that exogenous TSP1 can limit NO/cGMP signaling in human platelets but do not reveal whether endogenous TSP1 significantly influences this pathway. Based on FIG. 35A, basal plasma TSP1 levels in the WT mouse should be sufficient to limit NO/cGMP signaling. Using platelets from WT and TSP1-null mice, we found that both basal and NO-stimulated platelet cGMP levels were elevated in TSP1-null compared to WT platelets (FIG. 36A). Exogenous TSP1 decreased the NO-driven flux in platelet cGMP in both WT and null platelets, though inhibition was greater in TSP1-null platelets (FIG. 36B). Platelets are known to express eNOS, the absence of which in platelets decreases bleeding times (Wallerath et al., Thromb Haemost. 77:163-167, 1997; Freedman et al., Circ Res. 84:1416-1421, 1999), but the Tyrode's buffer typically used to study platelet function lacks the eNOS substrate L-arginine. Addition of 100 µM L-arginine to Tyrode's elevated cGMP levels in TSP1-null but not in WT platelets (FIG. 36C). Thus, endogenous TSP1 limits cGMP flux driven by both exogenous and endogenous NO.

Endogenous TSP1 is Necessary for Platelet Aggregation in the Presence of No

To determine the relevance of endogenous TSP1 to platelet aggregation, we compared thrombin induced aggregation at high shear using platelets from WT and TSP1-null mice. At low thrombin concentrations, null platelets demonstrated resistance to thrombin-driven aggregation compared to WT platelets as determined by titration with multiple additions of 0.1 U/mL thrombin (FIG. 37A). At sufficiently high thrombin levels, null and WT platelets aggregated at the same rate and to nearly the same extent (FIG. 37B). However, even at this thrombin dose, null platelets became completely refractory to thrombin in the presence of exogenous NO while WT platelets demonstrated only a modest decrement in the extent and stability of aggregation in response to NO (FIG. 37B). Under static conditions, similar patterns of response were found in murine platelets. Null platelets demonstrated aggregation in the presence of thrombin, though the lack of endogenous TSP1 in these platelets led to decreased aggregation as compared to WT (FIG. 37C). As with high shear conditions, exogenous NO delayed aggregation of WT murine platelets, but TSP1— null platelets were completely inhibited.

Endogenous TSP1 Also Limits Aggregation Downstream of cGMP

In addition to limiting cGMP synthesis by sGC, we previously showed that TSP1 inhibits signaling downstream of cGMP in endothelial cells (Isenberg et al., *Proc Natl Acad Sci USA*. 102:13141-13146, 2005). This second mechanism is also conserved in platelets. The membrane-permeable cGMP analog 8Br-cGMP substantially inhibited aggregation of WT murine platelets. As with NO, the cGMP analog rendered TSP1-null platelets resistant to thrombin-induced aggregation (FIG. 37D).

TSP1 Limits the Anti-Adhesive Activity of NO in Platelets

NO is known to inhibit activation of the platelet integrin αIIbβ3 (Walsh et al., *Biochemistry*. 43:473-480, 2004). Human platelet adhesion to the αIIbβ3 ligand fibrinogen (5 µg/ml) was partially inhibited by exogenous NO (FIG. 38A). Similar inhibition was observed for adhesion on type I collagen (3 µg/ml). The effect of NO on adhesion to fibrinogen is mediated by cGMP signaling because the sGC inhibitor ODQ prevented the decrease in platelet adhesion in response to exogenous NO (FIG. 38B). Treatment with TSP1 alone moderately increased basal adhesion of platelets on type I collagen and fibrinogen, but the ability of NO to significantly decrease platelet adhesion to fibrinogen or collagen was lost in the presence of TSP1 (FIG. 38C).

TSP1 Regulates Platelet Adhesion Via Rap1

The GTPase Rap1 plays important roles in promoting platelet aggregation and adhesion (Franke et al., *Mol Cell Biol*. 20:779-785, 2000; Han et al., *Curr Biol*. 16:1796-1806, 2006). cGMP activates cGK-I to phosphorylate Rap1GAP2 on Ser7, which in turn limits thrombinmediated activation of Rap1 (Schultess et al., *Blood*. 105:3185-3192, 2005; Danielewski et al., *Thromb Haemost*. 93:319-325, 2005). GTP-bound Rap1 activates platelet αIIbβ3 integrin by binding to the adapter protein RIAM (Lafuente et al., *Dev Cell*. 7:585-595, 2004). To determine whether TSP1 regulates Rap1 activation in platelets, we assessed GTP loading by pull-down using the Rap1-binding domain of RalGDS (FIG. 39A). As expected, thrombin stimulated Rap1 activation, and either NO or 8Br-cGMP inhibited this activation. Addition of 2.2 nM TSP1 reversed the inhibition of Rap1 activation in the presence of NO or 8Br-cGMP, indicating that TSP1 blocks this response both at the level of sGC and downstream of cGMP. TSP1 alone did not increase Rap1 activation (FIG. 39B). The geranylgeranyl transferase inhibitor GGTI-298 inhibits membrane translocation of Rap1 (Kanda & Watanabe, *Br J Pharmacol*. 151:476-482, 2007), and we verified that it inhibits basal and partially inhibits thrombin-stimulated Rap1 activation in platelets (FIG. 39B). Although other pathways may also be affected by this inhibitor, GGTI-298 was selective in adhesion assays for blocking thrombin-stimulated adhesion of platelets on fibrinogen but not on the α2β1 ligand collagen (FIG. 39C). The ability of TSP1 to stimulate thrombin-activated platelet adhesion to a substrate coated with the αIIbβ3 integrin ligand fibrinogen was lost following preincubation of platelets with GGTI-298 (FIG. 39D). Partial reversal of the TSP1 stimulation of adhesion was also seen in the presence of NO. In the presence of NO, the 55±9% stimulation of adhesion by TSP1 decreased to 25±8% following Rap1 blockade with GGTI-298. Thus, promotion of αIIbβ3-mediated platelet adhesion by TSP1 is at least partially Rap1-dependent. GGTI-298 preferentially delayed platelet aggregation at high shear in the presence of NO, consistent with the known stimulatory role of Rap1 signaling in platelet aggregation (FIG. 39E). However, TSP1 maintained its ability to accelerate platelet aggregation in the presence of both NO and GGTI-298. Thus, the positive effects of TSP1 on aggregation must require additional signaling pathways.

cGK-I is Regulated by TSP1 Signaling

VASP is another target of cGK, and in mice VASP is required for NO to delay aggregation (Aszodi et al., *Embo J*. 18:37-48, 1999). We first confirmed that treatment of platelets with 8Br-cGMP stimulates VASP phosphorylation at Ser239 and found that this was inhibited by pretreating the platelets with TSP1 (FIG. 39F). The ability of TSP1 to prevent phosphorylation of a direct cGK target stimulated by a cell-permeable cGMP analog implied that cGK itself is negatively regulated by TSP1 signaling. We tested this hypothesis using an in vitro kinase assay with a defined cGK-I selective peptide substrate (Hall et al., *J Biol Chem*. 274:3485-3495, 1999). Activation of cGK via sGC using DEA/NO in intact platelets strongly induced 32P-incorporation into the peptide, and this was prevented in platelets treated with TSP1 (FIG. 39G). This inhibition by TSP1 could occur at the level of sGC and/or cGK, so to specifically assess inhibition of cGK we activated intact platelets by treating with 100 µM 8Br-cGMP for 1 minute prior to washing and lysis for the kinase assay. Treatment with 2.2 nM TSP1 inhibited 32P incorporation stimulated by 8Br-cGMP to the same extent as the well characterized cGK-I inhibitor Rp-8 pCPT-cGMP (FIG. 39H). Therefore, cGK is a second target for TSP1 signaling in platelets.

Two Domains of TSP1 Block the NO-Driven Delay in Platelet Aggregation

To define the functional domains of TSP1 that block an NO-stimulated delay in platelet aggregation, we treated platelets with recombinant type 1 repeats (3TSR) and the C-terminal domains of TSP1 (E123CaG-1). Both TSP1 fragments blocked the ability of NO to delay thrombin-induced aggregation at high shear (FIG. 40A), whereas a trimeric recombinant construct containing the N-terminal region of TSP1 (NoC1) was inactive at the same concentration and further delayed aggregation at a higher dose (FIG. 40B). 3TSR and E123CaG1 also reversed the NO delay of aggregation under static conditions and even tended to enhance aggregation beyond control conditions (FIG. 40C). 3TSR and E123CaG1 inhibited NO stimulated cGMP flux in platelets with similar dose-dependencies as full length TSP, whereas NoC1 was also inactive in this assay (FIG. 40D). The type 1 repeats mediate TSP1 interactions with its receptor CD36, and the G module mediates CD47 binding. Thus, consistent with antagonism of NO signaling in vascular cells Isenberg et al., *J Biol Chem*. 281:26069-26080, 2006), engaging either TSP1 receptor on platelets appears to be sufficient to overcome the NO-driven delay in aggregation.

CD36- and CD47-Binding Peptides Mimic TSP1 Antagonism of NO in Platelet Aggregation Two CD47-binding sequences have been identified in the G module of TSP1 (Gao et al., *J Biol Chem*. 271:21-24, 1996). The NO-driven delay in platelet aggregation at high shear was blocked by a peptide from this region of TSP1 (7N3, $_{1102}$FIRVVMYEGKK$_{1112}$ (SEQ ID NO: 10)). Two control peptides in which the VVM sequence required for CD47 binding was mutated (604, FIRGGMYEGKK (SEQ ID NO: 11), and 605, FIRVAIYEGKK (SEQ ID NO: 12)) had no effect at 10 µM (FIG. 41A). Remarkably, 10 nM 7N3 was sufficient to significantly inhibit the NO delay (FIG. 41B). Peptide 4N1-1 ($_{1016}$RFYVVMWK$_{1023}$ (SEQ ID NO: 14)), comprising the first VVM sequence in TSP1, and a derivative of the 4N1-1 peptide with terminal lysines to increase its solubility (4N1K; Gao et al., *J Biol Chem*. 269:32389-32393, 1994) similarly prevented an NO-stimulated delay in platelet aggregation under static conditions (FIGS. 41C, 41D). A modified CD36-binding peptide derived from the second type 1 repeat (907, $_{434}$GDGV(D-I)TRIR$_{442}$ (SEQ ID NO: 19)) accelerated platelet aggregation in the presence of NO to a similar degree as the CD47-binding peptide 7N3 in high shear conditions (FIG. 41E). A second CD36-binding peptide derived from the third type 1 repeats of TSP1 (906, $_{488}$VTAGGGVQKRSRL$_{500}$ (SEQ ID NO: 18)) also reversed an NO-stimulated delay of platelet aggregation (FIG. 41F), but a heparin-binding peptide derived from the same region (246, $_{412}$KRFKQDGGWSHWSPWSS$_{428}$ (SEQ ID NO: 8)) was inactive (FIG. 41G). The CD47-(7N3) and CD36-binding peptides (p907) partially inhibited NO stimulated increases in platelet cGMP (FIG. 41H), but the respective control peptides did not. This peptide data supports the results using the recombinant TSP1 domains: engaging either CD36 or CD47 is sufficient to inhibit cGMP accumulation in platelets.

Discussion

Tonic NO/cGMP signaling acutely regulates vascular tone and tissue perfusion and, if sustained, can induce angiogenesis and vascular remodeling (Jones et al., Biochem Biophys Res Commun. 318:520-528, 2004; Dimmeler et al., Nature 399:601-605, 1999; Ignarro, J Physiol Pharmacol. 53:503-514, 2002; Ignarro et al., Circ Res. 90:21-28, 2002). TSP1 is a major endogenous antagonist of NO-dependent vasodilation (Isenberg et al., Proc Natl Acad Sci USA. 102:13141-13146, 2005; Isenberg et al., Cardiovasc Res. 71:785-793, 2006; Isenberg et al., Blood. 109:1945-1952, 2007) and restricts blood flow by vasoconstriction at sites of injury when released from platelets (Isenberg et al., Blood. 109:1945-1952, 2007). Here, we demonstrate that the hemostatic role of TSP1 extends to regulation of platelet function. Under both high and low shear conditions, NO significantly delays thrombin-stimulated aggregation and decreases adhesion of human and murine platelets. The differential effects of NO on aggregation of WT versus TSP1-null platelets demonstrate that endogenous TSP1 released from platelets in response to thrombin plays an important role to facilitate hemostasis by overcoming the tonic anti-thrombotic activity of NO. Thus, local release of TSP1 from activated platelets can simultaneously stimulate local vasoconstriction, platelet adhesion, platelet activation, recruitment of additional platelets, and stabilization of the thrombus. Unlike small molecule platelet agonists such as ADP, TSP1 is tethered to both platelets and the fibrin clot, ensuring its localization and persistence in controlling hemorrhage. TSP1 orthologs occur in all chordates examined and are presumed to have evolved by gene duplication and divergence from a single primordial thrombospondin gene whose present day descendants are found in lower animals (Adams & Lawler, Int J Biochem Cell Biol. 36:961-968, 2004; Brass, J Clin Invest. 115:3329-3331, 2005). Therefore, this potent antagonist of NO signaling has been present throughout vertebrate evolution, supporting a central role of TSP1 in regulating vascular NO signaling. This function of TSP1 was not previously appreciated because NO is a volatile gas that is lost during the isolation of platelets for in vitro functional assays. In vivo, endothelial eNOS provides a tonic inhibitory level of NO. Platelets also contain eNOS and use circulating L-arginine to generate NO (FIG. 42) (Wallerath et al., Thromb Haemost. 77:163-167, 1997; Freedman et al., Circ Res. 84:1416-1421, 1999; Signorello et al., Eur J Biochem. 270:2005-2012, 2003). Isolated platelets are rapidly depleted of the volatile NO, and the buffers employed in standard aggregation assays do not provide the L-arginine required for NO synthesis by endogenous platelet eNOS. Consequently, endogenous cGMP levels decay as platelets are "rested" before testing, explaining why washed TSP1-null behave like WT platelets in their response to thrombin activation (Lawler et al., J Clin Invest. 101:982-992, 1998; Bonnefoy et al., Blood. 107:955-964, 2006). The lack of a phenotype for TSP1-null mice in a tail snip bleeding assay may also be explained by limited dependence of this assay on NO as evidenced by the similar lack of a phenotype for eNOS-null mice (Ozuyaman et al., Thromb Haemost. 93:1161-1167, 2005). Our results also suggest that the magnitude of the anti-thrombotic activity of NO may have been underestimated due to tonic antagonism by endogenous platelet TSP1. In normal platelets at high or low shear, exogenous NO typically delays but does not prevent aggregation (Radomski et al., Proc Natl Acad Sci USA. 87:5193-5197, 1990; Rossiello et al., J Thromb Haemost. 3:2554-2562, 2005; Holmes et al., Br J Clin Pharmacol. 60:355-363, 2005 and our data). This implies that NO/cGMP signaling modulates but does not prevent the signal transduction downstream of thrombin that initiates platelet aggregation. One consequence of thrombin signaling is α-granule release, which rapidly makes TSP1 available to bind to its receptors CD36 and CD47. Signaling through these receptors limits NO signaling in platelets at the level of sGC and cGK, thereby promoting aggregation and adhesion (FIG. 42). By examining TSP1-null platelets, the potent inhibitory activity of NO in the absence of this positive feedback is revealed.

Our data provide a new interpretation of the previously described effects of TSP1 on αIIbβ3-fibrinogen interactions (Leung, J Clin Invest. 74:1764-1772, 1984; Bonnefoy et al., J. Biol. Chem. 276:5605-5612, 2001; Beiso et al., Biochim Biophys Acta. 1033:7-12, 2000). Independent of any direct interaction with fibrinogen or αIIbβ3, we propose that TSP1 promotes fibrinogen binding and platelet adhesion by activating αIIbβ3 via Rap1 (FIG. 42). We found that NO inhibits platelet adhesion on fibrinogen, whereas TSP1 increases basal adhesion and reverses the inhibition by NO. This probably occurs via blocking the tonic inhibitory effect of cGMP/cGK signaling on activation of this integrin via RAP1GAP2 phosphorylation and Rap1 activation (Massberg et al., J Exp Med. 189: 1255-1264, 1999; Schultess et al., Blood. 105:3185-3192, 2005; Danielewski et al., Thromb Haemost. 93:319-325, 2005), which occurs downstream of CD47-mediated activation of αIIbβ3 (Chung et al., J Biol Chem. 272:14740-14746, 1997). By these mechanisms, TSP1 can increase platelet adhesion and incorporation into fibrin clots. A different CD47 ligand, SHPS1 (also called SIRPα), was also shown to regulate αIIbβ3 function (Kato et al., J Thromb Haemost. 3:763-774, 2005). However, the activity of SHPS1 was to inhibit rather than stimulate the integrin. These results implicate either cGK or its substrate RAP1GAP2 as the downstream target through which TSP1 inhibits 8Br-cGMP responses in platelets. However, the ability of TSP1 treatment to prevent phosphorylation of a second cGK substrate VASP and to inhibit cGK activity in an in vitro kinase assay clearly establishes that cGK is a downstream target of TSP1 signaling. Based on studies in VASP null mice, VASP plays a critical role in the modulation of platelet aggregation by NO (Aszodi et al., Embo J. 18:37-48, 1999), and phosphorylation of Ser239 is both a direct and indirect target of NO/cGMP signaling to delay aggregation (Li et al., Blood. 107:965-972, 2006). Collagen is also an important physiological agonist for platelet activation. Platelet adhesion on collagen and activation in response to this adhesion is mediated by the platelet integrin α2β1 and the collagen signaling receptor glycoprotein VI (Sarratt et al., Blood. 106:1268-1277, 2005). Platelet adhesion to and aggregation induced by collagen is stimulated by peptide 4N1K (but not by the control 4NGG) and by TSP1 in WT but not in CD47-null platelets (Chung et al., *Blood.* 94:642-648, 1999). Here we found that NO inhibits platelet adhesion to type I collagen via a sGC-dependent mechanism, and TSP1 reverses this inhibition.

Thus, in addition to enhancing platelet aggregation, TSP1 can promote adhesive interactions with matrix collagen that induce platelet activation. The reported changes in von Willebrand factor processing in TSP1-null mice provides an additional mechanism by which platelet adhesion on collagen can be regulated, and the potential role of NO in this pathway merits further investigation (Bonnefoy et al., *Blood.* 107:955-964, 2006; Pimanda et al., *J Biol Chem.* 279:21439-21448, 2004). The role of endogenous TSP1 in the process of thrombus formation is less clear in severe vessel injury such as those created by guide wire endothelial stripping of arterial segments (Budhani et al., *J Mol Cell Cardiol.* 43:210-214, 2007). Consistent with previous reports that CD47-binding peptides increase platelet aggregation (Chung et al., *Blood.* 94:642-648, 1999; Dorahy et al., *J Biol Chem.* 272:1323-1330, 1997; Fujimoto et al., *J Biol Chem.* 278:26655-26665, 2003), we found that CD47-binding peptides potently antagonize NO-stimulated delays in aggregation. This occurred under high shear and static conditions. Both conditions are physiologically relevant since some agonist receptor signaling pathways are initiated only under low shear conditions (Verkleij et al., *Blood.* 91:3808-3816, 1998; Frojmovic, *Am Heart J.* 135: S119-131, 1998). Thus, CD47 may be a useful pharmacological target for controlling platelet activation in diseases associated with decreased blood flow and shear such as peripheral vascular disease. Vascular thrombus frequently complicates this process. Drugs that act as antagonists of CD47 may be useful for treating prothrombotic disorders, and agonists of CD47 could benefit bleeding disorders where thrombin activation is limited. CD47-binding peptides derived from TSP1 could provide leads for creating such mimetics. Such drugs might also be useful for individuals at risk for cardiovascular disease associated with TSP1 polymorphisms (Stenina et al., *Int J Biochem Cell Biol.* 36:1013-1030, 2004; Zwicker et al., *Blood.* 108:1280-1283, 2006). Our data suggests that CD36 could also be a useful target to control platelet activation. CD36-null platelets aggregate normally, but this was also assessed without NO (Yamamoto et al., *Br J Haematol.* 81:86-92, 1992). CD36-null mice and Naka-humans, who lack CD36, may have no phenotype with respect to NO signaling because CD47 can mediate this activity of TSP1 independent of CD36 (Isenberg et al., *J Biol Chem.* 281:26069-26080, 2006). However, because we show that engaging CD36 is sufficient to perturb NO signaling in platelets, CD36-directed drugs such as those currently in clinical testing as anti-tumor agents might be useful to modulate platelet function (Markovic et al., *Am J Clin Oncol.* 30:303-309, 2007).

Example 6

Blocking TSP1-CD47 Signaling Enhances Tissue Survival to Ischemia in a Porcine Model: Implications for Human Disease Insufficient tissue perfusion underlies many acute and chronic diseases. Tissue perfusion in turn requires adequate blood flow, determined in large part by the relative state of relaxation or constriction of arterial vessels. Nitric oxide (NO) produced by vascular cells modulates blood flow and tissue perfusion by relaxing and dilating arteries. Recently we reported that the secreted protein thrombospondin-1 (TSP1), through its cell surface receptor CD47, limits the ability of NO to relax and dilate blood vessels and thus decreases tissue perfusion. To determine the clinical potential of these discoveries we evaluated the therapeutic efficacy of targeting TSP1-CD47 in a porcine model of tissue ischemia.

Briefly, random cutaneous flaps 2×10 cm$^2$ were raised in white hairless Yucatan miniature pigs and were treated with a monoclonal antibody to TSP1, an antisense morpholino oligonucleotide to CD47 or control agents and tissue survival assessed. Primary vascular cells (VSMC) cultured from Yucatan pigs were also treated with the same agents±and an NO donor (DEA/NO) and cGMP quantified.

Antibody blockade of TSP1 or morpholino suppression of CD47 dramatically enhanced survival of random tissue flaps. These responses correlated with increased blood vessel patency and tissue blood flow on vessel injection studies. NO-stimulated cGMP flux in Yucatan VSMC was abrogated after antibody or morpholino treatment.

Antibody ligation of TSP1 or antisense morpholino knock down of CD47 greatly increased tissue survival to ischemia. Given the homology between porcine and human soft tissues these results suggest significant therapeutic potential for people.

Introduction

Impaired tissue healing is a well recognized phenomenon in the elderly (Ashcroft et al., *J Anat* 187 (Pt 1):1-26, 1995; Ashcroft et al., *Biogerontology* 3(6):337-345, 2002). Among the many factors that contribute to this consequence of aging, alterations in blood flow is central (Marin, *Mech Ageing Dev* 79(2-3):71-114, 19). Decreased tissue blood flow secondary to vascular disease not only impairs tissue responses to trauma, surgical or otherwise, but also leads to eventual ischemic tissue death (Reed & Edelberg, *Sci Aging Knowledge Environ* 2004(7):pe7, 2004). A majority of the population over 65 years of age will have varying degrees of vascular pathology and progressive diseases arising from the same (Sigvant et al., *J Vasc Surg* 45(6):1185-1191, 2007).

Nitric oxide (NO) is a central regulators of vascular health and blood flow (Ignarro, *J Physiol Pharmacol* 53(4 Pt 1):503-514, 2002). This bioactive gas increases blood flow in mature vasculature through its ability to relax vascular smooth muscle cells (Ignarro, *Circ Res* 65(1):1-21, 1989) and increases new blood vessel formation (angiogenesis) by stimulating vascular cell proliferation and migration[8, 9]. In the elderly, NO production in blood vessels is dramatically decreased (Napoli et al., *Nitric Oxide* 15(4):265-279, 2006), a problem that is further accelerated in the presence of vascular pathology (Desjardins & Balligand, *Acta Clin Belg* 61(6):326-334, 2006). Recently, we discovered that the secreted matricellular protein, thrombospondin-1 (TSP1) is the central modulator of NO stimulation of vascular cells (Isenberg et al., *Proc Natl Acad Sci USA* 102(37):13141-13146, 2005; Isenberg et al., *Cardiovasc Res* 71(4):785-793, 2006). In the absence of endogenous TSP1, NO-driven increases in tissue blood flow are dramatically increased (Isenberg et al., *Blood* 109(5):1945-1952, 2007). Likewise, the absence of TSP1 or its necessary receptor CD47 confers significant survival advantages to complex tissue units following ischemic insult and correlates directly with markedly improved blood flow. Blocking TSP1 directly with antibody engagement or suppressing CD47 (Isenberg et al., *J Biol Chem* 281(36):26069-26080, 2006) with a morpholino oligonucleotide leads to heightened blood flow under ischemic stress (Isenberg et al., *Circ Res* 100(5):712-720, 2007) and atherosclerotic vasculopathy in murine models.

The use of an appropriate animal model is required to critically evaluate the therapeutic potential of this strategy in humans. The pig (*Sus scrofa*) represents an ideal large animal model for analysis of therapeutic agents that modify blood flow (de Smet et al., *Cardiovasc Res* 39(1):224-232, 1998) and tissue perfusion because the structure and morphology of pig vasculature and skin is nearly identical to human (Zhang et al., *Plast Reconstr Surg* 106(7):1555-1565, 2000; Guyuron et al., *Plast Reconstr Surg* 101(3):816-819, 1998). We herein demonstrate that using monoclonal antibodies to target TSP1 or an antisense morpholino oligonucleotide to suppress CD47 expression greatly enhances ischemic soft tissue survival in a porcine tissue injury model. These results suggest that the identified therapeutics may be clinically efficacious in improving tissue blood flow and healing in people.

Materials and Methods

Cells and Reagents:

Vascular smooth muscle cell (VSMC) growth medium was obtained from Cambrex (SM-GM, Lonza, Basel, Switzerland). A CD47 morpholino antisense oligonucleotide complementary to human a 5'-UTR sequence conserved between murine and human CD47 mRNAs (CGTCACAG-GCAGGACCCACTGCCCA; SEQ ID NO: 21) and 5 base mismatched control morpholino were purchased from Gene-Tools (Philomath, Oreg.). A monoclonal antibody to TSP1 (clone A6.1) was prepared as described (Dixit et al., *J Biol Chem* 261(4):1962-1968, 1986). TSP1 antibody HB8432 was purified from conditioned medium of the corresponding hybridoma, obtained from the American Type Culture Collection (Manassas, Va.), by affinity chromatography on immobilized protein A. Fluorescein was purchased from Pierce (Rockford, Ill.). Monomeric type I collagen was obtained from Inamed (Fremont, Calif.).

Animals:

White hairless Yucatan miniature swine (*Sus scrofa* (Yuc: scr), Sinclair Research Center, Columbia, Mo.) between 15 and 30 kg and 6 months of age were housed in an AAALAC accredited facility in accordance with the standards in the Guide for the Care and Use of Laboratory Animals (NRC 1996). Animals were fed once daily with ~750 gm of Zeigler NIH SWINE (Zeigler Bros. Inc., Gardens, Pa.) and received water ad libitum. The animals were maintained on a 12:12 light dark cycle at 24±2 C and 30-70% relative humidity Animals were anesthetized by an intramuscular injection of ketamine 10-12 mg/kg and medetomidine 20-30 µg/kg followed by IV catheter placement and administration of propofol to effect. Following intubation, they were placed on isoflurane 1-3%. Buprenorphine 0.01 mg/kg was given intramuscularly and cefazolin 25 mg/kg was given intravenously before surgery. Animals received warm LRS at ~10 ml/kg/hr and were maintained on a hot-water blanket during the procedure. Following the indicated post-operative intervals animals were again anesthetized with 10-12 mg/kg ketamine and 20-30 µg/kg medetomidine and an intravenous catheter was placed, data acquisition was performed, and the animals were euthanized by administration of 80-100 mg/kg Euthasol intravenous.

White Hairless Yucatan Miniature Pig VSMC Cultures.

Under sterile technique, segments of the femoral artery were harvested, and the tissue was cut into small pieces and incubated in smooth muscle cell growth medium with 1% collagenase type II (Worthington Biochemical Corp., Lakewood, N.J.). The resultant cell suspension was then plated in sterile culture flasks in growth medium and cultured until confluence obtained.

Ischemic Soft Tissue Flap Model.

Animals underwent shaving of the dorsal surface hair and cleansing of the skin with soap and alcohol. Random dorsal cutaneous flaps 2×10×0.5 cm were elevated and immediately sutured in place with interrupted 4-0 nylon suture (Ethicon, Johnson & Johnson, N.J.). Treated flaps were injected with the indicated amounts of drug in sterile normal saline. On the 3 and 7 post-operative days tissue survival was determined and flaps excised for histology. In some instances animals received intravenous fluorescein prior to euthanasia and flap perfusion assessed under ultra violet illumination.

Determination of Flap Survival.

Clinical assessment of flap perfusion was performed with notation of color, capillary refill and bleeding to needle stick being recorded. Flap dimensions were then traced onto a clear plastic sheet and with demarcation of viable and non-viable areas made. Weights of segments of sheeting corresponding to viable versus non-viable portions of flaps were then determined and % survival expressed as a percentage versus total as previously described (Isenberg et al., *Blood* 109(5):1945-1952, 2007).

Indian Ink Studies.

The internal jugular vein and common carotid arteries were cannulated and the animals perfused with a volume of 5 L heparinized (50 U/mL) normal saline heated to 50° C. A mixture of India ink and gelatin (5%) heated to 50° C. (1 L) was administered by gently pressing and then releasing the plunger of the syringe to simulate the arterial pulse. The flaps were excised and placed in 100% glycerin and stored at 4° C. for 10 days. During this time flap tissue became thin, desiccated and transparent and allowed visualization of the vascular architecture under direct transillumination. Using 5× magnification patent vessels (defined as those demonstrating filling with India ink) were quantified and expressed as per $cm^2$ flap area.

Adhesion assay.

White hairless Yucatan miniature pig VSMC were plated at 10,000 cells/well onto 96-well plates (Maxisorb, Nunc) pre-coated with type I collagen (3 µg/ml). Cells were incubated for 1 h in basal medium (lacking additives and serum) with 0.1% BSA and the indicated concentrations of TSP1 and DEA/NO. Plates were then washed with PBS, fixed with glutaraldehyde, stained with crystal violet, and washed. Absorbed stain was solubilized with acetic acid from fixed cells and the resulting color signal determined on a MR580Microelisa Auto Reader, (Dynatech, Alexandria, Va.) at 450 nm wavelength. In other experiments cell were treated with a CD47 or mismatch control morpholino as described for 48 h prior to harvesting.

Morpholino Suppression of CD47.

White hairless Yucatan miniature pig VSMC were plated onto culture plates (Nunc, Roskilde, Denmark) at a the indicated cell density in smooth muscle cell growth medium+2% FCS and cultured until approximately 90% confluent. Cultured cells were treated according to the recommendation of the manufacturer with morpholinos (10 µM) and delivery agent (Endoporter® 6 µl/ml) and used within 48 hours of treatment.

Intracellular Cyclic Nucleotide Measurement.

White hairless Yucatan miniature pig VSMC ($10^4$ cells/well) grown overnight in 12-well culture in SM-GM containing 2% FCS and then weaned off serum over 48 h before treatment with NO donors and other agents in serum/additive free medium+0.1% BSA. Intracellular cGMP levels were determined using an enzyme immunoassay (Amersham, GE Health Care, UK).

Analysis of White Hairless Yucatan CD47 mRNA Sequence.

Approximately $2 \times 10^6$ white hairless Yucatan miniature pig lung endothelial cells were suspended in 1 mL TriZOL reagent (Invitrogen, Carlsbad, Calif.) and processed according to the manufacturer's specifications. 5 µg total RNA was used to create cDNA using SuperScript III (Invitrogen, Carlsbad, Calif.). A primer approximately 60 bp upstream of the predicted CD47 start codon and a primer approximately 60 bp downstream of the predicted CD47 stop codon were used to amplify CD47 cDNA with PCR Supermix (Invitrogen, Carlsbad, Calif.). Two independently-derived PCR products were purified using the Wizard purification kit (Promega, Madison, Wis.) and subjected to sequencing at the NCI Minicore with the primers used for PCR and two internal primers (to obtain higher-quality sequence of the ends of the PCR products). The following primers were employed: (porcine CD47) forward CTGCTCCAGACACCTGAGG (SEQ ID NO: 23) and reverse CGTCTTAGTACTCTCCAATC (SEQ ID NO: 24).

Histology.

Flaps were excised, fixed in 10% buffered formaldehyde, paraffin embedded and sectioned at a thickness of 5 μm. Sections were then stained with hematoxylin and eosin (H & E) according to standard procedures. Review of each slide was performed by an independent pathologist blinded to the origin of each tissue slide.

Statistics:

Results in a porcine model are presented as the mean±SD of a total of 23 animals. Each animal underwent 2-4 flaps dependent on the degree on non-pigment dorsal skin for a total of 76 random dorsal cutaneous flaps distributed into the following treatment groups: Untreated (vehicle only) n=22; CD47 morpholino n=22; mismatch morpholino (negative control) n=10; TSP1 monoclonal antibody A6.1 n=16; TSP1 monoclonal antibody HB8432 n=6. Experiments with harvested primary femoral artery vascular smooth muscle cells from the Yucatan white hairless pig were repeated a least four times and results are presented as the mean±SD. India ink analysis of flap perfusion was performed on 6 flaps from each treatment group described and results presented as the mean±SD. Significance was calculated with Student's t test or where appropriate one way and two way ANOVA using a standard soft ware package (Origin) with p<0.05.

Results

Yucatan Pig CD47 mRNA.

The antisense morpholino was designed to complement human and murine CD47, but the published sequence for porcine CD47 has four mismatched bases within this sequence (NM__213982; Shahein et al., *Immunology* 106(4): 564-576, 2002) (FIG. 43A). We first confirmed the sequence of Yucatan miniature pig CD47. Tissue from the Yucatan white hairless mini pig was digested, cDNA prepared and sequence analysis performed (gi EU179507; NCBI). Based upon DNA sequencing of two independently derived CD47 cDNAs, white hairless Yucatan miniature pig CD47 mRNA and predicted protein sequences are identical to those annotated for *Sus scrofa* (NM__213982). Based on their distribution in the sequence, 4 mismatches were not predicted to impact targeting (Gene Tools). The strength of interaction between the target RNA sequence and the CD47 morpholino was estimated by analysis of melting temperature. At concentrations of 1 μM and 10 μM morpholino, the calculated $T_M$ are 99.8° C. and 104.0° C. respectively for porcine and human CD47. Thus, the morpholino should form stable complexes with the porcine CD47 mRNA under physiological conditions.

Morpholino Suppression of CD47 Prevents TSP1 Inhibition of NO-Stimulated VSMC Adhesion.

To confirm that the morpholino effectively targets CD47 in porcine vascular cells, we first replicated our published results in human VSMC, where down regulation of CD47 using the same antisense morpholino blocked the ability of TSP1 to inhibit NO-stimulated effects[16]. Porcine VSMC demonstrated NO-stimulated enhancement of adhesion to type I collagen, which was inhibited by exogenous TSP1 at very low doses (FIG. 43B).

NO-Driven cGMP Accumulation in CD47 Morpholino-Treated Yucatan Pig VSMC is not Blocked by TSP1.

To further validate the CD47 morpholino, VSMC from the femoral arteries of Yucatan white hairless pigs were pre-treated with a CD47 oligonucleotide morpholino or a mismatched control, and cGMP responses to exogenous NO were measured. As expected untreated, mismatch- and target morpholino-treated cells showed similar increases in cGMP after incubation with an NO donor (FIG. 43C). Pre-incubation with TSP1 (2.2 nM) blocked the increase in cGMP in control and mismatch treated cells. However, NO-stimulated cGMP levels in VSMC treated with a CD47 morpholino were resistant to suppression by TSP1. Importantly, basal cGMP levels were also elevated in resting cells following treatment with the CD47 morpholino compared to untreated and mismatch treated cells (FIG. 43D).

TSP1 Antibody Treatment of Porcine VSMC Blocks TSP1 Inhibition of NO-Stimulated cGMP Accumulation.

Antibody A6.1 was raised against human TSP1 but recognizes TSP1 across several species of mammals (Annis et al., *J Thromb Haemost* 4(2):459-68, 2006). This TSP1 antibody improved survival of ischemic tissue in mice, but its ability to block cGMP signaling via CD47 has not been confirmed in vitro (Isenberg et al., *Circ Res* 100(5):712-720, 2007). To validate A6.1, white hairless Yucatan miniature pig VSMC were incubated in the presence of A6.1 (10 μg/ml) and TSP1 (2.2 nM), and then NO added. The ability of TSP1 to block an NO-driven accumulation of cGMP was substantially reduced in the cells that were pretreated with A6.1 (FIG. 43E).

Suppression of CD47 Increases Random Cutaneous Flap Survival in a Porcine Model.

20 cm² random cutaneous flaps were created in 6 month old white hairless Yucatan miniature pigs. Flaps that were treated with a CD47 morpholino via infiltration injection showed significantly more tissue survival compared to untreated flaps or flaps treated with a control morpholino (FIGS. 44A, 44B). Untreated and flaps treated with a mismatch control morpholino showed 47±5% and 34±6% necrosis respectively. In contrast morpholino treated flaps had minimal necrosis (12±3%).

Morpholino Suppression of CD47 is Associated with Increased Perfusion of Random Ischemic Flaps.

Perfusion injection studies of freshly euthanized white hairless Yucatan pigs demonstrated alterations in flap staining by India ink consistent with clinical findings of tissue survival (FIGS. 45A, 45B). Untreated flaps and flaps treated with a missense control morpholino showed lack of India ink staining of vessels that paralleled areas of tissue necrosis (FIG. 45C).

Antibody Ligation of TSP1 Alters Ischemic Tissue Survival.

Random dorsal cutaneous flaps were treated with a monoclonal antibody to TSP1 (A6.1), which was previously shown to enhance ischemic tissue survival in a murine model (Isenberg et al., *Circ Res* 100(5):712-720, 2007). Treated flaps demonstrated significantly increased tissue preservation compared to untreated flaps (FIGS. 46A, 46B). In contrast another monoclonal antibody to TSP1 (HB8432) did not increase tissue survival. Determination of tissue survival correlated with areas of fluorescein staining in flaps obtained in living animals.

Discussion

Tissue necrosis is a common complication secondary to traumatic injury or in the post-operative interval following elective surgery (Annis et al., *J Thromb Haemost* 4(2):459-468, 2006; Levin, *Orthop Clin North Am* 24(3):393-409, 1993), problems further enhanced by aging (Ryan, *Micron* 35(3):161-171, 2004; Harris & Rumbaut, *Pathophysiology* 8(1):1-10, 2001). Significant morbidity and mortality arise as a result. A number of agents designed to increase tissue blood flow and enhance tissue survival have been utilized in several experimental models, though results in the clinical environment have been disappointing (Hankey et al., *JAMA* 295(5): 547-553, 2006). A majority of currently employed agents are administered systemically and have non-specific and troublesome side effects. Thus, new agents are needed that can enhance tissue survival and wound healing and at the same time avoid systemic complications.

Nitric oxide is one of the central regulators of blood flow in the body based on its ability to relax VSMC and dilate blood vessels (Ignarro, *J Physiol Pharmacol* 53(4 Pt 1):503-514, 2002; Bolz et al., *Circulation* 107(24):3081-3087, 2003). Agents based on NO have been used in experimental models to enhanced tissue blood flow and survival under ischemic insult (Isenberg et al., *Microsurgery* 25(5):442-451, 2005; Knox et al., *Microsurgery* 15(10):708-711, 1994). In people NO elevating agents such as nitroglycerine and isosorbide dinitrate have been employed for many years in treating ischemic heart and vascular disease. Recently we discovered that TSP1, through CD47, potently blocks the ability of NO to relax contracting VSMC (Isenberg et al., *Blood* 109(5):1945-1952, 2007). In murine models of ischemia tissue survival, blood flow was dramatically enhanced by targeting TSP1 and CD47. Additionally tissue blood flow in both young and aged animals is substantially greater following an exogenous NO challenge in mice lacking TSP1 (Isenberg et al., *Blood* 109 (5):1945-1952, 2007; Isenberg et al., *Arterioscler Thromb Vasc Biol* Published on-line Oct. 4, 2007; DOI: 10.1161/ ATVBAHA.107.155390). However, it is widely appreciated that therapeutic results in murine disease models often do not translate into clinical gains for people.

We now present evidence that targeting TSP1-CD47 enhances NO-signaling in porcine vascular cells and increases ischemic tissue survival in higher mammals. In several in vitro assays, porcine VSMC demonstrated TSP1 inhibition of NO-driven cell signaling. NO-stimulated adhesion to collagen was blocked by TSP1. NO driven intracellular cGMP flux was also sensitive to blockade by TSP1. Treating porcine VSMC with a CD47 morpholino that decreases expression of the cell receptor renders the cells functionally insensitive to TSP1 blockade of NO-stimulated signals including alterations in adhesion and intracellular cGMP flux. Even more significant was the finding that TSP1-CD47 signaling modulated basal levels of intracellular cGMP in porcine VSMC. We previously reported that endogenous TSP1 altered resting levels of cGMP in murine endothelial and aortic-derived VSMC (Isenberg et al., *Proc Natl Acad Sci USA* 102(37):13141-13146, 2005; Isenberg et al., *Cardiovasc Res* 71(4):785-793, 2006) and that this response necessarily required CD47 (Isenberg et al., *J Biol Chem* 281(36):26069-26080, 2006). We also recently reported that TSP1 limits tissue cGMP at rest and after ischemic insult (Isenberg et al., *Blood* 109(5):1945-1952, 2007; Isenberg et al., *Arterioscler Thromb Vasc Biol* Published on-line Oct. 4, 2007; DOI: 10.1161/ATVBAHA.107.155390). We now extend these findings and show that interrupting TSP1-CD47 signaling by suppressing CD47 levels leads to elevation of basal cGMP in porcine VSMC. Additionally, a TSP1 monoclonal antibody (A6.1) minimized the ability of TSP1 to inhibit NO-stimulated cGMP flux in porcine VSMC. Together these findings suggest that in a porcine model of tissue ischemia a CD47 morpholino and a TSP1 antibody enhance tissue survival by increasing cGMP, maximizing vascular relaxation and increasing tissue perfusion.

To develop an experimental system with greater similarity to people we employed a porcine model of tissue ischemia. Pigs have been utilized in numerous studies of tissue healing and blood flow since they mimic human cutaneous and vascular anatomy (Bostick et al., *J Am Assoc Lab Anim Sci* 45(3):33-37, 2006' Van Dorp et al., *Wound Repair Regen* 6(6):556-568, 1998; Russell et al., *Plast Reconstr Surg* 117 (7):2259-2266; discussion 2267-2268, 2006; Harder et al., *J Surg Res* 119(1):100-105, 2004). The distribution of cutaneous vessels in the pig has recently been described and follows the same general rule as in humans with vessels traveling from deep to superficial and branching step-by-step into reduced-caliber divisions though the total number of segmental arcades in the porcine cutaneous envelope is greater than found in people (Zhang et al., *Plast Reconstr Surg* 106(7): 1555-1565, 2000). Clinically this enhanced redundancy in cutaneous perfusion required alteration of the traditional random flap dimensions from a ratio of 1:2 between width and length to 1:5 to insure a predictable degree of tissue necrosis. We have recently reported therapeutic efficacy in enhancing ischemic tissue survival with a CD47 morpholino also delivered directly to tissue units through syringe injection (Isenberg et al., *Circ Res* 100(5):712-720, 2007; Isenberg et al., *Arterioscler Thromb Vasc Biol* Published on-line Oct. 4, 2007; DOI: 10.1161/ATVBAHA.107.155390). Similar increases in tissue survival were obtained in flaps treated with a specific monoclonal antibody to TSP1 (clone A6.1). The monoclonal antibody can engage TSP1 directly at the cell surface and should persist in the soft tissues in the extravascular compartment for some time. In a murine model of tissue ischemia the A6.1 antibody was also tissue protective and enhanced survival and blood flow (Isenberg et al., *Circ Res* 100(5):712-720, 2007). This finding is consistent with the ability of A6.1 to bind to both human and murine TSP1 (Annis et al., *J Thromb Haemost* 4(2):459-468, 2006).

The results herein presented in a porcine model provide additional confirmation that blockade of TSP1-CD47 signaling regionally, via morpholino suppression of CD47, or direct ligation of TSP1 with a monoclonal antibody greatly enhances ischemic tissue survival. These results expand on our previous reports that therapeutic advantage can be obtained with the same treatments in murine ischemic tissue units. Combined with cellular data obtained in vascular cells from several different species including murine (Isenberg et al., *Proc Natl Acad Sci USA* 102(37):13141-13146, 2005' Isenberg et al., *Cardiovasc Res* 71(4):785-793, 2006), bovine, porcine and human (Isenberg et al., *Blood* 109(5):1945-1952, 2007) these findings provide strong evidence for the universality of NO regulation by TSP1 in mammals and suggest therapeutic potential for people.

Example 7

Thrombospondin-1 and CD47 Regulate Blood Pressure and Cardiovascular Responses to Vasoactive Stress Nitric oxide (NO) locally regulates vascular resistance and blood pressure by modulating blood vessel tone. Thrombospondin-1 (TSP1), via its receptor CD47, limits the ability of NO to relax vascular smooth muscle cells and increase regional blood flow under ischemic stress. Because NO also has central cardiovascular effects and nitrovasodilators are important therapeutic regulators of blood pressure and cardiac function, we examined global cardiovascular responses to stress in mice lacking TSP1 or CD47. Mice lacking TSP1 have normal resting blood pressure and pulse but show an exaggerated drop in mean arterial pressure in response to NO. CD47-deficient mice have elevated resting blood pressure and exhibit a greater decrease in response to NO. TSP1 null mice exhibit a similarly exaggerated hypotensive response to isoflurane anesthesia. With concurrent central autonomic blockade, this leads to premature cardiovascular collapse and death of the TSP1 null mice. Blood pressure and regional cutaneous perfusion responses to temperature change and epinephrine are also dysregulated in TSP1 and CD47 null mice. Thus, TSP1 signaling via CD47 is an acute physiological regulator of blood pressure and global hemodynamics.

Cardiovascular homeostasis requires constant regulation of tissue perfusion and blood flow. This process involves coordinated interactions of the autonomic nervous system, heart, lungs and blood vessels. Regional metabolic demands must be met by rapid and efficient redistribution of blood flow. The bioactive gas nitric oxide (NO) is a major physiological regulator of blood vessel diameter and blood flow (Ignarro, *J Physiol Pharmacol.* 53:503-514, 2002; Arnal et al., *Cell Mol Life Sci.* 55:1078-1087, 1999). Endothelial cells lining arteries, in response to specific stresses, increase their production of NO, which in turn diffuses into the adjacent vascular smooth muscle cells (VSMC) and causes cGMP-mediated relaxation. This results in vessel dilation and increased blood flow. Direct cGMP-dependent and indirect activation of the cGMP phosphodiesterase (PDE5) provides negative feedback to limit NO/cGMP signaling (Muller-shausen et al., *J Cell Biol.* 160:719-727, 2003). The matricellular protein, thrombospondin-1 (TSP1), which is produced by vascular cells and circulates at 100-200 μM levels in plasma (Bergseth et al., *Thromb Res.* 99:41-50, 2000), controls a second signaling pathway that limits the ability of NO to stimulate cGMP accumulation (Isenberg et al., *Proc Natl Acad Sci USA.* 102:13141-13146, 2005; Isenberg et al., *Cardiovasc Res.* 71:785-793, 2006). Physiological levels of TSP1 potently inhibit NO-driven relaxation of contracting VSMC and limit the ability of NO to increase tissue blood flow at rest and under stress (Isenberg et al., *Blood* 109:1945-1952, 2007). The ability of TSP1 to block NO/cGMP signaling in vascular cells requires its cell surface receptor CD47 (Isenberg et al., *J Biol Chem.* 281:26069-26080, 2006). Targeting of either TSP1 or CD47 significantly enhances tissue survival after local ischemic challenge (Isenberg et al., *Circ Res.* 100:712-720, 2007).

NO has central as well as local effects. Hypertensive phenotypes have been found in some NOS knockout mice (Ortiz & Garvin, *Am J Physiol Regul Integr Comp Physiol.* 284:R628-638, 2003). Central administration of NO donors or nitrovasodilators can alter blood pressure and cardiac function, leading to the extensive use of these agents for treating chronic and acute diseases of the cardiovascular system (Hermann et al., *J Clin Hypertens* (Greenwich) 8:17-29, 2006). Based on its ability to limit NO signaling, we hypothesized that TSP1 and CD47 might also play a role in regulating central cardiovascular responses. Data presented below now shows that awake CD47 null mice have elevated blood pressure, and both CD47 and TSP1 null mice show exaggerated hypotensive responsives to NO. Furthermore, responses of these mice to anesthesia, central autonomic blockade, temperature change, and adrenergic stimulation demonstrate additional roles for endogenous TSP1 and its receptor CD47 to limit global cardiovascular responses.

Materials and Methods

Animals.

Wild type, TSP1-null and CD47-null C57BL/6 mice were housed under pathogen free conditions and had ad libitum access to filtered water and standard rat chow. Handling and care of animals was in compliance with the guidelines established by the Animal Care and Use Committees of the National Cancer Institute.

Reagents.

The nitric oxide donor diethylamine NONOate (DEA/NO) was kindly provided by Dr. Larry Keefer (NCI, Frederick, Md.). The nitric oxide donor PAPA/NO was purchased from Cayman Chemical Company (Ann Arbor, Mich.). Isoflurane (Forane®, USP) was purchased from Baxter Healthcare Corp. (Deerfield, Ill.). Epinephrine hydrochloride and hexamethonium chloride were purchased from Sigma-Aldrich (St. Louis, Mo.).

Blood Pressure and Pulse Measurements.

Mean systolic, diastolic and arterial blood pressure (BP) and mean pulse was measured in age and sex matched mice using a computerized tail cuff system (Hatteras Systems, MC4000 Blood Pressure Analysis System, Cary, N.C.). The mice were allowed to acclimate to the apparatus for 5 min prior to the start of measurement. Each animal underwent a cycle of 10 preliminary and 50 experimental pressures measurements for data acquisition and data calculation. Animals were acclimated to the measuring system and protocol for 4 days with treatment with data acquisition being performed on the $5^{th}$ day. Pressures recordings were performed at the same time each day. Data was accepted if the mouse had valid readings for at least 20 consecutive pulse beats. All studies were performed at the same hour each day.

ECG Measurements.

ECG measurements were obtained in resting awake animals using the ECGenie™ ECG Screening System (Mouse Specifics, Inc., Boston, Mass.) Animals were placed on the recording stage and allowed to acclimate to the system and measurements were obtained passively as the animal's paws contacted the lead surfaces built into the platform floor surface. Sampling of collected tracings were then analyzed by the include manufacturer software package for standard physiologic parameters.

Skin Blood Flow.

Skin blood flow was measured using laser Doppler imaging (MoorLD1-2λ, Moor Instruments, Devon, England). Briefly, animals were placed in a prone position on a heating pad, and anesthesia was provided by 2% inhalation isoflurane in a 50:50 mixture of oxygen to room air. Core temperature was monitored by rectal probe and was further controlled with a heat lamp. The hair of the dorsum of the animals was clipped and depilated with Nare™ and a template with a 1 $cm^2$ area used to trace a region of interest (ROI). After equilibration to the experimental set-up analysis of cutaneous blood flow was obtained. The following instrument settings were used: override distance 21 cm; scan time 4 msec/pixel. Results are expressed as the change percent control from baseline of the ROI.

General Anesthesia.

Animals were induced with isoflurane via controlled vaporizer and maintained on 1.5% isoflurane and a 50:50 mixture of room air and oxygen administered via nose cone. Respirations were monitored continuously monitored by direct observation of the animal. Body core temperature was measured via rectal probe. Temperature control was performed using a water-circulating warming surface and heating lamp. Following a 15 minute period of stabilization mean systolic, diastolic and arterial blood pressure and mean pulse measurements were determined.

Statistics.

Results are presented as the mean±SD with significance calculated by the Student's t test and an assigned p value 0.05. Data represents results of studies performed in a total of 40 animals distributed as follows: Wild type, n=16; TSP1-null, n=16; CD47-null, n=8.

Results

CD47 Controls Resting Blood Pressure.

Age and sex matched wild type and TSP1 null C57BL/6 mice exhibited no significant differences in resting blood pressure (FIG. 47A). In contrast, CD47 null animals demonstrated significant elevations of systolic, diastolic and mean arterial pressure compared to wild type and TSP1-null animals. No significant difference in mean resting pulse (FIG. 47B) or ECG was found between any age, gender or strain cohort.

TSP1 and CD47 Limit Blood Pressure Responses to NO.

Age and sex matched wild type and TSP1 null C57BL/6 mice were challenged with a rapidly releasing NO donor (DEA/NO, t½=2-4 min (Thomas et al., *Methods Enzymol.* 359:84-105, 2002), 1 μl/gm body weight of a 100 mM stock solution) administered via i.p. injection, and awake resting blood pressure and pulse were determined. Both wild type and TSP1-null mice demonstrated significant decreases in systolic, diastolic and mean arterial pressure (FIG. 47C), but significantly greater decreases in blood pressure measurements were noted in the absence of TSP1. Mean pulse values tended to increase modestly in all animals following DEA/NO challenge. Analysis of time course data demonstrated that recovery of baseline pressure levels was delayed in TSP1 null animals as compared to wild type mice. Similar differences were found when animals were challenged using an NO donor agent with slower release kinetics (PAPA/NO, t½=15 minutes (Thomas et al., *Methods Enzymol.* 359:84-105, 2002), FIG. 47D), with the drop in mean arterial pressure always greater in the absence of TSP1. Interestingly, CD47 null animals treated with PAPA/NO showed the greatest drop in mean arterial blood pressure (FIG. 47D). Once again mean pulse was only modestly increased above resting values in animals treated with PAPA/NO (FIG. 47E).

TSP1 and CD47 Limit Cutaneous Perfusion Responses to NO.

Changes in blood pressure can also influence cutaneous perfusion (Takeuchi et al., *Jpn J Physiol.* 29:119-130, 1979). When age and sex matched animals at a fixed core temperature (34.5° C.) were treated with exogenous NO (DEA/NO 1 μl/gram weight of 100 mM stock) via rectal catheter bolus injection, the initial increase in cutaneous perfusion assessed by laser Doppler imaging was always significantly greater in TSP1 and CD47 null mice compared to wild type controls (FIG. 48A). By 30 minutes, perfusion in the TSP1 null returned to baseline, but flux remained elevated in the CD47-null (FIG. 48B).

TSP1 and CD47 Limit Blood Pressure Responses to Epinephrine.

Treatment with epinephrine (0.05 μg/animal in 50 μl of sterile saline via i.p. injection) produced the expected increase in mean arterial pressure in wild type animals (FIG. 49A). However, TSP1 null animals did not show a significant increase in mean arterial pressure. Mean pulse values were moderately increased in both wild type and TSP-null mice (FIG. 49B). However, the same dose of epinephrine proved fatal to CD47 null animals, precluding further measurements.

A reflex increase in cutaneous perfusion has also been reported in response to an i.p. epinephrine challenge (Ishida et al., *Biol Pharm Bull.* 26:170-181, 2003). Both wild type and TSP1 null animals had increased cutaneous perfusion secondary to an epinephrine bolus (FIG. 49C). However, the increase was greater and more sustained in the TSP1 null mice.

TSP1 Stabilizes Blood Pressure During General Anesthesia.

Induction of general anesthesia is associated with alterations in cardiovascular responses (Reich et al., *Anesth Analg.* 101:622-628, 2005). Isoflurane is a widely used agent for induction and maintenance of general anesthesia. After establishment of general anesthesia with isoflurane, wild type mice demonstrated the expected downward trend in systolic blood pressure and a very modest overall drop in mean arterial pressure (FIG. 50A). In contrast TSP1-null animals showed significant decreases in systolic, diastolic and mean arterial blood pressures.

TSP1 and CD47 Limit Alterations in Tissue Perfusion in Response to Temperature.

Alterations in core temperature are known to significantly alter skin blood flow (Stocks et al., *Aviat Space Environ Med.* 75:444-457, 2004), due in part to autonomic regulation of skin in-flow vessels (Charkoudian, *Mayo Clin Proc.* 78:603-612, 2003). Under controlled conditions of general anesthesia, the core temperature in animals was increased in 0.5 degree intervals from 34 to 37° C., and cutaneous perfusion was measured via laser Doppler imaging. Cutaneous perfusion increased in all animals with increasing core temperature (FIG. 50B). However, the increase as a percentage of the respective baseline values was always significantly greater in TSP1 and CD47 null animals.

TSP1 Limits Cardiovascular Collapse from Central Autonomic Blockade.

Maintenance of mean arterial blood pressure and minimization of larger alterations in systolic and diastolic pressure are central for homeostasis. Input from the autonomic nervous system is critical for the precise control and support of blood pressure. Autonomic blockade with a centrally active agent such as the ganglionic blocker hexamethonium removes sympathetic tone and is known to enhance cardiovascular responses to alterations in nitric oxide levels (Scrogin et al., *Am J Physiol.* 274:R367-374, 1998; Shibao et al., *Hypertension* 50:47-53, 2007). We induced and maintained general anesthesia with 1% isoflurane in wild type and TSP1 null mine. Core temperature was kept constant at 37° C., and the animals were challenged with hexamethonium. Cutaneous perfusion was then measured every 2.5 minutes via laser Doppler imaging (FIGS. 51A, 51B). Both wild type and TSP1 null animals demonstrated decreases in cutaneous perfusion and eventual cardiovascular collapse and death. However, the loss of perfusion was significantly more rapid in the absence of TSP1 and diverged from that of wild type mice after 5 min. Wild type mice sustained cutaneous perfusion for an additional 10 min, indicating an important role for endogenous TSP1 in maintaining perfusion under this stress.

Discussion

Aberrant vasoregulation contributes to the etiology of many chronic diseases including peripheral vascular disease, coronary heart disease and hypertension. Nitrovasodilators play a major role in the therapeutic management of these diseases. Previously, hydrolysis of cGMP by PDEs was considered the major regulator of NO signaling in vascular physiology (Mullershausen et al., *J Cell Biol.* 160:719-727, 2003; Rybalkin et al., *Circ Res.* 93:280-291, 2003). Inhibitors of PDE5 have proven therapeutically useful to increase NO responses in certain tissues. We have identified TSP1 as a physiological regulator of the activation of soluble guanylate cyclase by NO (Isenberg et al., *Proc Natl Acad Sci USA.* 102:13141-13146, 2005). Elevated basal cGMP levels in vascular cells from mice lacking endogenous TSP1 or CD47 show that cGMP signaling is continuously modulated by physiological concentrations of TSP1 independent of PDE activity (Isenberg et al., *J Biol Chem.* 281:26069-26080, 2006). In vivo, loss of TSP1 or CD47 results in enhanced perfusion of ischemic tissues as well as enhanced local and systemic cardiovascular responses to exogenous NO challenge. Thus, TSP1 constantly functions to temper regional and systemic blood flow distribution in healthy tissue and in response to injury or stress.

Homeostatic compensation mechanisms probably account for the normal resting blood pressure and pulse in TSP null mice. However, the modulating role of TSP1 becomes apparent in the face of centrally acting vasoactive stresses. The differential responses in TSP1 null and wild type mice show that endogenous TSP1 functions continuously to maintain blood pressure by modifying central cardiovascular responses to NO. We also identified a role for TSP1 in maintaining blood pressure and perfusion in response to temperature change, adrenergic challenge, and isoflurane anesthesia. In addition to being opposed by TSP1, the vasodilator activity of NO is also limited by baroreflex control. Blocking autonomic input revealed an important role of TSP1 in maintaining vascular tone.

The cardiovascular phenotype of the CD47 null mouse is more pronounced in that its resting blood pressure differs from that of a wild type mouse, and vasoactive challenges generally resulted in greater changes in blood pressure than were observed for TSP1 null mice. The stronger phenotype of the CD47 null relative to the TSP1 null could reflect some compensation for loss of TSP1 by other thrombospondins expressed in vascular cells such as TSP2 and TSP4 (Lamy et al., *J Immunol.* 178:5930-5939, 2007; Stenina et al., *Circulation* 108:1514-1519, 2003; Lopes et al., *Mol Cell Biol.* 23:5401-5408, 2003).

Cutaneous perfusion is also linked to central control and distribution of blood flow and is sensitive to pressure alterations. Under conditions of a controlled increase in core body temperature the absence of TSP1 or CD47 caused markedly enhanced blood flow through the cutaneous envelope. Thus, regional blood flow responses to core temperature changes are also limited by TSP1 via CD47. Identical experiments performed under general isoflurane anesthesia allowed correlation of mean arterial pressure with core body temperature and cutaneous perfusion. Here too, in the presence of similar mean arterial pressure, TSP1 was limiting for temperature-stimulated alterations in cutaneous perfusion.

Because loss of TSP1/CD47 signaling can alter blood pressure and global hemodynamic responses to stress, the potential for elevated plasma or vascular matrix TSP1 levels to increase blood pressure or decrease compliance in response to physiological NO signaling should also be considered. Elevated TSP1 expression in the blood vessel wall or surrounding matrix has been reported in atherosclerosis, restenosis, and diabetes (Riessen et al., *Am Heart J.* 135:357-364, 1998; Roth et al., *J Surg Res.* 74:11-16, 1998; Chen et al., *Circulation* 100:849-854, 1999; Stenina et al., *Circulation* 107:3209-3215, 2003). Some cancers are associated with elevated circulating plasma TSP1 levels (Yamashita et al., *Cancer* 82:632-638, 1998; Volpert et al., *Proc Natl Acad Sci USA.* 95:6343-6348, 1998; Hayden et al., *Ann Clin Biochem.* 37(Pt 3):319-325, 2000), but it remains unclear whether elevated circulating TSP1 could be hypertensive.

The present results suggest a central role for TSP1 in controlling blood pressure and are consistent with our previous finding that TSP1 null mice at rest demonstrate marked increases in skeletal muscle blood flow following an NO challenge as compared to the wild type animal (Isenberg et al., *Blood* 109:1945-1952, 2007).[7] Given the association between a coding polymorphism in TSP1 and early coronary artery disease (Topol et al., *Circulation* 104:2641-2644, 2001; Zwicker et al., *Blood* 108:1280-1283, 2006), our results raise the intriguing possibility that altering the antagonism between the TSP/CD47 and NO/cGMP pathways could lead to cardiovascular pathology in people. Further, these results suggest that targeting TSP1/CD47 may provide new therapeutic approaches to regulate blood pressure as well as regional blood flow.

Example 8

Blocking Thrombospondin-1/CD47 Signaling Alleviates Deleterious Effects of Aging on Tissue Responses to Ischemia Decreased blood flow secondary to peripheral vascular disease underlies a significant number of chronic diseases that account for the majority of morbidity and mortality among the elderly. Blood vessel diameter and blood flow are limited by the matricellular protein thrombospondin-1 (TSP1) through its ability to block responses to the endogenous vasodilator nitric oxide (NO). In this study we investigate the role TSP1 plays in regulating blood flow in the presence of advanced age and atherosclerotic vascular disease.

Briefly, mice lacking TSP1 or CD47 show minimal loss of their resistance to ischemic injury with age and increased preservation of tissue perfusion immediately following injury. Treatment of WT and apolipoprotein E null mice using therapeutic agents that decrease CD47 or enhance NO levels reverses the deleterious effects of age and diet-induced vasculopathy and results in significantly increased tissue survival in models of ischemia.

With increasing age and diet-induced atherosclerotic vascular disease, TSP1 and its receptor CD47 become more limiting for blood flow and tissue survival following ischemic injury. Drugs that limit TSP1/CD47 regulation of blood flow could improve outcomes from surgical interventions in the elderly and ameliorate vascular complications attendant to aging.

Introduction

Complications from peripheral vascular disease, including coronary artery disease and myocardial infarction, stroke and ischemic vascular disease affect some 80% of people over the age of 65. The elderly have significant alterations in vascular anatomy including a loss of vascular networks (Lamah et al., *Int J Microcirc Clin Exp.* 16:271-276, 1996) and alterations in vascular response to injury (Ryan T., *Micron.* 35:161-171, 2004). Age is a recognized risk factor for complications following surgery including delayed and incomplete wound healing and tissue loss and accounts for significant morbidity and mortality in this group (Gohel et al., *Eur J Vasc Endovasc Surg.* 29:74-77, 2005; Gosain et al., *World J Surg.* 28:321-326, 2004; Brem et al., *Surg Technol Int.* 11:161-167, 2003; Crooks A., *J Wound Care* 4:222-223, 2005)[3-6]. Animal studies have confirmed the impact of aging upon wound healing (Ashcroft et al., *Biogerontology* 3:337-345, 2002; Ashcroft et al., *J Anat.* 187(Pt 1):1-26, 1995; Kivirikko et al., *Med Biol.* 54:159-186, 1976).

Tissue perfusion is regulated through the control of blood vessel diameter, which itself is controlled by the contractile state of vascular smooth muscle cells (VSMC). Nitric oxide (NO) is a primary and ubiquitous dilator of blood vessels (Ignarro L J., *J Physiol Pharmacol.* 53:503-514, 2002). NO is constitutively produced in blood vessels by endothelial nitric oxide synthase (eNOS). NO activates soluble guanylate cyclase (sGC) leading to cGMP production and vasodilation. In aged vascular cells (Bernardini et al., *Biochim Biophys Acta.* 1745:265-272, 2005), animals and people, both eNOS expression and NO production (Qian et al., *J Cardiovasc Pharmacol.* 47:587-593, 2006) are decreased.

We recently reported that thrombospondin-1 (TSP1) blocks NO-driven VSMC relaxation in a CD47-dependent manner (Isenberg et al., *J Biol. Chem.* 281:26069-26080, 2006; Isenberg et al., *Blood* 109:1945-1952, 2007; Isenberg et al., *Circ Res.* 100:712-720, 2007). NO-driven alterations in blood flow are substantially greater in the absence of TSP1 or CD47. Given the deleterious effects of aging on the cardiovascular system, we wanted to determine if blocking of TSP1 inhibition of NO signaling would provide significant tissue protection in senescent animals. Aged WT and apolipoprotein E (apoE) null mice (with diet-driven vasculopathy) demonstrated increased tissue necrosis in response to a fixed ischemic challenge compared to young animals. In contrast, senescent TSP1-null and CD47-null animals subjected to the same ischemic challenge demonstrated tissue preservation comparable to that in young animals. Suppression of CD47 in senescent or apoE-null animals also resulted in increased tissue survival following ischemic injury.

Materials and Methods

Reagents.

Isosorbide dinitrate (ISDN) and L-nitro-N-methyl arginine (L-NAME) were purchased from Sigma (St. Louis, Mo.). A CD47 morpholino antisense oligonucleotide (CGTCACAG-GCAGGACCCACTGCCCA (SEQ ID NO: 21)) and a mismatched control morpholino were purchased from Gene-Tools (Philomath, Oreg.).

Animals.

C57BL/6 WT, TSP1-null (Lawler et al., *J Clin Invest.* 101: 982-992, 1998) and CD47-null (Gao et al., *J Cell Biol.* 135: 533-544, 1996) mice were maintained in a pathogen free environment with ad libitum access to standard rat chow and water. ApoE null mice (B6.129P2-Apoe<tmlUnc>/J) were purchased from Jackson Labs (Bar Harbor, Me.) and maintained on either a standard rat chow diet or a 40% fat diet (Harlan Teklan, Madison, Wis.) (Meir et al., *Arterioscler Thromb Vasc Biol.* 24:1006-1014, 2004) Animals used were 12-18 months of age, except as indicated when young animals (aged 2-4 months) were used for control purposes. Care and handling of animals was in accordance with the Animal Care and Use Committees of the National Cancer Institute and of Washington University School of Medicine.

Ischemic Soft Tissue Flap Model.

Animals underwent creation of a random myocutaneous (McFarlane) flap as previously described (Isenberg et al., *Blood* 109:1945-1952, 2007). Some animals received either ISDN (1 mg/mL) or L-NAME (0.5 mg/ml) ad libitum in the drinking water during the post-operative interval.

Estimation of Survival Area in Flaps.

The necrotic areas of dorsal myocutaneous McFarlane flaps were determined as previously described (Isenberg et al., *Blood* 109:1945-1952, 2007).

Laser Doppler Analysis of Tissue Perfusion.

Core temperature was monitored via rectal probe and maintained at 37° C. by a heated stage. Anesthesia was obtained with 1.5% isoflurane. A MoorLD1-2λ scanner (Moor Instruments, Devon, England) was used with the following parameters: scan area—1.6×2.5 cm; scan speed—4 ms/pixel, scan time 1 min 54 sec, override distance 25 cm. The override distance was 20 cm.

Hind Limb Ischemia.

Wild type, TSP1-null, CD47-null underwent ligation of the femoral artery at the level of the inguinal ligament as previously described (Isenberg et al., *Circ Res.* 100:712-720, 2007) with a 5-0 nylon ligature placed around the femoral artery and tied, resulting in complete vessel occlusion.

Blood Oxygen Level Dependent (BOLD) MRI Imaging.

WT and TSP1 null mice 14-18 months of age underwent in vivo analysis of tissue perfusion and blood flow using BOLD MRI. MRI images were acquired using a Bruker Biospin 4.7 T scanner and isoflurane anesthesia as previously described (Isenberg et al., *Blood* 109:1945-1952, 2007). T2 mapping spin echo images were obtained using a multi-slice multi-echo (MSME) sequence with a 10-echo train and an echo time of 15 ms. The scan time for a T2 mapping image set (NEX=1) by the MSME sequence was 10 min.

Hind Paw Perfusion Assay.

Fourteen month old mice underwent treatment of the hind paw with 5% mustard oil (Chem Services, Inc) in sesame oil (50 µl to dorsal paw), which is known to induce NO-dependent vasoactive responses (Bernatchez et al., *Proc Natl Acad Sci USA.* 102:761-766, 2005; Yang R et al., *Arterioscler Thromb Vasc Biol.* 19:2762-2768, 1999).

Morpholino Suppression of CD47.

Flap soft tissue units and underling wound beds were injected with control vehicle (normal saline), a CD47 morpholino or a control morpholino (10 µM) in sterile saline. Flap survival was determined as described.

Mitochondrial Viability Assay.

Mitochondrial viability of hindlimb muscle biopsies was assessed by the reduction of a tetrazolium salt to water insoluble formazan through mitochondrial oxidation as described (Bonheur et al., *J Surg Res.* 116:55-63, 2004). Results were expressed as absorbance normalized to dry tissue weight.

Determination of Tissue cGMP.

Skeletal muscle biopsies of equal wet weight were excised, frozen in liquid nitrogen and pulverized, and then washed with 6% (w/v) trichloroacetic acid at 4° C. Homogenates were centrifuged and supernatants washed 4 times with 5 volumes of water saturated diethyl ether. The extracts was lyophilized and resuspended in assay buffer for analysis via immunoassay (Amersham, GE Healthcare, UK).

Histology.

Tissue units were excised, fixed in 10% buffered formaldehyde, paraffin embedded, and sectioned at a thickness of 5 µm. Sections were then stained with hematoxylin and eosin (H&E). Review of each slide was performed by an independent pathologist blinded to the origin of each tissue slide.

Statistics.

Results are presented as the mean±SD of a total of 164 aged animals (12-18 months old) of the following genetic type: WT=67, TSP1-null=56, CD47-null=31, apo E-null=10. Where indicated studies were performed in comparable numbers of young WT, TSP1- and CD47-null mice aged 2-4 months. Significance was calculated with Student's t test and one way ANOVA using a soft ware package (Origin) with $p<0.05$.

Results

Thrombospondin-1 Limits Tissue Necrosis in Aged Animals.

Figure 52:
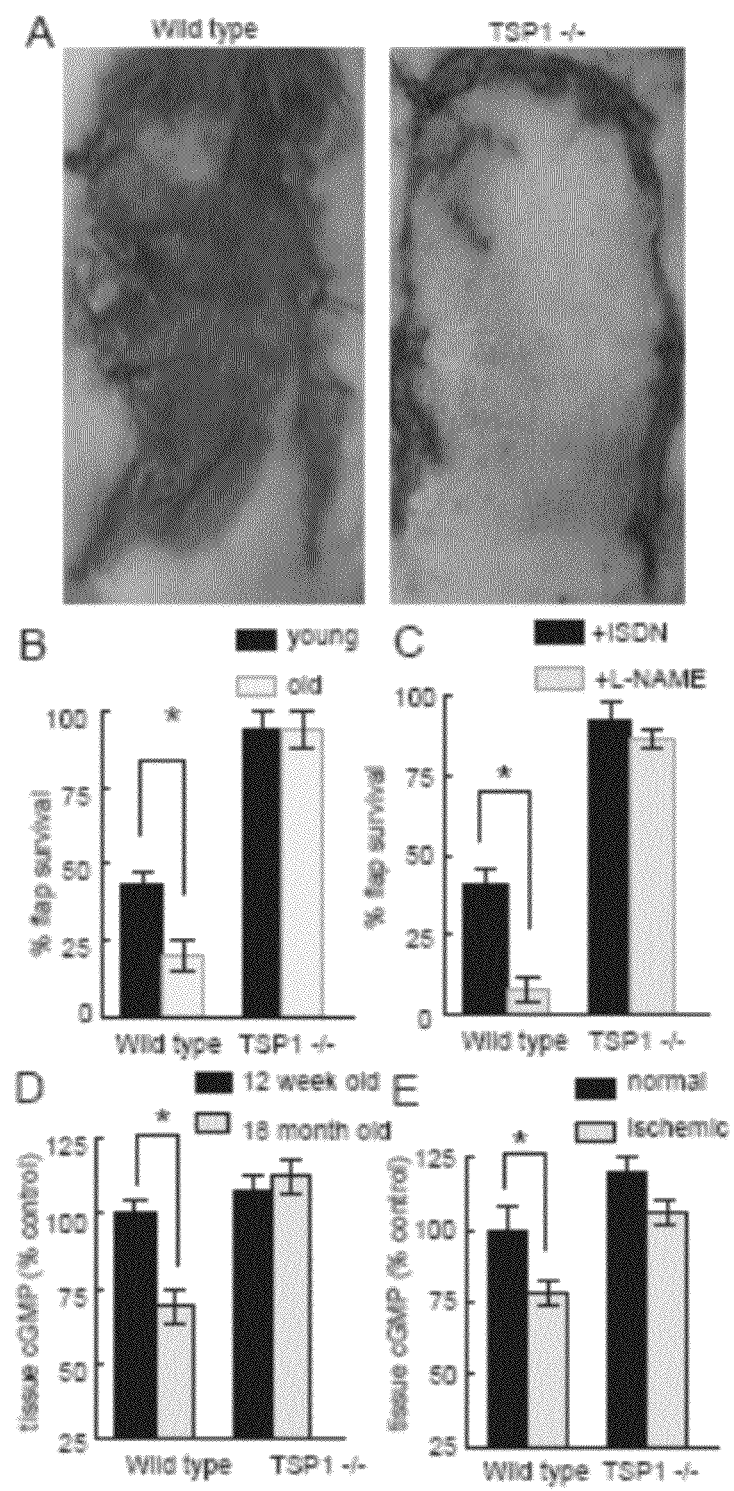

Aged (14-18 months old) sex matched WT and TSP1-null mice underwent McFarlane flap surgery. Wild type flaps demonstrated near total necrosis with only 20±6% survival obtained at 7 days (FIGS. 52A, 52B). This is significantly less than the survival seen in young mice of the same background (Isenberg et al., *Blood* 109:1945-1952, 2007) (p<0.05). Flaps in senescent TSP1-null mice demonstrated near total tissue survival with minimal necrosis (6±3%). Survival did not differ significantly from that of young TSP1-null mice (Isenberg et al., *Blood* 109:1945-1952, 2007) (p>0.05). Histologic review of WT tissue flaps from senescent mice demonstrated loss of the epidermis and ulceration, coagulative necrosis of subcutaneous collagen, and absence of hair follicles (FIGS. 58A & 58C). TSP1-null flaps demonstrated normal histology with minimal inflammatory cell infiltration (FIGS. 58B & 58D).

Nitric Oxide Increases Aged Tissue Survival after Ischemia.

WT aged mice that underwent random myocutaneous flaps and received ISDN ad libitum in the drinking water demonstrated a moderate but significant increase in tissue survival 41±5% (p<0.05) (FIG. 52C). Treatment of WT aged mice with L-NAME further decreased flap survival (8±4% versus 20±6%, p<0.05) compared to untreated (FIGS. 52A, 52C), while L-NAME failed to diminish flap survival in TSP1-null animals. Given the near complete survival of random flaps in untreated aged TSP1-null animals treatment with ISDN did not dramatically alter flap survival (FIG. 52C).

Tissue cGMP is Limited by TSP1 and Age.

Skeletal muscle from WT and TSP1-null young (12 week old) and aged (18 month old) (FIG. 52D) or old mice alone (FIG. 52E) was analyzed for cGMP. Consistent with previous reports (Wheeler et al., *Mol Cell Biochem.* 169:115-124, 1997; Khatib et al., *Mech Ageing Dev.* 101:21-32, 1998), cGMP levels decreased significantly in aged WT animals. In contrast, cGMP was slightly elevated in muscle samples from young TSP1-null mice and did not fall with age. Following 24 hours of ischemia, old TSP1-null animals demonstrated significantly less decrease in tissue cGMP compared to wild type (FIG. 52E).

SP1 Limits Immediate Responses to Ischemia in Senescent Animals.

Mice (14-18 months old) underwent random myocutaneous flaps and laser Doppler analysis of tissue perfusion (FIG. 53A). TSP1-null and CD47-null flaps demonstrated greater flap perfusion than WT flaps (FIG. 53B) (FIG. 59). Null flaps exhibited less overall loss of tissue perfusion immediately after flap elevation and a progressive increase in tissue perfusion during the post-operative interval. WT flaps demonstrated progressive decreases in flap perfusion and showed no tendency to recovery.

Thrombospondin-1 Limits Hind Limb Survival of Ischemia in Aged Animals.

Mice (age 14-18 months) underwent ligation of the femoral artery. Aged wild type animals demonstrated minimal remodeling of existing collateral vessels in the ischemic limb and significantly less than young mice (FIGS. 54A, 54D). In contrast TSP1-null limbs demonstrated extensive vascular remodeling of existing collateral vessels with both young and old animals performing equally well (FIGS. 54B, 54D). Laser Doppler analysis of hind limb perfusion 72 hours post-ligation demonstrated less restoration of perfusion in wild type (FIGS. 54A, 54C) than in TSP1-null limbs (FIGS. 54B, 54C). Mitochondrial viability of muscle biopsies from hind limbs was only minimally decreased in limbs undergoing vascular ligation compared to contralateral control limbs in TSP1-null specimens (FIG. 54E) Aged WT samples showed a pronounced decrease in MTT signal between ischemic limb muscle compared to normal limb muscle, and between young and old tissue samples (FIG. 54E). H&E sections of hind limbs demonstrated marked sterile necrosis of muscle fibers and loss of cell nuclei in ischemic WT tissue (FIGS. 60A, 60B). Ischemic TSP1-null muscle demonstrated minimal sterile necrosis of muscle fibers and increased cell nuclei.

Loss of TSP1 Immediately Enhances Tissue Perfusion Following Hindlimb Ligation in Older Animals.

Aged WT and TSP1-null animals showed a profound decrease in perfusion immediately following vascular ligation of the hindlimb (FIGS. 55A, 55B). However, the TSP1-null animals showed a progressive increase in hindlimb perfusion compared to WT limbs and had significantly more restoration of flow within the first post-operative hour.

Aged TSP1 Null Animals Demonstrate Enhanced Responses to Exogenous NO in Ischemic Tissue.

To further define the role of TSP1/NO signaling in acute responses to tissue ischemia, WT and TSP1-null mice (14-18 months of age) underwent ligation of the femoral artery. Three days following the procedure, animals underwent BOLD MRI in the presence of an NO challenge (10 µM DEA/NO). In the absence of TSP1, NO-driven blood flow changes showed a progressive increase to levels slightly above those found in the control limb (FIG. 55D). WT animals demonstrated a significant deficit in tissue blood flow responses to exogenous NO challenge following proximal ligation compared to the non-operated limb (FIG. 55C). $T_2$ maps showed dramatic differences in WT animals between control and ischemic hind limbs (FIG. 55c). In contrast, blood flow was the same in ischemic and control hind limbs in TSP1-null mice (FIG. 55d).

CD47 Limits Tissue Survival to Ischemia in Aged Animals.

We have reported that the effects of TSP1 on tissue ischemia are mediated by CD47 (Isenberg et al., *Circ Res.* 100:712-720, 2007). Following random myocutaneous flap surgery, tissue survival in senescent CD47-null mice (93±4%) resembled levels obtained in aged TSP1-null animals (FIG. 56A). In contrast to the decrease with age in WT animals, flap tissue survival in CD47-null animals did not decrease age (FIG. 56A).

TSP1 and CD47 Limit Vasodilatory Responses in Aged Animals.

WT and CD47-null mice aged 2-4 months underwent mustard oil application to the right hind paw and perfusion measured by Doppler. Young WT and CD47-null animals demonstrated equivalent levels of hind paw perfusion under basal conditions (FIGS. 56B, 56C). However, upon application of mustard oil, CD47-null animals experienced a marked increase of the baseline perfusion as compared to WT. Likewise, young TSP1-null mice demonstrated enhanced perfusion in response to a mustard oil challenge compared to WT (FIG. 56D). Senescent CD47- and TSP1-null animals had 20-25% greater perfusion compared to WT animals following mustard oil treatment, with persistence of perfusion gains over time (FIG. 56E).

Morpholino Suppression of CD47 Increases Aged Tissue Survival after Ischemia.

WT mice 14-18 months in age underwent random myocutaneous flaps and were treated with control vehicle, a CD47 morpholino (FIGS. 61A, 61B) or control morpholino (data not shown) injected directly to the flap and wound bed at the time of surgery. Post-operative tissue survival was increased in animals treated with a CD47 morpholino as compared to control treated animals (91±4% vs 31±6% respectively) (FIG. 57A). Control morpholino treated flaps displayed degrees of tissue necrosis comparable to untreated aged WT animals. Interestingly, CD47 morpholino treated WT flaps demonstrated substantial remodeling of existing collateral flap vessels (FIG. 61C). Mitochondrial viability was markedly increased in flaps that received the CD47 morpholino as compared to vehicle, missense morpholino or untreated flaps (FIG. 57B).

Ischemic Tissue Necrosis in Aged Animals with Atherosclerotic Peripheral Vascular Disease is Minimized by CD47 Suppression.

ApoE-null mice 12-16 months of age fed a high fat diet for a minimum of 8 months underwent flap elevation. On postoperative day 7 apoE-null animals demonstrated significantly decreased tissue survival comparable to or even slightly worse than changes seen in WT animals of comparable age (FIGS. 61D, 61E). Despite diet induced atherosclerosis, these animals showed increased tissue survival following CD47 morpholino treatment (84±7% vs 5±5% respectively) (FIG. 57C). Routine histological staining of an artery from an aged apoE-null animal on a high fat diet three weeks following temporary ligation demonstrated significant neointimal enlargement and plaque formation (FIG. 61F).

Discussion

Altered tissue perfusion secondary to atherosclerotic peripheral vascular disease is a common cause of numerous diseases of the elderly (Marin J., *Mech Ageing Dev.* 79:71-114, 1995; Bilato et al., *Aging (Milano).* 8:221-234, 1996). Such vasculopathy is endemic in Western societies (Sontheimer D L, *Am Fam Physician* 73:1971-1976, 2006). The consequences of atherosclerotic vascular disease in the elderly are altered blood flow (Mackey et al., *Adv Cardiol.* 44:234-244, 2007) and inadequate delivery of nutrients and oxygen to tissues with attendant tissue ischemia, necrosis and loss. Even in the absence of atherosclerotic changes, age-related decreases in nitric oxide synthase activity (Muller-Delp et al., *Am J Physiol Heart Circ Physiol.* 283:H1662-1672, 2002; Muller-Delp et al., *Am J Physiol Heart Circ Physiol.* 282:H1843-1854, 2002) and cellular and tissue cGMP (Wheeler et al., *Mol Cell Biochem.* 169:115-124, 1997; Khatib et al., *Mech Ageing Dev.* 101:21-32, 1998) can impair the ability of senescent vasculature to dilate, thereby limiting the delivery of blood to tissues.

Recently, we demonstrated that NO-driven relaxation of VSMC is regulated by TSP1 (Isenberg et al., *Cardiovasc Res.* 71:785-793, 2006). In both endothelial and VSMC (Isenberg et al., *Cardiovasc Res.* 71:785-793, 2006; Isenberg et al., *Proc Natl Acad Sci USA.* 102:13141-13146, 2005), TSP1 via CD47, blocks the ability of endogenous or exogenous NO to elevate cGMP levels. As a physiologic consequence, tissue perfusion in response to NO is significantly greater in the absence of TSP1 or CD47 (Isenberg et al., *Blood* 109:1945-1952, 2007). Although the absence of TSP1 or CD47 conferred a survival advantage on ischemic tissues in young animals (10-16 weeks of age), it was not clear that ischemia in the elderly or in the presence of age-associated vasculopathy would be ameliorated by blocking the TSP1-CD47 pathway.

In the present study we found that TSP1, in a CD47 dependent manner, limits ischemic tissue survival under conditions of advanced age and atherosclerotic vasculopathy. In the absence of TSP1 or CD47, senescent mice were able to maintain perfusion following an ischemic insult. The acute effects of TSP1/CD47 signaling on perfusion of aged ischemic tissues is consistent with the immediate enhancement of tissue perfusion in muscle units of TSP1-null animals exposed to exogenous NO (Isenberg et al., *Blood* 109:1945-1952, 2007). Even more remarkable, senescent TSP1-null animals demonstrate a greater perfusion increase in response to exogenous NO than young WT animals (see FIG. 55D and Isenberg et al., *Blood* 109:1945-1952, 2007). Superior perfusion and tissue survival responses of aged TSP1- and CD47-null animals were observed consistently for random cutaneous flaps, hindlimb vascular ligation, and a noninvasive mustard oil/hind paw assay despite the comparable soft tissue vascular densities in wild type and null animals (Agah et al., *Am J. Pathol.* 161:831-839, 2002). The NO-dependence for tissue survival of ischemic injury in WT animals is supported by positive effects of NO supplementation with ISDN and negative effects of NOS inhibition with L-NAME. In the absence of TSP1, tissue survival is less sensitive to NO modulation. This is not surprising since TSP1 limits cGMP accumulation in both vascular cells (Isenberg et al., *Cardiovasc Res.* 71:785-793, 2006; Isenberg et al., *Proc Natl Acad Sci USA.* 102:13141-13146, 2005) and tissue (FIGS. 52D, 52E), and prior studies have documented increased tissue TSP1 levels with age (Riessen et al., *Am Heart J.* 135:357-364, 1998). Thus, we propose that the NO-insufficiency of aging may be due to increased TSP1 antagonism of NO/cGMP signaling as well as loss of NOS activity.

ApoE-null mice on a high-fat diet develop a hyperlipidemic state analogous to that in humans. Blood vessels of these mice show luminal narrowing and hypertrophy of the medial layers with atherosclerotic plaque (Li et al., *Circulation* 110:1701-1705, 2004). Comparable atherosclerotic changes in people have been associated with decreased local NO production by vascular endothelium (Desjardins et al., *Acta Clin Belg.* 61:326-334, 2006; Napoli et al., *Nitric Oxide* 15:265-279, 2006). Interestingly, TSP1 expression has been found to increase with age in atherosclerotic blood vessels (Riessen et al., *Am Heart J.* 135:357-364, 1998; Favier et al., *J Pathol.* 207:358-366, 2005) and in several end organs (Kang et al., *Am J Kidney Dis.* 37:601-611, 2001; Hiscott et al., *Prog Retin Eye Res.* 25:1-18, 2006; Buee et al., *Am J Pathol.* 141:783-788, 1992). Morpholino suppression of CD47 improved ischemic tissue survival in apoE-null animals in the presence of diet-induced atherosclerotic vasculopathy, and also in aged wild type animals. These results suggest that targeting of TSP1 or CD47 in regional vascular beds could improve tissue perfusion under conditions of both advanced age and peripheral vascular disease.

Example 9

Bioactivities of Additional TSP1-based Peptides

NO is a prime physiologic regulator in mammals and can stimulate pro-survival and pro-angiogenic responses. The ability to selectively enhance or block NO-driven effects has remained a therapeutic goal for decades. Discovery that TSP1 and TSP1-based agents can block NO-driven effects provides therapies that either synergize or antagonize NO. Both approaches permit the harnessing of NO as a therapeutic drug by selectively increasing or decreasing NO-driven cellular responses.

This example demonstrates selected bioactivities of TSP1-based peptides.

Methods

Adhesion Assay.

Vascular cells (VSMC or endothelial) were plated at 10,000 cells/well onto 96-well plates (Maxisorb, Nunc) pre-coated with type I collagen (3 µg/ml). Cells were incubated for 1 h in basal medium (lacking additives and serum) with 0.1% BSA and the indicated concentrations of TSP1 and DEA/NO. Plates were then washed with PBS, fixed with glutaraldehyde, stained with crystal violet, and washed. Absorbed stain was solubilized with acetic acid from fixed cells and the resulting color signal determined on a MR580Microelisa Auto Reader, (Dynatech, Alexandria, Va.) at 450 nm wavelength.

Intracellular Cyclic Nucleotide Measurement.

Vascular cells (endothelial) or HT-1080 cells ($10^4$ cells/well) grown overnight in 12-well culture in SM-GM containing 2% FCS or RPMI+10% FCS respectively and then weaned off serum over 48 h before treatment with NO donors and other agents in serum/additive free medium+0.1% BSA. Intracellular cGMP levels were determined using an enzyme immunoassay (Amersham, GE Health Care, UK). In other experiments fresh washed human platelets were incubated in Tyrode's buffer and the indicated treatment agents±NO and cGMP determined.

Results.

NO-Stimulated Adhesion of VSMC and Endothelial Cells to Collagen Matrix is Blocked by TSP1-Based Peptides C6B and C6D.

Figure 62:
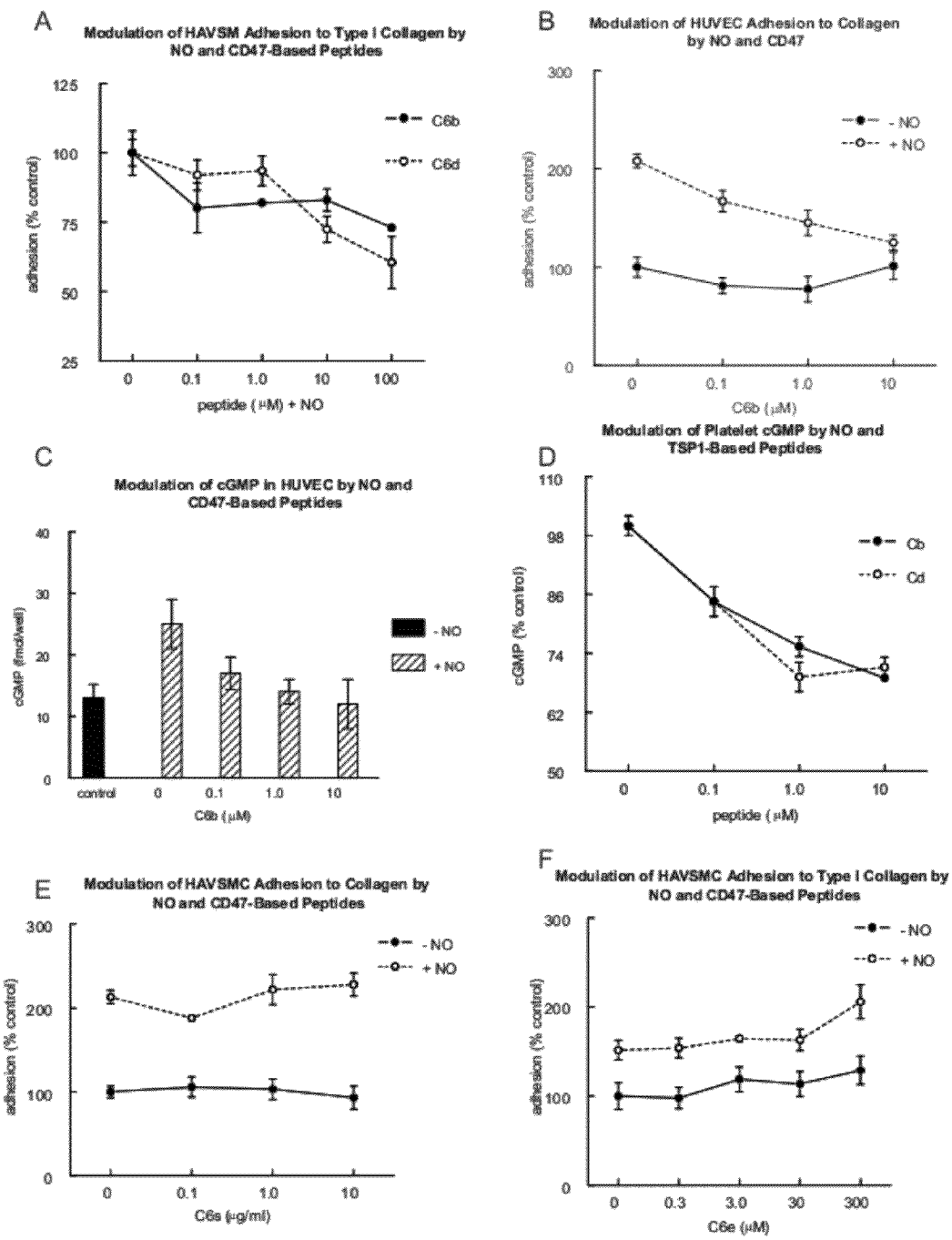

VSMC and endothelial cells demonstrated increased adhesion to type I collagen in the presence of NO (10 µM DEA/NO), which was blocked in a dose-dependent manner by peptide C6b and C6d (FIGS. 62A, 62B).

NO-Stimulated cGMP Flux in Endothelial Cells and Platelets is Blocked by Peptides C6b and C6d.

Endothelial cells (FIG. 62C) and platelets (FIG. 62D) in basal medium without serum or Tyrode's buffer respectively were treated with the indicated peptides±NO (10 µM DEA/NO) and cGMP levels determined.

NO-Stimulated Vascular Cell Adhesion to Type I Collagen is not Blocked by Several Other TSP1-Based Peptides.

HAVSMC were treated with several TSP1 based peptides C6e (FIG. 62F) and C6s (FIG. 62E)±NO (DEA/NO 10 µM), and adhesion to type I collagen determined. The ability of NO to increase cell adhesion was not blocked by these peptides.

NO-Stimulated cGMP Flux in HT-1080 Cells is Inhibited by Several TSP1 Based Peptides.

HT-1080 cells were plated in 12-well plates in RPMI medium, weaned off serum over 48 hrs and treated with the indicated peptides at the given concentrations and cGMP determined via immunoassay (FIGS. 63A-C).

Example 10

Peptide C6d Promotes Aggregation

This example demonstrates that TSP1-derived peptides, such as C6d can be used to promote platelet aggregation by blocking effects of NO.

Methods

Fresh human platelets were suspended in Tyrode's buffer and under low shear conditions thrombin-stimulated aggregation measured as described. Platelets were then treated with peptide C6d (1 µM)±NO (10 µM DEA/NO) and thrombin and aggregation measure.

Results

Thrombin-stimulated aggregation under low shear conditions was markedly delayed by NO. Concurrent treatment with peptide C6d completely reversed the anti-coagulation effects on NO on thrombin-stimulated aggregation. See FIG. 64.

This example demonstrates that peptides based on the sequences of C6d (SEQ ID NO: 1), including C6b (SEQ ID NO: 7) and other peptides described herein, can promote platelet aggregation and blood clotting. These peptides and similar peptides can be used to stop bleeding from congenital bleeding disorders and acquired bleeding disorders. The will also be effective as topically applied hemostatic agents and may be used directly or incorporated into wound dressings and bandages for use in emergency situations and in treating victims of trauma. They can be used in the operating room to achieve bleeding control from large wound surfaces such as found during burn or liver surgery.

This disclosure demonstrates that blocking CD47 and/or TSP1, and particular the functional interaction between these proteins, increases tissue survival to ischemia, alters platelet function and blood clotting, and influences and modulates responses to aging. The disclosure further provides compositions and methods for exploiting these discoveries. It will be apparent that the precise details of compositions and methods described may be varied or modified without departing from the spirit of the described invention. We claim all such modifications and variations, and equivalents thereof, that fall within the scope and spirit of the claims below.

We claim:

1. A method of increasing tissue perfusion in a subject, comprising:
   selecting a subject in need of increased tissue perfusion; and
   administering to the subject a therapeutically effective amount of a pharmaceutical composition comprising an oligonucleotide or oligonucleotide analog of about 15 to about 300 bases that hybridizes to the mRNA of CD47 under high stringency conditions and a suitable delivery vehicle,
   thereby increasing tissue perfusion in the subject.

2. The method of claim 1, wherein the oligonucleotide analog is an antisense morpholino that binds specifically to a nucleic acid encoding CD47.

3. The method of claim 2, wherein the morpholino comprises an antisense morpholino that binds specifically to a nucleic acid encoding CD47 and comprises the sequence CGTCACAGGCAGGACCCACTGCCCA (SEQ ID NO: 21) or a sequence at least 90% identical to SEQ ID NO: 21.

4. The method of claim 3, wherein the antisense morpholino comprises a sequence that varies at no more than four positions from the sequence of SEQ ID NO: 21.

5. The method of claim 4, wherein the antisense morpholino consists essentially of the sequence CGTCACAGGCAGGACCCACTGCCCA (SEQ ID NO: 21).

6. The method of claim 1, wherein the subject has or is at risk of developing at least one disease or condition selected from the group consisting of: ischemia/reperfusion injury, burn injury, organ transplant, tissue transplant, myocardial infarction, myocardial ischemia, stroke, cerebral ischemia, sickle cell anemia, hypertension, atherosclerosis, vasculopathy, ischemia secondary to diabetes, peripheral vascular disease, scleroderma and pulmonary hypertension.

7. The method of claim 1, further comprising administering to the subject a therapeutically effective amount of one or more of: a nitric oxide donor or precursor, an activator of soluble guanylyl cyclase (sGC), or an inhibitor of a cyclic nucleotide phosphodiesterase.

8. The method of claim 1, wherein the need for increased tissue perfusion arises because the subject has had, is having, or will have a surgery selected from the group consisting of: integument surgery, soft tissue surgery, composite tissue surgery, organ transplant surgery, skin graft surgery, skin autograft surgery, limb reattachment surgery, acral part reattachment, and free flap surgery.

9. A method comprising:
   selecting a subject to be subjected to ischemia; and
   administering to the subject a therapeutically effective amount of a pharmaceutical composition comprising an oligonucleotide or oligonucleotide analog of about 15 to about 300 bases that hybridizes to the mRNA of CD47 under high stringency conditions and a suitable delivery vehicle,
   thereby reducing direct ischemic injury and/or ischemia/reperfusion injury in the subject when the subject is subjected to ischemia.

10. The method of claim 9, wherein the oligonucleotide analog is an antisense morpholino that binds specifically to a nucleic acid encoding CD47.

11. The method of claim 10, wherein the morpholino comprises an antisense morpholino that binds specifically to a nucleic acid encoding CD47 and comprises the sequence CGTCACAGGCAGGACCCACTGCCCA (SEQ ID NO: 21) or a sequence at least 90% identical to SEQ ID NO: 21.

12. The method of claim 11, wherein the antisense morpholino comprises a sequence that varies at no more than four positions from the sequence of SEQ ID NO: 21.

13. The method of claim 12, wherein the antisense morpholino consists essentially of the sequence CGTCACAGGCAGGACCCACTGCCCA (SEQ ID NO: 21).

14. The method of claim 9, wherein the ischemia arises because the subject will have or is having a surgery selected from the group consisting of: integument surgery, soft tissue surgery, composite tissue surgery, organ transplant surgery, skin graft surgery, skin autograft surgery, limb reattachment surgery, acral part reattachment, free flap surgery and stent implantation.

15. The method of claim 9, further comprising administering to the subject a therapeutically effective amount of one or more of: a nitric oxide donor or precursor, an activator of soluble guanylyl cyclase (sGC), or an inhibitor of cyclic nucleotide phosphodiesterase(s).

16. The method of claim 9, wherein the pharmaceutical composition is administered as a coating or additive to a vascular stent or other reservoir implanted into the subject.

17. A method of treating a subject, comprising:
   selecting a subject that has or is at risk of direct ischemic injury or ischemia/reperfusion injury; and
   administering to the subject a therapeutically effective amount of a pharmaceutical composition comprising an oligonucleotide or oligonucleotide analog of about 15 to about 300 bases that hybridizes to the mRNA of CD47 under high stringency conditions and a suitable delivery vehicle,
   thereby treating the direct ischemic injury and/or ischemia/reperfusion injury in the subject.

18. The method of claim 17, wherein the oligonucleotide analog is an antisense morpholino that binds specifically to a nucleic acid encoding CD47.

19. The method of claim 18, wherein the morpholino comprises an antisense morpholino that binds specifically to a nucleic acid encoding CD47 and comprises the sequence CGTCACAGGCAGGACCCACTGCCCA (SEQ ID NO: 21) or a sequence at least 90% identical to SEQ ID NO: 21.

20. The method of claim 19, wherein the antisense morpholino comprises a sequence that varies at no more than four positions from the sequence of SEQ ID NO: 21.

21. The method of claim 10, wherein the antisense morpholino consists essentially of the sequence CGTCACAGGCAGGACCCACTGCCCA (SEQ ID NO: 21).

22. The method of claim 17, wherein the subject has or is at risk of a disease or condition selected from the group consisting of: burn injury, organ transplant, tissue transplant, myocardial infarction, myocardial ischemia, stroke, cerebral ischemia, sickle cell anemia, hypertension, atherosclerosis, vasculopathy, ischemia secondary to diabetes, peripheral vascular disease, a non-healing wound of skin, soft tissue, joint or bone, scleroderma and pulmonary hypertension.

23. The method of claim 17, wherein the pharmaceutical composition is administered before, during, or after the subject undergoes surgery.

24. The method of claim 23, wherein the surgery is selected from the group consisting of: integument surgery, soft tissue surgery, composite tissue surgery, organ transplant surgery, skin graft surgery, skin autograft surgery, limb reattachment surgery, acral part reattachment, and free flap surgery.

25. The method of claim 17, further comprising administering a therapeutically effective amount of a nitric oxide donor or precursor to the subject.

26. A method, comprising:
  selecting a donor organ;
  administering to the donor organ, prior to its transplantation into the recipient, a therapeutically effective amount of a pharmaceutical composition comprising an oligonucleotide or oligonucleotide analog of about 15 to about 300 bases that hybridizes to the mRNA of CD47 under high stringency conditions and a suitable delivery vehicle, thereby reducing direct ischemic injury and/or ischemia/reperfusion injury in the donor organ.

27. The method of claim 26, wherein the oligonucleotide analog is an antisense morpholino that binds specifically to a nucleic acid encoding CD47.

28. The method of claim 27, wherein the morpholino comprises an antisense morpholino that binds specifically to a nucleic acid encoding CD47 and comprises the sequence CGTCACAGGCAGGACCCACTGCCCA (SEQ ID NO: 21) or a sequence at least 90% identical to SEQ ID NO: 21.

29. The method of claim 28, wherein the antisense morpholino comprises a sequence that varies at no more than four positions from the sequence of SEQ ID NO: 21.

30. The method of claim 29, wherein the antisense morpholino consists essentially of the sequence CGTCACAGGCAGGACCCACTGCCCA (SEQ ID NO: 21).

31. The method of claim 26, further comprising administering a therapeutically effective amount of a nitric oxide donor or precursor to the recipient.

* * * * *